US011224647B2

(12) United States Patent
Horwitz et al.

(10) Patent No.: US 11,224,647 B2
(45) Date of Patent: Jan. 18, 2022

(54) SAFE POTENT SINGLE PLATFORM VACCINE AGAINST TIER 1 SELECT AGENTS AND OTHER PATHOGENS

(71) Applicant: THE REGENTS OF THE UNIVERSITY OF CALIFORNIA, Oakland, CA (US)

(72) Inventors: Marcus A. Horwitz, Los Angeles, CA (US); Qingmei Jia, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/319,812

(22) PCT Filed: Jul. 31, 2017

(86) PCT No.: PCT/US2017/044741
§ 371 (c)(1),
(2) Date: Jan. 22, 2019

(87) PCT Pub. No.: WO2018/026729
PCT Pub. Date: Feb. 8, 2018

(65) Prior Publication Data
US 2019/0240310 A1 Aug. 8, 2019

Related U.S. Application Data

(60) Provisional application No. 62/369,654, filed on Aug. 1, 2016.

(51) Int. Cl.
A61K 39/114 (2006.01)
A61P 37/04 (2006.01)
C07K 14/32 (2006.01)
A61K 39/02 (2006.01)
A61K 39/07 (2006.01)
C12N 1/36 (2006.01)
C07K 14/195 (2006.01)
C12N 1/20 (2006.01)
A61K 9/00 (2006.01)
A61K 39/04 (2006.01)
A61K 39/235 (2006.01)
C07K 14/20 (2006.01)
C07K 14/36 (2006.01)
A61K 39/00 (2006.01)

(52) U.S. Cl.
CPC .......... *A61K 39/114* (2013.01); *A61K 9/0019* (2013.01); *A61K 9/0043* (2013.01); *A61K 9/0053* (2013.01); *A61K 39/02* (2013.01); *A61K 39/0291* (2013.01); *A61K 39/04* (2013.01); *A61K 39/07* (2013.01); *A61K 39/235* (2013.01); *A61P 37/04* (2018.01); *C07K 14/195* (2013.01); *C07K 14/20* (2013.01); *C07K 14/32* (2013.01); *C07K 14/36* (2013.01); *C12N 1/20* (2013.01); *C12N 1/36* (2013.01); *A61K 2039/522* (2013.01); *A61K 2039/523* (2013.01); *Y02A 50/30* (2018.01)

(58) Field of Classification Search
None
See application file for complete search history.

(56) References Cited

U.S. PATENT DOCUMENTS

| 8,206,700 | B2 | 6/2012 | Horwitz et al. |
| 8,481,024 | B2 | 7/2013 | Horwitz et al. |
| 2007/0190604 | A1 | 8/2007 | Horwitz et al. |
| 2010/0092518 | A1 | 4/2010 | Horwitz et al. |
| 2010/0183547 | A1 | 7/2010 | Horwitz et al. |
| 2010/0215679 | A1 | 8/2010 | Horwitz et al. |
| 2011/0129492 | A1 | 6/2011 | Horwitz et al. |
| 2012/0052085 | A1 | 3/2012 | Horwitz et al. |
| 2015/0056242 | A1 | 2/2015 | Horwitz et al. |
| 2016/0002591 | A1 | 1/2016 | Berka et al. |

OTHER PUBLICATIONS

Jia, Q., et al., "*Francisella tularensis* Live Vaccine Strain deficient in capB and overexpressing the fusion protein of IglA, IglB, and IglC from the bfr promoter induces improved protection against *F. tularensis* respiratory challenge", Vaccine, Sep. 2016, pp. 4969-4978, vol. 34, No. 41.

Jia, Q., et al., "A heterologous prime-boost vaccination strategy comprising the *Francisella tularensis* live vaccine strain capB mutant and recombinant attenuated *Listeria monocytogenes* expressing *F. tularensis* IglC induces potent protective immunity in mice against virulent *F. tularensis* aerosol challenge", Infection and Immunity, May 2013, pp. 1550-1561, vol. 81, No. 5.

Zaide, G., et al., "Identification and Characterization of Novel and Potent Transcription Promoters of *Francisella tularensis*", Applied and Environmental Microbiology, Mar. 2011, pp. 1608-1618, vol. 77, No. 5.

Valentino, M.D., et al., "A broadly applicable approach to T cell epitope identification: Application to improving tumor associated epitopes and identifying epitopes in complex pathogens", Journal of Immunological Methods, 2011, pp. 111-126, vol. 373.

(Continued)

*Primary Examiner* — Jennifer E Graser
(74) *Attorney, Agent, or Firm* — Gates & Cooper LLP

(57) ABSTRACT

A method of immunizing a susceptible host against a pathogen comprising administering to the host a vaccine that comprises an attenuated recombinant live vaccine strain lacking a polynucleotide encoding CapB (LVS ΔcapB), wherein the LVS ΔcapB expresses an antigen of at least one pathogen from Table 1; or administering to the host a vaccine that comprises an attenuated *Listeria monocytogenes* expressing the antigen of the pathogen from Table 1; or administering to the host a prime vaccine and a heterologous booster vaccine where the prime vaccine comprises an attenuated recombinant live vaccine strain lacking a polynucleotide encoding CapB (LVS ΔcapB), wherein the LVS ΔcapB expresses an antigen of at least one pathogen from Table 1 and the heterologous booster vaccine comprises an attenuated *Listeria monocytogenes* expressing the antigen of the pathogen from Table 1.

14 Claims, 32 Drawing Sheets
Specification includes a Sequence Listing.

(56) References Cited

OTHER PUBLICATIONS

Valentino, M.D., et al., "Identification of T-cell epitopes in *Francisella tularensis* using an ordered protein array of serological targets", Immunology, 2011, pp. 348-360, vol. 132.
Extended European Search Report dated Jun. 29, 2020 for European Patent Application No. 17837480.7.
PCT International Preliminary Report on Patentability (IPRP) dated Feb. 14, 2019, International Application No. PCT/US17/44741.
Jia et al., "Francisella tularensis Live Vaccine Strain deficient in capB and overexpressing the fusion protein of IgIA, IgIB, and IgIC from the bfr promoter induces improved protection against F. tularensis respiratory challenge", Vaccine, vol. 34, No. 41, Sep. 1, 2016 (Sep. 1, 2016), pp. 4969-4978.
Jia et al., "A Heterologous Prime-Boost Vaccination Strategy Comprising the Francisella tularensis Live Vaccine Strain capB Mutant and Recombinant Attenuated Listeria monocytogenes Expressing F. tularensis IgIC Induces Potent Protective Immunity in Mice against Virulent F. tularensis Aerosol Challenge11", Infection and Immunity, vol. 81, No. 5, Apr. 15, 2013 (Apr. 15, 2013), pp. 1550-1561.
Valentino et al., "Identification of T-cell epitopes in Francisella tularensis using an ordered protein array of serological targets : T-cell epitope discovery in F. tularensis SchuS411", Immunology, vol. 132, No. 3, Mar. 1, 2011 (Mar. 1, 2011), pp. 348-360.
Valentino et al., "A broadly applicable approach to T cell epitope identification: Application to improving tumor associated epitopes and identifying epitopes in complex pathogens11", Journal of Immunological Methods, Elsevier Science Publishers B.V.,Amsterdam, NL, vol. 373, No. 1, Aug. 11, 2011 (Aug. 11, 2011), pp. 111-126.
Zaide et al., "Identification and Characterization of Novel and Potent Transcription Promoters of Francisella tularensis11", Applied and Environmental Microbiology, vol. 77, No. 5, Ronmental Microbiology, vol. 77, No. 5, Mar. 1, 2011 (Mar. 1, 2011), pp. 1608-1618.
Extended European Search Report dated Jun. 29, 2020 for EP Application No. EP 17837480 .
PCT International Search Report & Written Opinion dated Dec. 26, 2017, Application No. PCT/US17/44741.
Jia, et al. 'Recombinant Attenuated Listeria Monocytogenes Vaccine Expressing Francisella Tularensis IgIc Induces Protection In Mice Against Aerosolized Type AF. Tularensis'2008, Vaccine, vol. 27, No. 8, pp. 1216-1229; p. 3, second paragraph.

A. 5 h post infection

| | |
|---|---|
| 1 | Un-stained Protein standard 1 |
| 2 | Uninfected THP-1 cells |
| 3 | rLVS ΔcapB |
| 4 | rLVS ΔcapB/BaLFPA(L1) |
| 5 | rLVS ΔcapB/YpF1V(D) |
| 6 | rLVS ΔcapB/YpF1V(L1) |
| 7 | PA protein |
| 8 | Yp LF-LcrV monomer protein |

B. 24 h post infection

| | |
|---|---|
| 1 | Un-stained Protein standard 1 |
| 2 | Uninfected THP-1 cells |
| 3 | rLVS ΔcapB |
| 4 | rLVS ΔcapB/BaLFPA(L1) |
| 5 | rLVS ΔcapB/YpF1V(D) |
| 6 | rLVS ΔcapB/YpF1V(L1) |
| 7 | Pre-stained Protein standard |
| 8 | PA protein |
| 9 | Yp LF-LcrV monomer protein |

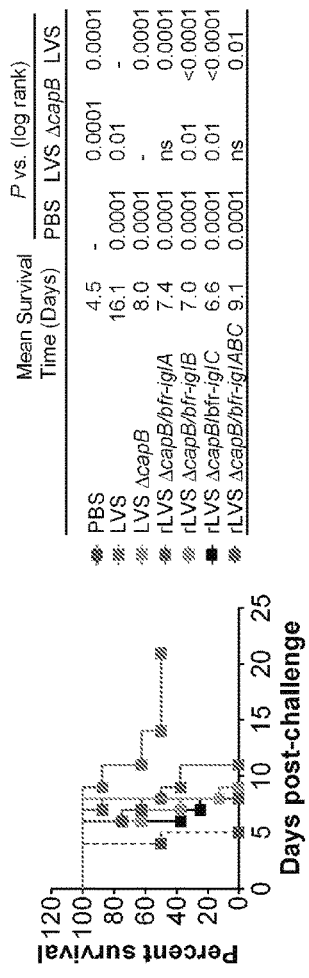
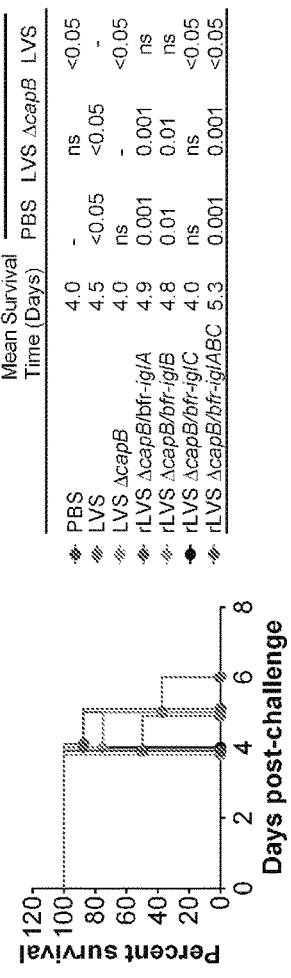
FIG. 20.

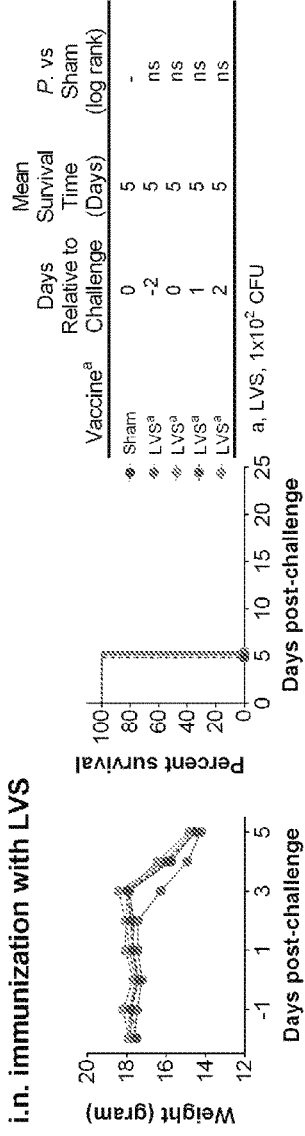
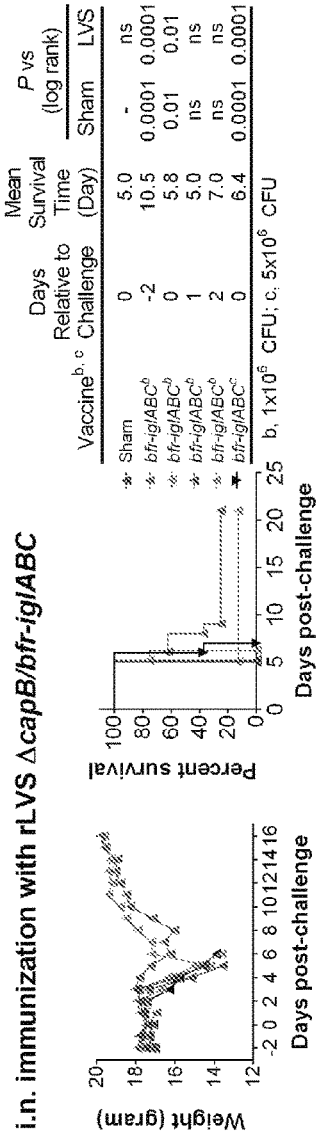
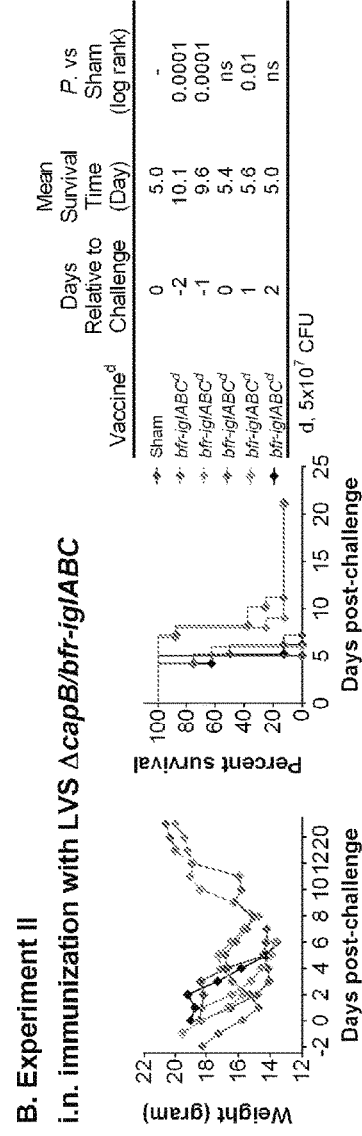
FIG. 22.

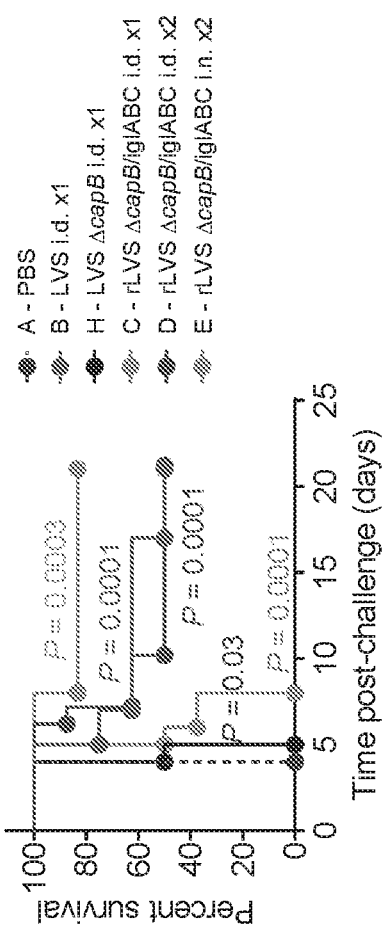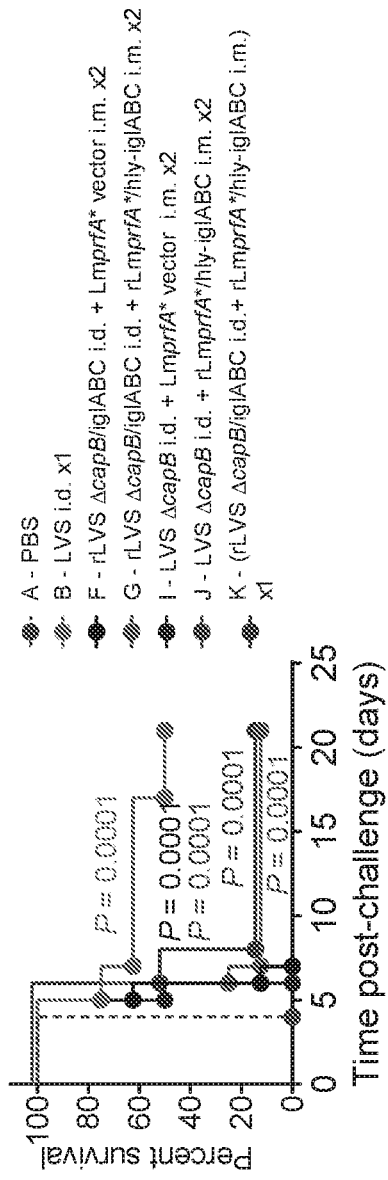
FIG. 27

SAFE POTENT SINGLE PLATFORM VACCINE AGAINST TIER 1 SELECT AGENTS AND OTHER PATHOGENS

CROSS-REFERENCE TO RELATED APPLICATIONS

This application claims priority under Section 119(e) from U.S. Provisional Application Ser. No. 62/369,654, filed Aug. 1, 2016, entitled "SAFE POTENT SINGLE PLATFORM VACCINE AGAINST TIER 1 SELECT AGENTS AND OTHER PATHOGENS" the contents of which are incorporated herein by reference.

STATEMENT AS TO RIGHTS TO INVENTION MADE UNDER FEDERALLY SPONSORED RESEARCH AND DEVELOPMENT

This invention was made with government support under Grant No. AI101189 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 18, 2017, is named 30435_320-WO-U1_SL.txt and is 176,302 bytes in size.

TECHNICAL FIELD

The invention relates to single platform homologous and heterologous priming and boosting vaccines for preventing diseases caused by pathogens and in particular, Tier 1 Select Agents including tularemia, anthrax, and plague in humans and animals.

BACKGROUND OF THE INVENTION

When *Francisella tularensis, Bacillus anthracis*, and *Yersinia pestis* infect humans by the respiratory route, the route of greatest concern in an intentional bioterrorist attack, they cause highly fatal diseases—pneumonic tularemia, pulmonary anthrax, and pneumonic plague, resp. Pneumonic tularemia has a mortality of up to 40--60% for infections with the highly virulent Type A Ft untreated and can be highly fatal even with appropriate antibiotic treatment (1). Pulmonary anthrax has a mortality as high as 100% untreated, and 45% with treatment (2); and pneumonic plague is rapidly lethal (~50-90%) untreated (3). Because these pathogens are relatively easy to manufacture, environmentally hardy, and cause high mortality, they are considered the most likely pathogens to be employed by bioterrorists; indeed, they were developed as bioweapons during WWII and the Cold War (4, 5).

However, there are no licensed vaccines against *F. tularensis* and *Y. pestis*, and the licensed vaccine against *B. anthracis* is suboptimal. The currently available licensed human anthrax vaccines are the U.S. anthrax vaccine absorbed (AVA) and the U.K. anthrax vaccine precipitated (AVP); both are undefined acellular subunit vaccines, containing primarily the Ba Protective Antigen (PA) with a lesser amount of lethal factor (LF) and other proteins. AVA requires 3 prime and 3 boost vaccinations followed by annual boosters and its duration of efficacy is unknown. In addition, AVA causes adverse reactions such as local soreness, redness, itching and swelling at the site of injection. The complexity of the immunization schedule and adverse effects of AVA make it unattractive. There are currently no licensed vaccines against plague or tularemia. The *Y. pestis* EV76 strain was developed and used in humans in the former Soviet Union; however, it has significant toxicity and is not licensed in the U.S. (3). The *F. tularensis* Live Vaccine Strain (LVS) has been extensively studied in the U.S.; this unlicensed vaccine is relatively toxic and provides incomplete protection against aerosolized Ft (6).

Accordingly, there is a great need for vaccines and methods designed to protect military and non-military personnel from diseases caused by Tier 1 Select Agents as well as other pathogens and toxic agents. Furthermore, there is a need for a single platform vaccine that can provide protection from multiple pathogens and toxic agents.

SUMMARY OF THE INVENTION

The present invention is useful for preventing infection caused by pathogens and in particular, Tier 1 Select Agents of bioterrorism including *F. tularensis*, the agent of tularemia, *B. anthracis*, the agent of anthrax and *Y. pestis*, the agent of plague. Though the vaccines described herein are generally illustrated with the antigens for *F. tularensis, B. anthracis*, and/or *Y. pestis*, the same platform can be modified to accommodate antigens of other Tier 1 Select Agents, e.g. *Burkholderia pseudomallei*, as well as other pathogens and toxic agents known in the art such as those identified by the National Institute of Allergy and Infectious Diseases as emerging infectious diseases/pathogens and/or those identified by the Center for Disease Control as USDA Federal select agents and toxins.

Generally, the single platform vaccine comprises one or both of two types of vaccines. One vaccine is a recombinant LVS ΔcapB overexpressing antigens of *F. tularensis* and/or expressing antigens of *B. anthracis* and/or *Y. pestis* and/or other pathogens. The second vaccine is a recombinant attenuated *Listeria monocytogenes* expressing antigens of *F. tularensis, B. anthracis, Y. pestis*, and/or other pathogens. Each vaccine is administered intradermally (i.d.) or by another route, e.g. subcutaneously (s.q.), intramuscularly (i.m.), intranasally (i.n.), inhaled, or even orally to a mammalian host. The vaccine can be administered as part of a homologous or heterologous prime-boost vaccination strategy. The vaccine induces a strong cell-mediated immune response to pathogen antigens in the vaccine and a strong antibody response.

This single platform simplifies manufacture, regulatory approval, clinical evaluation, and vaccine administration, and would be more acceptable to people than multiple individual vaccines, and be less costly. Currently, no single platform vaccine against Tier 1 Select Agents is available. Regarding manufacture, vaccines constructed from the same vectors can be manufactured under the same conditions. That is, the manufacture of the LVS ΔcapB vector will be the same regardless of which antigen it is expressing or overexpressing. Similarly, manufacture of the *L. monocytogenes* vector will be the same regardless of which antigen it is expressing.

Furthermore, a single platform vaccine also has the advantage of vaccines comprising any particular vector being able to be administered at the same time. That is, LVS ΔcapB overexpressing *F. tularensis* antigens and LVS ΔcapB expressing *B. anthracis* antigens and LVS ΔcapB expressing *Y. pestis* antigens can be administered together. Similarly, *L. monocytogenes* expressing *F. tularensis* antigens and *L.* monocytogenes expressing *B. anthracis* antigens and *L. monocytogenes* expressing *Y. pestis* antigens can be administered together. Thus, vaccination against all three pathogens would only require one prime vaccination and one or two booster vaccinations. Obviously, these same vectors expressing antigens of other pathogens, such as Tier 1 Select Agents, can be administered together as well.

The invention disclosed herein has a number of embodiments. One embodiment is a method of immunizing a susceptible host against an infection from at least one pathogen from Table 1. The method comprises administering to the host a prime vaccine and a homologous and/or heterologous booster vaccine. The prime vaccine comprises an attenuated recombinant live vaccine strain lacking a polynucleotide encoding CapB (LVS ΔcapB), wherein the LVS ΔcapB expresses an antigen of at least one pathogen from Table 1. The heterologous booster vaccine comprises an attenuated *L. monocytogenes* expressing the antigen of the same pathogen(s) from Table 1. Alternatively, using the homologous prime-boost vaccination strategy, the prime and boost vaccines are the same and can comprise either an attenuated recombinant live vaccine strain lacking a polynucleotide encoding CapB (LVS ΔcapB), wherein the LVS ΔcapB expresses an antigen of at least one pathogen from Table 1 or an attenuated recombinant *L. monocytogenes* expressing an antigen of at least one pathogen from Table 1. Typically, each vaccine is administered intradermally, subcutaneously, intramuscularly, intranasally, by inhalation or orally. Each vaccine is administered to the host in an amount sufficient to induce an immune response in the host to the pathogen antigen. In certain implementations, the host is administered a single dose of the prime vaccine and one or more doses of the homologous or heterologous booster vaccine.

In one or more embodiments, the pathogen is selected from the group of Tier 1 Select Agents consisting of *Francisella tularensis, Bacillus anthracis, Yersinia pestis, Burkholderia pseudomallei,* and *Burkholderia mallei.* In certain embodiments, the LVS ΔcapB and attenuated *Listeria monocytogenes* express antigens of two or more pathogens selected from the group consisting of *Francisella tularensis, Bacillus anthracis, Yersinia pestis, Burkholderia pseudomallei,* and *Burkholderia mallei.* In one instance, the LVS ΔcapB and attenuated *Listeria monocytogenes* express antigens of *Francisella tularensis, Bacillus anthracis,* and *Yersinia pestis.*

In one illustrative embodiment, the pathogen is *Francisella tularensis* (*F. tularensis*) and the LVS ΔcapB overexpresses a fusion protein comprising the immunodominant epitopes of IglA, IglB, and IglC (IglABC). In specific instances, the fusion protein is expressed by LVS ΔcapB under the control of a *F. tularensis* bfr promoter and/or omp promoter. The attenuated *Listeria monocytogenes* also expresses the fusion protein comprising the immunodominant epitopes of IglA, IglB, and IglC (IglABC). In specific instances, the fusion protein is expressed by *L. monocytogenes* under the control of a *L. monocytogenes* hly or actA promoter.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 3. Expression of *B. anthracis* and *Y. pestis* fusion proteins by *F. tularensis* rLVS ΔcapB from infected macrophage-like THP-1 cells. Monocytic THP-1 cells were seeded at 3×10$^5$ cells/well on 24-well plates and differentiated in the presence of PMA for 3 days. Vaccine vector (LVS ΔcapB) (lane 3) and vaccines (lanes 4-6) were grown on Chocolate agars supplemented without or with kanamycin (7.5 µg/ml) for 3 days. The differentiated THP-1 cells were infected with the vaccines or vaccine vector opsonized with human serum and incubated at 37° C. for 1 h. The cells were then washed with RPMI three times, incubated with complete RPMI supplemented with gentamycin (0.1 µg/ml) to inhibit extracellular bacterial growth. At 5 and 24 h post infection, medium was removed from wells; cells were lysed in 0.125 ml SDS buffer and boiled for 5 min. The cell lysates were analyzed by Western blotting using antibodies to *B. anthracis* PA antigen (mAb to *B. anthracis* PA) plus goat polyclonal antibody to *Y. pestis* LcrV antigen. These antibodies detected protein bands of ~50- and 52-kDa in cells infected rLVS ΔcapB/BaLFPA(L1) (panels A & B: lane 4) and ~50 kDa proteins in cells infected with rLVS ΔcapB/YpF1V(L1) (panels A & B: lanes 5 and 6 resp.).

FIG. 4. Growth kinetics of *F. tularensis* rLVS ΔcapB expressing *B. anthracis* and *Y. pestis* fusion proteins in infected macrophage-like THP-1 cells. Monocytic THP-1 cells were infected as described above in the legend for FIG. 3. At various times post infection, medium was removed from wells; the cells lysed with PBS containing 0.1% Saponin for 3-5 min at room temperature; and the lysates serially diluted and assayed for colony forming units (CFU).

Figure 5:
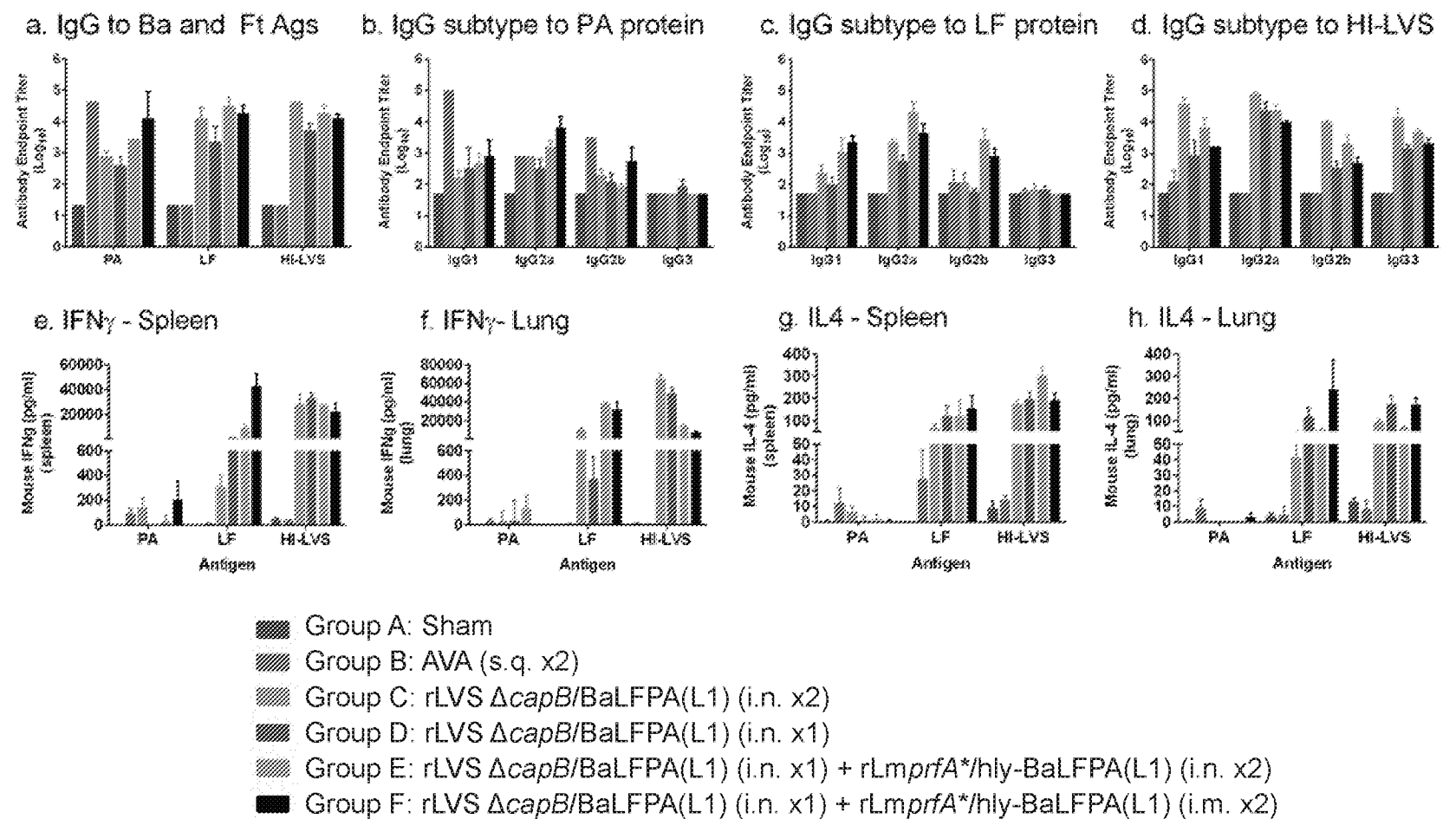

FIG. 5. Humoral and cell-mediated immune responses induced by immunization with LVS ΔcapB- and Lm-vectored *B. anthracis* vaccines. As indicated by the colors and letters to right, mice (n=4/group) were vaccinated with PBS i.n. at week 0 (Sham, A), AVA subcutaneously (s.q.) twice at weeks 0 and 4 (B), rLVS ΔcapB/BaLFPA(L1) i.n. twice at weeks 0 and 4 (C) or once at week 4 (D), or primed with rLVS ΔcapB/BaLFPA(L1) i.n. at week 0 and boosted with rLmprfA*/hly-BaLFPA(L1) (rLm ΔactA ΔinlB prfA*hly-BaLFPA(L1)) twice at weeks 4 and 6 i.n (E) or i.m. (F). At week 7, all mice were bled and spleens and lungs removed. Antibody responses: Sera were assayed for IgG to Ba LF and PA proteins and heat inactivated Ft Live Vaccine Strain (HI-LVS) (a) or IgG subtypes IgG1, IgG2a, IgG2b, and IgG3 to these antigens as indicated (b to d). Cell-mediated Responses: Spleen and lung cells were stimulated with PA, LF or HI-LVS and their supernatants assayed for secretion of IFN-γ and IL-4 (e to h). Values are mean±SD.

FIG. 7. Cytokine production induced by immunization with *Francisella*- and Lm-vectored *B. anthracis* vaccines. Mice (n=4/group) were vaccinated intranasally (i.n.) at week 0 with PBS (Sham, Group A), subcutaneously twice at weeks 0 and 4 with AVA (Group B), i.n. twice at weeks 0 and 4 (group C) or once at week 4 (Group D) with rLVS ΔcapB/BaLF-PA(L1), or primed intranasally with rLVS ΔcapB/BaLFPA(L1) at week 0 and boosted twice at weeks 4 and 6 i.n. (Group E) or intramuscularly (i.m.) (Group F) with rLmprfA*/hly-BaLFPA(L1) (rLm ΔactA ΔinlB prfA*/hly-BaLFPA(L1)). At week 7, all mice were bled, euthanized, their spleens (panels A, B, and C) and lung (Panels D, E, and F) cells isolated and stimulated with *B. anthracis* LF or PA antigen, or *Francisella* HI-LVS for 3 days. Supernatants of the spleen and lung cell culture were collected and assayed for interferon gamma (IFN-γ) secretion by ELISA. Values are mean±SD. P<0.01; *, P<0.001, ****, P<0.0001 by ANOVA (Prism 6.04).

FIG. 13. Protective efficacy of rLVS ΔcapB/Yp & rLm/Yp against respiratory challenge with virulent Yp. Mice, 8/group, were sham-immunized, or immunized subcutaneously (SC) twice with EV76 ($10^6$), intradermally (ID) or intranasally (IN) twice with rLVS ΔcapB/Yp (rLVS ΔcapB/YpF1V(L1)) or prime-boosted with rLVS ΔcapB/Yp once and rLm/Yp (rLm ΔactA ΔinlB prfA*/hly-YpF1V(L1)) once intramuscularly (ID/IM) or intranasally (IN/IN) ($10^6$ of each) at Week 0 and 4, as indicated on the right of the panels, challenged at week 9 with Yp (CO92), and monitored for survival for 14 days. Survival curves were compared by log-rank test (Mantel-cox, Prism).

FIG. 14B discloses "GGSG" and "GGSG2" as SEQ ID NOS 62 and 63, respectively. C. Relative intensity of protein expression. The intensity of protein bands detected by various antibodies were analyzed by QuantityOne (Bio-Rad) and compared with the same protein expressed by the parental LVS ΔcapB (IglA, IglB, IglC, and Bfr, left panel) or with the endogenous protein from the same strain (IglA or IglC, right panel). Results were representative of multiple protein expression experiments tested in broth culture (CDM and TSBC) and in infected human (THP-1) and mouse macrophage-like cell lines. FIG. 14C discloses "GGSG" and "GGSG2" as SEQ ID NOS 62 and 63, respectively.

FIG. 20. Mice immunized with attenuated rLVS ΔcapB/bfr-iglABC, comprising immunodominant epitopes of IglA, IglB, and IglC, survive longer than sham-immunized mice and mice immunized with the parental LVS ΔcapB. BALB/c mice (8/group) were immunized i.d. with various vaccines, challenged with (A) 16 CFU at 49 days post-immunization (A, Experiment I) or with 31 (B) or 310 (C) CFU *F. tularensis* Schu S4 at 42 days (B, Experiment II) and monitored for signs of illness and death for 21 days. Mean Survival Day was calculated by dividing the sum of the surviving days of all mice by the total number of mice examined, with animals surviving until the end of the experiment given a survival time of 21 days, when the experiment was terminated. Survival curves between different groups were compared by log-rank test (Mantel-Cox) (Prism 6.04).

FIG. 22. Immediate pre- or post-exposure prophylaxis with rLVS ΔcapB/bfr-iglABC but not LVS induces partial protective immunity against respiratory challenge with *F. tularensis* Schu S4. BALB/c mice were sham-immunized or immunized i.n. with $10^2$ CFU of LVS (A, Experiment I, upper panel), $1\times10^6$ CFU or $5\times10^6$ CFU of rLVS ΔcapB/bfr-iglABC (A, Experiment I, lower panel), or $5\times10^7$ CFU of rLVS ΔcapB/bfr-iglABC (B, Experiment II) 2 days before (−2), 1 day before (−1), the day of (0), 1 day after (1), or 2 days after (2) challenge i.n. with 10 CFU *F. tularensis* Schu S4, and monitored for signs of illness and death for up to 21 days. Shown are the results from two independent experiments (one in A&B and the other in C). Mean Survival Day was calculated by dividing the sum of the surviving days of all mice by the total number of mice examined, with animals surviving until the end of the experiment given a survival time of 21 days, when the experiment was terminated. Survival curves between different groups were compared by log-rank test (Mantel-Cox) (Prism 6.04). In Experiment I, at day 3 post challenge, before any mice had died, the mean weight of mice immunized with LVS on day −2 was significantly lower than that of the sham-immunized mice (p<0.05), mice immunized with $1\times10^6$ rLVS ΔcapB/bfr-iglABC at day −2, 0, and 2, and mice immunized with $5\times10^6$ rLVS ΔcapB/bfr-iglABC at day 0 (A, left panels). At days 4 and 5 post challenge, the mean weight of mice immunized with rLVS ΔcapB/bfr-iglABC (Day −2, $1\times10^6$) was significantly greater than that of sham-immunized mice and mice immunized with rLVS ΔcapB/bfr-iglABC at day 0 and day 1 post challenge (A, lower left panel). In Experiment II, mice immunized with 5×10$^7$ rLVS ΔcapB/bfr-iglABC had transient weight loss that partially or fully recovered if they were immunized at day −2 or −1 before challenge (B, left panel).

FIG. 27. Protective efficacy of homologous prime-boost vaccination with rLVS ΔcapB/bfr-iglABC and heterologous prime-boost vaccination with rLVS ΔcapB/bfr-iglABC—rLm/hly-iglABC against respiratory challenge with the virulent *F. tularensis* SchuS4 strain. BALB/c mice, 8/group, were immunized i.d. once at week 0 with PBS (Sham, Group A), 10$^4$ CFU LVS (Group B), 10$^6$ CFU LVS ΔcapB (Group H), or 10$^6$ rLVS ΔcapB/bfr-iglABC (Group C); immunized i.d. or i.n. twice at weeks 0 and 4 with 10$^6$ rLVS ΔcapB/bfr-iglABC (Groups D & E, resp.) (panel a); primed i.d. once at week 0 with rLVS ΔcapB/bfr-iglABC (Groups F & G) or LVS ΔcapB (Groups I & J) and boosted intramuscularly (i.m.) twice at weeks 4 and 6 with rLmprfA* Vector (Lm ΔactA ΔinlB prfA*) (Groups F & I) or rLmprfA*/hly-iglABC (rLm ΔactA ΔinlB prfA*/hly-iglABC, Groups G & J); or immunized simultaneously i.d. with rLVS ΔcapB/bfr-iglABC and i.m. with rLmprfA*/hly-iglABC (Group K) (panel b). All the mice were challenged i.n. with 10 CFU (3× LD$_{50}$) *F. tularensis* Schu S4 at week 10, and monitored for signs of illness, weight change and death for up to 21 days post challenge. Survival curves were compared between vaccine groups and the sham group by log-rank test (Mantel-cox, Prism); the P value for the comparison of a specific vaccine vs. Sham is color-coded to the color of the vaccine symbol.

FIG. 28. Humoral immune responses induced by immunization with LVS ΔcapB- and Lm-vectored *B. anthracis* vaccines. As indicated by the colors and letters to right, mice (n=8/group) were vaccinated i.d. with PBS once at week 0 (Sham, Group A), subcutaneously (s.c.) with AVA three times at weeks 0, 4, and 8 (Group B), i.n. or i.d. with rLVS/BaLFPA (rLVS ΔcapB/BaLFPA[L1]) three times at weeks 0, 4, and 8 (Groups C & D, resp.), three times i.n. or i.m. with rLm/BaLFPA (rLm ΔactA ΔinlB prfA*/hly-BaLFPA[L1]) (Groups E & F, resp.), primed i.n. (Groups G & H) with rLVS/BaLFPA once at week 0 and boosted i.n. once (Groups G) or twice (Group H), or primed i.d. with rLVS/BaLFPA once at week 0 (Groups I & J) and boosted i.m. once (Groups I) or twice (Group J) with rLm/BaLFPA. All the mice were bled at week 11, challenged at week 12, and monitored for 3 weeks post challenge (see FIG. 29 below). Sera were assayed for IgG or IgG subtypes IgG1 and IgG2a to Ba PA (A) and LF proteins (B). Values are mean±SE. Data were analyzed by two-way ANOVA with Tukey's post multiple comparisons test (Prism). Values that are significantly different from the Sham group are marked with asterisks over the comparison groups. *, P<0.05; , P<0.01; **, P<0.0001 by two-way ANOVA with Tukey's multiple comparisons test.

FIG. 29. Protective efficacy induced by immunization with LVS ΔcapB- and Lm-vectored *B. anthracis* vaccines against respiratory challenge with virulent *B. anthracis*. Mice (n=8/group) were immunized as described in the legend to FIG. 28 (the same experiment as the one for FIG. 28) and as indicated by colors, groups, and vaccines to the right, challenged at week 12 with Ba Ames spores (371,000 CFU), and monitored for survival. Survival curves between vaccinated groups and the sham group were compared by log-rank test (Mantel-cox, Prism); the P value for the comparison of a specific vaccine vs. Sham are color-coded to the color of the vaccine symbol.

FIG. 30. Humoral immune responses induced by immunization with LVS ΔcapB- and Lm-vectored *Y. pestis* vaccines. As indicated by the colors and letters to the right, mice (n=8/group) were vaccinated i.d. with PBS once at week 0 (Sham, Group A), subcutaneously (s.c.) with *Y. pestis* vaccine strain EV76 once at week 0 (Group B), i.n. or i.d. with rLVS ΔcapB/YpF1V (rLVS ΔcapB/YpF1V[L1]) three times at weeks 0, 4, and 8 (Groups C & D, resp.), i.m. with rLmprfA*/hly-YpF1V (rLm ΔactA ΔinlB prfA*/hly-YpF1V [L1]) three times at weeks 0, 4, and 8 (Group E), or primed i.d. with rLVS ΔcapB/YpF1V once at week 0 (Groups F & G) and boosted i.m. once (Group F) or twice (Group G) with rLmprfA*/hly-YpF1V. All the mice were bled at week 11, challenged with Yp CO92 at week 12, and monitored for 3 weeks for survival (see FIG. 31 below). Sera were assayed for IgG or IgG subtypes IgG1 and IgG2a to Yp F1 (A) and LcrV proteins (B). Values are mean±SE. Values that are significantly different from the Sham group are marked with asterisks over the comparison groups. , P<0.01; *, P<0.001; ****, P<0.0001 by two-way ANOVA with Tukey's multiple comparisons test.

FIG. 31. Protective efficacy induced by immunization with LVS ΔcapB- and Lm-vectored *Y. pestis* vaccines against respiratory challenge with virulent *Y. pestis*. Mice (n=8/group) were immunized as described in legend to FIG.

30 and as indicated by colors, groups, and vaccines to the right, challenged at week 12 with Yp CO92 (1,800 CFU), and monitored for 21 days for survival. Survival curves between vaccinated groups and the Sham group were compared by log-rank test (Mantel-cox, Prism); the P value for the comparison of a specific vaccine vs. Sham are color-coded to the color of the vaccine symbol.

Figure 32:
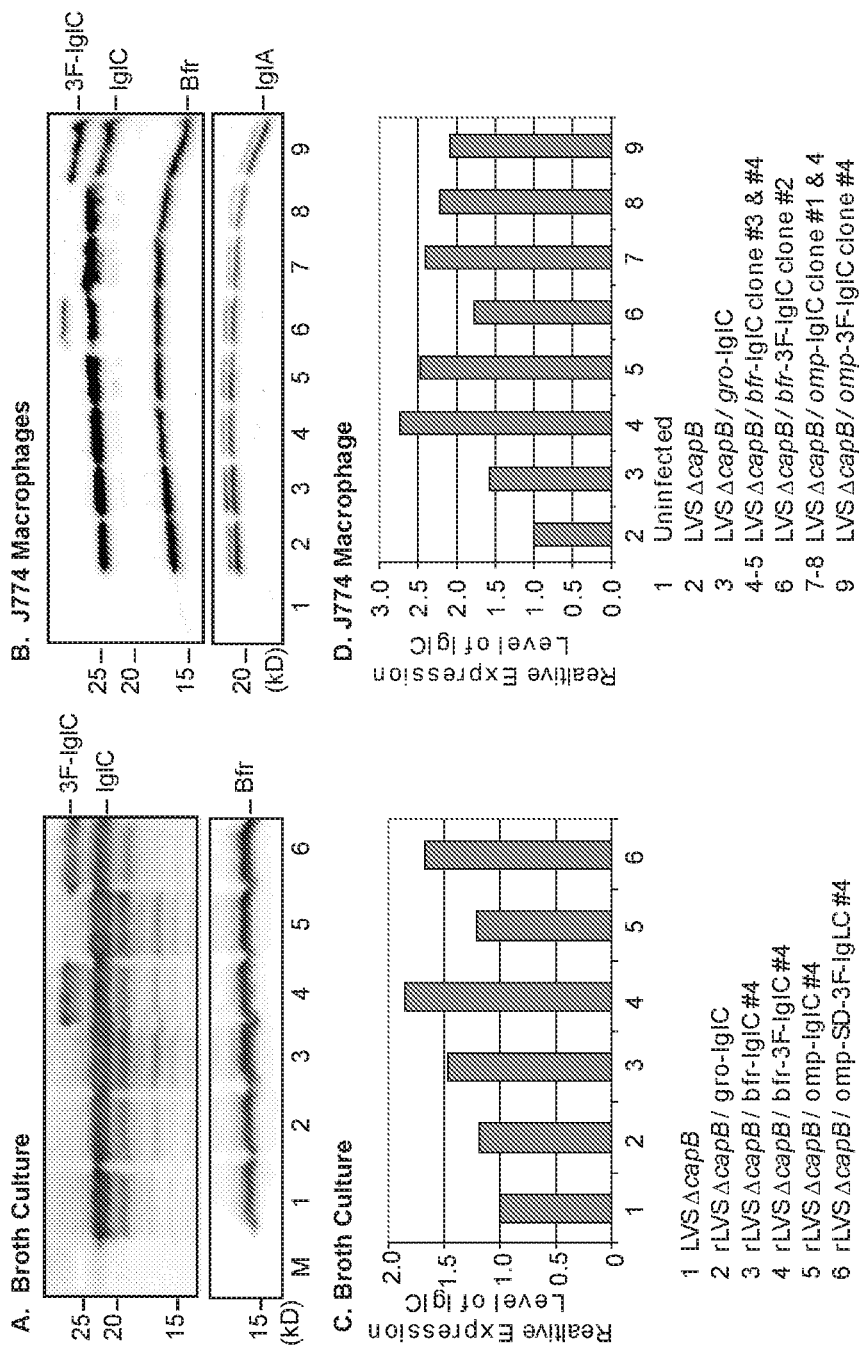

FIG. 32. Over-expression of IglC by rLVS ΔcapB strains in broth and in macrophages. rLVS ΔcapB strains carrying IglC protein expression cassette downstream of the Ft groE, bfr and omp promoter were cultured in Tryptic soy broth supplemented with L-cysteine (TSBC) or used to infected mouse macrophage-like J774 cells. Protein expression was analyzed using polyclonal antibodies specific for IglC, IglA, or Bfr (loading control). IglC fused with a 3×FLAG tag (3F-IglC) was expressed by the rLVS ΔcapB strains as a detection control for IglC. A. Protein expression in TSBC. B. Protein expression in J774 macrophages. C. Relative expression level of IglC in TSBC. D. Relative expression level of IglC in J774 macrophages.

DETAILED DESCRIPTION OF THE INVENTION

In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention.

All publications mentioned herein are incorporated by reference to disclose and describe aspects, methods and/or materials in connection with the cited publications. For example, U.S. Pat. No. 8,481,024, titled "VACCINES AGAINST TULAREMIA", filed by Marcus A. Horwitz et al. and U.S. Pat. No. 8,206,700, titled "METHODS AND COMPOSITIONS FOR TREATING TULAREMIA", filed by Marcus A. Horwitz et al., are incorporated by reference in their entirety herein.

Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As previously described, there is a need for a safe and effective tularemia vaccine, anthrax vaccine, and plague vaccine. The only currently available tularemia vaccine is an unlicensed toxic vaccine known as Live Vaccine Strain (LVS). An improved heterologous prime-boost vaccine against tularemia is described herein where the prime is LVS ΔcapB expressing or not expressing a F. tularensis protein (IglA or IglC) or fusion protein (IglABC), and the booster vaccine is a heterologous vector, attenuated L. monocytogenes expressing a F. tularensis protein (IglA or IglC) or fusion protein (IglABC). This heterologous prime-boost vaccine against tularemia is safer and more potent than the current unlicensed and toxic LVS vaccine. The prime LVS ΔcapB based vaccines described herein are >10,000 fold less virulent than LVS and hence much safer. The heterologous prime-boost vaccine is also more potent than LVS. See also the "Illustrative embodiments of multiantigenic live attenuated prime and booster vaccines against Tularemia" section below.

With respect to individual anthrax vaccines, the acellular AVA vaccine contains various amounts of PA and small amounts of LF and other secreted proteins; PA plays the major role in the protective immunity. The major drawback of AVA is its requirement for extensive repetitive vaccinations, suggesting that PA delivered via adjuvant is limited in its capacity to induce-long-lasting protective immunity. The only commercially available anthrax vaccine (AVA) requires six immunizations plus frequent boosters and is poorly effective. Currently, two major approaches are being used to improve PA-based anthrax vaccines: a) delivering and presenting PA more effectively, e.g. via live attenuated heterologous vectors such as viral vectors (however, pre-existing immunity adversely affects their efficacy) (15-18), *Bacillus subtilis* (19), or *Salmonella typhimurium* (20, 21); and b) complementation of PA with additional bacterial components of protective value (e.g., LF and EF). A fusion protein of LFD1-PAD4 adsorbed to alum has been shown to induce 100% protection against Ba spore challenge in mice (12). Hence, in the present invention, live attenuated vaccine vectors have been constructed expressing this LFD1-PAD4 fusion protein. Since this approach not only induces strong antibody responses but also T cell responses, this approach is more likely to induce long-lasting immunity. The heterologous prime-boost and homologous prime-boost vaccines against anthrax described herein are safe and found to be much more effective than AVA in animal studies.

With respect to individual plague vaccines, several new vaccines have been described based primarily on the antigens expressed herein (22-25) but also others (26). However, the only currently available plague vaccine is unlicensed and toxic (EV76). The heterologous prime-boost vaccine against plague described herein is safe and effective.

In aspects of the invention, the prime-boost vaccine described herein comprises a prime vaccine and a booster vaccine. With respect to the prime vaccine, the vector LVS ΔcapB and recombinant LVS ΔcapB overexpressing individual proteins of *F. tularensis* including IglA and IglC have been previously described. In an illustrative embodiment of a prime vaccine against *F. tularensis*, the present invention provides a LVS ΔcapB vector expressing a fusion protein (IglABC) of three immunodominant epitopes of three different proteins—IglA, IglB, and IglC. These vaccines are safer than the unlicensed and toxic Live Vaccine Strain (LVS) and highly immunogenic. In other embodiments, the same vector is used for expressing immunoprotective antigens of *B. anthracis* and *Y. pestis*. This vector may also be used to express antigens of other pathogens including other Tier 1 Select Agents, as well as agents and toxins listed in Table 1 and known in the art such as those identified by the National Institute of Allergy and Infectious Diseases as emerging infectious diseases/pathogens and/or those identified by the Center for Disease Control as USDA Federal select agents and toxins.

With respect to the booster vaccine, an attenuated recombinant *Listeria monocytogenes* vaccine expressing individual proteins of *F. tularensis* including IglA and IglC has been previously described. In an illustrative embodiment of a booster vaccine against *F. tularensis*, the present invention provides an attenuated *Listeria monocytogenes* vaccine expressing a fusion protein (IglABC) of three immunodominant epitopes of three different proteins—IglA, IglB, and IglC. In other embodiments, the same vector is used for expressing immunoprotective antigens of *B. anthracis* and *Y. pestis*. This vector may also be used to express antigens of other pathogens including other Tier 1 Select Agents, as well as agents and toxins listed in Table 1 and known in the art such as those identified by the National Institute of Allergy and Infectious Diseases as emerging infectious diseases/pathogens and/or those identified by the Center for Disease Control as USDA Federal select agents and toxins.

Typically, the vaccine is administered to humans or animals by injection intradermally or by another route, e.g. subcutaneously, intramuscularly, orally, intranasally, or by inhalation.

In another aspect, the present invention provides the first known single platform vaccine against multiple Tier 1 Select Agents, for instance *F. tularensis* (tularemia), *B. anthracis* (anthrax), and *Y. pestis* (plague). As noted above, a single platform simplifies manufacture, regulatory approval, clinical evaluation, and vaccine administration, and would be more acceptable to people than multiple individual vaccines, and be less costly. This single vaccine platform may be designed to express the antigens of multiple pathogens, for instance one, two or all three illustrative pathogens (i.e. *F. tularensis*, *B. anthracis*, and *Y. pestis*). That is, the LVS ΔcapB vector, which already contains antigens of *F. tularensis*, may be designed to also express *B. anthracis* and/or *Y. pestis* antigens and the *L. monocytogenes* vector may similarly be designed to express antigens of one, two or all three illustrative pathogens. The same platform may be used to express additional immunoprotective antigens of Tier 1 Select Agents or other pathogens.

As noted above, the invention disclosed herein has a number of embodiments. An exemplary embodiment of the invention is a method of immunizing a susceptible host against an infection from at least one pathogen from Table 1 (e.g. *Francisella tularensis, Bacillus anthracis, Yersinia pestis, Burkholderia pseudomallei* or *Burkholderia mallei*), comprising administering to the host a vaccine comprising an attenuated recombinant live vaccine strain lacking a polynucleotide encoding CapB (LVS ΔcapB), wherein the LVS ΔcapB expresses an antigen of at least one pathogen from Table 1; or alternatively administering to the host a vaccine comprising an attenuated *Listeria monocytogenes* expressing the antigen of the pathogen from Table 1; or alternatively administering to the host a prime vaccine comprising an attenuated recombinant live vaccine strain lacking a polynucleotide encoding capB (LVS ΔcapB), wherein the LVS ΔcapB expresses an antigen of at least one pathogen from Table 1; and a heterologous booster vaccine comprising an attenuated *Listeria monocytogenes* expressing the antigen of the pathogen from Table 1. Optionally, the LVS ΔcapB and attenuated *Listeria monocytogenes* express antigens of two or more pathogens selected from the group consisting of *Francisella tularensis, Bacillus anthracis, Yersinia pestis, Burkholderia pseudomallei,* and *Burkholderia mallei*. Typically, the prime vaccine and/or heterologous booster vaccine are each administered intradermally, subcutaneously, intramuscularly, intranasally, by inhalation or orally. In an illustrative embodiment, the pathogen is *Francisella tularensis* (*F. tularensis*) and the LVS ΔcapB over-expresses a fusion protein comprising IglA, IglB, and IglC (IglABC).

Embodiments of the invention include an immunogenic composition comprising a recombinant attenuated *Francisella tularensis* subspecies *holarctica* live vaccine Strain (LVS) having a deleted capB gene (SEQ ID NO: 1) which comprises a heterologous promoter that expresses a fusion protein comprising an antigenic polypeptide epitope present in a *Francisella tularensis, Bacillus anthracis, Yersinia pestis, Burkholderia pseudomallei* or *Burkholderia mallei* polypeptide. While it is desirable to include large segments of *Francisella tularensis, Bacillus anthracis, Yersinia pestis, Burkholderia pseudomallei* or *Burkholderia mallei* polypeptides in this invention in order to present a large number of immunoreactive epitopes to the mammalian immune system, for example, one that is up to 250 killidatltons in size. Surprisingly, certain larger fusion proteins are observed to make the immunogenic composition unstable. For this unexpected reason, in some embodiments of the invention, the fusion protein expressed by the heterologous promoter is less than 100 (or 90 or 80 or 70 or 60) kilodaltons in size. This size delineation therefore facilitates the vaccines in this embodiment ability to elicit an immune response in a mammalian host when the immunogenic composition is administered orally, intradermally (i.d.), subcutaneously (s.q.), intramuscularly (i.m.), or intranasally (i.n.) to the mammalian host. Optionally the LVS expresses two or more antigenic polypeptide epitopes present in a *Francisella tularensis, Bacillus anthracis, Yersinia pestis, Burkholderia pseudomallei* or *Burkholderia mallei* polypeptide.

In an exemplary working example of this embodiment of the immunogenic composition, the heterologous promoter (e.g. a heterologous promoter that comprises a bfr promoter (SEQ ID NO: 13) and/or an omp promoter (SEQ ID NO: 14)) expresses a fusion protein comprising at least 8 contiguous amino acids of IglA (SEQ ID NO: 2); a fusion protein comprising at least 8 contiguous amino acids of IglB (SEQ ID NO: 3); and/or a fusion protein comprising at least 8 contiguous amino acids of IglC (SEQ ID NO: 4). In a very specific desirable working embodiment, the heterologous promoter is designed to express the fusion protein in an amount at least 1.5, 2.0 or 2.5 fold greater than the expression of endogenous IglA protein, endogenous IglB protein and/or endogenous IglC protein expressed in the LVS (see e.g. FIG. 32).

MHC class I molecules bind short peptides, whose N- and C-terminal ends are anchored into the pockets located at the ends of the peptide binding groove. While the majority of the peptides are of length 9, longer peptides can be accommodated by the bulging of their central portion, resulting in binding peptides of length 8 to 15. Peptides binding to class II proteins are not constrained in size and can vary from 11 to 30 amino acids long. In embodiments of the invention, while 8 amino acids or more are sufficient to elicit immunological reaction of MHC Class I (which bind peptides of 8-15 amino acids), typically larger stretches of amino acids are used. For example, 11 or more amino acids are sufficient to elicit immunological reaction of MHC Class II (which binds peptides of 11-30 amino acids). See e.g., Meydan et al., BMC Bioinformatics 201314 (Suppl 2): S13. Optionally the at least 8 contiguous amino acids of a polypeptide such as IglA, the at least 8 contiguous amino acids of a polypeptide such as IglB, and the at least 8 contiguous amino acids of a polypeptide such as IglC are covalently linked together in a single fusion protein. In a typical example, the LVS expresses a major histocompatibility class I or a major histocompatibility class II epitope present in amino acid residues 33-132 of IglA (SEQ ID NO: 2), a major histocompatibility class I or a major histocompatibility class II epitope present in amino acid residues 446-506 of IglB (SEQ ID NO: 3), and/or a major histocompatibility class I or a major histocompatibility class II epitope present in amino acid residues 29-149 of IglC (SEQ ID NO: 4).

In another of the immunogenic composition embodiments, the antigenic polypeptide epitope is present in a

*Bacillus anthracis* polypeptide selected from lethal factor domain I (SEQ ID NO: 7), the extended domain IV of protective antigen (SEQ ID NO: 8); and AhpC (SEQ ID NO: 9). In another of the immunogenic composition embodiments, the antigenic polypeptide epitope is present in a *Yersinia pestis* polypeptide selected from F1 (SEQ ID NO: 8), LcrV (SEQ ID NO: 9), YscF (SEQ ID NO: 10), YopE (SEQ ID NO: 11), and Psn (SEQ ID NO: 12). In another of the immunogenic composition embodiments, the antigenic polypeptide epitope is present in a *Burkholderia pseudomallei* polypeptide selected from Hcp-1 (SEQ ID NO: 35), Hcp-2 (SEQ ID NO: 36), Hcp-3 (SEQ ID NO: 37), Hcp-4 (SEQ ID NO: 38), Hcp-6 (SEQ ID NO: 39), Lo1C (SEQ ID NO: 40), TypA (SEQ ID NO: 41), BipB (SEQ ID NO: 42), BipC (SEQ ID NO: 43), BipD (SEQ ID NO: 44), Omp3 (SEQ ID NO: 45), Omp7 (SEQ ID NO: 46), Omp85 (SEQ ID NO: 47), OmpW (SEQ ID NO: 48), PotF (SEQ ID NO: 49), OppA (SEQ ID NO: 50), BopA (SEQ ID NO: 51), BimA (SEQ ID NO: 52), BPSL1897 (SEQ ID NO: 53), BPSL3369 (SEQ ID NO: 54), BPSL2287 (SEQ ID NO: 55), BPSL2765 (SEQ ID NO: 56), and VgrG5 (SEQ ID NO: 57). In another of the immunogenic composition embodiments, the antigenic polypeptide epitope is present in a *Burkholderia mallei* polypeptide selected from BMA_A0768 (SEQ ID NO: 58), BMA_2821 (SEQ ID NO: 59), BMA 0816 (SEQ ID NO: 60), and GroEL (SEQ ID NO: 61).

Another embodiment of the invention is a method of generating an immune response in a mammal comprising administering one or more of immunogenic compositions disclosed herein to the mammal so that an immune response is generated to the antigenic polypeptide epitope present in a *Francisella tularensis, Bacillus anthracis, Yersinia pestis, Burkholderia pseudomallei* or *Burkholderia mallei* polypeptide. In one such embodiment, the method comprises administering a LVS immunogenic composition disclosed herein in a primary vaccination; and administering the same immunogenic composition of LVS immunogenic composition disclosed herein in a subsequent homologous booster vaccination. Typically, the method consists essentially of administering the immunogenic composition of an LVS immunogenic composition disclosed herein in a primary vaccination; and administering the immunogenic composition of LVS immunogenic composition disclosed herein in a subsequent homologous booster vaccination. Optionally, the method comprises administering the immunogenic composition to the mammal less than 4 times.

In another embodiment of the invention, the method comprises administering an LVS composition as disclosed herein in a primary vaccination; and administering a second heterologous immunogenic composition comprising the antigenic polypeptide epitope present in a *Francisella tularensis, Bacillus anthracis, Yersinia pestis, Burkholderiapseudomallei,* or *Burkholderia mallei polypeptide* in a subsequent booster vaccination. Optionally, the second immunogenic composition comprises an attenuated strain of *Listeria monocytogenes* expressing the antigenic polypeptide epitope. For example, in an illustrative embodiment of the invention, the attenuated *Listeria monocytogenes* expresses a fusion protein comprising at least 8 contiguous amino acids of IglA (SEQ ID NO: 2), a fusion protein comprising at least 8 contiguous amino acids of IglB (SEQ ID NO: 3); and/or a fusion protein comprising at least 8 contiguous amino acids of IglC (SEQ ID NO: 4). Optionally, the amino acid residues of IglA, the amino acid residues of IglB, and the amino acid residues of IglC are covalently linked in a single fusion protein, one that is less than 50, 60, 70 or kilodaltons in size. In certain embodiments, the method comprises administering LVS immunogenic composition disclosed herein and a second immunogenic composition to the mammal less than a total of four times. Optionally for example, the method comprises administering a single dose of a LVS immunogenic composition disclosed herein, and one or more doses of the second immunogenic composition.

As already noted, *F. tularensis, B. anthracis* and *Y. pestis* are Tier I bioterrorist threats and a vaccine is needed to protect against use of these agents as a bioweapon. In illustrative implementations, this vaccine may be used by the military to protect its personnel. Health care workers upon whom the public is relying for assistance in a bioterrorist attack would also be high priority candidates for a vaccine such as this. Finally, if the vaccine is sufficiently benign on human testing, the general public worldwide could benefit from this vaccine to protect them from a bioterrorist attack.

It should be emphasized that a major drawback to widespread use of the currently available but unlicensed LVS and EV76 vaccines is toxicity. Since the vaccines provided herein are non-toxic or of exceedingly low toxicity, but comparably efficacious or more efficacious, these vaccines would likely be much better accepted than the LVS vaccine for widespread use among the military, first responders, and the public. Furthermore, the AVA vaccine requires at least six administrations and is not highly efficacious. Since the vaccines provided herein are more efficacious and require only two or three vaccinations, these vaccines would likely be much better accepted than the AVA vaccine for widespread use among the military, first responders, and the public.

Illustrative Embodiments of Multiantigenic Live Attenuated Prime and Booster Vaccines Against Tularemia In one or more illustrative embodiments, a multivalent prime and booster vaccine for preventing tularemia in humans and animals is provided. The invention is useful for preventing infection caused by *Francisella tularensis*, the agent of tularemia, and a potential agent of bioterrorism. *F. tularensis* is a Tier I bioterrorism agent that has previously been stock-piled as a germ-warfare agent and may have been used as such in World War II. Especially when spread by the air-borne route, *F. tularensis* can cause a highly fatal pneumonia. The present vaccine is designed to prevent military and non-military personnel from disease caused by *F. tularensis*.

A safe, well-characterized, stable and effective vaccine against *F. tularensis* is needed to protect against potential use of this agent as a bioterrorist weapon. A vaccine against *F. tularensis* was developed a half-century ago, but it has not been approved for general use. This vaccine, called Live Vaccine Strain, or LVS, is an attenuated form of *Francisella tularensis* subspecies *holarctica*, a much less virulent subspecies of *F. tularensis* than the highly virulent subspecies of concern as a bioterrorist agent, *F. tularensis* subspecies *tularensis*. The LVS vaccine is unstable in that different colonial morphology types emerge on culture, and somewhat toxic to humans vaccinated with it. Moreover, it may not protect against the high doses of *F. tularensis* subspecies *tularensis* that might be released in an airborne bioterrorism attack. Hence, a vaccine that is safer, more stable, and more effective against airborne highly virulent *F. tularensis* is needed.

Previously, mutants of the LVS vaccine that lack the O-Antigen have been investigated, i.e. the LPS molecule. These LPS-deficient mutants (LVS ΔwbtDEF and LVS Δwzy) were highly attenuated vs. LVS. Immunization of mice with these mutants conferred some protective immunity, but very little. The LVS strain was several orders of magnitude more potent. LVS mutants with deletions in the capA, B, and/or C genes have also been previously described (27, 28). These mutants were attenuated compared with LVS. However, each of these transposon insertion mutants contains the sequence for transposons and kanamycin resistant genes in their chromosome. Moreover, the capacity of the mutants to induce protective immunity against F. tularensis challenge was not evaluated.

A first generation vaccine and vaccine vector comprised of an un-marked attenuated deletional mutant of the LVS vaccine has also been previously described. The deletion is in a gene called capB. The LVS ΔcapB mutant, like the previously evaluated LVS ΔwbtDEF mutant, is highly attenuated compared with LVS. Surprisingly, however, the LVS ΔcapB mutant induces protective immunity against F. tularensis intranasal challenge comparable to LVS. Recombinant versions of LVS ΔcapB expressing single key F. tularensis immunoprotective proteins including IglA or IglC have also been described. Additionally, a heterologous prime-boost vaccination strategy where the prime was LVS ΔcapB expressing one F. tularensis protein, and the booster vaccine was a heterologous vector, attenuated L. monocytogenes expressing one F. tularensis proteins has been described. Intradermal immunization with the heterologous prime-boost vaccine induced protection greater than that of the LVS vaccine. Boosting also included immunizing with the F. tularensis protein or proteins in adjuvant.

The present invention describes improved versions of both the aforementioned prime and booster vaccines. The improved prime vaccine (rLVS ΔcapB/bfr-iglABC—See Table 3 for complete definition) and booster vaccine (rLm ΔactA ΔinlB prfA*/hly-iglABC) express a fusion protein (IglABC) comprising immunogenic portions of three major F. tularensis proteins vs. one protein for the predecessor vaccines. This prime vaccine (rLVS ΔcapB/bfr-iglABC) has demonstrated improved immunogenicity and immunoprotection compared with the first generation rLVS ΔcapB vaccines. The booster vaccine (rLm ΔactA ΔinlB prfA*/hly-iglABC) has also demonstrated improved immunogenicity compared with the first generation rLm vaccines.

The invention consists of two types of vaccines. One vaccine is a recombinant LVS ΔcapB overexpressing a fusion protein consisting of immunodominant epitopes of F. tularensis Francisella Pathogenicity Island (FPI) and Type VI Secretion System (T6SS) proteins IglA, IglB, and IglC (IglABC). The second vaccine is a heterologous booster vaccine: an attenuated Listeria monocytogenes expressing the fusion protein IglABC. Each vaccine is administered intradermally or by another route, e.g. subcutaneously, intramuscularly, intranasally, inhaled, or even orally to a mammalian host. The vaccine can be administered as part of a homologous or heterologous prime-boost vaccination strategy. The vaccine induces a strong cell-mediated immune response to pathogen antigens in the vaccine and a strong antibody response.

With respect to the prime vaccine, the vector LVS ΔcapB and recombinant LVS ΔcapB overexpressing individual proteins of F. tularensis including IglA and IglC have been previously described. These vaccines were safer than the unlicensed and toxic Live Vaccine Strain (LVS) and highly immunogenic. Here, the vaccine is improved in two ways. First, a fusion protein of three different proteins—IglA'B'C'—is overexpressed. Second, the fusion protein is expressed from a stronger promoter—the bfr promoter and omp promoter instead of the previously used groEL promoter.

With respect to the booster vaccine, an attenuated recombinant Listeria monocytogenes vaccine (rLm) expressing individual proteins of F. tularensis including IglA and IglC has been previously described. Here, the vaccine is improved by expressing a fusion protein of three different proteins—IglABC.

There is a need for a safe and effective tularemia vaccine. The only currently available vaccine is an unlicensed toxic vaccine known as Live Vaccine Strain (LVS). The prime LVS ΔcapB based vaccines described herein are >10,000 fold less virulent than LVS and hence much safer. In the case of first generation rLVS ΔcapB vaccines expressing a single F. tularensis protein from a weak promoter (e.g. groEL), intranasal immunization yielded high level protection, equivalent to LVS and intradermal immunization yielded protection comparable to or slightly less than LVS. The multiantigenic high-expressing vaccine described herein is more immunogenic and protective than the first generation vaccine.

In the case of a first generation booster vaccine, rLm expressing single F. tularensis proteins, when used in a heterologous prime-boost vaccination strategy with rLVS ΔcapB vaccines as the prime, was more potent than LVS by the intradermal route. Thus, the first-generation prime-boost vaccination strategy provided a vaccine that is safer and more potent than the LVS vaccine. The multiantigenic version of the rLm booster vaccine is more immunogenic and therefore more protective than the previous vaccine as well in a prime-boost vaccination strategy.

As already noted, F. tularensis is a Tier I bioterrorist threat and a vaccine is needed to protect against use of this agent as a bioweapon. In illustrative implementations, this vaccine may be used by the military to protect its personnel. Health care workers upon whom the public is relying for assistance in a bioterrorist attack would also be high priority candidates for a vaccine such as this. Finally, if the vaccine is sufficiently benign on human testing, the general public worldwide could benefit from this vaccine to protect them from a bioterrorist attack. It should be emphasized that a major drawback to widespread use of the currently available but unlicensed vaccine, LVS, is its toxicity. Since the present vaccines are much less toxic, but comparably efficacious, the present vaccine would likely be much better accepted than the LVS vaccine for widespread use among the military, first responders, and the public.

Illustrative Aspects and Embodiments of the Invention

The invention disclosed herein has a number of embodiments. One embodiment is a method of immunizing a susceptible host against an infection from at least one pathogen from Table 1. The method comprises administering to the host a prime vaccine and a heterologous booster vaccine. The prime vaccine comprises an attenuated recombinant live vaccine strain lacking a polynucleotide encoding CapB (LVS ΔcapB), wherein the LVS ΔcapB expresses an antigen of at least one pathogen from Table 1. The heterologous booster vaccine comprises an attenuated Listeria monocytogenes expressing the antigen of the pathogen from Table 1. Typically, each vaccine is administered intradermally, subcutaneously, intramuscularly, intranasally, by inhalation or orally. Each vaccine is administered to the host in an amount sufficient to induce an immune response in the host to the pathogen antigen. In certain implementations, the host is administered a single dose of the prime vaccine and one or more doses of the booster vaccine.

In one or more embodiments, the pathogen is selected from the group of Tier 1 Select Agents consisting of *Francisella tularensis, Bacillus anthracis, Yersinia pestis, Burkholderia pseudomallei*, and *Burkholderia mallei*. In certain embodiments, the LVS ΔcapB and attenuated *Listeria monocytogenes* express antigens of two or more pathogens selected from the group consisting of *Francisella tularensis, Bacillus anthracis, Yersinia pestis, Burkholderia pseudomallei*, and *Burkholderia mallei*. In one instance, the LVS ΔcapB and attenuated *Listeria monocytogenes* express antigens of *Francisella tularensis, Bacillus anthracis*, and *Yersinia pestis*.

In one illustrative embodiment, the pathogen is *Francisella tularensis* (*F. tularensis*) and the LVS ΔcapB overexpresses a fusion protein comprising the immunodominant epitopes of IglA, IglB, and IglC (IglABC). In specific instances, the fusion protein is expressed by rLVS ΔcapB under the control of a bfr promoter and/or omp promoter. The attenuated *Listeria monocytogenes* also expresses the fusion protein comprising the immunodominant epitopes of IglA, IglB, and IglC (IglABC). In specific instances, the fusion protein is expressed by rLm under the control of a actA promoter and/or hly promoter.

EXAMPLES

Example 1

Construction and Characterization of LVS ΔcapB and Recombinant *Listeria monocytogenes* Expressing *B. anthracis* and *Y. pestis* Antigens and Demonstration of their Immunogenicity and Efficacy Concept of Using Attenuated *Francisella* as a Prime and booster Vaccine in a Homologous Prime Boost Vaccination Strategy; or *Listeria monocytogenes* as a Prime and Booster Vaccine in a Homologous Prime-Boost Vaccination Strategy; or *Francisella* as a Prime Vaccine and *Listeria monocytogenes* as a Booster Vaccine in a Heterologous Prime-Boost Vaccination Strategy as Delivery Platforms for *B. anthracis* and *Y. pestis* Immunoprotective Antigens

*Bacillus anthracis* (Ba), *Yersinia pestis* (Yp), and *Francisella tularensis* (Ft), causing anthrax, plague, and tularemia, respectively, are classified as Tier 1 Select Agents of bioterrorism as they have extraordinarily high infectivity, cause high morbidity and mortality—especially when inhaled, are relatively easily cultured and dispersed, and have previously been weaponized. As post-exposure prophylaxis is not a practical public health alternative for countering an outbreak of pneumonic tularemia, anthrax or plague, a safe and effective pre-exposure vaccine is needed. Currently, there are no licensed vaccines against pneumonic tularemia and plague and the only currently available human anthrax vaccine is suboptimal as it requires 6 doses followed by annual boosters and its duration of efficacy is unknown. Practically speaking, a multivalent vaccine is needed as it would simplify manufacture, regulatory approval, clinical evaluation, and vaccine administration, and be more acceptable to people than multiple individual vaccines. Our strategy for a multivalent vaccine platform is to use LVS ΔcapB as a single vector platform to express *B. anthracis, Y. pestis* and *F. tularensis* immunoprotective proteins in a homologous prime-boost vaccination strategy; or to use an attenuated *Listeria monocytogenes* (Lm) as a single vector platform to express *B. anthracis, Y. pestis* and *F. tularensis* immunoprotective proteins in a homologous prime-boost vaccination strategy; or to use LVS ΔcapB expressing recombinant *B. anthracis, Y. pestis*, and *F. tularensis* immunoprotective proteins as the prime vaccine and an attenuated *Listeria monocytogenes* (Lm) vector expressing recombinant Ba, Yp, and Ft immunoprotective proteins as the booster vaccine in a heterologous prime-boost vaccination strategy. The same vectors can be used to express antigens of other pathogens including other Tier 1 Select Agents.

Figure 31:
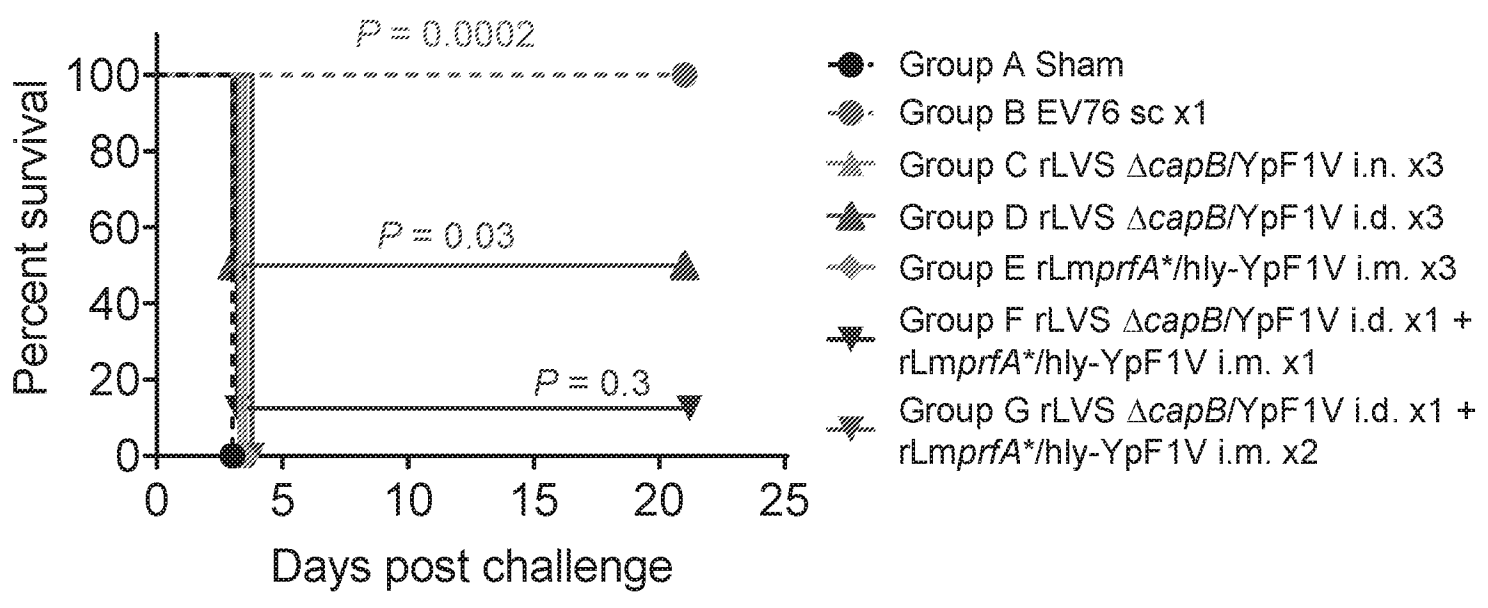

In preliminary studies, we have developed vaccines using LVS ΔcapB as a vector to express *F. tularensis* (IglABC) *B. anthracis* (Ba), or *Y. pestis* (Yp) antigens and rLm ΔactA ΔinlB prfA*(G155S) (rLmprfA*) as a vector to express Ft, Ba or Yp antigens, and shown that these vaccines are highly immunogenic. In a recent study in mice, two doses of rLVS ΔcapB/bfr-iglABC yielded greater protection than one dose against intranasal (i.n.) challenge with highly virulent Ft SchuS4; protection was equivalent to (i.d.) or better than (i.n.) that from LVS, indicating that homologous prime-boost vaccination is sufficient for high-level protection against virulent Ft SchuS4 (FIG. 27). Similarly, three doses of rLVS ΔcapB/BaLFPA given i.d. or i.n. provided protection superior to the AVA vaccine (FIG. 29); and three doses of rLVS ΔcapB/Yp provided excellent protection against respiratory challenge with virulent Yp CO92 (FIG. 31).

Ultimately, we envision construction of a trivalent Ft rLVS ΔcapB (prime) vaccine expressing Ba+Yp antigens downstream of a strong Ft promoter, *bacterioferritin* (bfr, FTL_0617) or outer membrane protein 26 (omp, FTN_1451) and a trivalent rLm ΔactA ΔinlB prfA* booster vaccine expressing Ba+Yp+Ft antigens downstream of a strong Lm promoter (actA/hly) [or, alternatively, a bivalent rLm ΔactA ΔinlB prfA*/Ba+Yp used in concert with our rLm ΔactA ΔinlB prfA*/IglABC vaccine]. Both the Ft LVS and Lm ΔactA ΔinlB "parental" strains have been tested in humans. LVS ΔcapB is a fully defined further attenuated LVS with three major attenuating deletions (capB, pilA, and FTT 0918). rLm ΔactA ΔinlB prfA* comprises Lm ΔactA ΔinlB with an additional mutation in prfA*(G155S)—shown not to affect the virulence of this strain (7, 8). Thus, both the prime and boost vectors are anticipated to be exceedingly safe. Moreover, we have shown that both vectors are capable of inducing strong humoral and cellular immune responses to expressed antigens (9, 10); such responses play key roles in immunoprotection against these pathogens. These vectors can express immunoprotective antigens of Ba and Yp. Ba and Yp antigens expressed by these vectors in our studies include the immunogenic domains of the protective antigen (PA) and lethal factor (LF) for Ba and fraction 1 capsular antigen (F1) and low-calcium-response V antigen (LcrV) for Yp.

The translated amino acid sequences of the fusion protein of *B. anthracis* lethal factor domain 1 and the extended Protective Antigen domain 4 separated by GGSG (SEQ ID NO: 62) (designated L1) or GSSGGSSG (SEQ ID NO: 65) (L2) and the fusion protein of *Y. pestis* F1, LcrV, and/or YscF either linked directly (designated "D") or separated by a GGSG (SEQ ID NO: 62) (L1) or (GGGS)3 (SEQ ID NO: 66) (L3) linker are listed below:

A. *B. anthracis* LFPA(L1) (LFD1-GGSG-PAD4)
(SEQ ID NO: 16)
MAGGHGDVGMHVKEKEKNKDENKRKDEERNKTQEEHLKEIMKHIVKIEVKGEEAVKKEAAEKLLEKVPS
DVLEMYKAIGGKIYIVDGDITKHISLEALSEDKKKIKDIYGKDALLHEHYVYAKEGYEPVLVIQSSEDY
VENTEKALNVYYEIGKILSRDILSKINQPYQKFLDVLNTIKNASDSDGQDLLFINQLKEHPIDFSVEFL
EQNSNEVQEVFAKAFAYYIEPQHRDVLQLYAPEAFNYMDKFNEQEINLGGSGNFDQQTSQNIKNQLAEL
NATNIYTVLDKIKLNAKMNILIRDKRFHYDRNNIAVGADESVVKEAHREVINSSTEGLLLNIDKDIRKI
LSGYIVEIEDTEGLKEVINDRYDMLNISSLRQDGKTFIDFKKYNDKLPLYISNPNYKVNVYAVIKENT
IINPSENGDISINGIKKILIFSKKGYEIG B. *B. anthracis* LFPA(L2) (LFD1-GSSGGSSG-PAD4)
(SEQ ID NO: 17)
MAGGHGDVGMHVKEKEKNKDENKRKDEERNKTQEEHLKEIMKHIVKIEVKGEEAVKKEAAEKLLEKVPS
DVLEMYKAIGGKIYIVDGDITKHISLEALSEDKKKIKDIYGKDALLHEHYVYAKEGYEPVLVIQSSEDY
VENTEKALNVYYEIGKILSRDILSKINQPYQKFLDVLNTIKNASDSDGQDLLFINQLKEHPIDFSVEFL
EQNSNEVQEVFAKAFAYYIEPQHRDVLQLYAPEAFNYMDKFNEQEINLGSSGGSSGNFDQQTSQNIKNQ
LAELNATNIYTVLDKIKLNAKMNILIRDKRFHYDRNNIAVGADESVVKEAHREVINSSTEGLLLNIDKD
IRKILSGYIVEIEDTEGLKEVINDRYDMLNISSLRQDGKTFIDFKKYNDKLPLYISNPNYKVNVYAVIK
ENTIINPSENGDISINGIKKILIFSKKGYEIG C. *Y. pestis* F1V(D) (F1-LcrV)
(SEQ ID NO: 18)
MKKISSVIAIALFGTIATANAADLTASTTATATLVEPARITLTYKEGAPITIMDNGNIDTELLVGTLTL
GGYKTGTTSTSVNFTDAAGDPMYLTFTSQDGNNHQFTTKVIGKDSRDFDISPKVNGENLVGDDVVLATG
SQDFFVRSIGSKGGKLAAGKYTDAVTVTVSNQMIRAYEQNPQHFIEDLEKVRVEQLTGHGSSVLEELVQ
LVKDKNIDISIKYDPRKDSEVFANRVITDDIELLKKILAYFLPEDAILKGGHYDNQLQNGIKRVKEFLE
SSPNTQWELRAFMAVMHFSLTADRIDDDILKVIVDSMNHHGDARSKLREELAELTAELKIYSVIQAEIN
KHLSSSGTINIHDKSINLMDKNLYGYTDEEIFKASAEYKILEKMPQTTIQVDGSEKKIVSIKDFLGSE
NKRTGALGNLKNSYSYNKDNNELSHFATTCSDKSRPLNDLVSQKTTQLSDITSRFNSAIEALNRFIQK
YDSVMQRLLDDTSGK D. *Y. pestis* F1V(L1) (F1-GGSG-LcrV)
(SEQ ID NO: 19)
MKKISSVIAIALFGTIATANAADLTASTTATATLVEPARITLTYKEGAPITIMDNGNIDTELLVGTLTL
GGYKTGTTSTSVNFTDAAGDPMYLTFTSQDGNNHQFTTKVIGKDSRDFDISPKVNGENLVGDDVVLATG
SQDFFVRSIGSKGGKLAAGKYTDAVTVTVSNQGGSGMIRAYEQNPQHFIEDLEKVRVEQLTGHGSSVLE
ELVQLVKDKNIDISIKYDPRKDSEVFANRVITDDIELLKKILAYFLPEDAILKGGHYDNQLQNGIKRVK
EFLESSPNTQWELRAFMAVMHFSLTADRIDDDILKVIVDSMNHHGDARSKLREELAELTAELKIYSVIQ
AEINKHLSSSGTINIHDKSINLMDKNLYGYTDEEIFKASAEYKILEKMPQTTIQVDGSEKKIVSIKDF
LGSENKRTGALGNLKNSYSYNKDNNELSHFATTCSDKSRPLNDLVSQKTTQLSDITSRFNSAIEALNR
FIQKYDSVMQRLLDDTSGK E. *Y. pestis* VF1YscF(L3) (LcrV-[GGGS]3-F1-[GGGS]3-YscF)
(SEQ ID NO: 20)
MIRAYEQNPQHFIEDLEKVRVEQLTGHGSSVLEELVQLVKDKNIDISIKYDPRKDSEVFANRVITDDIE
LLKKILAYFLPEDAILKGGHYDNQLQNGIKRVKEFLESSPNTQWELRAFMAVMHFSLTADRIDDDILKV
IVDSMNHHGDARSKLREELAELTAELKIYSVIQAEINKHLSSSGTINIHDKSINLMDKNLYGYTDEEIF
KASAEYKILEKMPQTTIQVDGSEKKIVSIKDFLGSENKRTGALGNLKNSYSYNKDNNELSHFATTCSDK
SRPLNDLVSQKTTQLSDITSRFNSAIEALNRFIQKYDSVMQRLLDDTSGKGGGSGGGGSGGGSSADLT
ASTTATATLVEPARITLTYKEGAPITIMDNGNIDTELLVGTLTLGGYKTGTTSTSVNFTDAAGDPMYLT -continued

```
FTSQDGNNHQFTTKVIGKDSRDFDISPKVNGENLVGDDVVLATGSQDFFVRSIGSKGGKLAAGKYTDAV

TVTVSNQGGGGSGGGGSGGGGSMSNFSGFTKGTDIADLDAVAQTLKKPADDANKAVNDSIAALKDKPDN

PALLADLQHSINKWSVIYNINSTIVRSMKDLMQGILQKFP
```

Construction and Verification of Bivalent rLVS ΔcapB Prime Vaccines Expressing the Fusion Protein of *B. anthracis* Immunogenic Domains of the Lethal Factor (LF) and Protective Antigen (PA) and the Fusion Protein of *Y. pestis* Fraction 1 Capsular Antigen (F1), Low-Calcium-Response V Antigen (LcrV), and/or the Type III Secretion System Needle Protein YscF We have constructed the following *Francisella*-vectored vaccine candidates expressing *B. anthracis* and *Y. pestis* antigens (Table 2): 1) rLVS ΔcapB expressing a fusion protein comprising the *B. anthracis* lef-encoded LF amino terminal domain [domain 1 (LFD1), aa 1-254] (11) and pagA-encoded PA carboxy-terminal host cell receptor-binding domain [domain 4 (PAD4), aa 552-735] (12) separated by a GGSG (SEQ ID NO: 62) (L1) or GSSGGSSG (SEQ ID NO: 65) (L2) flexible linker, resulting in rLVS ΔcapB/BaLFPA(L1) and rLVS ΔcapB/BaLFPA(L2); 2) rLVS ΔcapB expressing the fusion protein comprising the *B. anthracis* LFD1-GGSG-PAD4 ligated in frame with the carboxy-terminal of the *F. tularensis* KatG signal sequence (KatGss) or the *F. novicida* PepO signal sequence (PepOss), resulting in rLVS ΔcapB/katGss-BaLFPA(L1) and rLVS ΔcapB/PepOss-BaLFPA(L1); 3) rLVS ΔcapB expressing the *Y. pestis* cafI-encoded F1 antigen and lcrV-encoded LcrV antigen either linked directly (D) or separated by a flexible linker GGSG (SEQ ID NO: 62) (L1), downstream of the Ft omp promoter, resulting in rLVS ΔcapB/YpF1V(D) and rLVS ΔcapB/YpF1V(L1); 4) rLVS ΔcapB expressing the *Y. pestis* F1V(L1) ligated in frame with the C-terminal of *F. novicida* PepPOss, resulting in rLVS ΔcapB/PepOss-YpF1V (L1); 5) rLVS ΔcapB expressing the *Y. pestis* lcr V-encoded LcrV antigen, cafI-encoded F1 antigen, and yscF-encoded YscF separated by a flexible linker GGGSGGGSGGGS (SEQ ID NO: 66) (L3) and downstream of the Ft bfr promoter, resulting in rLVS ΔcapB/YpVF1YscF(L3).

Construction and Verification of Monovalent rLm Booster Vaccines Expressing Ba Fusion Protein LFD1-GGSG-PAD4 and Yp Fusion Protein F1-GGSG-LcrV We have constructed: 1) rLm expressing Ba LFD1-L-PAD4 downstream of Lm hly or actA promoter and fused with the listeriolysin O signal sequence (LLOs.s.) or the ActA N-terminal 100 amino acids (ActAN100) using Lm ΔactA and Lm ΔactA ΔinlB prfA*Lm vectors, resulting in rLm ΔactA/actA-BaLFPA(L1), rLm ΔactA ΔinlB prfA*/actA-BaLFPA(L1), rLm ΔactA/hly-BaLFPA(L1), and rLm ΔactA ΔinlB prfA*/hly-BaLFPA(L1); and 2) rLm expressing Yp F1-LcrV under the control of Lm hly and actA promoters by using two different version of Lm vectors, resulting in rLm ΔactA/actA-YpF1V(L1), rLm ΔactA ΔinlB prfA*Lm/actA-YpF1V(L1), rLm ΔactA/hly-YpF1V(L1), and rLm ΔactA ΔinlB prfA*/hly-YpF1V(L1). See Table 2 for a complete list of the rLm vaccines constructed.

Figure 1:
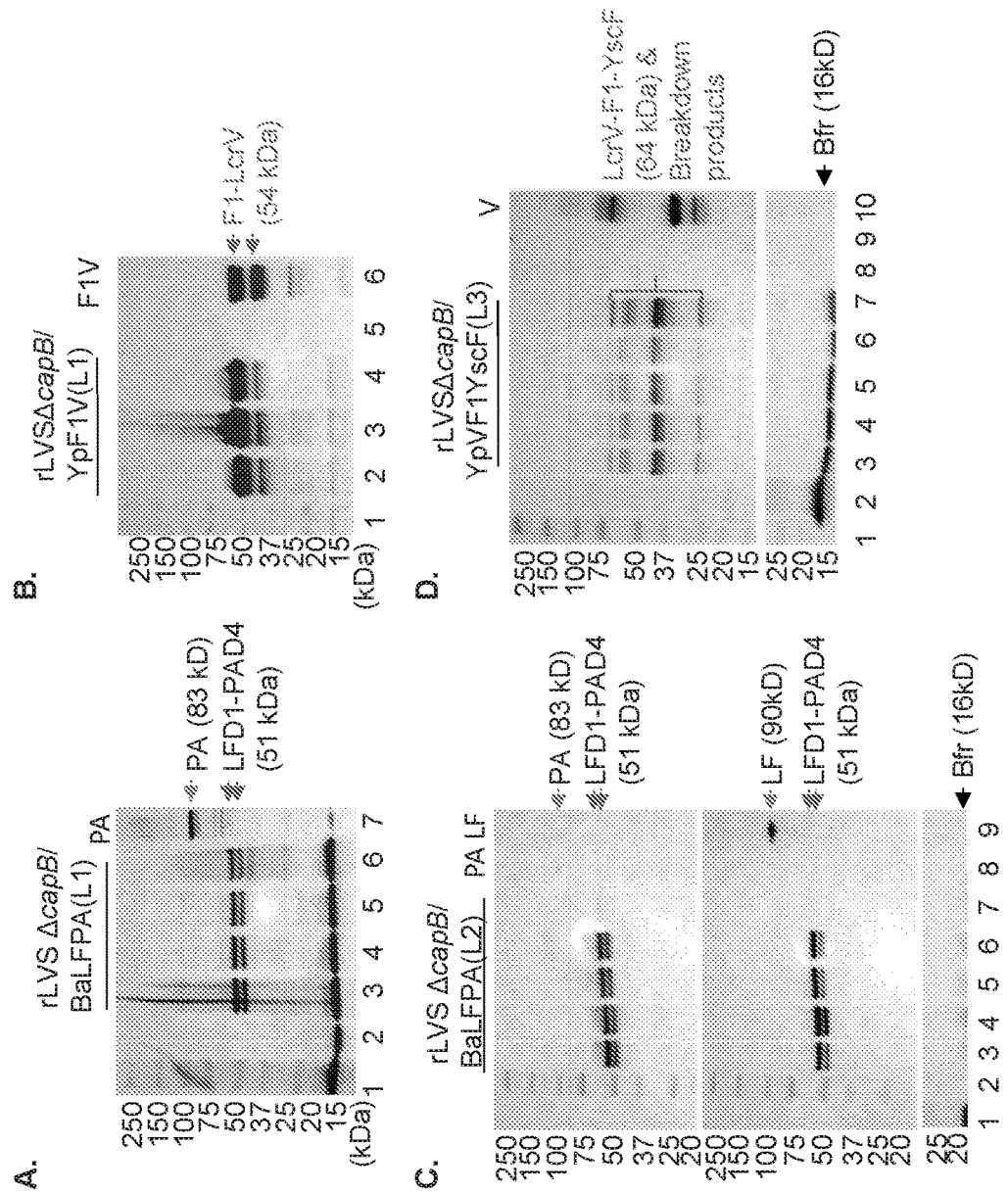
FIG. 1. Expression of fusion proteins Ba LFPA(L1), Ba LFPA(L2), Yp F1V(L1), and Yp VF1YscF(L3) by rLVS ΔcapB. rLVS ΔcapB/BaLFPA(L1) (A, lanes 3-6), rLVS ΔcapB/BaLFPA(L2) (C, lanes 3-6), rLVS ΔcapB/YpF1V (L1) (B, lanes 2-4), and rLVS ΔcapB/YpVF1YscF(L3) (D, lanes 3-7) were grown on agar plates and lysates analyzed by Western blotting using monoclonal antibody to Ba PA (A; C, top panel) or LF (C, middle panel), goat polyclonal antibody to Yp LcrV (B; D, top panel), or to Ft Bfr (C & D, bottom panels, serving as vector control). Lysate of LVS ΔcapB (A, lane 2; C, lane 1; D, lane 2), PA protein (A, lane 7; C, lane 8), LF (C, lane 9), monomer of F1-LcrV (B, lane 6), F1 (D, lane 9) or LcrV (D, lane 10) served as controls. B, lane 5, empty; C, lane 7, lysate of culture supernatant of rLVS ΔcapB/KatGS S-BaLFPA(L1).
Figure 2:
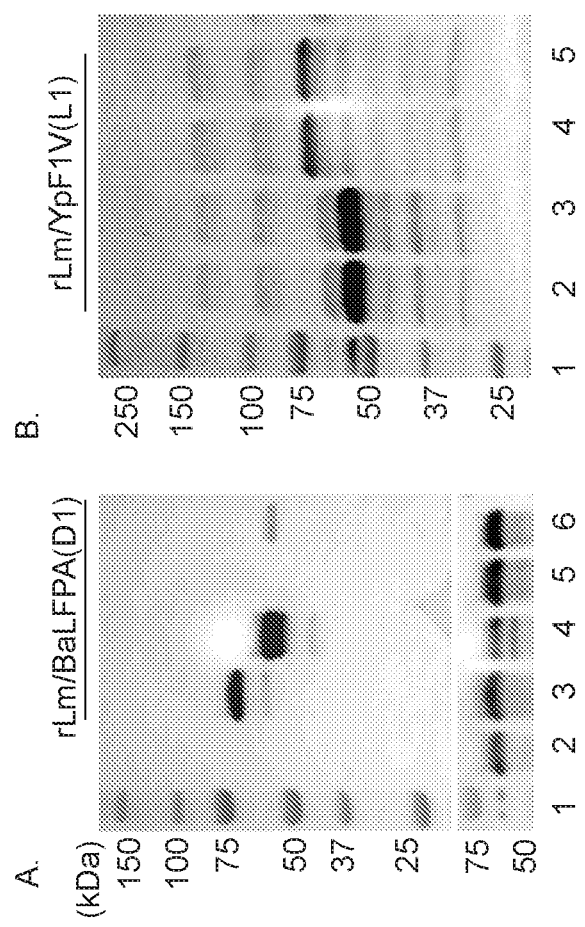
FIG. 2. Expression of the fusion protein Ba LFPA(L1) and Yp F1V(L1) by recombinant *L. monocytogenes.* Culture filtrates of rLm ΔactA ΔinlB prfA* (A, top panel, Lanes 3 & 4) or rLm ΔactA (A, top panel, Lanes 5 & 6) expressing Ba fusion protein actA-BaLFPA(L1) (~62 kDa, lanes 3, 5; ~62 kDa band visible in lane 5 in over-exposed blot—not shown) and hly-BaLFPA(L1) (without/with LLOs.s of ~51 & 54 kDa, resp., lanes 4, 6) or culture filtrates of rLm ΔactA ΔinlB prfA* expressing Yp fusion proteins hly-F1V(L1) (~55 & 58 kDa) (B, lanes 2 & 3.) or actA-YpF1V(11) (~66 kDa) (B, Lanes 4 & 5) were analyzed by Western blotting using monoclonal antibody to Ba PA (A, top panel) or polyclonal antibody to Lm P60 (A, bottom panel, loading control), or goat antibody to Yp LcrV (B). Lysate of Lm vector (A, lane 2) served as control.

Demonstration that *B. anthracis* and *Y. pestis* Fustion Proteins are Expressed by *F. tularensis* and Lm Platforms rLVS ΔcapB and rLm vaccines express Ba and Yp fusion proteins in broth (FIG. 1 and FIG. 2).

Demonstration that *B. anthracis* and *Y. pestis* Fusion Proteins are Expressed by rLVS ΔcapB from Infected Macrophase-Like THP-1 Cells To examine whether the *F. tularensis* rLVS ΔcapB platform can express the *B. anthracis* and *Y. pestis* fusion proteins from infected macrophage-like cells, we seeded THP-1 cells at $3 \times 10^5$ cells/well on 24-well plates and differentiated them in the presence of PMA for 3 days. Vaccine vector (LVS ΔcapB) and vaccines were grown on Chocolate agar supplemented without or with kanamycin (7.5 µg/ml) for 3 days. Differentiated THP-1 cells were infected with 0.5 ml of vaccines or vaccine vector opsonized with human serum for 10 min at 37° C., spun at 1000×g for 30 min at 4° C., and incubated at 37° C. for 1 h. The cells were then washed with RPMI three times, incubated with complete RPMI supplemented with gentamycin (0.1 µg/ml) to inhibit extracellular bacterial growth. At 5 and 24 h post infection, medium was removed from wells and cells were lysed in 0.125 ml SDS buffer and boiled for 5 min. The cell lysates were loaded onto 4-15% SDS gels and proteins separated by electrophoresis; the proteins transferred to a nitrocellulose membrane; and the proteins probed with antibodies to *B. anthracis* PA antigen (mAb to *B. anthracis* PA) plus goat polyclonal antibody to *Y. pestis* LcrV antigen (FIG. 3). At five hours post infection (FIG. 3A), double protein bands of ~51-52 kDa (expected size of the Ba fusion protein) were detected from THP-1 cells infected with rLVS ΔcapB/BaLFPA(L1) (lane 4), but not from the uninfected THP-1 cells (lane 2), or THP-1 cells infected with the parental LVS ΔcapB (lane 3), rLVS ΔcapB/YpF1V(D) (lane 5) or the rLVS ΔcapB/YpF1V(L1) (lane 6) strains. The mAb antibody to PA also detected the full length PA protein and its degraded forms (lane 8). Also at five hours post infection (FIG. 3A), a major single protein band of ~50 kDa (expected size of the Yp fusion protein) was also detected from THP-1 cells infected with rLVS ΔcapB/YpF1V(L1) (lane 5) and the rLVS ΔcapB/YpF1V(L1) (lane 6), similar to the positive control of F1-LcrV monomer protein (lane 9). At 24 h post infection (FIG. 3B), the fusion protein of *B. anthracis* LFD1-PAD4 (lane 4) was expressed at a level similar to that expressed at 5 hours post infection; the fusion protein of *Y. pestis* F1-LcrV (lane 5) and *Y. pestis* F1-GGSG-LcrV (lane 6) were expressed to a level higher than that detected at 5 hours post infection. These results indicated that the *F. tularensis* LVS ΔcapB platform could be used as a multi-valent vaccine platform for expressing *B. anthracis* and *Y. pestis* antigens.

Figure 4:
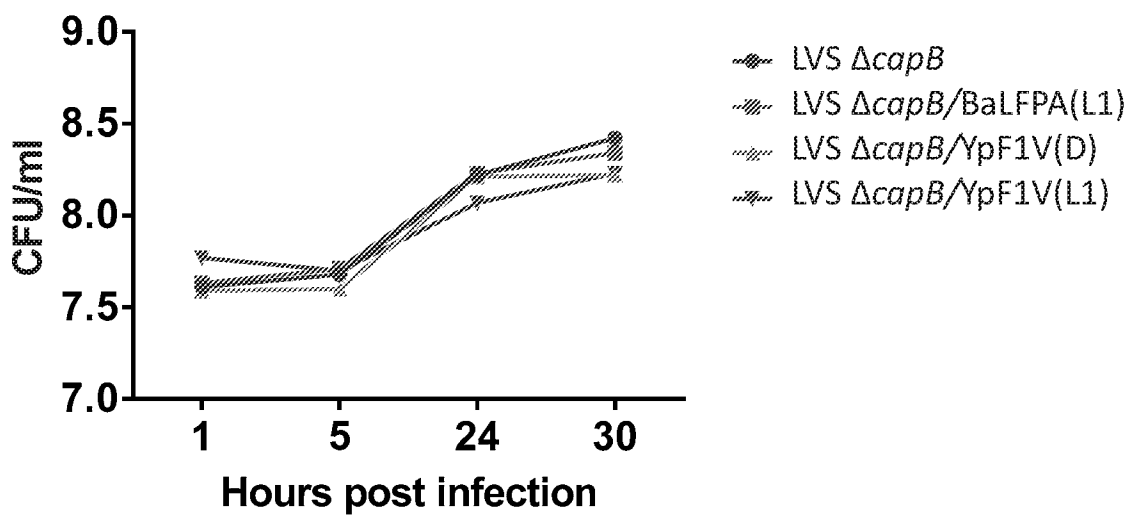

Demonstration that *F. tularensis* rLVS ΔcapB Expressing Fusion Proteins of *B. anthracis* and *Y. pestis* Grow SImilarly to the Parental LVS ΔcapB in Infected THP-1 Cells To examine the growth kinetics of the rLVS ΔcapB vaccine candidates expressing *B. anthracis* and *Y. pestis* antigens, we infected THP-1 cells as described above for FIG. 3. At various times post infection, we lysed the cells; serially diluted the lysates, plated on chocolate agar supplemented with kanamycin, incubated at 37° C. in a $CO_2$ incubator for 3-5 days, and enumerated colonies. As shown in FIG. 4, the rLVS ΔcapB strains expressing *B. anthracis* or the *Y. pestis* antigens grew similarly to the parental LVS ΔcapB strain in infected THP-1 cells.

Figure 6:
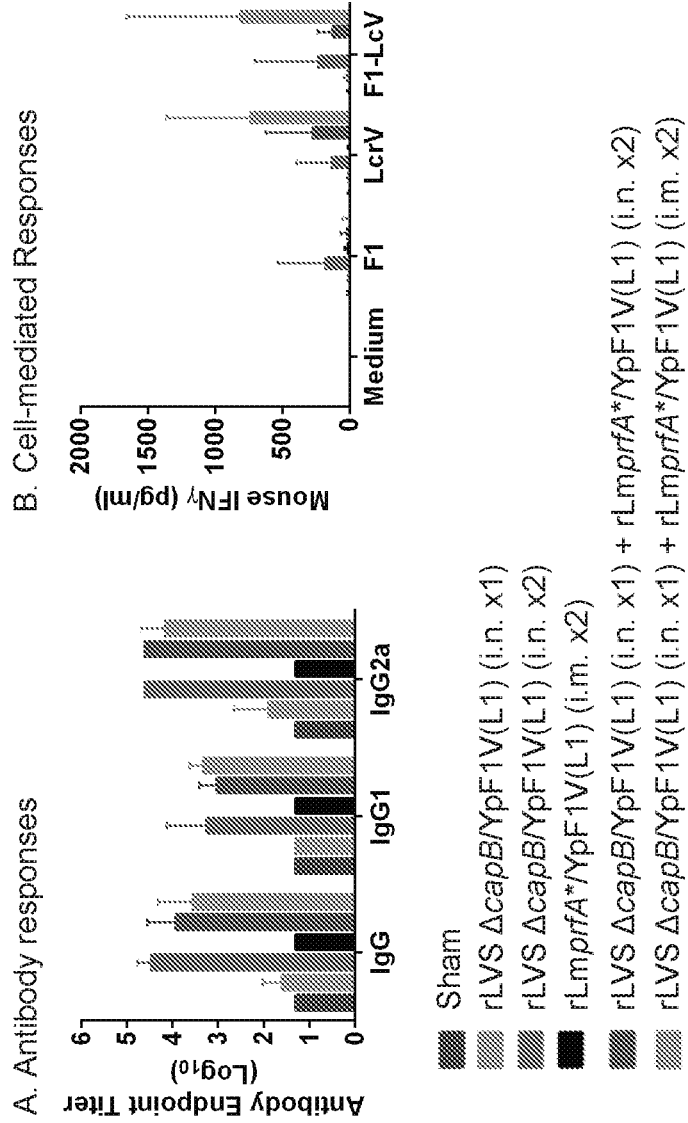
FIG. 6. immunogenicity of LVS ΔcapB- and Lm-vectored Yp vaccines. Mice were vaccinated with PBS at week 0 (Sham, blue bars), rLVS ΔcapB/YpF1V(L1) intranasally (i.n.) once at weeks 0 (green bars) or twice at weeks 0 and 4 (red bars), or with rLmprfA*/YpF1V(L1) (rLm ΔactA ΔinlBprfA*/hly-YpF1V(L1)) intramuscularly (i.m.) twice at weeks 0 and 4 (black bars), or primed with rLVS ΔcapB/YpF1V(L1) i.n. at week 0 and boosted with rLmprfA*/YpF1V twice at weeks 4 and 6 i.n. (purple bars) or i.m. (orange bars). At week 7, all mice were bled and spleens and lungs removed. A. Antibody responses: Sera were assayed for IgG, subtypes IgG1 and IgG2a to *Y. pestis* antigen F1/V monomer protein (BE1 Resources). B. Cell-mediated Responses: Spleen and lung cells were stimulated with medium alone or medium supplemented with F1, LcrV, or F1-LcrV monomer protein and their supernatants assayed for secretion of IFN-γ. Values are mean±SD.

Demonstration that Immunization with rLVS ΔcapB- and/or rLm ΔactA ΔinlB prfA*—Vectored Ba and Yp Vaccines Includes Antigen-Specific Functional Humoral and Strong LF—Specific T-cell Mediated Immune Responses Mice immunized with rLVS ΔcapB/BaLF-PA (rLVS ΔcapB/BaLFPA[L1]) or prime-boosted with rLVS ΔcapB/BaLF-PA and rLmprfA*/BaLF-PA (rLm ΔactA ΔinlB prfA*/hly-BaLFPA(L1)) produced significantly greater amounts of Ba (LF and PA) and Ft (HI-LVS) antigen specific serum IgG antibody than sham-immunized mice, dominated by subtype IgG2a, and with appreciable amounts of IgG1 and IgG2b, and minimal amounts of IgG3 to LF/PA (FIG. 5a-5d). Importantly, heterologously prime-boosted mice also produced higher titers of serum antibodies that neutralized anthrax toxin (assayed in mouse macrophage cell line J774A.1) than sham-immunized mice and mice vaccinated with only the LVS ΔcapB-vectored vaccine (data not shown). Priming with LVS ΔcapB-vectored Ba vaccine with or without boosting with Lm-vectored Ba vaccines induces Francisella (HI-LVS) and anthrax antigen (LF>PA)-specific Th1- and Th2-type cytokine secretion (FIG. 5e-5h) and LF- and HI-LVS specific multifunctional CD4 T cells (data not shown). In contrast, AVA vaccine immunization yielded little or no cytokine secretion to Ba antigens. Homologous prime-boosting with LVS ΔcapB/YpF1-V (LVS ΔcapB/YpF1V[L1]) [but not rLmprfA */Yp (rLm ΔactA ΔinlB prfA*/hly-YpF1V(L1)] or heterologous prime-boosting with the LVS ΔcapB/YpF1-V (i.n.)+rLmprfA */YpF1-V (i.n. or i.m.) vaccines similarly induce Yp F1/LcrV antigen-specific antibody responses (FIG. 6A) and T-cell mediated immune responses (FIG. 6B).

Figure 7:
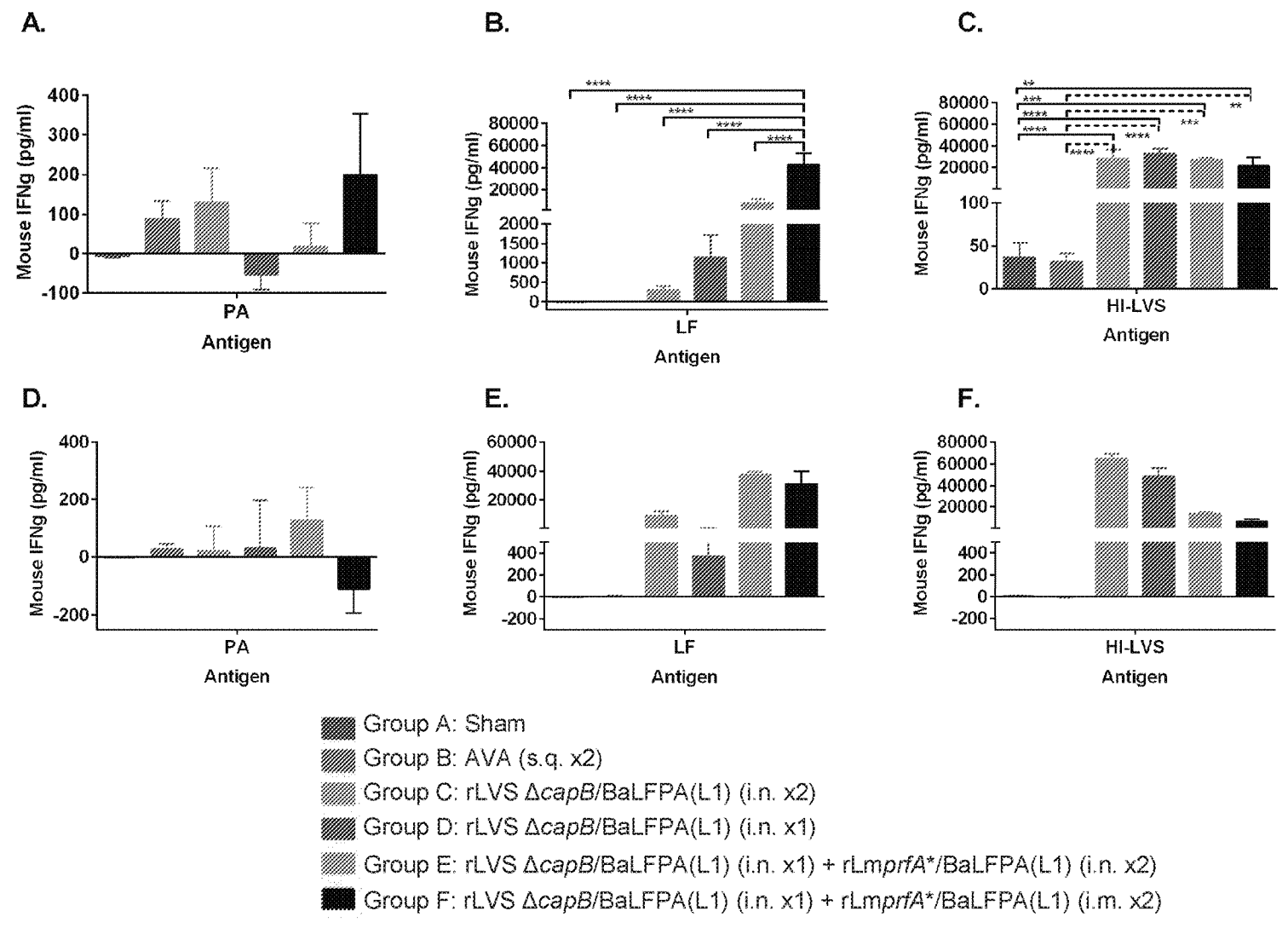
Figure 8:
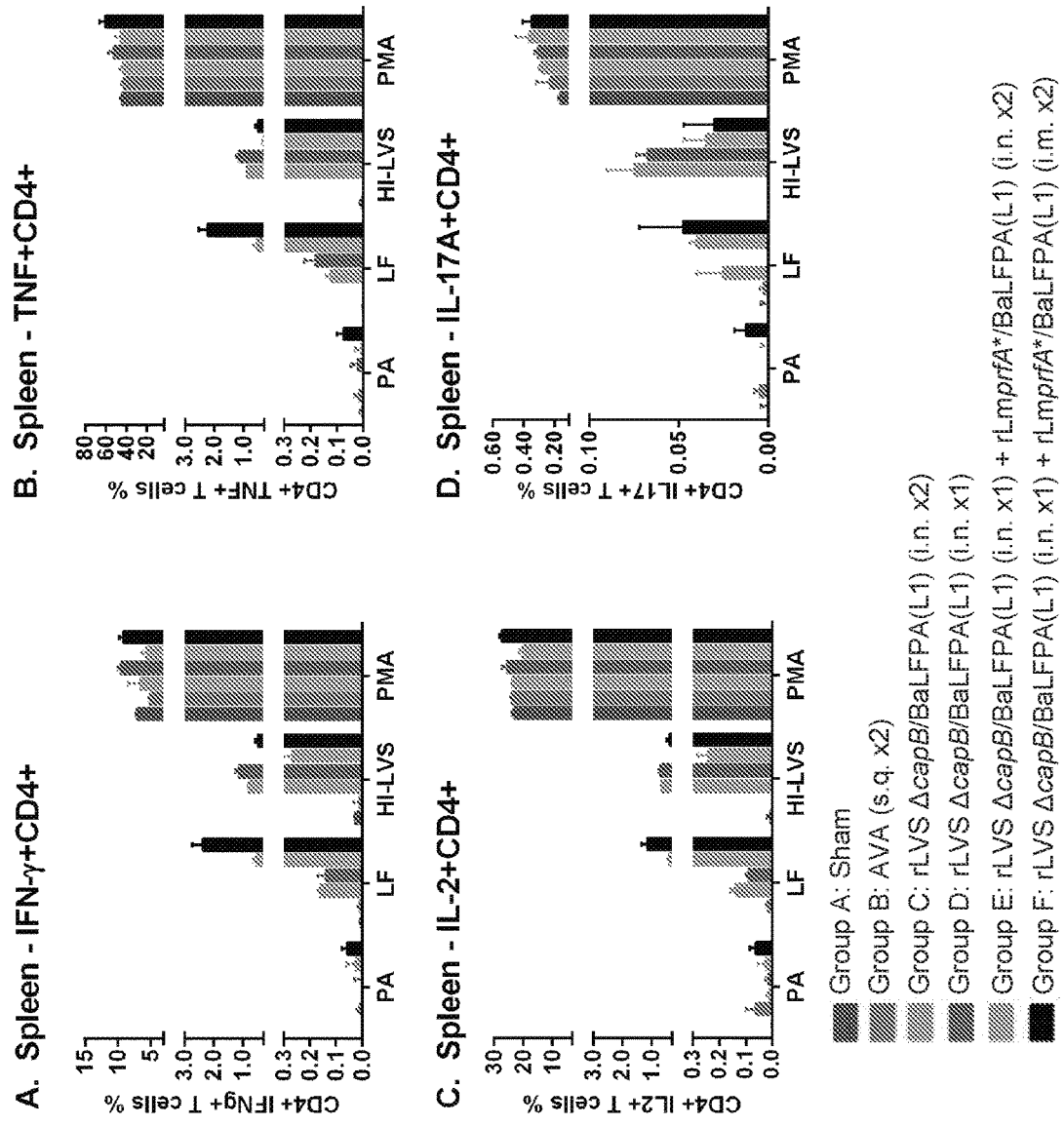
FIG. 8. Immunization with LVS ΔcapB- and Lm-vectored *B. anthracis* vaccines induces elevated frequencies of spleen CD4+ T cells producing IFN-γ, IL-2, TNF, and IL17. Mice were immunized as described in legend to FIG. 5. Spleen cells were stimulated with PA, LF or HI-LVS, or PMA and assayed by intracellular cytokine staining for CD4+ T cells expressing IFN-γ (A), TNF (8), IL-2 (C), and IL-17A (D) as indicated. Values are means±SEM.
Figure 9:
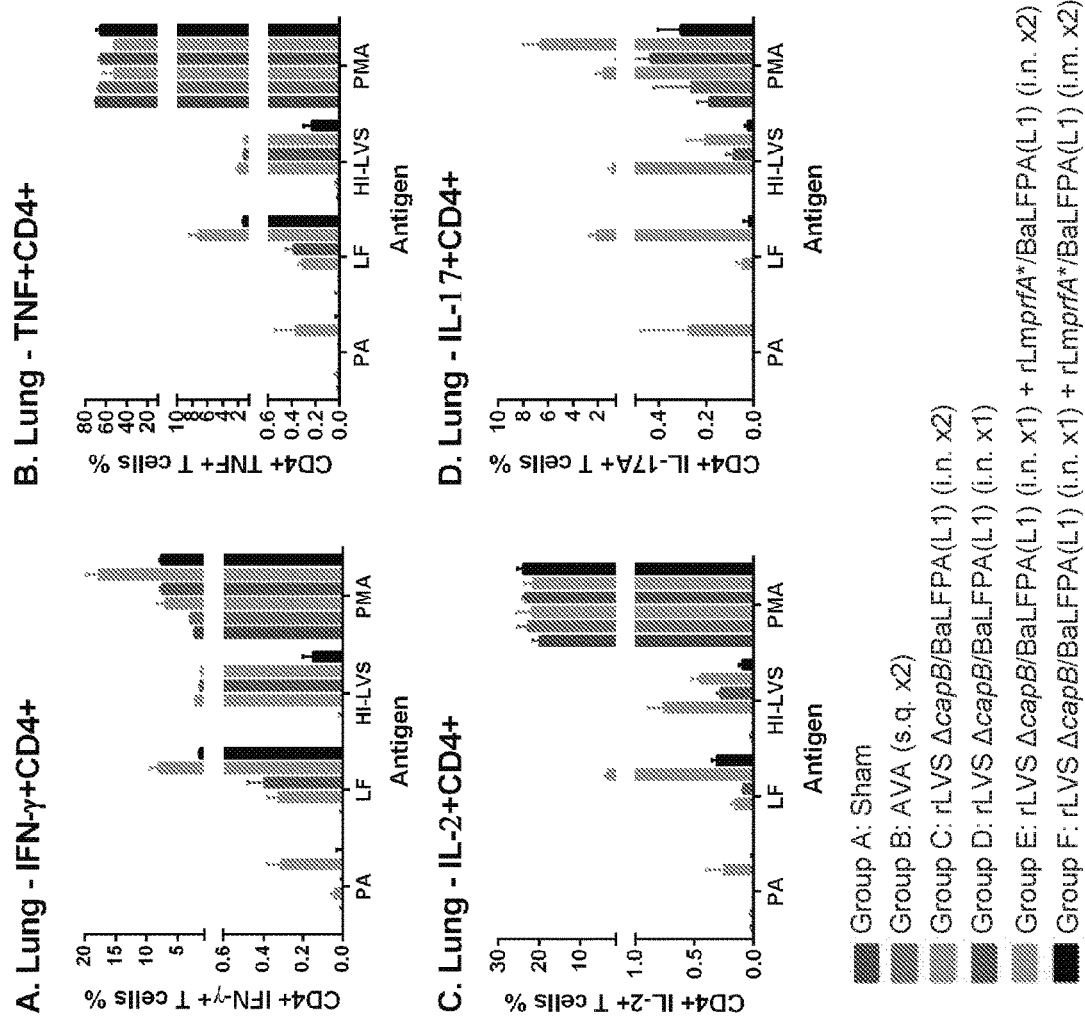
FIG. 9. Immunization with LVS ΔcapB- and Lm-vectored *B. anthracis* vaccines induces elevated frequencies of lung CD4+ T cells producing IFN-γ, IL-2, TNF, and IL-17. Mice were immunized as described in legend to FIG. 5. Spleen cells were stimulated with PA, LF or HI-LVS, or PMA and assayed by intracellular cytokine staining for CD4+ T cells expressing IFN-γ (A), TNF (B), IL-2 (C), and IL-17A (D) as indicated. Values are means±SEM.
Figure 10:
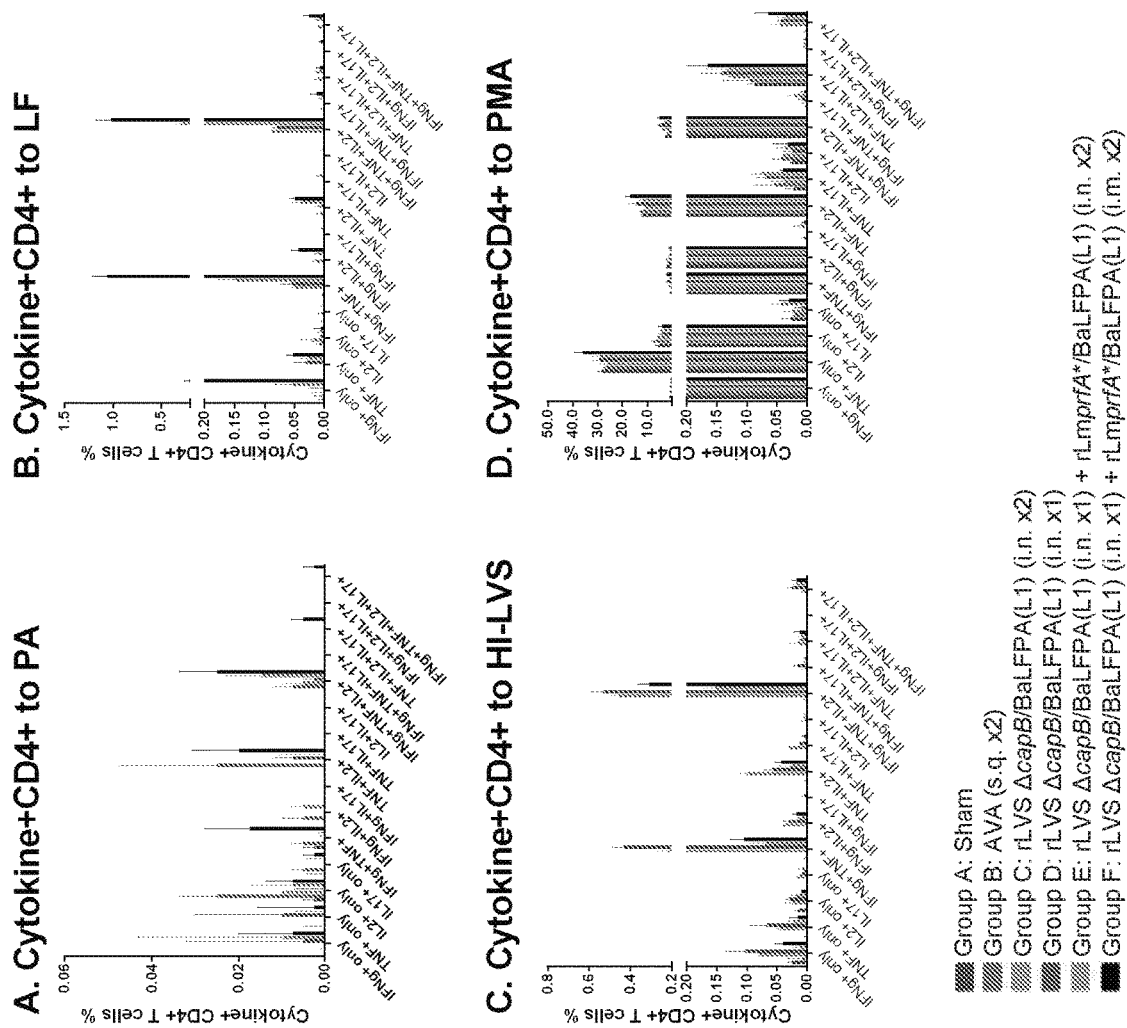
FIG. 10. Immunization with LVS ΔcapB- and Lm-vectored *B. anthracis* vaccines induces elevated frequencies of multifunctional spleen CD4+ T cells producing IFN-γ, IL-2, TNF, and IL-17. Mice were immunized as described in legend to FIG. 5. Spleen cells were stimulated with PA (A), LF (B), HI-LVS (C), or PMA (D) and assayed by intracellular cytokine staining for 15 possible combinations of CD4+ T cells expressing IFN-γ, TNF, IL-2, and/or IL-17A. Values are means±SEM.
Figure 11:
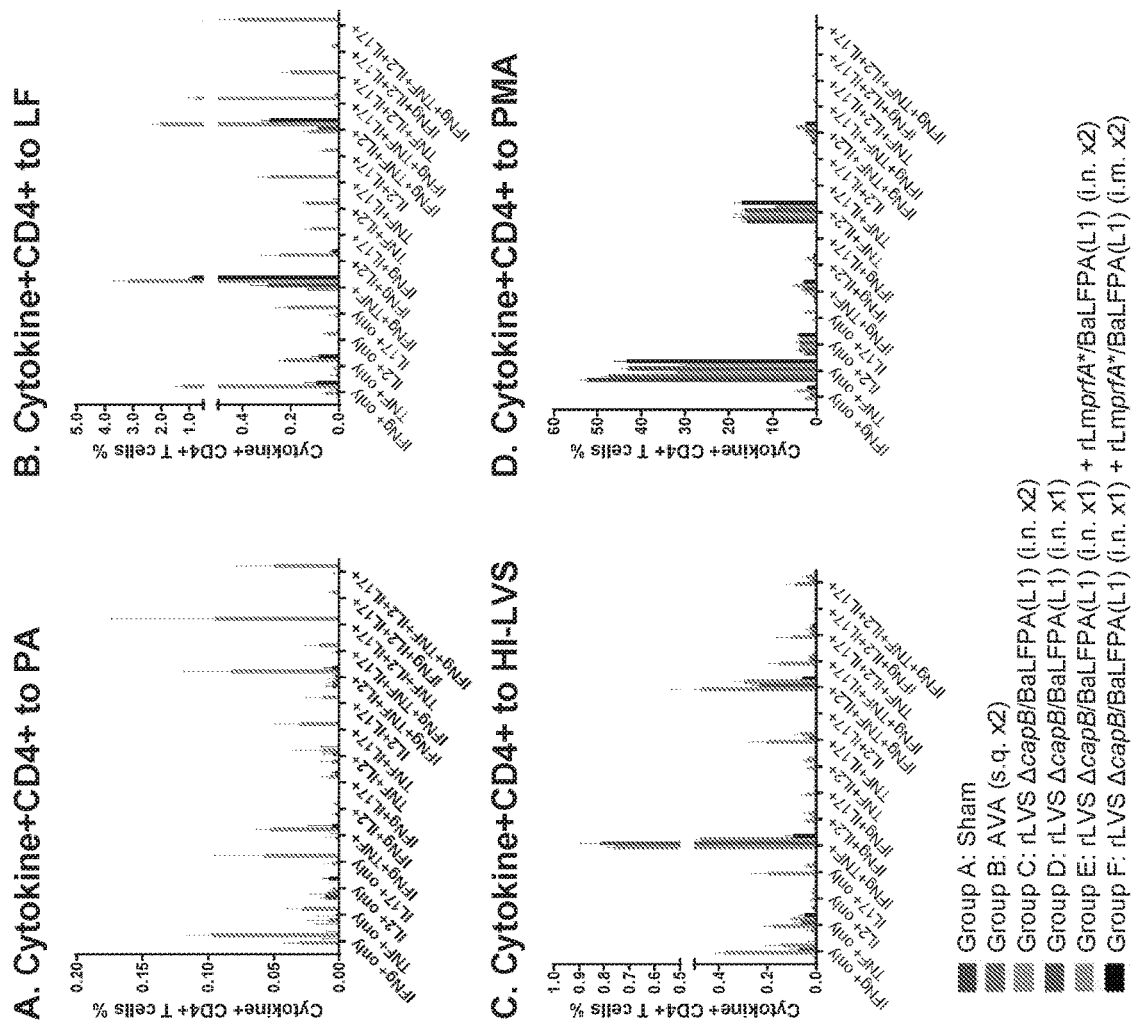
FIG. 11. Immunization with LVS ΔcapB- and Lm-vectored *B. anthracis* vaccines induces elevated frequencies of multifunctional lung CD4+ T cells producing IFN-γ, IL-2, TNF, and IL17. Mice were immunized as described in legend to FIG. 5. Lung cells were stimulated with PA (A), LF (B), HI-LVS (C), or PMA (D) and assayed by intracellular cytokine staining for 15 possible combinations of CD4+ T cells expressing IFN-γ, TNF, IL-2, and/or IL-17A. Values are means±SEM.

Demonstration that Immunization with Francisella- and Lm-Vectored B. anthracis Vaccines Induces Antigen specific T-cell Mediated Immune Responses To examine whether immunization with B. anthracis vaccines delivered by Francisella and Lm platforms induces T-cell immune responses, we immunized groups of mice as described above, isolated their spleen and lung cells, and assayed T-cell mediated immune responses by measuring cytokine secretion and intracellular cytokine staining. Our results show that in response to PA antigen, spleen cells from mice immunized with the AVA vaccine subcutaneously twice, rLVS ΔcapB/BaLFPA(L1) intranasally twice, or primed with rLVS ΔcapB/BaLFPA(L1) intranasally and boosted twice with rLmprfA */hly-BaLFPA intramuscularly produced greater amounts of interferon gamma (IFN-γ) than sham-immunized mice, mice immunized only once with rLVS ΔcapB/BaLFPA(L1) intranasally, or mice primed with rLVS ΔcapB/BaLFPA(L1) intranasally and boosted twice with rLmprfA */hly-BaLFPA intranasally, although the difference did not reach statistical significance (FIG. 7A). In response to LF, spleen cells from mice primed with rLVS ΔcapB/BaLFPA(L1) intranasally and boosted twice with rLmprfA */hly-BaLFPA intramuscularly produced significantly greater amounts of IFN-γ than mice from all other groups (FIG. 7B); lung cells from heterologously prime-boosted mice, whether the boost was intranasal or intramuscular, also produced the highest amounts of IFN-γ in response to LF (FIG. 7E). In response to HI-LVS, spleen and lung cells from all mice immunized with rLVS ΔcapB/BaLFPA(L1), whether once or twice, or whether heterologously boosted or not, produced significantly greater amounts of IFN-γ than sham-immunized mice or mice immunized with the AVA vaccine (FIGS. 7C and F). Consistently, spleen and lung cells from mice primed with Francisella and boosted with Lm vaccines produced significantly greater frequencies of T cells producing IFN-γ, TNF, IL-2, and IL17, especially in response to LF and HI-LVS (FIGS. 8 & 9). Spleen and lung cells from mice primed with Francisella and boosted with Lm vaccines produced significantly greater frequencies of multifunctional CD4+ T cells expressing IFN-γ, TNF and IL2 in response to in vitro stimulation with PA and LF antigens, especially LF antigen (FIGS. 10 & 11, Panels A & B); lung cells from mice prime-boosted by these vaccines intranasally also produced large numbers of multifunctional CD4+ T cells expressing IFN-γ, TNF, IL2, and IL17 in response to in vitro stimulation with PA and LF antigens (FIG. 11, Panels A & B). Spleen and lung cells from mice primed with Francisella-vectored vaccines produced significantly greater frequencies of multifunctional CD4+ T cells in response to HI-LVS (FIGS. 10 & 11, Panel C). In contrast, in response to stimulation with PMA, spleen and lung cells from all groups produced comparable frequencies of cytokine-producing CD4+ T cells (FIGS. 8, 9, 10 & 11). These results indicate that priming with Francisella-vectored B. anthracis vaccines and boosting with Lm-vectored B. anthracis vaccines induce Francisella and anthrax antigen specific Th1-type cytokine secretion and multifunctional CD4 T cells.

Figure 12:
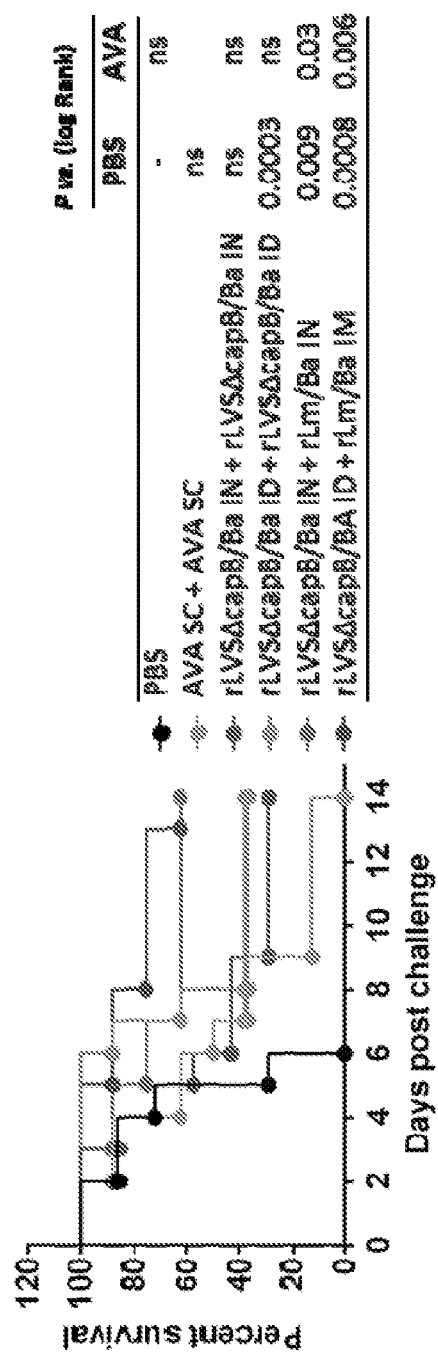
FIG. 12. Protective efficacy of rLVS ΔcapB/Ba & rLm/Ba against respiratory challenge with virulent Ba Ames spores. Mice, 8/group, were sham-immunized, or immunized subcutaneously (SC) twice with AVA (Biothrax, 0.025 ml), intradermally (ID) or intranasally (IN) twice with rLVS ΔcapB/Ba (rLVS ΔcapB/BaLFPA(L1)) or prime-boosted with rLVS ΔcapB/Ba once and rLm/Ba (rLm ΔactA ΔinlB prfA*/hly-BaLFPA(L1)) once systemically (ID/IM) or mucosally (IN/IN) ($10^6$ of each) at Week 0 and 4, as indicated in FIG. 8, challenged 4 weeks later with Ba Ames spores (5× LD50), and monitored for survival.

Demonstration that Systemic Homologous Vaccination with rLVS ΔcapB/Ba LFPA(L1) and Both Systemic and i.n. Heterologous Prime-Boost Vaccination with rLVS ΔcapB/BaLFPA(L1) and rLm ΔactA ΔinlB prfA*/hly-BaLFPA Induces Strong Protective Immunity Against Respiratory Challenge wih Ba and protection is Superior to Systemic Homologous Boosting with the AVA Vaccine Mice were sham-immunized, or immunized subcutaneously twice with AVA (Biothrax, 0.025m1), i.d. or i.n. twice with rLVS ΔcapB/Ba (rLVS ΔcapBIBaLFPA(L1)) or prime-boosted with rLVS ΔcapB/Ba once and rLm/Ba (rLm ΔactA ΔinlB prfA*/hly-BaLFPA) once systemically (i.d./i.m.) or mucosally (i.n./i.n.) ($10^6$ of each) at Week 0 and 4, as indicated in FIG. 12, challenged at week 8 with Ba Ames spores (5× LD50), and monitored for survival. Homologous vaccination i.d. and heterologous prime boosting by either route of immunization showed significant protection and heterologous prime-boost vaccination was significantly better than the AVA vaccine (P=0.03 and 0.006 by mucosal and systemic route, respectively).

Demonstration that Systemic Heterologous Prime-Boost Vaccination with rLVS ΔcapB/YpF1V and rLm ΔactA ΔinlB prfA*/hly-YpF1V Protects Against Respiratory Challenge with Yp (CO92)

Figure 13:
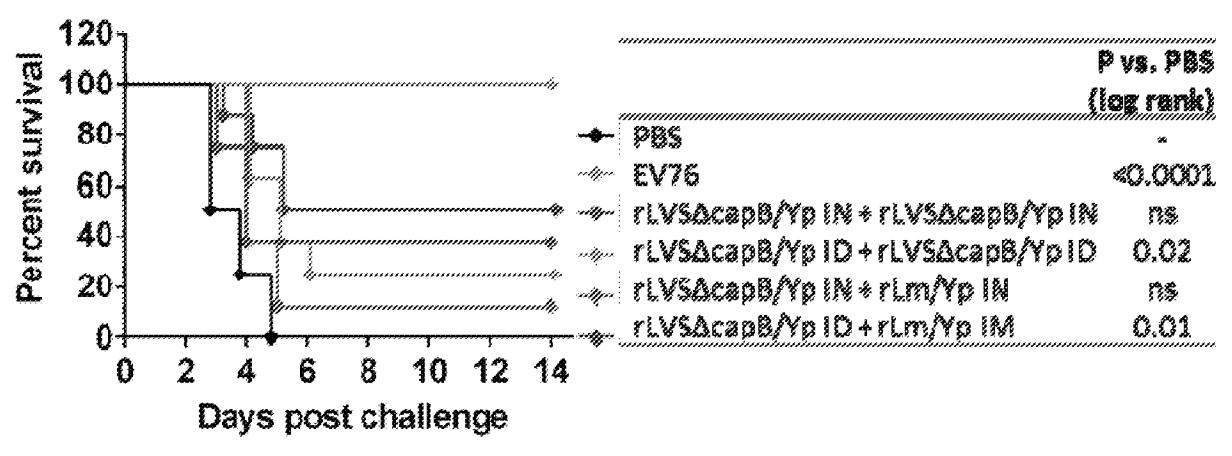

Mice were sham-immunized, or immunized subcutaneously with EV76 ($10^6$), i.d. or i.n. twice with rLVS ΔcapB/Yp (rLVS ΔcapB/YpF1V[L1]) or prime-boosted with rLVS ΔcapB/Yp once and rLm/Yp (ΔactA ΔinlB prfA*/hly-YpF1V) once systemically (i.d./i.m.) or mucosally (i.n./i.n.) ($10^6$ of each) at Week 0 and 4, as indicated in FIG. 13, challenged 5 weeks later with Yp (CO92, 10×$LD_{50}$), and monitored for survival. Homologous or heterologous prime-boosting by the systemic route (intradermally/intramuscularly), with only one boost, showed significant protection (P=0.02/0.01), albeit less than EV76.

Figure 28:
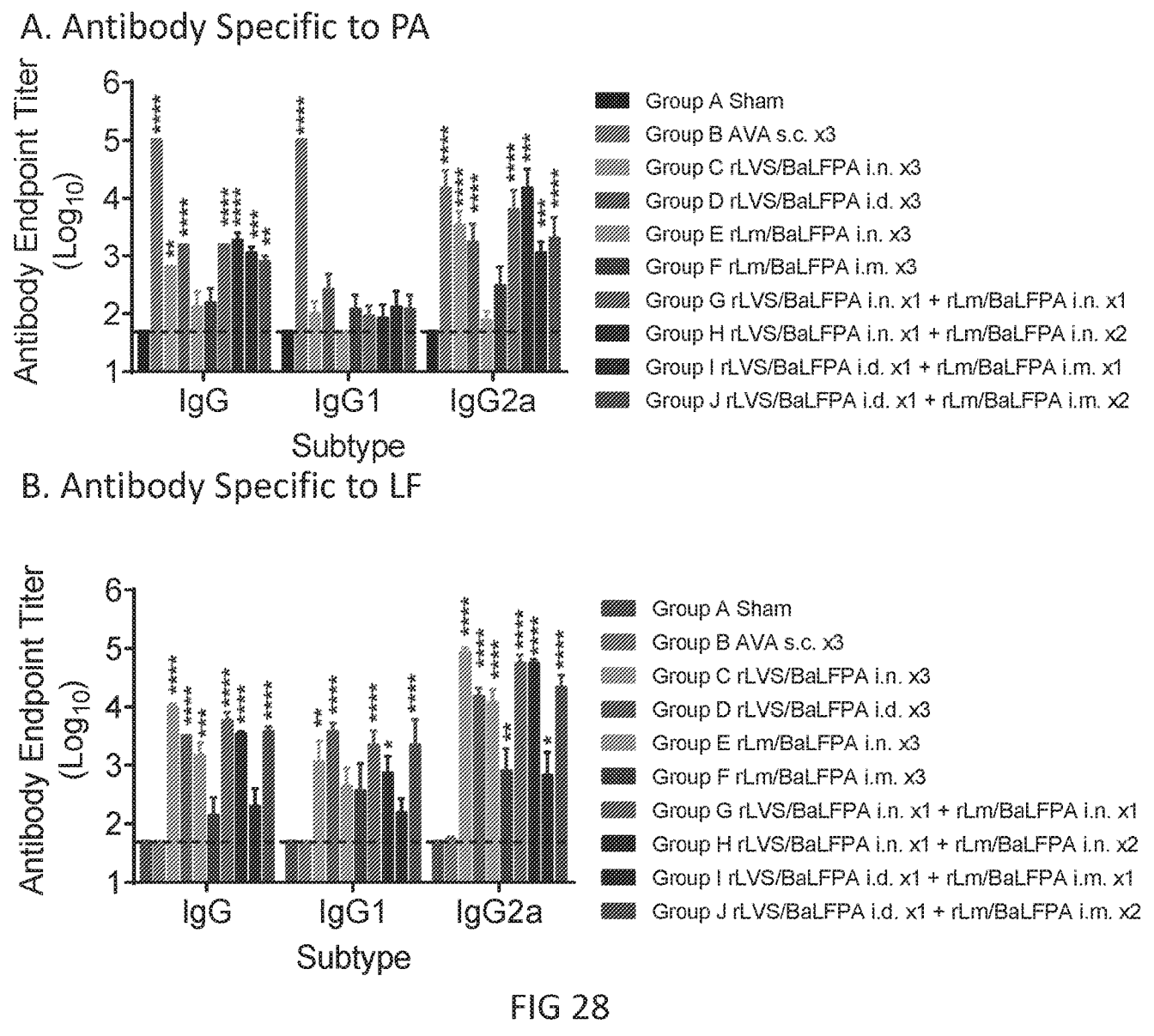

Demonstration that Homologous Prime-Boost Vaccination with rLVS ΔcapB/BaLFPA(L1) or with rLm ΔactA ΔinlB prfA*/hly-BaLFPA(L1) and Heterologous Prime-Boost Vaccination with rLVS ΔcapB/BaLFPA(L1)—rLm ΔactA ΔinlB prfA*hly-BaLFP A(L1) via Systemic and Mucosal Routes Induce Antigen-Specific Functional Humoral Immune Responses As described and indicated in the legend to FIG. 28, mice were sham-immunized, or immunized subcutaneously (s.c.) with AVA three times at weeks 0, 4, and 8 (Biothrax, 0.025 ml), i.d. or i.n. with rLVS ΔcapB/BaLFPA three times at weeks 0, 4, and 8 (rLVS ΔcapB/BaLFPA[L1]) or rLm/BaLFPA (rLm ΔactA ΔinlB prfA*/hly-BaLFPA), or primed i.n. or i.d. with rLVS ΔcapB/BaLFPA once at week 0 and boosted i.n. or i.m. with rLm/BaLFPA ($10^6$ of each) once at week 0 or twice at weeks 4 and 8, bled at week 11, challenged at week 12 and monitored for 3 weeks. Sera were analyzed for antigen specific antibody. Similar to mice immunized with AVA, mice homologously primed-boosted (immunized three times) with rLVS ΔcapB/BaLFPA (rLVS ΔcapB/BaLFPA[L1]) and heterologously primed-boosted with rLVS ΔcapB/BaLFPA-rLm/BaLFPA (rLm ΔactA ΔinlB prfA*/hly-BaLFPA) produced significantly greater amounts of Ba PA antigen—specific serum IgG antibody than sham-immunized mice, dominated by subtype IgG2a (FIG. 28a). Mice homologously primed-boosted (immunized three times) with rLm/BaLFPA (rLm ΔactA ΔinlB prfA*/hly-BaLFPA) showed increased IgG and IgG2a when immunized by either the i.n. or i.m. routes and increased IgG1 when immunized by the i.m. route, but the differences were not statistically significant. In contrast to mice immunized with AVA, mice homologously primed-boosted with rLVS ΔcapB/BaLFPA or rLm/BaLFPA, and mice heterologously primed-boosted with rLVS ΔcapB/BaLFPA—rLm/BaLFPA produced significantly greater amounts of Ba LF antigen—specific serum IgG antibody than sham-immunized mice, balanced between subtypes IgG1 and IgG2a (FIG. 28b).

Figure 29:
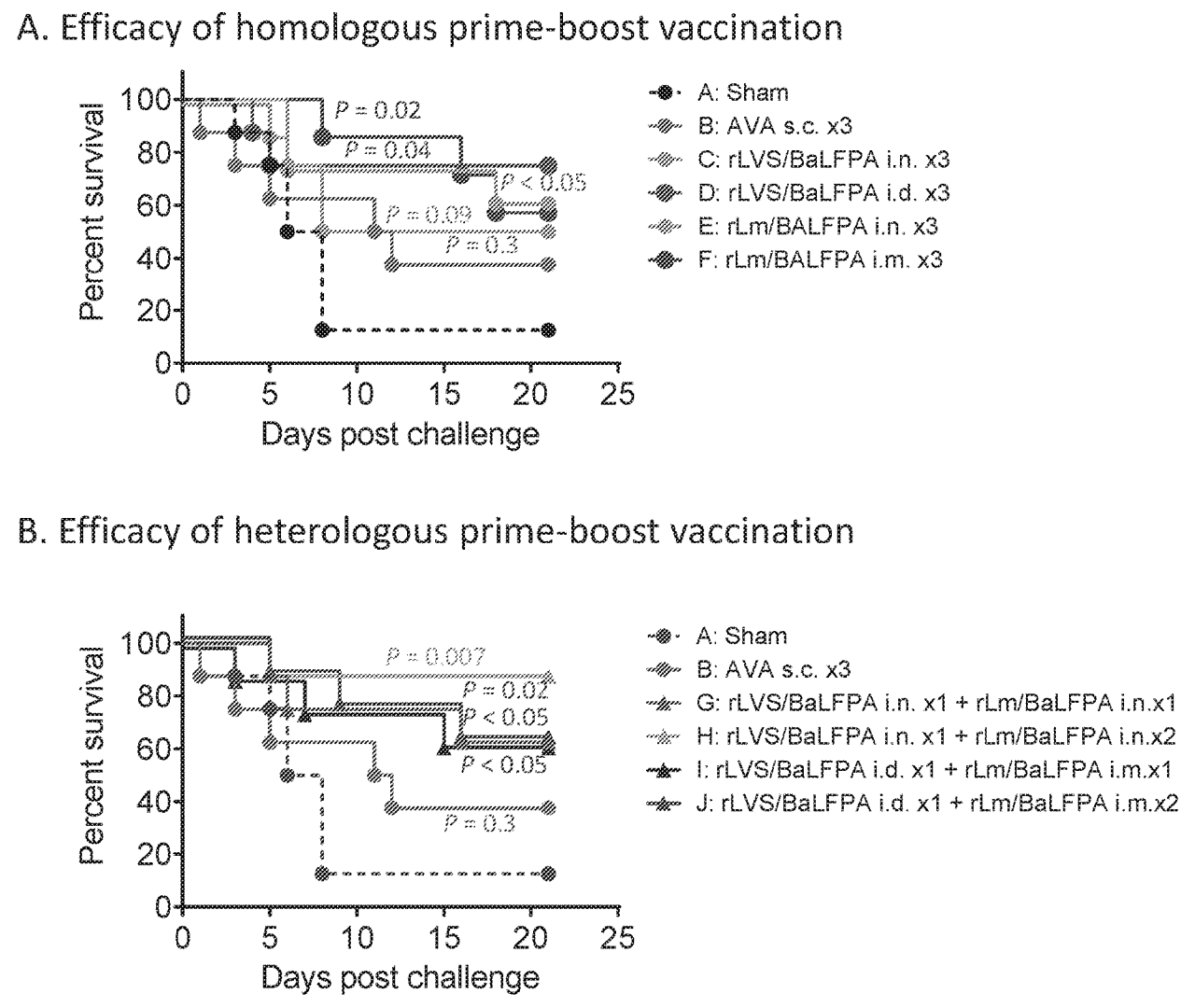

Demonstration that Both Systemic and Mucosal Homologous Prime-Boost Vaccination with rLVS ΔcapB/BaLFPA or rLm ΔactA ΔinlB prfA*/hly-BaLFPA and Heterologous Prime-Boost Vaccination with rLVS ΔcapB/BaLFPA—rLm ΔactA ΔinlB prfA*/hly-BaLFPA Induces Strong Protective Immunity Against Respiratory Challenge with Ba and Protection is Superior to Systemic Homologous Prime-Boosting with the AVA Vaccine Mice were immunized as described above and as indicated in FIG. 29, challenged at week 12 with Ba Ames spores (371,000 CFU), and monitored for 21 days for survival. Mice homologously primed-boosted i.d. with rLVS ΔcapB/BaLFPA or i.m. or i.n. with rLm ΔactA ΔinlB prfA*/hly-BaLFPA and heterologously primed with rLVS ΔcapB/BaLFPA and boosted with rLm ΔactA ΔinlB prfA*/hly-BaLFPA by either route of immunization showed significantly increased survival compared with sham immunized mice. In contrast, survival of mice immunized with the AVA vaccine was not significantly different from that of sham-immunized mice (P=0.3) (FIG. 29).

Figure 30:
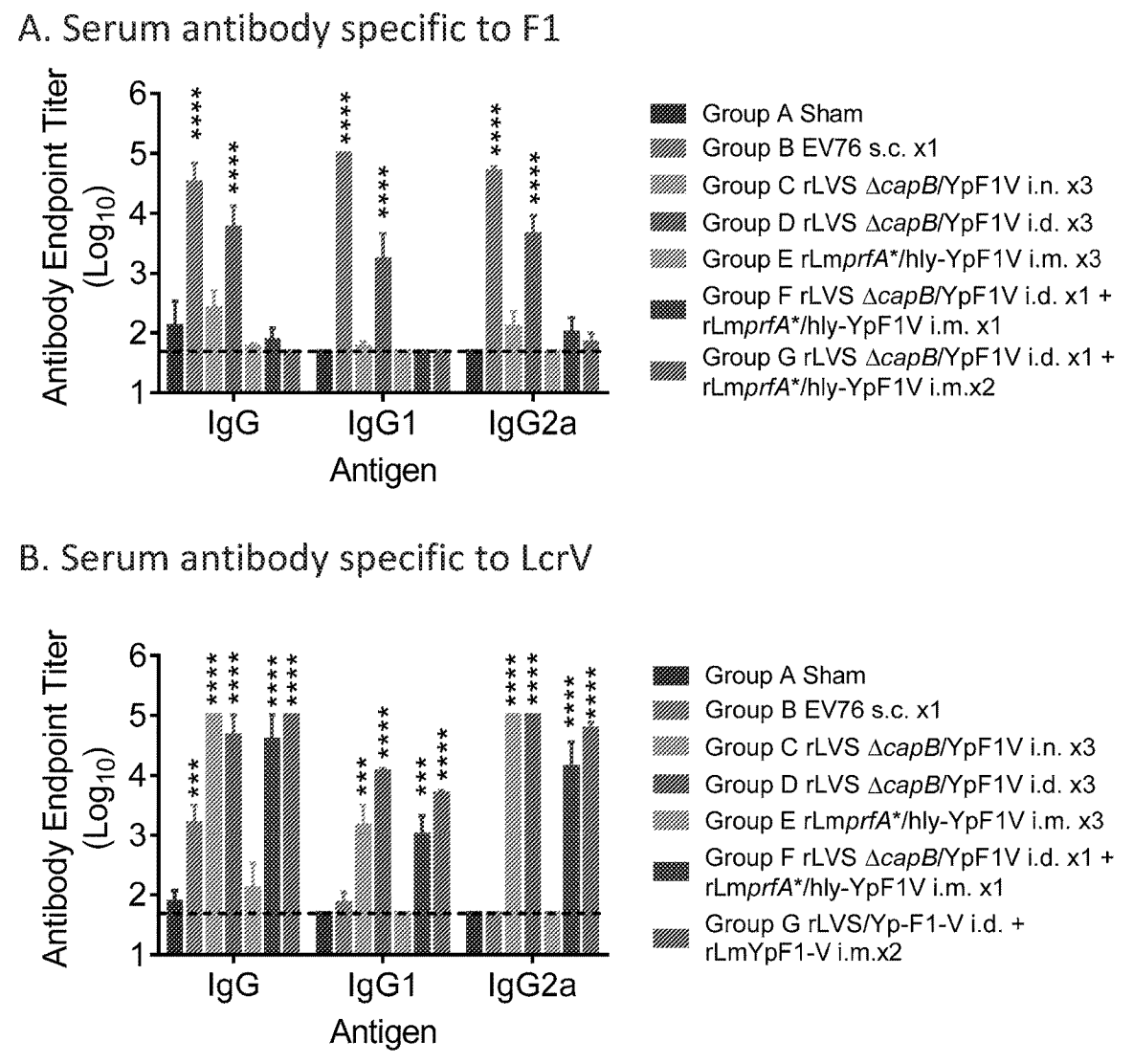

Demonstration that Systemic and Mucosal Homologous Prime-Boost Vaccination with rLVS ΔcapB/YpF1V and Systemic Heterologous Prime-Boost Vaccination with rLVS ΔcapB/YpF1V—rLm ΔactA ΔinlB prfA*/hly-YpF1V Induce Antigen-Specific Humoral Immune Responses Mice were sham-immunized, or immunized subcutaneously (s.c.) with EV76 ($10^6$) once, i.n. or i.d. with rLVS ΔcapB/YpF1V or rLm ΔactA ΔinlB prfA*/hly-YpF1V three times at weeks 0, 4, and 8, or primed i.d. with rLVS ΔcapB/YpF1V once at week 0 and boosted i.m. with rLm ΔactA ΔinlB prfA*/hly-YpF1V ($10^6$ of each) once at week 4 or twice at weeks 4 and 8, as indicated in FIG. 30, bled at week 11 and sera assayed for antigen-specific antibody. Among all the vaccine regimens tested, systemic (i.d.) homologous prime-boost vaccination with rLVS ΔcapB/YpF1V induced significantly elevated serum antibody to F1 antigen in comparison with Sham-immunized mice, balanced between subtypes IgG1 and IgG2a (FIG. 30A), similar to mice vaccinated with EV76. In response to LcrV antigen, homologous prime-boost vaccination i.n. and i.d with rLVS ΔcapB/YpF1V but not i.m. with rLm ΔactA ΔinlB prfA*/hly-YpF1V, and systemic heterologous prime-boost vaccination induced significantly elevated LcrV-specific IgG antibody in comparison with Sham-immunized mice, balanced between subtypes IgG1 and IgG2a (FIG. 30B).

Demonstration that Systemic Homologous Prime-Boost Vaccination with rLVS ΔcapB/YpF1V Induces Strong Protective Immunity against Yp CO92 Respiratory Challenge Mice were immunized as described above and in the legend to FIG. 30, challenged at week 12 with Yp CO92 (1,800 CFU), and monitored for 21 days for survival. Mice immunized three times i.d. with rLVS ΔcapB/YpF1V survived significantly longer than sham-immunized mice (P=0.03); mice primed-boosted with rLVS ΔcapB/YpF1V—rLm ΔactA ΔinlB prfA*/hly-YpF1V also survived longer than sham-immunized mice, although the difference was not statistically significant (FIG. 31).

Example 2

Figure 14:
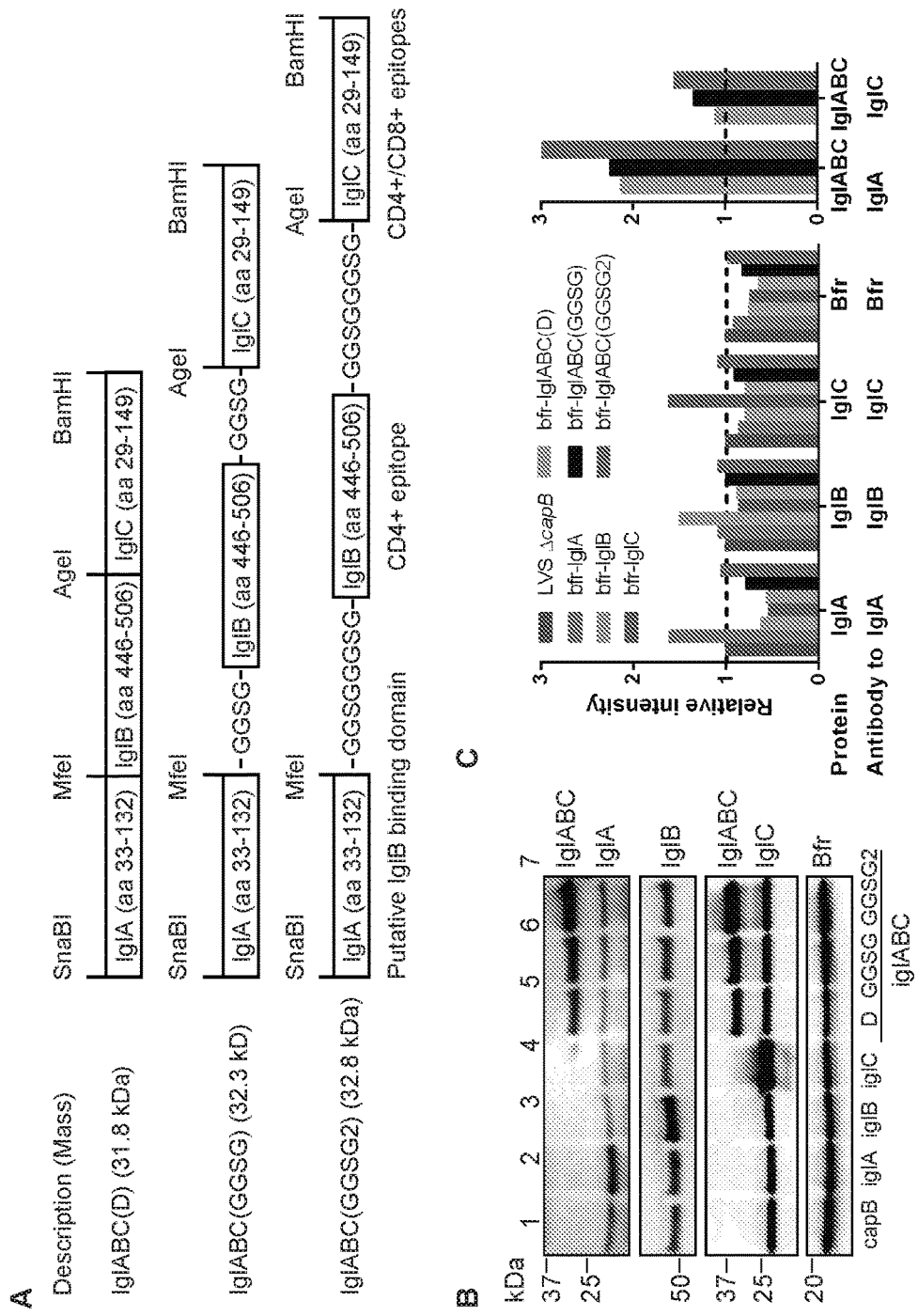
FIG. 14. Construction of shuttle plasmids for antigen expression cassettes of IglABC(D), IglABC(GGSG), and IglABC(GGSG2) and expression of *F. tularensis* FPI T6SS proteins by the recombinant LVS ΔcapB strains. A. Antigen expression cassette for fusion protein of IglABC. The coding sequences for IglA (residues 33-132), IglB (residues 446-506), and IglC (residues 29-149) either fused directly in frame with each other [IglABC(D)] or linked by a flexible linker GGSG (SEQ ID NO: 62) [IglABC(GGSG)] or GGSGGGSG (SEQ ID NO: 63) [IglABC (GGSG2)] was amplified by using overlap PCRs from the genomic DNA of a recent clinical isolate of *F. tularensis* subsp. tularensis and primer pairs listed in Supplemental Table 1 as described in the supplemental methods. B. The *F. tularensis* IglA, IglC, IglC and IglABC are overexpressed by rLVS ΔcapB cultured in broth medium. Various rLVS ΔcapB glycerol stocks were grown in TSBC for overnight with agitation; the overnight culture was sub-cultured to mid-log phase in TSBC; cells collected by centrifugation and lysed in SDS buffer; cell lysates equivalent to $1 \times 10^8$ bacteria were analyzed by SDS-PAGE and Western blotting using polyclonal antibodies (pAb) to IglA (top), monoclonal antibody (mAb) to IglB (upper middle), pAb to IglC (lower middle) and pAb to Bacterioferritin (Bfr, bottom) (loading control). Note, the membrane probed with mAb to IglB was stripped and re-probed with pAbs to IglA and Bacterioferritin; a separated membrane applied with the same amount of cell lysates was probed with pAb to IglC. Lane 1, LVS ΔcapB; Lane 2, rLVS ΔcapB/bfr-iglA; Lane 3, rLVS ΔcapB/bfr-iglB; Lane 4, rLVS ΔcapB/bfr-iglC; Lane 5, rLVS ΔcapB/bfr-iglABC(D); Lane 6, rLVS ΔcapB/bfr-iglABC [by definition expressing IglABC(GGSG); see Table 3]; Lane 7, rLVS ΔcapB/bfr-iglABC(GGSG2).

Construction and Characterization of LVS ΔcapB and Recombinant Listeria monocytogenes Overexpressing/Expressing the Fusion Protein of IglA, IglB, and IglC In Vitro and In Vivo and Demonstration of their Improved Immunogenicity as a Vaccine Against F. tularensis A. Recombinant LVS ΔcapB Overexpressing the Fusion Protein of IglA, IglB, and IglC Rationale and Construction of LVS ΔcapB Overexpressing the Fusion Protein of IglA, IglB, and IglC as a Vaccine Candidate against F. tularensis Previously, we have constructed recombinant LVS ΔcapB (rLVS ΔcapB) overexpressing a single immunogenic protein of Francisella tularensis at a time, including proteins expressed by the genes located in the Francisella pathogenicity Island (FPI)—intracellular growth locus A (iglA, FTT1714/1359) (27), iglB (FTT1713/1358), iglC (FTT1712/1357), and vgrG (1702/1347) from a shuttle plasmid under the control of the Francisella tularensis groEL (FTL_1715) promoter (28)—rLVS ΔcapBlgro-iglA, rLVS ΔcapBlgro-iglB, rLVS ΔcapBlgro-iglC and rLVS ΔcapB/gro-vgrG. IglA, IglB, IglC, and VgrG are major components of the Francisella Type VI Secretion System (T6SS) apparatus that is required by F. tularensis to escape from its phagosome and multiply intracellularly in host cells; the heterodimers of IglA/IglB assemble to form the Francisella T6SS outer sheath (29), which upon contraction, thrusts an inner tube likely comprising IglC through the bacterial wall and into the target phagosomal membrane. We have shown that mice immunized with rLVS ΔcapBlgro-iglA and rLVS ΔcapBlgro-iglC survive longer than sham-immunized mice and mice immunized with the parental rLVS ΔcapB vaccine against lethal aerosol challenge with virulent F. tularensis Schu S4 strain (27). To improve the potency of the rLVS ΔcapB vaccine, we sought to improve the activity of the transcription promoter for antigen expression in the shuttle plasmid and to increase the F. tularensis antigen pool. To improve the transcription promoter activity, we constructed rLVS ΔcapB strains expressing FPI proteins IglA, IglB, IglC or the fusion protein of IglA, IglB, and IglC (IglABC) under the control of the groEL promoter and two additional Francisella promoters, the promoter of the F. tularensis bacterioferritin (bfr, FTL 0617), which is about 10 times more potent than the groEL promoter (30), and the promoter of F. novicida outer membrane protein 26 (omp, FTN_1451) (31). To increase the antigen pool without compromising the stability of the shuttle plasmid, we constructed rLVS ΔcapB expressing the fusion protein of the immunodominant epitopes of IglA (residues 33-132), IglB (residues 446-506) and IglC (residues 29-149), either directly fused in-frame [IglABC(D)] or separated by a flexible linker GGSG (SEQ ID NO: 62) [IglABC(GGSG)] or GGSGGGSG (SEQ ID NO: 63) [IglABC(2GGSG)] downstream of the bfr or omp promoter and the Shine-Dalgarno sequence (FIG. 14A).

The translated amino acid sequences of IglABC(D), IglABC(GGSG), and IglABC(2GGSG) are listed below:

A. IglABC(D)
(SEQ ID NO: 21)
MLVVGDLSKGRSVDAKKEFADREVRRVNNGVDRVLEEMNISFDFEAPNFV

SKDRSNLKVNYRIESVKDFRPDAVAKKVPEIRALLEMKEILASFAKDIEN

NQLPLEMARYPFRNVSIEVETIPGKPGWYSCKINVIPHIQFEGMNITMTI

DIRLEPELFGINNNTGNCRLFIDSLTIAGEKLDKNIVAIDGGEDVIKADS

ATAAASVIRLSITPGSINPTISITLGVLIKSNVRTKIEEKVSSILQASAT

DMKIKLGNSNKKQEYKTDEAWGIMIDLSNLELYPI

B. IglABC(GGSG)
(SEQ ID NO: 22)
MLVVGDLSKGRSVDAKKEFADREVRRVNNGVDRVLEEMNISFDFEAPNFV

SKDRSNLKVNYRIESVKDFRPDAVAKKVPEIRALLEMKEILASFAKDIEN

NQLGGSGPLEMARYPFRNVSIEVETIPGKPGWYSCKINVIPHIQFEGMNI

TMTIDIRLEPELFGINNNGGSGTGNCRLFIDSLTIAGEKDKNIVAIDGGE

DVIKADSATAAASVIRLSITPGSINPTISITLGVLIKSNVRTKIEEKVSS

ILQASATDMKIKLGNSNKKQEYKTDEAWGIMIDLSNLELYPI

C. IglABC(2GGSG)
(SEQ ID NO: 23)
MLVVGDLSKGRSVDAKKEFADREVRRVNNGVDRVLEEMNISFDFEAPNFV

SKDRSNLKVNYRIESVKDFRPDAVAKKVPEIRALLEMKEILASFAKDIEN

NQLGGSGGGSGPLEMARYPFRNVSIEVETIPGKPGWYSCKINVIPHIQFE

GMNITMTIDIRLEPELFGINNNGGSGGGSGTGNCRLFIDSLTIAGEKLDK

NIVAIDGGEDVIKADSATAAASVIRLSITPGSINPTISITLGVLIKSNVR

TKIEEKVSSILQASATDMKIKLGNSNKKQEYKTDEAWGIMIDLSNLELYPI

Demonstration that rLVS ΔcapB Overexpresses IglC and IglIABC in Broth and in Infected Human Macrophage-like THP-1 Cells To examine the protein expression by rLVS ΔcapB, we cultured each vaccine strain in TSBC (Tryptic Soy Broth with 0.1% Cysteine), collected the bacteria, and performed Western blotting. Western blotting analyses using polyclonal antibodies specific to IglA (BEI Resources) or IglC (prepared by our laboratory) or monoclonal antibody to IglB (BEI Resources) showed that IglA, IglB, and IglC expression by rLVS ΔcapB/bfr-iglA, rLVS ΔcapB/bfr-iglB, and rLVS ΔcapB/bfr-iglC was 1.5-1.6-fold higher than that of the parental LVS ΔcapB (FIG. 14B, 14C). IglABC fusion proteins, whether the three protein residues were directly fused or linked by flexible linkers, were expressed by each rLVS ΔcapB/bfr-iglABC and detected by antibody to IglA or IglC; fusion protein expression was higher when the protein residues were linked by flexible linkers than when fused directly, and the IglABC fusion protein with two linkers had a higher expression level than the one with one linker. To examine further the protein expression by rLVS ΔcapB, we infected PMA-differentiated THP-1 cells with rLVS ΔcapB overexpressing IglA, IglB, IglC, or IglABC under the control of the bfr promoter (rLVS ΔcapB/bfr-iglA, rLVS ΔcapB/ bfr-iglB, rLVS ΔcapB/bfr-iglC, and rLVS ΔcapB/bfr-iglABC) for 72 hours, lysed the cells, and analyzed the cell lysates for F. tularensis protein expression by Western blotting using polyclonal antibodies specific to IglA, IglB, or IglC. Our results showed that IglC expression by rLVS ΔcapB/pbfr-iglC was approximately 1.7-fold higher than the parental LVS ΔcapB; IglA and IglB expression by rLVS ΔcapB/pbfr-iglA and rLVS ΔcapB/pbfr-iglB, respectively, were equivalent to LVS ΔcapB; and the IglABC fusion protein, whether the three protein residues were directly fused or linked by flexible linkers, was expressed by rLVS ΔcapB/bfr-iglABC (data not shown) (FIG. 14B). rLVS ΔcapB/bfr-iglABC induced greater IglC- and HI-LVS-specific humoral and cell-mediated immune responses than rLVS ΔcapB expressing IglABC linked directly or by GGSGGGSG (SEQ ID NO: 63) (data not shown). We chose the rLVS ΔcapB/bfr-iglABC for further analysis.

Figure 15:
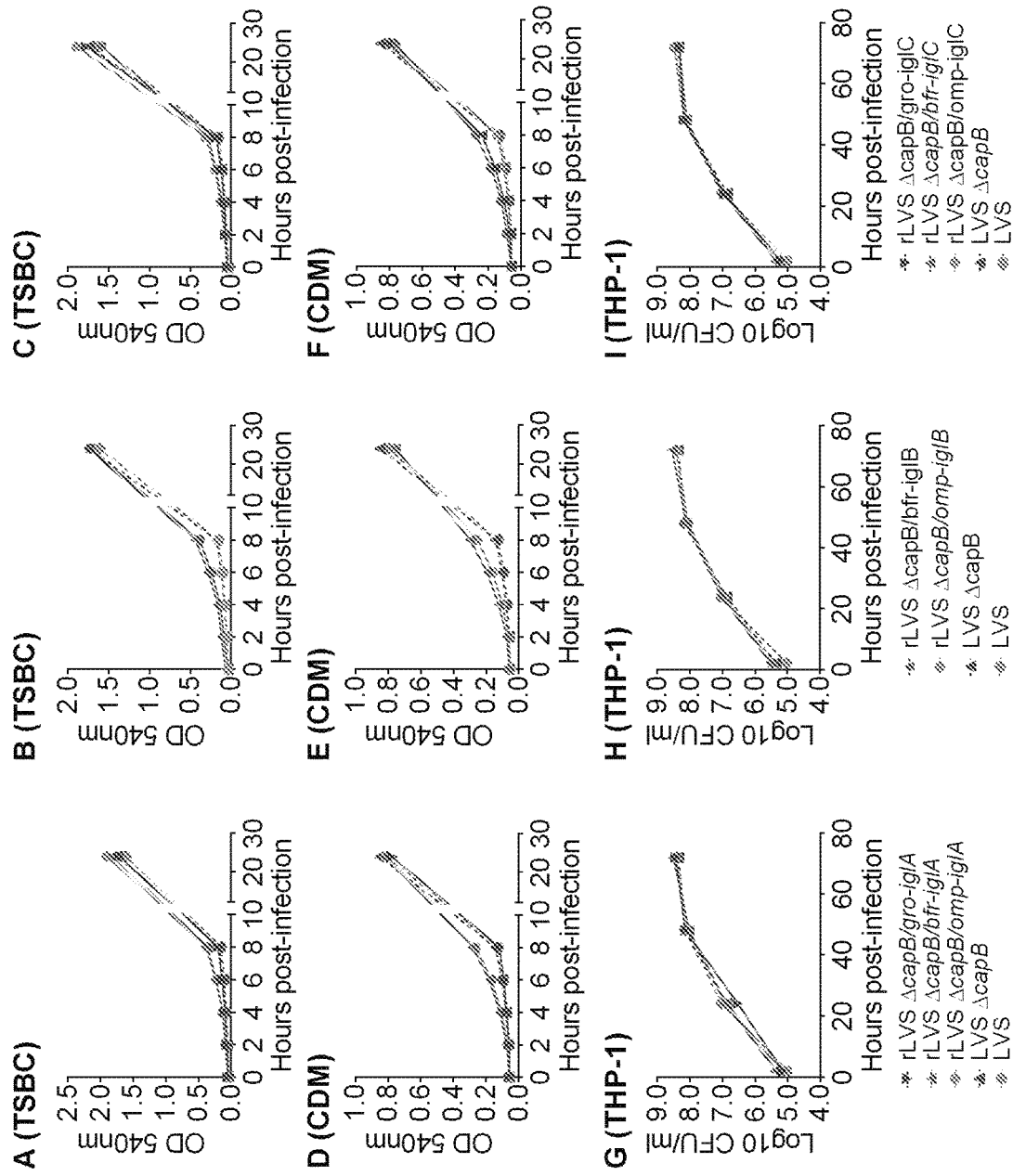
FIG. 15 Growth kinetics of rLVS ΔcapB candidate vaccines in broth and in human macrophage-like THP-1 cells. (A-F) Chocolate agar-grown rLVS ΔcapB vaccines expressing IglA, IglB, or IglC downstream of the groE, bfr, or outer membrane protein (omp) promoter were subcultured in tryptic soy broth-L-cysteine (TSBC, a-c) medium or Chamberlain Defined Medium (CDM, d-f) for up to 24 hours. At the indicated times post-infection, the optical density of each strain (a-f) was measured. (G-I) THP-1 cells were infected with chocolate agar-grown vaccines for 1 h at 37° C., washed, replaced with fresh medium, and cultured for 24, 48 or 72 hours. At the indicated times post infection, cells were harvested, lysed with 0.1% saponin/PBS, serially diluted, plated on Chocolate agar, and incubated for 3 days before CFU were enumerated.
Figure 16:
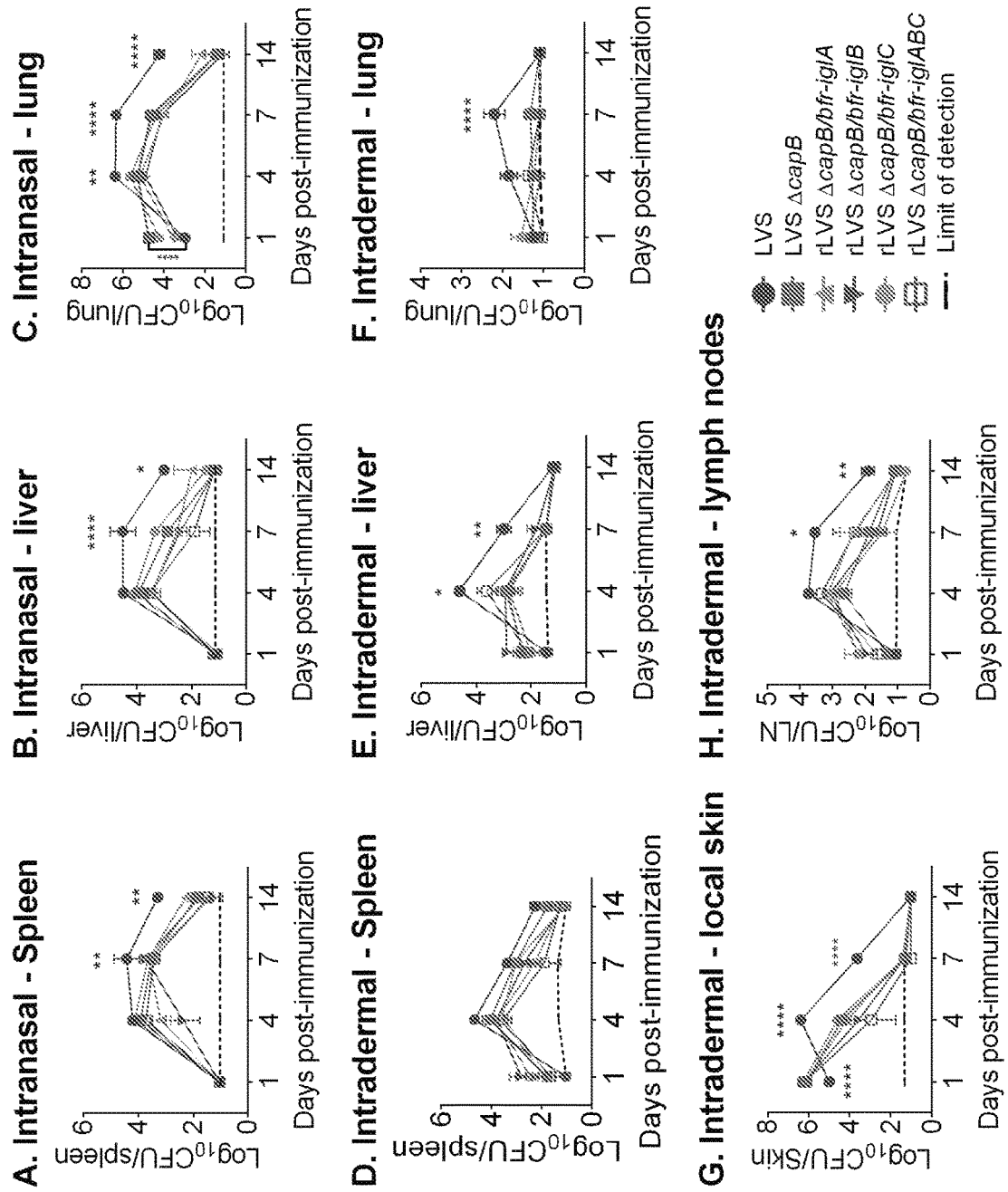
FIG. 16. The rLVS ΔcapB vaccines are disseminated and cleared similarly to the parental strain after i.n. and i.d. vaccination. Mice (4/group) were immunized i.n. (top panels) with $10^2$ CFU of LVS or $10^5$ CFU of LVS ΔcapB or rLVS ΔcapB/bfr-iglA, iglB, iglC or iglABC vaccines, or immunized i.d. (middle and bottom panels) with $10^4$ CFU of LVS or $10^6$ CFU of LVS ΔcapB or rLVS ΔcapB/bfr-iglA, iglB, iglC, or iglABC vaccines; euthanized at various times post-vaccination, as indicated on the X-axis; and their organs removed and assayed for *F. tularensis* bacterial burden. Values are means±SE. Shown are the results combined from 3 independent experiments comprising 4-8 mice per group.

Demonstration that rLVS ΔcapB Overexpressing IglABC (rLVS ΔcapB/bfr-iglABC) Grows Similarly to the Parental LVS ΔcapB in Broth Culture and Intracellularly in Infected Human Macrophage-like THP-1 Cells To examine whether the protein expression cassette driven by the groE, bfr or omp promoter in the shuttle plasmid affects the growth kinetics of rLVS ΔcapB vaccine candidates in broth, we cultured the vaccines on chocolate agar, inoculated them into Chamberlain defined medium (CDM) or 3% Tryptic Soy Broth supplemented with 0.1% L-cysteine (TSBC) medium, and followed their growth kinetics by measuring optical density at 540 nm. As shown in FIG. 15, rLVS ΔcapB strains overexpressing IglA, IglB, or IglC under the control of the groE, bfr or omp promoter grew similarly to LVS and LVS ΔcapB in TSBC (FIG. 15A-C) and CDM (FIG. 15D-F). Moreover, these vaccines grew similarly in PMA-differentiated THP-1 cells (FIG. 15G-I). These results indicate that the shuttle plasmids carried by the rLVS ΔcapB vaccines did not affect their growth kinetics. The shuttle plasmids were stable under non-selective conditions in infected THP-1 cells (FIG. 15). Demonstration that a) rLVS ΔcapB Overexpressing IglA, IglB, IglC are Safe in Mice; b) rLVS ΔcapB Overexpressing IglA, IglB, IglC Disseminate and are Cleared Similarly to the Parental rLVS ΔcapB Strain in Mice; and c) the Shuttle Plasmid for Overexpressing IglA, IglB, or IglC is Stable in Mice To evaluate the safety, dissemination and clearance of rLVS ΔcapB/iglA, iglB, iglC, and iglABC, we infected BALB/c mice i.n. or i.d. with LVS, LVS ΔcapB, or rLVS ΔcapB/bfr-iglA, iglB, iglC, or iglABC and monitored them for signs of illness for 14 days. At 1, 4, 7, and 14 days post-immunization, we assayed the bacterial burden in various organs. As shown in FIG. 16, after i.n. vaccination, rLVS ΔcapB/bfr-iglA, iglB, iglC, and iglABC peaked in the spleen (FIG. 16A), liver (FIG. 16B), and lung (FIG. 16C) at Day 4 post-vaccination and were largely cleared by most mice at day 14 post-vaccination, similar to parental LVS ΔcapB in all three organs. LVS grew to much higher levels (1-2 logs higher) at Day 4 and/or Day 7 and maintained higher levels through Day 14, at which point its level was >1 log higher than the other vaccines in all three organs. After i.d. vaccination (FIG. 16D-H), rLVS ΔcapB/pbfr-iglA, iglB, iglC, and iglABC peaked at Day 4 post-vaccination in the spleen and liver and had minimal growth in the lung, and these vaccines were cleared from spleen, liver, and lung of all mice at Day 14 post-vaccination. In the local skin, the rLVS ΔcapB strains were detected on Day 1 and Day 4 post-vaccination and cleared by all mice at Day 7 post-vaccination. In the inguinal lymph nodes, the rLVS ΔcapB strains were detected at 1, 4, and 7 days post-vaccination and cleared (Limit of Detection) at Day 14 post-vaccination, similarly to the parental LVS ΔcapB. LVS grew to higher levels in all these sites, peaking at Day 4 (spleen, liver, skin, and lymph nodes) or Day 7 (lung) and was not cleared from the spleen and lymph nodes by Day 14. Both i.n. and i.d. vaccination with rLVS ΔcapB strains did not induce any signs of illness, indicating that these vaccines were as safe as the LVS ΔcapB parental strain. In contrast, ~25% of mice immunized i.n. with 200 CFU LVS died and mice immunized i.d. with $10^6$ CFU LVS showed ruffled fur in some of our experiments, evidence of toxicity of LVS by both the i.n. and i.d. route in BALB/c mice.

To examine whether the shuttle plasmid with the bfr promoter is stable in vivo in the absence of antibiotic selection, we harvested animal organs at various days post-vaccination, cultured organ homogenates on chocolate agar in the presence or absence of kanamycin for 3-5 days, and tested the colonies by colony PCR, amplifying the *F. tularensis* antigen expression cassette in the shuttle plasmid. We found that the shuttle plasmids for IglA and IglC were more stable than the one for IglB (Tables 4 & 5). That the expression cassette for the large protein IglB was slightly less stable than the others may indicate that stability depends to some degree on the size of the antigen expression cassette.

Demonstration that Higher Doses of rLVS ΔcapB Overexpressing IglABC are well Tolerated by Mice after Intranasal Vaccination To test the safety of rLVS ΔcapB/bfr-iglABC at relatively high doses, we immunized BALB/c mice intranasally, 4 per group, with six different doses of rLVS ΔcapB/bfr-iglABC, ranging from $1 \times 10^7$ to $4 \times 10^8$ CFU/mouse. Mice immunized with $1$-$2.5 \times 10^7$ CFU of rLVS ΔcapB/bfr-iglABC lost ~6% of their weight at 3-4 days post immunization and showed signs of mild illness (ruffled fur); mice immunized with rLVS ΔcapB/bfr-iglABC $5$-$20 \times 10^7$ CFU lost 6-12% of their weight at 3-4 days post immunization (FIG. 17) and showed signs of moderate illness (ruffled fur and inactive). However, all the mice immunized with rLVS ΔcapB/bfr-iglABC recovered by 7 days post immunization and none of them died. These results suggest that intranasal immunization with as many as $4 \times 10^8$ CFU rLVS ΔcapB/bfr-iglABC is reasonably safe.

Figure 18:
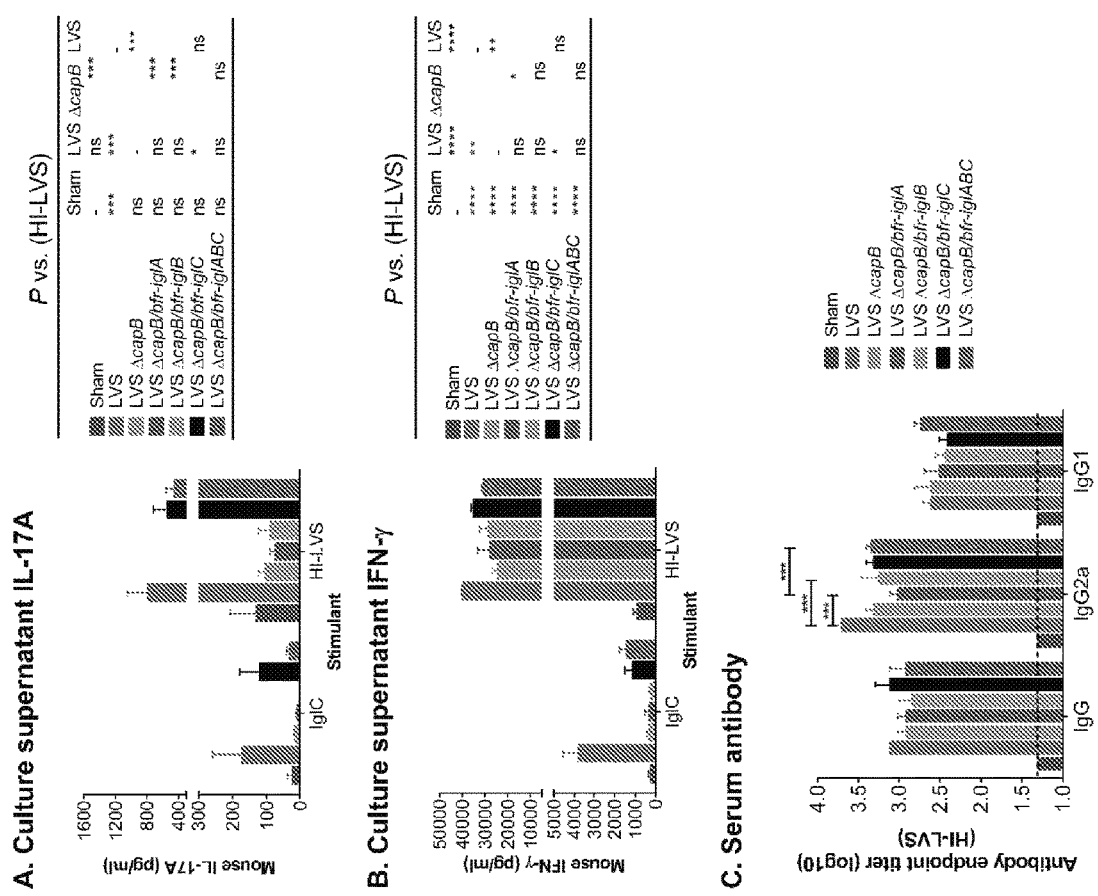
FIG. 18. Immunization with rLVS ΔcapB overexpressing FPI T6SS proteins induces greater antigen-specific cytokine production and a Th1-type antibody response. Mice (3/group) were immunized i.d. with various vaccines; euthanized 4 weeks later; their splenocytes isolated and stimulated with IglC or HI-LVS for 3 days; and the culture supernatant assayed for IL-17A (A) or IFN-γ (B). Their sera were isolated and assayed for antibodies specific to HI-LVS (C). Values are means±SE. *, $P<0.05$; , $P<0.01$; *, $P<0.001$; ****, $P<0.0001$ by ANOVA (Prism 6.04).
Figure 19:
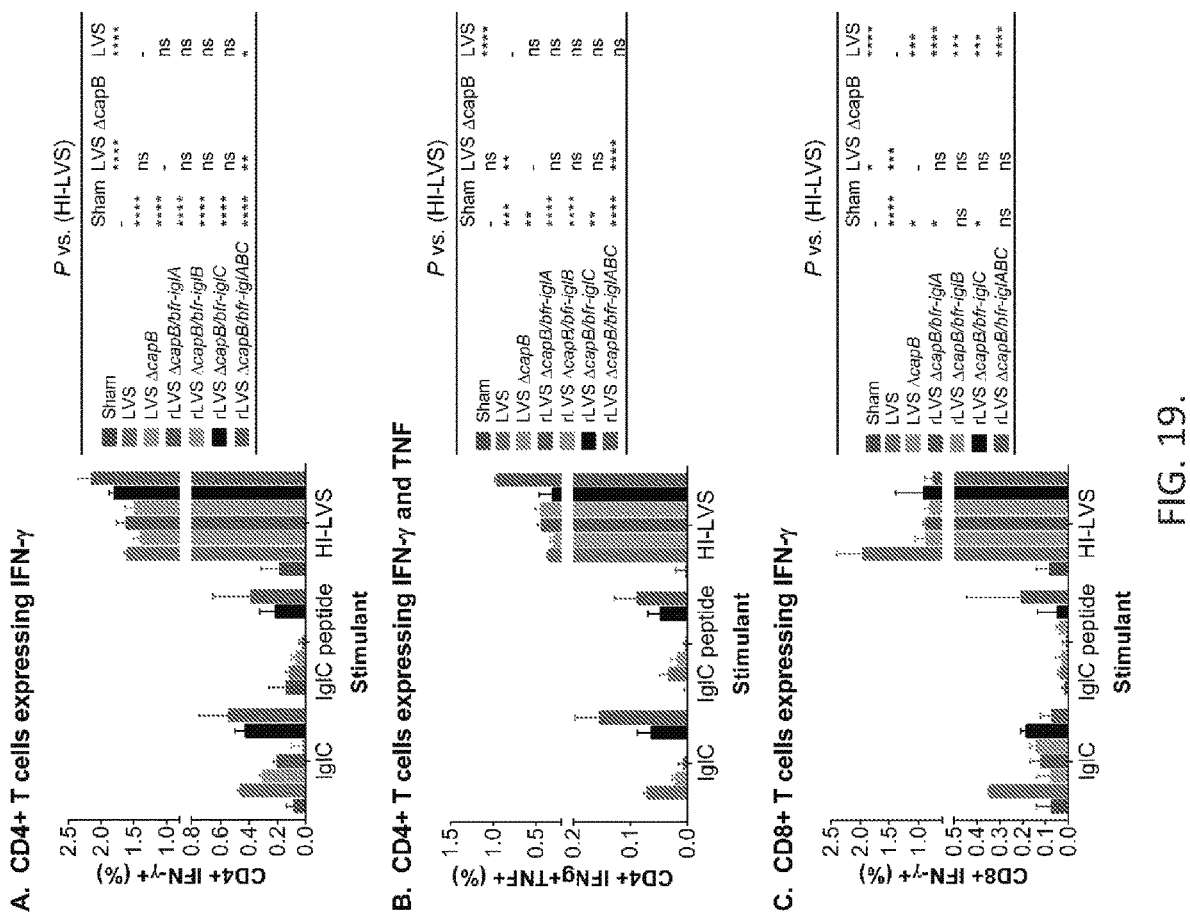
FIG. 19. Immunization with rLVS ΔcapB vaccines induces elevated frequencies of CD4+ and CD8+ T cells producing IFN-γ or IFN-γ+ TNF. Mice (3/group) were immunized i.d. once with various vaccines; euthanized 4 weeks later; and their splenocytes isolated, stimulated with IglC or HI-LVS, and assayed for CD4+ (A) or CD8+ (B) T cells expressing IFN-γ or IFN-γ+ TNF as indicated. Values are means±SE. *, $P<0.05$; , $P<0.01$; *, $P<0.001$; ****, $P<0.0001$ by ANOVA (Prism 6.04).

Demonstration that Immunization with rLVS ΔcapB Overexpressing FPI T6SS Proteins Induces Antigen-Specific Cytokine Production and Th1-Type Antibody Responses To examine T cell immune responses generated by the rLVS ΔcapB vaccines, we immunized BALB/c mice i.d. with various vaccines at Week 0, sacrificed them at Week 4, and assayed T-cell mediated immune responses and serum antibody. In response to in vitro stimulation with IglC protein, splenocytes from mice immunized with rLVS ΔcapB/iglC or iglABC secreted greater amounts of IL-17A (FIG. 18A) and IFN-γ (FIG. 18B) into the culture supernatant than sham- or LVS ΔcapB-immunized mice, although the differences did not reach statistical significance. In response to in vitro stimulation with HI-LVS, splenocytes from mice immunized with rLVS ΔcapB/iglC or iglABC also secreted greater amounts of IL-17A into the culture supernatant than sham- or LVS ΔcapB-immunized mice, comparable to splenocytes from LVS-immunized mice. Consistently, splenocytes from these mice generated significantly greater frequencies of Th1-type CD4+ T cells expressing IFN-γ (FIG. 19A), or IFN-γ+TNF (FIG. 19B), TNF+IL-2, or IFN-γ+TNF+IL-2 in response to in vitro stimulation with IglC, IglC peptide or HI-LVS than splenocytes from LVS ΔcapB-immunized mice (data not shown). Splenocytes from mice immunized with rLVS ΔcapB/bfr-iglABC showed the highest frequencies of Th1-type CD4+ T cells expressing IFN-γ (FIG. 19A) or IFN-γ+TNF (FIG. 19B) in response to in vitro stimulation with IglC and HI-LVS. However, splenocytes from LVS ΔcapB- and rLVS ΔcapB-immunized mice had lower frequencies of CD8+ IFN-γ+ T cells in response to HI-LVS (FIG. 19C) than splenocytes from LVS-immunized mice. With respect to humoral immune responses, all vaccine candidates induced HI-LVS-specific IgG2a and IgG1 antibodies (differences not statistically significant) (FIG. 18C). Thus, overall, the rLVS ΔcapB vaccines overexpressing IglC or the fusion protein of IglABC had enhanced T-cell mediated immune responses.

Demonstration that Immunization with rLVS ΔcapB/bfr-iglABC Induces Improved Protective Immunity Against Respiratory Challenge with *F. tularensis* Schu S4

To evaluate rLVS ΔcapB/bfr-iglA, iglB, iglC, or iglABC for efficacy in mice against respiratory challenge with virulent *F. tularensis* Schu S4, we immunized mice i.d. with PBS (Sham), LVS, LVS ΔcapB, or rLVS ΔcapB, challenged them 7 weeks later i.n. with a high lethal dose of *F. tularensis* Schu S4 (16 CFU, equivalent to $5 \times LD_{50}$), and observed the mice closely for signs of illness and death. Mice immunized with rLVS ΔcapB/bfr-iglABC survived longer (mean survival time 9.1 days) than sham-immunized mice (mean survival time 4.5 days) (p<0.0001) and mice immunized with the parental LVS ΔcapB or rLVS ΔcapB/bfr-iglA, iglB, or iglC; (mean survival time 6.6-8.0 days; difference not statistically significant (FIG. 20A).

To verify further the efficacy of rLVS ΔcapB vaccines against challenge with *F. tularensis* Schu S4, we repeated the above experiment and challenged mice i.n. 6 weeks later with two higher lethal doses (31 and 310 CFU) of *F. tularensis* Schu S4, equivalent to approximately 10 and 100 $LD_{50}$, respectively. Consistently, after i.n. challenge with 31 CFU of Schu S4, mice immunized with rLVS ΔcapB/bfr-iglA, iglB, iglC, or iglABC survived longer than sham-immunized mice (P<0.0001) and generally longer than LVS ΔcapB-immunized mice (differences not significant). In this experiment, mice immunized with rLVS ΔcapB/bfr-iglA were especially well protected—mean survival time 11.6 days vs. 4 days for sham-immunized mice and 7.1 days for LVS ΔcapB-immunized mice—but not as well protected as LVS-immunized mice (mean survival time 15.8 days), but this difference was not statistically significant (FIG. 20B, upper section). After i.n. challenge with 310 CFU of Schu S4, although all mice died by day 6 post-challenge, mice immunized with rLVS ΔcapB/bfr-iglABC survived significantly longer than all other mice including LVS-immunized mice (FIG. 20B, lower section). Mice immunized with rLVS ΔcapB/bfr-iglA or iglB survived significantly longer than sham- and LVS ΔcapB-immunized mice, comparable to LVS-immunized mice.

Figure 21:
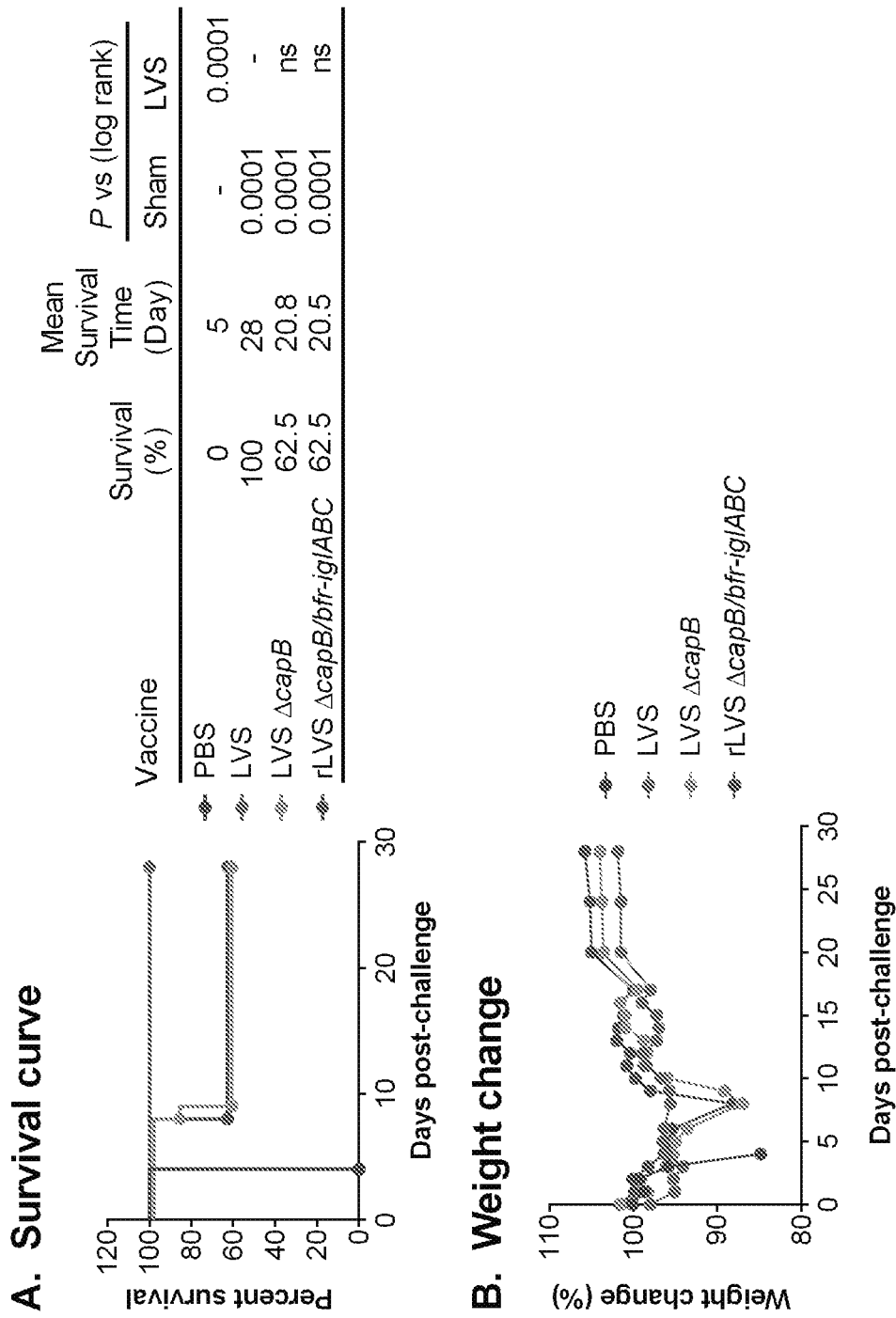
FIG. 21. Mice immunized with attenuated rLVS ΔcapB over-expressing fusion protein IglABC, comprising immunodominant epitopes of IglA, IglB, and IglC, survive longer than sham-immunized mice and comparable to mice immunized with LVS and the parental LVS ΔcapB. BALB/c mice, 8/group, were immunized i.n. once with PBS (Sham), 100 CFU LVS, $1\times10^6$ CFU LVS ΔcapB, or $1\times10^6$ rLVS ΔcapB/bfr-iglABC, challenged i.n. with 26 CFU *F. tularensis* Schu S4 at week 6 post immunization, and monitored for signs of illness, weight change and death for up to 28 days post challenge. The survival curves were compared by the log-rank test (Prism 6.04).
Figure 23:
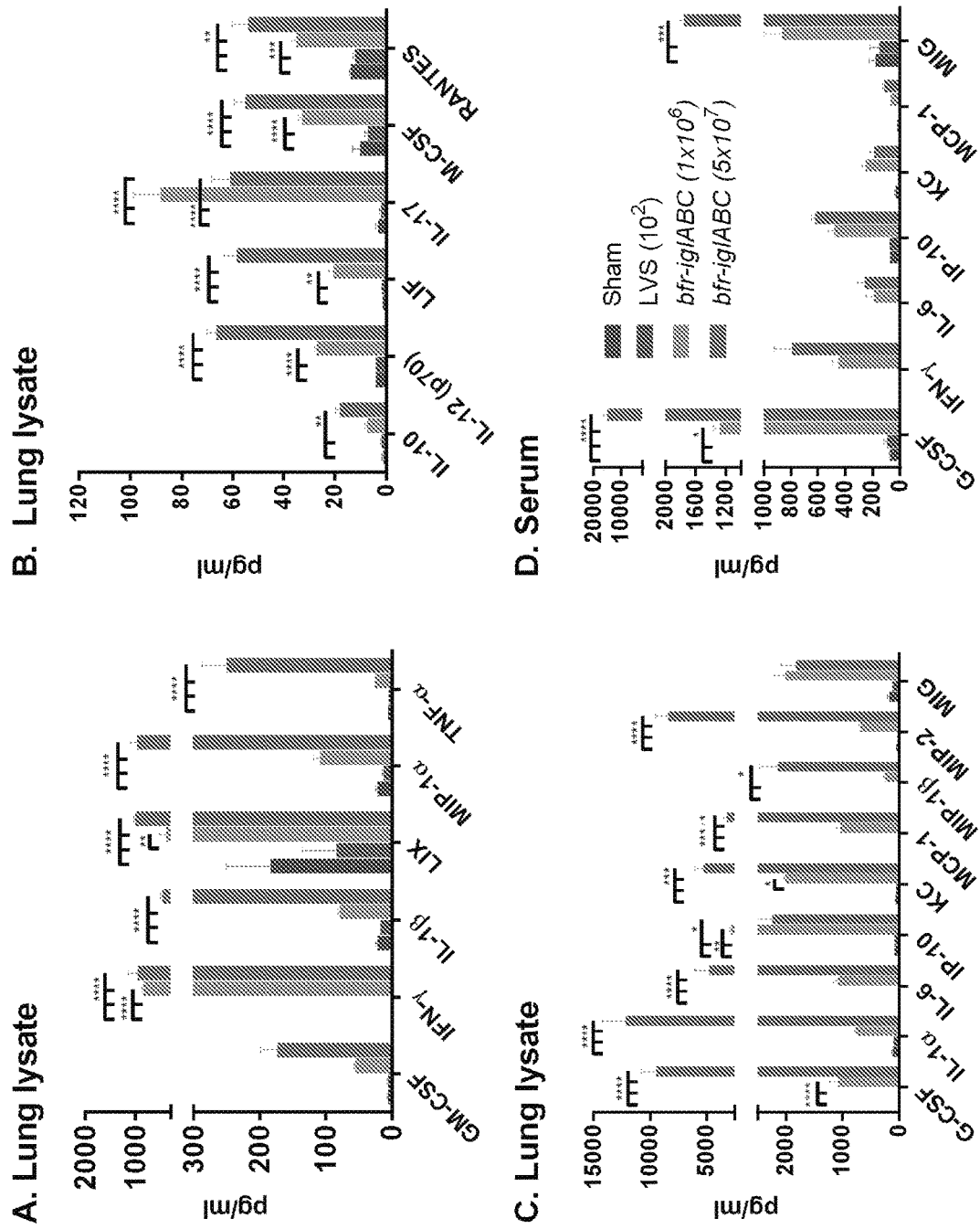
FIG. 23. Immediate pre-exposure prophylaxis with rLVS ΔcapB/bfr-iglABC but not LVS induces strong innate immunity. Mice were immunized with PBS (Sham), 10$^2$ of LVS, or 1×10$^6$ or 5×10$^7$ of rLVS ΔcapB/bfr-iglABC (bfr-iglABC) as indicated and euthanized at day 2 post immunization. Their lung lysates (A-C) and sera (D) were assayed for cytokine/chemokine production by a mouse 32-Plex kit. Shown are means±SE (n=3 mice) for each cytokine/chemokine. *, P<0.05; , P<0.01; *, P<0.001; ****, P<0.0001 by Two-Way ANOVA with multiple comparisons (Prism 6.04).

To explore further the efficacy of rLVS ΔcapB/bfr-iglABC by the i.n. route, we immunized mice i.n. and challenged them 6 weeks later with 26 CFU of *F. tularensis* SchuS4. As shown in FIG. 21, mice immunized with rLVS ΔcapB/bfr-iglABC survived significantly longer than sham-immunized mice, comparable to LVS-immunized mice (FIG. 21A). Mice immunized with rLVS ΔcapB/bfr-iglABC that survived challenge recovered from temporary weight loss such that their weights were similar to mice immunized with LVS by 2 weeks post-challenge (FIG. 21B).

Demonstration that Immediate Pre- or Post-Exposure Prophylaxis with rLVS ΔcapB/bfr-iglABC but not LVS Induces Partial Protective Immunity Against Respiratory Challenge with F. tularensis Schu S4 Strain and Protection is Correlated with the Induction of a Strong Innate Immune Response To evaluate the efficacy of rLVS ΔcapB/bfr-iglABC as a pre- or post-exposure vaccine, we immunized mice with PBS (Sham), 100 CFU LVS, or $1\times10^6$ or $5\times10^6$ CFU rLVS ΔcapB/bfr-iglABC two days before (−2 days), the same day as (0 day), or one day (1 day) or two days (2 days) after Schu S4 challenge and monitored mice closely for signs of illness and weight change. We evaluated mice for illness using a Clinical Score (CS) of 0-4 as follows: 0, normal; 1, questionable illness; 2, mild but definitive illness; 3, moderate to severe illness (euthanized if poorly responsive); 4, severe illness, moribund and euthanized. All sham- and LVS-immunized mice became ill by 3 or 4 days post-challenge and became moribund and were euthanized at day 5 post-challenge (FIG. 22A, upper section). In contrast, mice immunized with $1\times10^6$ CFU of rLVS ΔcapB/bfr-iglABC at −2 days were not sick until day 6 post-challenge and survived significantly longer (mean survival time 10.5 days) than both sham- and LVS-immunized mice (mean survival time 5 days). Mice immunized with $1\times10^6$ CFU or $5\times10^6$ CFU (FIG. 22A, lower section) of rLVS ΔcapB/bfr-iglABC on the day of challenge (Day 0) also survived significantly longer (mean survival times 5.8 and 6.4 days, respectively) than both sham-immunized mice and mice immunized with LVS at Day 0. When immunized at 1 or 2 days post-challenge, mice immunized with rLVS ΔcapB/bfr-iglABC had mean survival times comparable to sham- and LVS-immunized mice (FIG. 22A, lower section).

Figure 17:
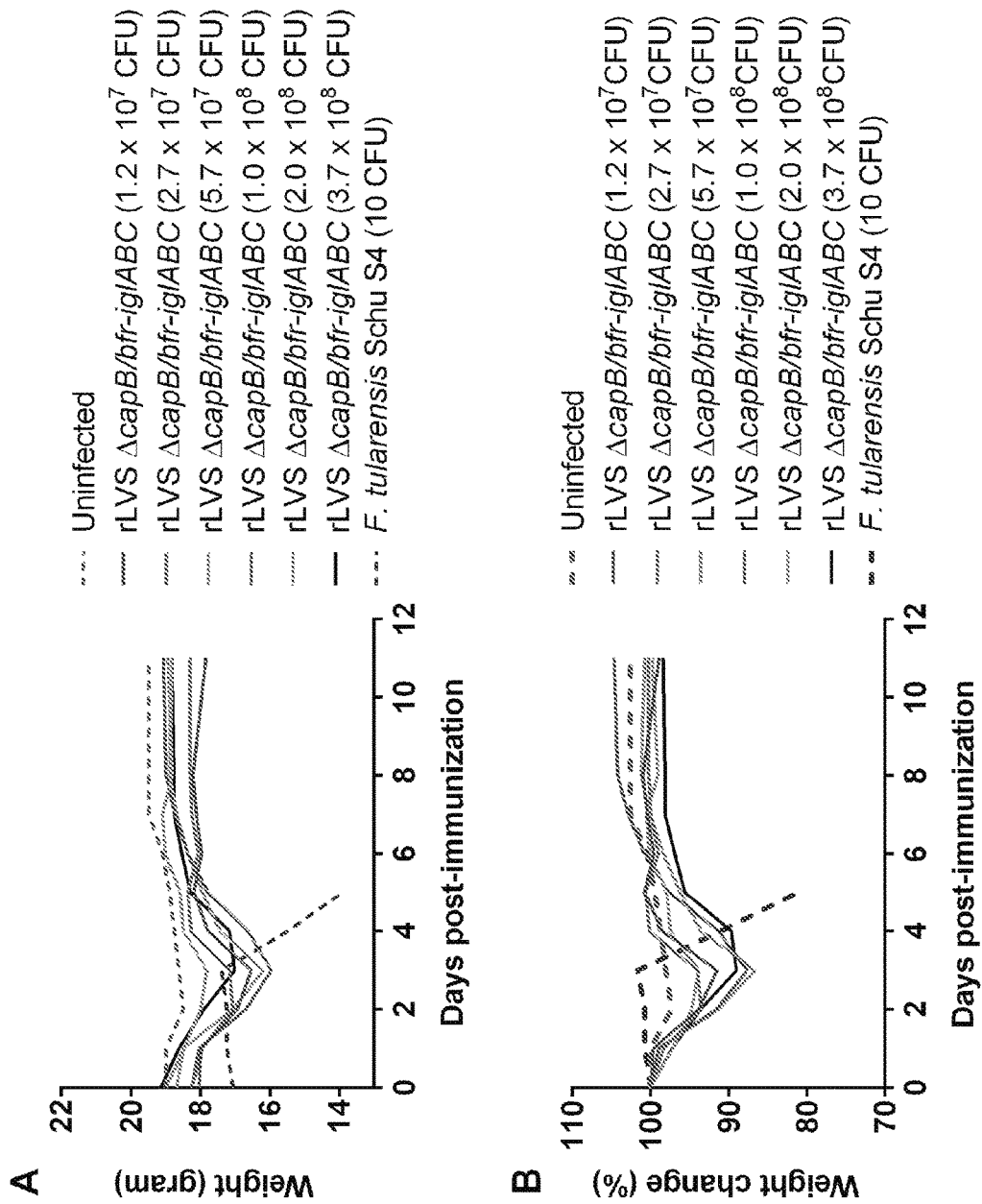
FIG. 17. Higher doses of rLVS ΔcapB/bfr-iglABC were well tolerated by BALB/c mice after intranasal vaccination. BALB/mice, 4 per group, were immunized intranasally with rLVS ΔcapB/bfr-iglABC at 6 different doses as shown in the Figure legend and monitored for signs of illness and weight change. Mice infected with virulent *F. tularensis* Schu S4 in a separate experiment were included as a control. Shown are mean of weight (top) or change of weight compared with the day of immunization (bottom).

To explore the efficacy of a higher dose of rLVS ΔcapB/bfr-iglABC as immediate pre- and post-exposure prophylaxis against Schu S4 challenge, we repeated the experiment described above with an immunizing dose of $5\times10^7$ CFU (tested as safe, FIG. 17). The extent of protection was directly dependent upon the time relative to challenge, with mice immunized sooner surviving longer. Mice immunized with $5\times10^7$ CFU rLVS ΔcapB/bfr-iglABC at −2, −1, or even 1 day post-challenge with Schu S4 survived significantly longer than sham-immunized mice (FIG. 22B, middle and right panel).

To explore the mechanism of protection provided by immediate pre-exposure prophylaxis with rLVS ΔcapB/bfr-iglABC, we immunized mice in groups of 3 i.n. with PBS (Sham), $10^2$ CFU LVS, or $1\times10^6$ or $5\times10^7$ CFU rLVS ΔcapB/bfr-iglABC; euthanized them 2 days later; and assayed lung lysates and sera for cytokine/chemokine production using a mouse 32-Plex cytokine/chemokine kit. We found that mice immunized with $1\times10^6$ or $5\times10^7$ rLVS ΔcapB/bfr-iglABC had significantly higher levels of pro-inflammatory cytokines/chemokines in their lungs (21 out of 32 cytokines/chemokines assayed) and sera (7 out of the 32) than sham-immunized mice and mice immunized with LVS (FIG. 23A-23D); many of the cytokines in rLVS ΔcapB/bfr-iglABC-immunized mice were orders of magnitude higher than in sham- and LVS-immunized mice. In most but not all cases, mice immunized with the higher dose of rLVS ΔcapB/bfr-iglABC had higher cytokine/chemokine levels than mice immunized with the lower dose of this vaccine. In contrast, there were no significant differences in cytokine/chemokine levels between LVS- and sham-immunized mice in the lungs or sera (FIG. 23A-23D). These results show that mice immunized with rLVS ΔcapB/bfr-iglABC, which could be administered safely at very high doses, rapidly develop a strong innate immune response in the lung and blood, whereas mice immunized with LVS, which could be administered safely at only very low doses, do not. Taken together with the above results on the efficacy of immediate pre-exposure prophylaxis, where rLVS ΔcapB/bfr-iglABC but not LVS provided near-term protection, these data show that the level of near-term protection correlates with the level of the innate immune response.

B. Recombinant *Listeria monocytogenes* Expressing the Fusion Protein of IglA, IglB, and IglC; Heterologous Prime-Boost Vaccination Construction of Attenuated Recombinant *Listeria monocytogenes* Vaccine Candidates Expressing Immunodominant Epitopes of F. tularensis IglA, IglB, and IglC Antigens Previously, we constructed attenuated recombinant *Listeria monocytogenes* stably expressing each of the seven F. tularensis proteins, including IglC (32). We showed that mice immunized intradermally with rLm/iglC develop cellular immune responses to F. tularensis IglC as evidenced by lymphocyte proliferation and CD4+ and CD8+ T-cell intracellular expression of interferon-gamma. Moreover, mice immunized with rLm/iglC are protected against lethal challenge with F. tularensis LVS administered by the intranasal route, a route chosen to mimic airborne infection, and, most importantly, against aerosol challenge with the highly virulent Type A F. tularensis SchuS4 strain. To develop a more potent vaccine without sacrificing safety, we utilized a heterologous prime-boost vaccination strategy with LVS ΔcapB or LVS ΔcapB overexpressing F. tularensis IglA or IglC as the prime vaccine and rLm/iglC as the booster vaccine. We show that the LVS ΔcapB-rLm/iglC prime-boost vaccine induces strong cellular immune responses and confers protective immunity against F. tularensis Schu S4 aerosol challenge that is comparable to or greater than that conferred by LVS (27).

Figure 24:
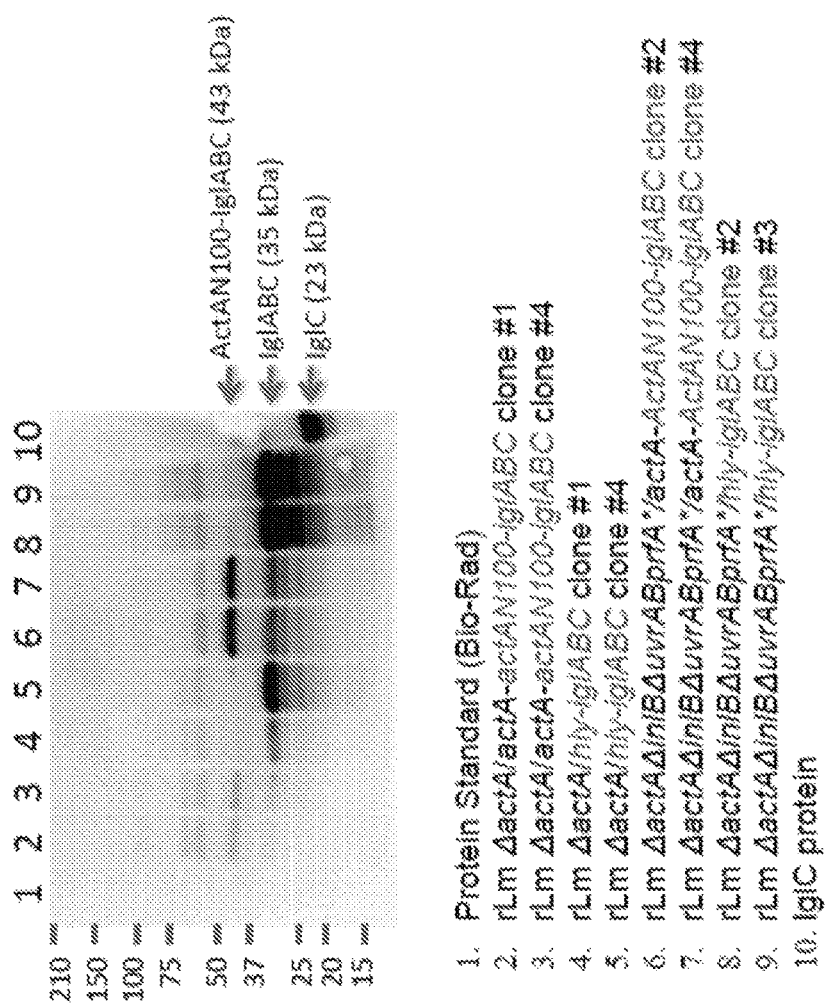
FIG. 24. Expression of *F. tularensis* IglABC by rLm vector in culture supernatant of recombinant *L. monocytogenes*. Broth culture filtrates of each recombinant rLm strain (two clones per strain) were concentrated and a volume of filtrate equivalent to 1ml of the bacterial culture was analyzed by Western blotting using rabbit polyclonal antibody to IglC. On the right border of the blot are listed the proteins of interest and their predicted mass. On the left border are listed the sizes of the molecular mass standards. Note that proteins expressed by the Lm ΔactA ΔinlB prfA* vector (lanes 6-9) were generally more abundant than those expressed by the Lm ΔactA vector (lanes 2-5) and that proteins expressed downstream of the hly promoter (lanes 4, 5, 8, 9) were generally more abundant than those expressed downstream of the actA promoter (lanes 2, 3, 6, 7) in the broth culture supernatant.

To expand the F. tularensis immunogenic antigen pool in the *Listeria monocytogenes* booster vaccines, we now have constructed 4 different versions of attenuated rLm expressing the immunodominant epitopes of F. tularensis IglA, IglB, and IglC antigens, IglABC, by using Lm ΔactA or Lm ΔactA ΔinlB prfA* as a vector to express F. tularensis IglABC fused with the Lm LLO signal sequence and downstream of the hly promotor or fused with the amino-terminal 100 amino acids including the signal sequence of Lm ActA (ActAN100) downstream of the actA promoter, resulting in four vaccine candidates: rLm ΔactA/hly-iglABC, rLm ΔactA/actA-iglABC, rLm ΔactA ΔinlB prfA*/hly-iglABC, and rLm ΔactA ΔinlB prfA*/actA-iglABC. We have shown that all four rLm vaccine candidates express the F. tularensis IglABC (FIG. 24).

Figure 25:
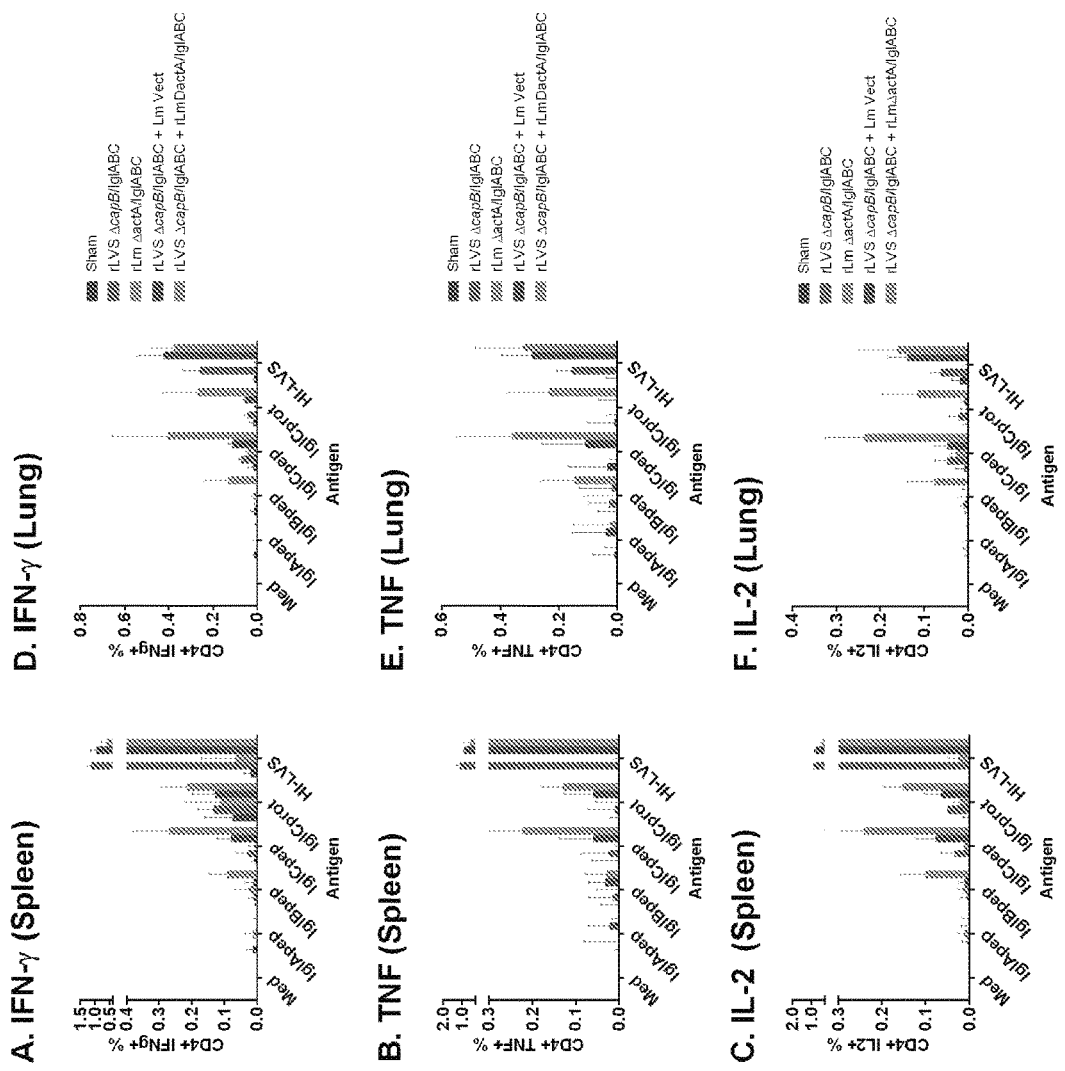
FIG. 25. Priming with rLVS ΔcapB/bfr-iglABC and boosting with rLm/hly-iglABC induces antigen specific CD4+ T cells expressing Th1 type cytokines. Mice (n=4/group) were vaccinated, bled, euthanized, their spleen and lung cells stimulated with medium alone or with a IglC peptide (IglCpep, TDEAWGIMIDLSNLE (SEQ ID NO: 64)), peptide pools of IglA (IglApep) or IglB (IglBpep), IglC protein (IglCprot), or heat-inactivated LVS (HI-LVS), and assayed for intracellular cytokine staining. Values=mean±SD.

Demonstration that Priming with rLVS ΔcapB/bfr-iglABC and Boosting with rLmprfA*/hly-iglABC Induces Antigen Specific T Cell-Mediated and Humoral Immune Responses To examine the immune responses induced by priming with rLVS ΔcapB/bfr-iglABC and boosting with rLmprfA*/hly-iglABC (rLm ΔactA ΔinlB prfA*/hly-iglABC), we immunized mice i.d. at week 0 with rLVS ΔcapB/bfr-iglABC and boosted them at week 4 with rLm/hly-iglABC. Sham-immunized mice and mice immunized i.d. once at week 0 with rLVS ΔcapB/bfr-iglC and mice immunized i.d. once at week 4 with rLm/hly-iglABC served as controls. At week 5, we anesthetized the mice, bled and euthanized them, isolated their splenocytes and lung cells, stimulated the cells with IglC peptide (TDEAWGIMIDLSNLE (SEQ ID NO: 64)), peptide pools of IglA or IglB, IglC protein, or heat-inactivated LVS and assayed antigen-specific T-cell immune response by intracellular cytokine staining. In response to stimulation with IglB peptides, IglC peptides, or IglC protein, mice primed with rLVS ΔcapB/bfr-iglABC and boosted with rLmprfA*/hly-iglABC produced significantly greater frequencies of CD4+ T cells expressing IFN-γ, TNF, or IL-2 in their spleens (FIG. 25A, 25B, 25C) and lungs (FIG. 25D, 25E, 25F) than sham-immunized mice, mice immunized with only rLVS ΔcapB/bfr-iglABC, or mice immunized with only rLm/hly-iglABC. In response to stimulation with HI-LVS, mice primed with rLVS ΔcapB/bfr-iglABC and boosted with rLmprfA*/hly-iglABC produced significantly greater frequencies of CD4+ T cells expressing IFN-γ, TNF, or IL-2 in their spleens and lungs than sham-immunized mice and mice immunized with only the booster vaccine, rLm/hly-iglABC, and comparable to that produced by mice immunized with only the prime vaccine, rLVS ΔcapB/bfr-iglABC (FIG. 25).

Figure 26:
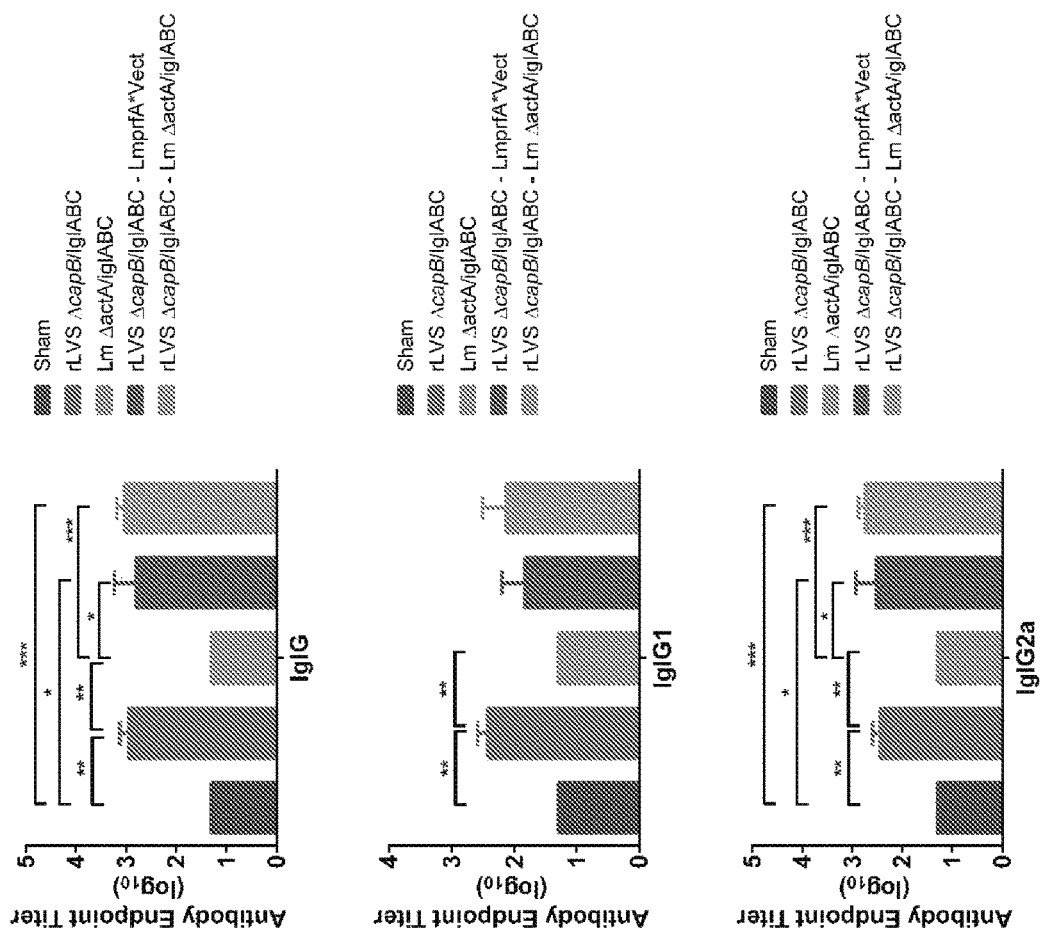
FIG. 26. Priming with rLVS ΔcapB/bfr-iglABC and boosting with rLm/hly-iglABC induces antigen (HI-LVS)-specific Th1/Th2-type antibody. Mice (n=4/group) were vaccinated, bled, euthanized and tested for serum antibody as described in the text. Values=mean±SD.

After analysis of the 7 possible combinations of CD4+ T cells producing one or more cytokines among IFN-γ, IL-2 and TNF, we found that in response to stimulation with IglB peptide, IglC peptide, IglC protein, or HI-LVS, the largest subsets of T cells were CD4+ T cells producing only IFN-γ, TNF, and IL-2 or multi-functional CD4+ T cells producing both IFN-y and TNF (data not shown). These results show that priming with rLVS ΔcapB/bfr-iglABC and boosting with rLmprfA*/hly-iglABC produced T-cell-mediated immune responses. We assayed humoral immune response on the sera collected from the immunized mice. Mice prime-boosted with rLVS ΔcapB/bfr-iglC—rLm/hly-iglABC produced HI-LVS specific Ig1G antibody at a significantly higher level than sham-immunized mice and mice immunized with the only the booster vaccine, comparable to mice immunized with the prime vaccine only or mice prime-boosted with rLVS ΔcapB/bfr-iglC—rLm vector (FIG. 26A). The IgG antibody is balanced between IgG1 and IgG2a (FIG. 26B and 26C).

Demonstration that Priming with rLVS ΔcapB/bfr-iglABC and Boosting with rLmprfA*/hly-iglABC Induces Strong Protective Immunity to Respiratory Challenge with F. tularensis SchuS4. To explore the capacity of a heterologous prime boost vaccine comprising a rLVS ΔcapB/bfr-iglABC prime and rLmprfA*/hly-iglABC boost to induce protective immunity to F. tularensis Schu S4 challenge, we immunized mice intradermally once with rLVS ΔcapB/bfr-iglABC (1×10⁶ CFU) at Week 0 and boosted them once at Week 4 or twice at Week 4 and 6 with rLm vaccines (1×10⁶ CFU) expressing IglABC where the genes encoding IglABC are expressed by the LmprfA* vector (Lm ΔactA ΔinlB prfAG155S) and downstream of hemolysin promoter (hly) fused with the LLO (listeriolysin O, encoded by hly) signal peptide (hly-iglABC) or downstream of the actA promoter fused with the N-terminal 100 amino acids of ActA (including the signal peptide) (actA-iglABC) as indicated in Table 6. Control mice were sham-immunized, not boosted, or boosted with the LmprfA* vector (1×10⁶ CFU). The mice were challenged intranasally with 29 CFU of F. tularensis Schu S4 (equivalent to 10×LD$_{50}$) and monitored for survival for 21 days. Sham-immunized mice had a mean survival time (MST) of 4 days. Whereas mice not boosted had a MST of 7.9 days, mice boosted with the vector alone had a MST of 6.4 days, and mice boosted once with rLmprfA* vaccine expressing IglABC from hly-iglABC or actA-iglABC had a MST of 7.6 and 7.1 days, respectively, the mice prime-boosted twice with rLmprfA* expressing IglABC from hly-iglABC or actA-iglABC had the longest survival times—both with MST of 9.4 days.

C. Homologous Prime-Boosting with rLVS ΔcapB/bfr-iglABC and Heterologous Prime-Boosting with rLVS ΔcapB/bfr-iglABC as the Prime Vaccine and rLm/iglABC as the Booster Vaccine Demonstration that Homologous Prime-Boosting with rLVS ΔcapB/bfr-iglABC or Heterologous Prime-Boosting with rLVS ΔcapB/bfr-iglABC as the Prime Vaccine and rLmprfA*/hly-iglABC as the Booster Vaccine Induces Strong Protective Imunity to Respiratory Challenge with F. tularensis SchuS4.

To further evaluate homologous prime-boosting with rLVS ΔcapB/hfr-iglABC or heterologous prime-boosting with rLVS ΔcapB/bfr-iglABC as the prime vaccine and rLmprfA*/hly-iglABC as the booster vaccine for efficacy in mice against respiratory challenge with virulent F. tularensis Schu S4, we immunized BALB/c mice, 8/group, i.d. once at week 0 with PBS (Sham, group A), 10⁴ CFU LVS (Group B), 10⁶ CFU LVS ΔcapB vector (Group H), or 10⁶ rLVS ΔcapB/bfr-iglABC (Group C); immunized them i.d. or i.n. twice at weeks 0 and 4 with 10⁶ rLVS ΔcapB/bfr-iglABC (Groups D & E, resp.); primed them i.d. once at week 0 with rLVS ΔcapB/bfr-iglABC (Groups F & G) or LVS ΔcapB (Groups I & J) and boosted them intramuscularly (i.m.) twice at weeks 4 and 6 with rLmprfA* Vector (Lm ΔactA ΔinlB prfA*) (Groups F & I) or rLmprfA*/hly-iglABC (Groups G & J); or immunized them simultaneously i.d. with rLVS ΔcapB/bfr-iglABC and i.m. with rLmprfA*/hly-iglABC once at week 6 (Group K). We challenged the mice with 10 CFU F. tularensis Schu S4 at week 10 and monitored them for signs of illness and survival for 3 weeks. As shown in FIG. 27, mice immunized i.d. once or twice with rLVS ΔcapB/bfr-iglABC and mice immunized i.n. twice with rLVS ΔcapB/bfr-iglABC (Groups C, D, and E, respectively) survived significantly longer than sham-immunized mice (P=0.03, P=0.0001, and P=0.0003, respectively) and survived significantly longer than mice immunized once with the LVS ΔcapB vector (P=0.006, P=0.0001, and P=0.0005, respectively); the survival of mice immunized i.d. or i.n. twice with rLVS ΔcapB/bfr-iglABC (Groups D and E) was equivalent to mice immunized with LVS (Group B) (Panel a). Mice primed with rLVS ΔcapB/bfr-iglABC or LVS ΔcapB vector and boosted with LmprfA* vector or rLmprfA*/hly-iglABC (Groups F, G, I and J) survived significantly longer than sham-immunized mice (P=0.0001, P=0.0001, P=0.0001, and P=0.0001, respectively); the survival of mice primed once with rLVS ΔcapB/bfr-iglABC and boosted twice with rLmprfA*/hly-iglABC (Groups G) was not statistically different from LVS-immunized mice. Mice immunized simultaneously with rLVS ΔcapB/bfr-iglABC and rLmprfA*/hly-iglABC (Groups K) survived longer than sham-immunized mice and their survival was not statistically different from LVS-immunized mice (Panel b).

Aspects of Working Embodiments with Antigenic Polypeptide Epitopes Present in a Francisella tularensis IglA, IglB, and IglC Epitopoes We hypothesized that proteins abundantly secreted by Ft or upregulated by Ft inside mononuclear phagocytes may be immunogenic antigens. Starting with 7 proteins, we found that Ft IglC (intracellular growth factor subunit C, FTT1712/1357) is a potent immunoprotective antigen, consistent with other studies showing that IglC is one of the most prominent Ft immunogenic antigens in murine tularemia models and in human immune sera. IglC is a 23-kDa protein encoded by the iglABCD operon in the Francisella Pathogenicity Island (FPI). It has no homology to other proteins, which is important because vaccines targeting IglC are less likely to cause a non-specific immune response to host proteins. IglC is one of the most upregulated Ft proteins during macrophage intracellular infection, required for intracellular survival, growth, and phagosome escape, and based on studies of iglC mutants in Ft subsp. *novicida, holarctica*, and *tularensis*, essential for virulence (6).

Other proteins upregulated by Ft in macrophages and therefore of interest to us as immunogens are IglA (FTT1714/1359), IglB (FTT1713/1358), and VgrG (valine glycine repeat protein G, FTT1702/1347) encoded by genes located within the FPI. Similar to every other gene located in the FPI, iglA, iglB and vgrG are required for intramacrophage growth and virulence in mice. More importantly, IglA, IglB and VgrG have been found to be immunogenic in murine models and in human tularemia [FIG. 4]. IglA is localized to the cytoplasm of Ft and its expression/stability is dependent on IglB. In particular, residues 33 to 132 of IglA are necessary for efficient binding to IglB, for the stability of IglB and for the intramacrophage growth of LVS. The T-cell epitopes of IglB were recently found to be within residues 454-514, especially residues 471-514. Bioinformatic analysis identifies the FPI including IglA, IglB, and VgrG, IcmF/pdpB, and DotU as a putative Type VI secretion system (T6SS) cluster as found in pathogens like *Pseudomonas aeruginosa, Aeruginosa hydrophila, Vibrio cholerae, enteroaggregative E. coli, S. typhimurium*, and others. The IglA and IglB homologues VipA and VipB in *V. cholerae* are shown to form tubular structures that are remodeled by ClpV into small complexes, a proposed essential step in T6SS formation. We show that IglA/IglB heterodimers assemble to form Francisella T6SS sheaths. Ft VgrG, significantly smaller than any known VgrG and lacking an active C-terminal domain, is secreted into Ft culture supernatant and the cytosol of infected macrophages. In view of these discoveries, one focus will be on tularemia vaccines expressing these highly immunogenic secreted FPI-encoded Ft proteins.

Fustion Protein Promoters

We cloned the GFP expression cassette driven by the groE or bfr promoter into the pFNLTP6-derived plasmid. The resulting plasmids, pFNLTP6/pgroE-GFP and pFNLTP6/pbfr-GFP, were electroporated into LVS; transformants selected on chocolate agar supplemented with kanamycin; and transformants verified by colony PCR. LVS/pbfr-GFP and LVS/pgro-GFP were grown in CDM for 24 h and protein expression analyzed. GFP was expressed at a higher level by LVS/pbfr-GFP than that by LVS/pgro-GFP. This study prompted us to construct rLVS ΔcapB strains expressing Ft-Ag downstream of the bfr promoter.

Demonstration that IglC driven by the Ft bfr and omp promoter was expressed at a level higher than IglC driven by the groE promoter. To improve the expression of IglC by the rLVS ΔcapB strains, we engineered the IglC coding sequence downstream of the Ft bfr or outer membrane protein (omp26) promoter. Consistent with the GFP expression, expression of IglC driven by the bfr or omp promoter was greater than that driven by the groE promoter (FIG. 32)

Route of Immunization (e.g., Intradermal [I.D.] vs. Intranasal [I.N.])

We have tested systemic routes (intradermal [i.d.] or intramuscular [i.m.]) vs. mucosal route of immunization (i.n.).

*B. anthracis*: As shown in FIGS. 12 & 29, homologous prime-boost vaccination with rLVS ΔcapB/Ba and heterologous prime-boost vaccination with rLVS ΔcapB/Ba—rLm/Ba vaccines by either systemic (intradermal) or mucosal (intranasal) route induces strong protection against challenge with Ba Ames spores.

*Y. pestis*: As shown in FIGS. 13 & 31, heterologous prime-boost vaccination with rLVS ΔcapB/Yp—rLm/Yp vaccines by the systemic (intradermal/intramuscular) route is superior to mucosal (intranasal) route against challenge with virulent *Y. pestis* CO92 challenge. Three doses of systemic (intradermal) homologous prime-boost vaccination with rLVS ΔcapB/Yp is also superior to the same vaccines administered by the intranasal route (FIG. 31).

*F. tularensis*: Mucosal route (intranasal) is generally superior to systemic (intradermal) route. However, two doses of rLVS ΔcapB/bfr-iglABC is comparable to LVS at the safe dose by the intradermal route (FIG. 27).

TABLES

TABLE 1

| Tier 1 Select Agents |
| --- |
| *Francisella tularensis* (Tularemia) |
| *Bacillus anthracis* (Anthrax) |
| *Yersinia pestis* (Plague) |
| *Burkholderia pseudomallei* (melioidosis) |
| *Burkholderia mallei* (glanders) |
| Category B Pathogens |
| *Coxiella burnetii* (Q Fever) |
| *Brucella species* (Brucellosis) |
| *Chlamydia psittaci* (Psittacosis) |
| *Rickettsia prowazekii* (Typhus) |
| *Listeria monocytogenes* (Listeriosis) |
| *Campylobacter jejuni* (Gastroenteritis) |
| *Yersinia enterocolitica* (Yersiniosis) |
| Additional Pathogens |
| *Chlamydia pneumonia* |
| *Chlamydia trachomatis* |
| *Mycoplasma pneumonia* |
| *Legionella pneumophila* |
| *Staphylococcus aureus* |
| *Streptococcus pneumoniae* |

TABLE 2

Plasmids, recombinant *F. tularensis* subsp. *holarctica*, *Listeria monocytogenes* for *B. anthracis* and *Y. pestis* vaccines

| Plasmids | | |
| --- | --- | --- |
| Name | Description | Reference |
| pFNLTP6 groE-gfp | *E. coli-Francisella* shuttle vector with gfp driven by *Francisella* groE promoter; Amp$^r$ Kan$^r$ | (13) |
| pBC11 Pomp-Ypcaf1-D-lcrV | pFNLTP6-derived *E. coli-Francisella* shuttle vector for expressing the fusion protein of *Y. pestis* F1 (encoded by caf1) and LcrV (encoded by lcrV) linked directly and downstream of *F. tularensis* omp promoter | This study |

TABLE 2-continued

Plasmids, recombinant *F. tularensis* subsp. *holarctica*, *Listeria monocytogenes* for *B. anthracis* and *Y. pestis* vaccines

| | | |
|---|---|---|
| pBC12/ Pomp-Ypcaf1-GGSG-lcrV | pFNLTP6-derived *E. coli-Francisella* shuttle vector for expressing the fusion protein of *Y. pestis* F1 (encoded by caf1) and LcrV (encoded by lcrV) separated by a GGSG linker (SEQ ID NO: 62) and downstream of *F. tularensis* omp promoter | This study |
| pSG39/ Pomp-pepOss-Ypcaf1-GGSG-lcrV | pFNLTP6-derived *E. coli-Francisella* shuttle vector for expressing the fusion protein of *Y. pestis* F1 (encoded by caf1) and LcrV (encoded by lcrV) separated by a GGSG linker (SEQ ID NO: 62) and downstream of *F. tularensis* omp promoter and PepO signal peptide | This study |
| pBC14/ Pbfr-BalefD1-GGSG-pagAD4 | pFNLTP6-derived *E. coli-Francisella* shuttle vector for expressing *B. anthracis* lethal factor (encoded by lef) domain 1 and Protective antigen (encoded by pagA) domain 4 separated by a GGSG linker (SEQ ID NO: 62) and downstream of *F. tularensis* bfr promoter | This study |
| pSG37/ Pomp-pepOss-Balef1D1-GGSG-pagAD4 | pFNLTP6-derived *E. coli-Francisella* shuttle vector for expressing the fusion protein of *B. anthracis* lethal factor (encoded by lef) domain 1 and Protective antigen (encoded by pagA) domain 4 with a GGSG linker (SEQ ID NO: 62) and downstream of *F. tularensis* omp promoter and PepO signal peptide | This study |
| pSG38/ Pomp-katGss Balef1D1-GGSG-pagAD4 | pFNLTP6-derived *E. coli-Francisella* shuttle vector for expressing the fusion protein of *B. anthracis* lethal factor (encoded by lef) domain 1 and Protective antigen (encoded by pagA) domain 4 with a GGSG linker (SEQ ID NO: 62) and downstream of *F. tularensis* omp promoter and KatG signal peptide | This study |
| pSG28/ ActAN100-Ypcaf1-GGSG-lcrV | pPL2-derived conjugation vector for integration of the antigen expression cassette ActAN100-Ypcaf1-GGSG-lcrV into the tRNA$^{arg}$ locus of the rLm chromosome | (14) & This study |
| pSG29/ hly-Ypcaf1-GGSG-lcrV | pPL2-derived conjugation vector pPL2-derived conjugation vector for integration of the antigen expression cassette hly-Ypcaf1-GGSG-lcrV into the tRNA$^{arg}$ locus of the rLm chromosome | (14) & This study |
| pSG40/ ActAN100-Balef1-GGSG-pagA4 | pPL2-derived conjugation vector for integration of the antigen expression cassette ActAN100-Balef1-GGSG-pa4 into the tRNA$^{arg}$ locus of the rLm chromosome | (14) & This study |
| pSG41/ hly-Balef1-GGSG-pagA4 | pPL2-derived conjugation vector for integration of the antigen expression cassette hly-Balef1-GGSG-pa4 into the tRNA$^{arg}$ locus of the rLm chromosome | (14) & This study |
| pQJ137/ Phfr-BalefD1-(GSSG)2-pagAD4 | pFNLTP6-derived *E. coli-Francisella* shuttle vector for optimized expression in Ft LVS of *B. anthracis* lethal factor (encoded by lef) domain 1 and Protective antigen (encoded by pagA) extended domain 4, separated by a GSSGGSSG linker (SEQ ID NO: 65) and downstream of *F. tularensis* bfr promoter | This study |
| pQJ138/ Pbfr-YplcrV-(GGGS)3-caf1-(GGGS)3-YscF | pFNLTP6-derived *E. coli-Francisella* shuttle vector for optimized expression in Ft LVS of the fusion protein of *Y. pestis* LcrV (encoded by lcrV), F1 (encoded by caf1), and YscF (encoded by yscF), separated by GGGSGGGSGGGS linker (SEQ ID NO: 66) and downstream of *F. tularensis* bfr promoter | This study |

| Strain | Description | Reference |
|---|---|---|
| | Attenuated recombinant *F. tularensis* subsp. *holarctica* | |
| LVS | Live vaccine strain | CDC |
| LVS ΔcapB | Unmarked LVS with deletion of capB | (10) |
| rLVS ΔcapB/ YpF1V(D) | LVS ΔcapB carrying pBC11/Pomp-Ypcaf1-D-lcrV | This study |
| rLVS ΔcapB/YpF1V(L1) | LVS ΔcapB carrying pBC12/Pomp-Ypcaf1-GGSG-lcrV | This study |
| rLVS ΔcapB/ BaLFPA(L1) | LVS ΔcapB carrying pBC14/Pbfr-BalefD1-GGSG-pagAD4 | This study |

TABLE 2-continued

Plasmids, recombinant *F. tularensis* subsp. *holarctica*, *Listeria monocytogenes* for *B. anthracis* and *Y. pestis* vaccines

| | | |
|---|---|---|
| rLVS ΔcapB/pepOss-YpF1V(L1) | LVS ΔcapB carrying pSG39/Pomp-pepOss-Ypcaf1-GGSG-lcrV | This study |
| rLVS ΔcapB/katGss-BaLFPA(L1) | LVS ΔcapB carrying pSG38/Pomp-katGss-Balef1D1-GGSG-pagAD4 | This study |
| rLVS ΔcapB/pepOss-BaLFPA(L1) | LVS ΔcapB carrying pSG37/Pomp-pepOss-Balef1D1-GGSG-pagAD4 | This study |
| rLVS ΔcapB/BaLFPA(L2) | LVS ΔcapB carrying pQJ137/Pbfr-BalefD1-(GSSG)2-pagAD4 optimized for expression in Ft LVS | This study |
| rLVS ΔcapB/YpVF1YscF(L3) | LVS ΔcapB carrying pQJ138/Pbfr-YplcrV-(GGGS)3-caf1-(GGGS)3-YscF optimized for expression in Ft LVS | This study |

Attenuated recombinant *Listeria monocytogenes*

| | | |
|---|---|---|
| Lm ΔactA ΔinlB prfA* | Lm ΔactA ΔinlB ΔuvrAB prfA*(G155S) | [7] |
| rLm ΔactA/actA-BaLFPA(L1) | rLm ΔactA integrated with the actAN100-Balef1-GGSG-pa4 antigen expression cassette at the tRNA$^{arg}$ locus | This study |
| rLm ΔactA ΔinlB prfA*/actA-BaLFPA | rLm ΔactA ΔinlB ΔuvrAB prfA*(G155S) integrated with the actA-Balef1-GGSG-pagA4 antigen expression cassette at the tRNA$^{arg}$ locus | This study |
| rLm ΔactA/hly-BaLF-PA | rLm ΔactA integrated with the hly-Balef1-GGSG-pagA4 antigen expression cassette at the tRNA$^{arg}$ locus | This study |
| rLm ΔactA ΔinlB prfA*/hly-BaLFPA | rLm ΔactA ΔinlB ΔuvrAB prfA*(G155S) integrated with the hly-Balef1-GGSG-pa4 antigen expression cassette at the tRNA$^{arg}$ locus | This study |
| rLm ΔactA/actA-YpF1V | rLm ΔactA integrated with the actAN100-Ypcaf1-GGSG-lcrV antigen expression cassette at the tRNA$^{arg}$ locus | This study |
| rLm ΔactA ΔinlB prfA*/actA-YpF1V | rLm ΔactA ΔinlB ΔuvrAB prfA*(G155S) integrated with the actAN100-Ypcaf1-GGSG-lcrV antigen expression cassette at the tRNA$^{arg}$ locus | This study |
| rLm ΔactA/hly-YpF1V | rLm ΔactA integrated with the hly-Ypcaf1-GGSG-lcrV antigen expression cassette at the tRNA$^{arg}$ locus | This study |
| rLm ΔactA ΔinlB prfA*/hly-YpF1V | rLm ΔactA ΔinlB ΔuvrAB prfA*(G155S) integrated with the hly-Ypcaf1-GGSG-lcrV antigen expression cassette at the tRNA arg locus | This study |

TABLE 3

Plasmids, recombinant F. tularensis subsp. holarctica, Listeria monocytogenes for F. tularensis vaccines

| Plasmids Name | Description | Reference |
|---|---|---|
| pFNLTP6 groE-gfp | E. coli-Francisella shuttle vector with gfp driven by Francisella groE promoter; Amp$^r$ Kan$^r$ | [2] |
| pFNL/bfr-iglA | E. coli-Francisella shuttle vector for over-expressing IglA downstream of bfr promoter | [34] |
| pFNL/bfr-iglB | E. coli-Francisella shuttle vector for over-expressing IglB downstream of bfr promoter | [34] |
| pFNL/bfr-iglC | E. coli-Francisella shuttle vector for over-expressing IglC downstream of bfr promoter | [34] |
| pFNL/bfr-iglABC(D) | E. coli-Francisella shuttle vector for over-expressing IglABC downstream of bfr promoter | [34] |

TABLE 3-continued

Plasmids, recombinant F. tularensis subsp. holarctica, Listeria monocytogenes for F. tularensis vaccines

| | | |
|---|---|---|
| pFNL/bfr-iglABC(GGSG) | E. coli-Francisella shuttle vector for over-expressing IglABC with a GGSG linker (SEQ ID NO: 62) and downstream of bfr promoter | [34] |
| pFNL/bfr-iglABC(GGSG2) | E. coli-Francisella shuttle vector for over-expressing IglABC with GGSG2 linker (SEQ ID NO: 63) and downstream of bfr promoter | [34] |
| pFNL/omp-iglA | E. coli-Francisella shuttle vector for over-expressing IglA downstream of omp promoter | [34] |
| pFNL/omp-iglB | E. coli-Francisella shuttle vector for over-expressing IglB downstream of omp promoter | [34] |
| pFNL/omp-iglC | E. coli-Francisella shuttle vector for over-expressing IgIC downstream of omp promoter | [34] |
| pFNL/omp-iglABC(D) | E. coli-Francisella shuttle vector for over-expressing IglABC downstream of omp promoter | [34] |
| pFNL/omp-iglABC(GGSG) | E. coli-Francisella shuttle vector for over-expressing IglABC with a GGSG linker (SEQ ID NO: 62) and downstream of omp promoter | [34] |
| pFNL/omp-iglABC(GGSG2) | E. coli-Francisella shuttle vector for over-expressing IglABC with GGSG2 linker (SEQ ID NO: 63) and downstream of omp promoter | [34] |

F. tularensis subsp. holarctica

| Strain | Description | Reference |
|---|---|---|
| LVS | Live vaccine strain | CDC |
| LVS ΔcapB | Unmarked LVS with deletion of capB | [10] |
| rLVS ΔcapB/gro-iglA | LVS ΔcapB carrying pFNL/gro-iglA | [27] |
| rLVS ΔcapB/gro-iglC | LVS ΔcapB carrying pFNL/gro-iglC | [27] |
| rLVS ΔcapB/gro-iglABC | LVS ΔcapB carrying pFNL/gro-iglABC | [34] |
| rLVS ΔcapB/bfr-iglA | LVS ΔcapB carrying pFNL/bfr-iglA | [34] |
| rLVS ΔcapB/bfr-iglB | LVS ΔcapB carrying pFNL/bfr-iglB | [34] |
| rLVS ΔcapB/bfr-iglC | LVS ΔcapB carrying pFNL/bfr-iglC | [34] |
| rLVS ΔcapB/bfr-iglABC(D) | LVS ΔcapB carrying pFNL/bfr-iglABC(D) | [34] |
| rLVS ΔcapB/bfr-iglABC | LVS ΔcapB carrying pFNL/bfr-iglABC(GGSG) | [34] |
| rLVS ΔcapB/bfr-iglABC(GGSG2) | LVS ΔcapB carrying pFNL/bfr-iglABC(GGSG2) | [34] |
| rLVS ΔcapB/omp-iglA | LVS ΔcapB carrying pFNL/omp-iglA | [34] |

TABLE 3-continued

Plasmids, recombinant F. tularensis subsp. *holarctica*, *Listeria monocytogenes* for F. tularensis vaccines

| | | |
|---|---|---|
| rLVS ΔcapB/omp-iglABC(D) | LVS ΔcapB carrying pFNL/omp-iglABC(D) | [34] |
| rLVS ΔcapB/omp-iglABC(GGSG) | LVS ΔcapB carrying pFNL/omp-iglABC(GGSG) | [34] |
| rLVS ΔcapB/omp-iglABC(GGSG2) | LVS ΔcapB carrying pFNL/omp-iglABC(GGSG2) | [34] |

Attenuated recombinant *Listeria* monocytogenes

| | | |
|---|---|---|
| rLm/iglC | Lm ΔactA integrated with the hly-iglC antigen expression cassette at the tRNA$^{arg}$ locus | [9] |
| rLm ΔactA/hly-iglABC | Lm ΔactA integrated with the hly-iglABC antigen expression cassette at the tRNA$^{arg}$ locus | [34] |
| rLm ΔactA/actA-iglABC | Lm ΔactA integrated with the actA-iglABC antigen expression cassette at the tRNA$^{arg}$ locus | [34] |
| rLm ΔactA ΔinlB prfA*/hly-iglABC | Lm ΔactA ΔinlB ΔuvrAB prfA*(G155S) integrated with the hly-iglABC antigen expression cassette at the tRNA$^{arg}$ locus | [34] |
| rLm ΔactA ΔinlB prfA*/actA-iglABC | Lm ΔactA ΔinlB ΔuvrAB prfA*(G155S) integrated with the actA-iglABC antigen expression cassette at the tRNA$^{arg}$ locus | [34] |

Primers

| Description | Sequence (5'-3')* | [34] |
|---|---|---|
| SnaB_iglA33_F | agatgctacgtaatgctagttgttggcgatttatca (SEQ ID NO: 25) | [34] |
| iglA132_R | attattttcaatgtccttagcaa (SEQ ID NO: 26) | [34] |
| iglA_Mfe_iglB446_F | gacattgaaaataatcaattgcctttagaaatggcgagatatcctttc (SEQ ID NO: 27) | [34] |
| iglB506_R | gttattatttgtaccgaataattc (SEQ ID NO: 28) | [34] |
| iglB_Age_iglC29_F | ggtacaaataataacaccggtaattgtagattatttattgattcttta (SEQ ID NO: 29) | [34] |
| BamH_iglC149_R | agatgcggatccctattatattggatataactctaaattaga (SEQ ID NO: 30) | [34] |
| MfeI_GGSG_iglB446_F | aagtaacaattgggtggttctggtcctttagaaatggcgagatatccttc (SEQ ID NO: 31) | [34] |
| AgeI_GGSG_iglB506_R | aagtaaaccggttccagaaccaccgttattatttgtaccgaataattctgg (SEQ ID NO: 32) | [34] |
| MfeI_GGSG2_iglB446_F | Aagtaacaattgggtggttctggtggtggttctggtcctttagaaatggcgagatatcctttc (SEQ ID NO: 33) | [34] |
| AgeI_GGSG2_iglB506_R | Aagtaaaccggttccagaaccaccaccagaaccaccgttattatttgtaccgaataattctgg (SEQ ID NO: 34) | [34] |

*Restriction sites underlined in the primers.

TABLE 4

Plasmid stability in vivo (I)

| | Percentage of Kanamycin resistance (# of KanR/# of total clones) on days post infection | | | |
|---|---|---|---|---|
| | 1[a)] | 4[b)] | 7[c)] | 14[d)] |
| LVS | 0 (0/15) | 0 (0/15) | 0 (0/15) | 0 (0/24) |
| LVS ΔcapB | 0 (0/2) | 0 (0/15) | 0 (0/10) | 0 (0/15) |
| LVS ΔcapB/bfr-iglA | 100 (46/46) | 100 (30/30) | 100 (30/30) | 100 (36/36) |
| LVS ΔcapB/bfr-iglB | 100 (40/40) | 100 (30/30) | 93 (26/28) | 71 (5/7) |
| LVS ΔcapB/bfr-iglC | 100 (48/48) | 100 (30/30) | 100 (30/30) | 100 (26/26) |

[a)]Day 1 post infection: Colonies were patched from chocolate agars plated with lung lysates of a randomly chosen single animal.
[b)]Day 4 post infection: colonies were from patched from chocolate agars plated with lung lysates of a randomly chosen single animals.
[c)]Day 7 post infection: colonies were from patched from chocolate agars plated with lung and/or spleen lysates of a single randomly chosen animal.
[d)]Day 14 post infection: colonies were from patched from chocolate agars plated with lung, spleen, liver, and lymph node lysates of 1-2 animals that still had colonies.

TABLE 5

Plasmid stability in vivo (II)

| | Percentage of plasmid persistence [# of PCR (+) clones/# of Total clones tested] | | | |
|---|---|---|---|---|
| | 1 | 4 | 7 | 14 |
| LVS | — | — | — | — |
| LVS ΔcapB | — | — | — | — |
| LVS ΔcapB/bfr-iglA | 100 (8/8) | 100 (8/8) | 100 (8/8) | 100 (4/4) |
| LVS ΔcapB/bfr-iglB | 100 (8/8) | 100 (8/8) | 87.5 (7/8) | 100 (4/4) |
| LVS ΔcapB/bfr-iglC | 100 (8/8) | 100 (8/8) | 100 (8/8) | 100 (3/3) |

TABLE 6

Efficacy of Heterologous Prime-Boost Vaccine Expressing IglABC

| Vaccine (week 0) | Vaccine (week 4) | Boost (week 6) | Challenge (week 10) | Mean Survival Time (Days) (weeks 10-13) |
|---|---|---|---|---|
| PBS | PBS | ID | 29 CFU SchuS4 | 4.0 |
| rLVS ΔcapB/bfr-iglABC | — | — | 29 CFU SchuS4 | 7.9 |
| rLVS ΔcapB/bfr-iglABC | rLm prfA* (vector) | rLm prfA* (vector) | 29 CFU SchuS4 | 6.4 |
| rLVS ΔcapB/bfr-iglABC | rLm prfA*/hly-iglABC | — | 29 CFU SchuS4 | 7.6 |
| rLVS ΔcapB/bfr-iglABC | rLm prfA*/hly-iglABC | rLm prfA*/hly-iglABC | 29 CFU SchuS4 | 9.4 |
| rLVS ΔcapB/bfr-iglABC | rLm prfA*/ActA-iglABC | — | 29 CFU SchuS4 | 7.1 |
| rLVS ΔcapB/bfr-iglABC | rLm prfA*/ActA-iglABC | rLm prfA*/ActA-iglABC | 29 CFU SchuS4 | 9.4 |

REFERENCES

Note: This application references a number of different publications as indicated throughout the specification by reference numbers enclosed in parenthesis, e.g., (x). A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

1. Matyas B T, Nieder H S, Telford S R, 3rd. Pneumonic tularemia on Martha's Vineyard: clinical, epidemiologic, and ecological characteristics. Ann NY Acad Sci. 2007; 1105:351-77. Epub 2007/04/20. doi: annals.1409.013 [pii] 10.1196/annals.1409.013. PubMed PMID: 17442781.
2. Jernigan D B, Raghunathan P L, Bell B P, Brechner R, Bresnitz E A, Butler J C, Cetron M, Cohen M, Doyle T, Fischer M, Greene C, Griffith K S, Guarner J, Hadler J L, Hayslett J A, Meyer R, Petersen L R, Phillips M, Pinner R, Popovic T, Quinn C P, Reefhuis J, Reissman D, Rosenstein N, Schuchat A, Shieh W J, Siegal L, Swerdlow D L, Tenover F C, Traeger M, Ward J W, Weisfuse I, Wiersma S, Yeskey K, Zaki S, Ashford D A, Perkins B A, Ostroff S, Hughes J, Fleming D, Kaplan J P, Gerberding J L. Investigation of bioterrorism-related anthrax, United States, 2001: epidemiologic findings. Emerg Infect Dis. 2002; 8(10):1019-28. Epub 2002/10/25. PubMed PMID: 12396909.
3. Rosenzweig J A, Jejelowo O, Sha J, Erova T E, Brackman S M, Kirtley M L, van Lier C J, Chopra A K. Progress on plague vaccine development. Appl Microbial Biotechnol. 2011; 91(2):265-86. Epub 2011/06/15. doi: 10.1007/s00253-011-3380-6. PubMed PMID: 21670978.
4. Alibek K. Biohazard: the chilling true story of the largest covert biological weapons program in the world, told from the inside by the man who ran it. New York: Random House, Inc.; 1999. 319 p.
5. Inglesby T V, Dennis D T, Henderson D A, Bartlett J G, Ascher M S, Eitzen E, Fine A D, Friedlander A M, Hauer J, Koerner J F, Layton M, McDade J, Osterholm M T, O'Toole T, Parker G, Perl T M, Russell P K, Schoch- Spana M, Tonat K. Plague as a biological weapon: medical and public health management. Working Group on Civilian Biodefense. JAMA. 2000; 283(17):2281-90. Epub 2000/05/12. doi: jst90013 [pii]. PubMed PMID: 10807389.
6. Titball R W, Oyston P C. A vaccine for tularaemia. Expert opinion on biological therapy. 2003; 3(4):645-53. PubMed PMID: 12831369.
7. Lauer P, Hanson B, Lemmens E E, Liu W, Luckett W S, Leong M L, Allen H E, Skoble J, Bahjat K S, Freitag N E, Brockstedt D G, Dubensky T W, Jr. Constitutive Activation of the PrfA regulon enhances the potency of vaccines based on live-attenuated and killed but metabolically active *Listeria monocytogenes* strains. Infect lmmun. 2008; 76(8):3742-53. Epub 2008/06/11. doi: IAI.00390-08 [pii] 10.1128/IAI.00390-08. PubMed PMID: 18541651; PMCID: PMC2493200.
8. Yan L, Qiu J, Chen J, Ryan-Payseur B, Huang D, Wang Y, Rang L, Melton-Witt J A, Freitag N E, Chen Z W. Selected prfA* mutations in recombinant attenuated *Listeria monocytogenes* strains augment expression of foreign immunogens and enhance vaccine-elicited humoral and cellular immune responses. Infect lmmun. 2008; 76(8):3439-50. Epub 2008/05/14. doi: IAI.00245-08 [pii] 10.1128/IAI.00245-08. PubMed PMID: 18474644; PMCID: PMC2493218.
9. Jia Q, Lee B Y, Clemens D L, Bowen R A, Horwitz M A. Recombinant attenuated *Listeria monocytogenes* vaccine expressing *Francisella tularensis* lgiC induces protection in mice against aerosolized Type A *F. tularensis*. Vaccine. 2009; 27(8):1216-29. Epub 2009/01/08. doi: 10.1016/j.vaccine.2008.12.014. PubMed PMID: 19126421; PMCID: PMC2654553.
10. Jia Q, Lee B Y, Bowen R, Dillon B J, Som S M, Horwitz M A. A *Francisella tularensis* live vaccine strain (LVS) mutant with a deletion in capS, encoding a putative capsular biosynthesis protein, is significantly more attenuated than LVS yet induces potent protective immunity in mice against *F. tularensis* challenge. Infect lmmun. 2010; 78(10):4341-55. Epub 2010/07/21. doi: 10.1128/iai.00192-10. PubMed PMID: 20643859; PMCID: PMC2950357.
11. Pannifer A D, Wong T Y, Schwarzenbacher R, Renatus M, Petosa C, Bienkowska J, Lacy D B, Collier R J, ParkS, Leppla S H, Hanna P, Liddington R C. Crystal structure of the anthrax lethal factor. Nature. 2001; 414(6860):229-33. doi: 10.1038/n35101998. PubMed PMID: 11700563.
12. Baillie L W, Huwar T B, Moore S, Mellado-Sanchez G, Rodriguez L, Neeson B N, Flick-Smith H C, Jenner D C, Atkins H S, Ingram R J, Altmann O M, Nataro J P, Pasetti M F. An anthrax subunit vaccine candidate based on protective regions of *Bacillus anthracis* protective antigen and lethal factor. Vaccine. 2010; 28(41):6740-8. Epub 2010/08/10. doi: 50264-410X(10)01086-8 [pii] 10.1016/j.vaccine.2010.07.075. PubMed PMID: 20691267; PMCID: 3008506.
13. Maier T M, Havig A, Casey M, Nano F E, Frank O W, Zahrt T C. Construction and characterization of a highly efficient Francisella shuttle plasmid. Appl Environ Microbial. 2004; 70(12):7511-9. PubMed PMID: 15574954; PMCID: PMC535190.
14. Lauer P, Chow M Y, Loessner M J, Portnoy D A, Calendar R. Construction, characterization, and use of two *Listeria monocytogenes* site-specific phage integration vectors. J Bacterial. 2002; 184(15):4177-86. PubMed PMID: 12107135; PMCID: PMC135211.
15. Friedlander A M, Little S F. Advances in the development of next-generation anthrax vaccines. Vaccine. 2009; 27 Suppl 4:028-32. Epub 2009/10/20. doi: S0264-410X(09)01312-7 [pii] 10.1016/j.vaccine.2009.08.102. PubMed PMID: 19837282.
16. Langley W A, Bradley K C, Li ZN, Smith M E, Schnell M J, Steinhauer D A. Induction of neutralizing antibody responses to anthrax protective antigen by using influenza virus vectors: implications for disparate immune system priming pathways. J Virol.84(16):8300-7. Epub 2010/05/28. doi: JVI.00183-10 [pii] 10.1128/JVI.00183-10. PubMed PMID: 20504926; PMCID: 2916528.
17. Langley W A, Bradley K C, Li Z N, Talekar G R, Galloway S E, Steinhauer D A. The effects of preexisting immunity to influenza on responses to influenza vectors in mice. Vaccine.28(38):6305-13. Epub 2010/07/27. doi: S0264-410X(10)00953-9 [pii] 10.1016/j.vaccine.2010.06.112. PubMed PMID: 20656032.
18. McConnell M J, Hanna P C, Imperiale M J. Adenovirus-based prime-boost immunization for rapid vaccination against anthrax. Mol Ther. 2007; 15(1):203-10. Epub 2006/12/14. doi: 6300034 [pii] 10.1038/sj.mt.6300034. PubMed PMID: 17164792.
19. Due le H, Hong H A, Atkins H S, Flick-Smith H C, Durrani Z, Rijpkema S, Titball R W, Cutting S M. Immunization against anthrax using *Bacillus* subtilis spores expressing the anthrax protective antigen. Vaccine. 2007; 25(2):346-55. Epub 2006/09/30. doi: 50264-410X(06)00889-9 [pii] 10.1016/j.vaccine.2006.07.037. PubMed PMID: 17007969.
20. Coulson N M, Fulop M, Titball R W. *Bacillus anthracis* protective antigen, expressed in *Salmonella typhimurium* SL 3261, affords protection against anthrax spore challenge. Vaccine. 1994; 12(15):1395-401. Epub 1994/11/01. PubMed PMID: 7887017.
21. Garmory H S, Titball R W, Griffin K F, Hahn U, Bohm R, Beyer W. *Salmonella* enterica serovar typhimurium expressing a chromosomally integrated copy of the *Bacillus anthracis* protective antigen gene protects mice against an anthrax spore challenge. Infect lmmun. 2003; 71 (7):3831-6. Epub 2003/06/24. PubMed PMID: 12819066.
22. Leary S E, Williamson E D, Griffin K F, Russell P, Eley S M, Titball R W. Active immunization with recombinant V antigen from *Yersinia pestis* protects mice against plague. Infect lmmun. 1995; 63(8):2854-8. PubMed PMID: 7622205; PMCID: 173387.
23. Williamson E D, Eley S M, Griffin K F, Green M, Russell P, Leary S E, Oyston P C, Easterbrook T, Reddin K M, Robinson A, et al. A new improved sub-unit vaccine for plague: the basis of protection. FEMS lmmunol Med Microbial. 1995; 12 (3-4):223-30. PubMed PMID: 8745007.
24. Oyston P C, Williamson E D, Leary S E, Eley S M, Griffin K F, Titball R W. Immunization with live recombinant *Salmonella* typhimurium aroA producing F1 antigen protects against plague. Infect lmmun. 1995; 63(2): 563-8. Epub 1995/02/01. PubMed PMID: 7822022.
25. Smiley S T. Immune defense against pneumonic plague. lmmunol Rev. 2008; 225:256-71. Epub 2008/10/08. doi: IMR674 [pii] 10.1111/j.1600-065X.2008.00674.x. PubMed PMID: 18837787.
26. Sanapala S, Rahav H, Patel H, Sun W, Curtiss R. Multiple antigens of *Yersinia pestis* delivered by live recombinant attenuated *Salmonella* vaccine strains elicit 27. Jia Q, Bowen R, Sahakian J, Dillon B J, Horwitz M A. 2013. A heterologous prime-boost vaccination strategy comprising the *Francisella tularensis* live vaccine strain capB mutant and recombinant attenuated *Listeria monocytogenes* expressing *F. tularensis* IglC induces potent protective immunity in mice against virulent *F. tularensis* aerosol challenge. Infect Immun 81:1550-1561.
28. Maier T M, Havig A, Casey M, Nano F E, Frank D W, Zahrt T C. 2004. Construction and characterization of a highly efficient *Francisella* shuttle plasmid. Appl Environ Microbiol 70:7511-7519.
29. Clemens D L, Ge P, Lee B Y, Horwitz M A, Zhou Z H. 2015. Atomic structure of T6SS reveals interlaced array essential to function. Cell 160:940-951.
30. Zaide G, Grosfeld H, Ehrlich S, Zvi A, Cohen O, Shafferman A. 2011. Identification and characterization of novel and potent transcription promoters of *Francisella tularensis*. Appl Environ Microbiol 77:1608-1618.
31. Gallagher L A, Ramage E, Jacobs M A, Kaul R, Brittnacher M, Manoil C. 2007. A comprehensive transposon mutant library of *Francisella* novicida, a bioweapon surrogate. Proc Natl Acad Sci U S A 104:1009-1014.
32. Jia Q, Lee B Y, Clemens D L, Bowen R A, Horwitz M A. 2009. Recombinant attenuated *Listeria monocytogenes* vaccine expressing *Francisella tularensis* IglC induces protection in mice against aerosolized Type A *F. tularensis*. Vaccine 27:1216-1229.
33. Jia Q, Lee B Y, Bowen R, Dillon B J, Som S M, Horwitz M A. 2010. A *Francisella tularensis* live vaccine strain (LVS) mutant with a deletion in CapB, encoding a putative capsular biosynthesis protein, is significantly more attenuated than LVS yet induces potent protective immunity in mice against *F. tularensis* challenge. Infect Immun 78:4341-4355.
34. Jia Q, Bowen R, Lee B Y, Dillon B J, Maslesa-Galic S, Horwitz M A. *Francisella tularensis* Live Vaccine Strain deficient in CapB and overexpressing the fusion protein of IglA, IglB, and IglC from the bfr promoter induces improved protection against *F. tularensis* respiratory challenge. Vaccine. 2016; 34(41):4969-78. doi: 10.1016/j.vaccine.2016.08.041. PubMed PMID: 27577555; PMCID: PMC5028307.

SEQUENCES

```
B. anthracis polypeptide sequences
a. Anthrax protective antigen precursor
AAA22637.1 protective antigen precursor [Bacillus anthracis]
MKKRKVLIPLMALSTILVSSTGNLEVIQAEVKQENRLLNESESSSQGLLGYYFSDLNFQAPMVVTSSTTG
DLSIPSSELENIPSENQYFQSAIWSGFIKVKKSDEYTFATSADNHVTMWVDDQEVINKASNSNKIRLEKG
RLYQIKIQYQRENPTEKGLDFKLYWTDSQNKKEVISSDNLQLPELKQKSSNSRKKRSTSAGPTVPDRDND
GIPDSLEVEGYTVDVKNKRTFLSPWISNIHEKKGLTKYKSSPEKWSTASDPYSDFEKVTGRIDKNVSPEA
RHPLVAAYPIVHVDMENIILSKNEDQSTQNTDSETRTISKNTSTSRTHTSEVHGNAEVHASFFDIGGSVS
AGESNSNSSTVAIDHSLSLAGERTWAETMGLNTADTARLNANIRYVNTGTAPIYNVLPTTSLVLGKNQTL
ATIKAKENQLSQILAPNNYYPSKNLAPIALNAQDDFSSTPITMNYNQFLELEKTKQLRLDTDQVYGNIAT
YNFENGRVRVDTGSNWSEVLPQIQETTARIIENGKDLNLVERRIAAVNPSDPLETTKPDMILKEALKIAF
GFNEPNGNLQYQGKDITEFDFNFDQQTSQNIKNQLAELNATNIYTVLDKIKLNAKMNILIRDKRFHYDRN
NIAVGADESVVKEAHREVINSSTEGLLLNIDKDIRKILSGYIVEIEDTEGLKEVINDRYDMLNISSLRQD
GKTFIDFKKYNDKLPLYISNPNYKVNVYAVIKENTIINPSENGDISTNGIKKILIFSKKGYEIG (SEQ
ID NO: 6)

b. Anthrax toxin lethal factor precursor; lef, plasmid pXO1,
Protein ID: NP_052803.1
NP_052803.1 pXO1-107 (plasmid) [Bacillus anthracis]
MNIKKEFIKVISMSCLVTAITLSGPVFIPLVQGAGGHGDVGMHVKEKEKNKDENKRKDEERNKTQEEHLK
EIMKHIVKIEVKGEEAVKKEAAEKLLEKVPSDVLEMYKAIGGKIYIVDGDITKHISLEALSEDKKKIKDI
YGKDALLHEHYVYAKEGYEPVLVIQSSEDYVENTEKALNVYYEIGKILSRDILSKINQPYQKFLDVLNTI
KNASDSDGQDLLFINQLKEHPIDFSVEFLEQNSNEVQEVFAKAFAYYIEPQHRDVLQLYAPEAFNYMDKF
NEQEINLSLEELKDQRMLSRYEKWEKIKQHYQHWSDSLSEEGRGLLKKLQIPIEPKKDDIIHSLSQEEKE
LLKRIQIDSSDFLSTEEKEFLKKLQIDIRDSLSEEEKELLNRIQVDSSNPLSEKEKEFLKKLKLDIQPYD
INQRLQDTGGLIDSPSINLDVRKQYKRDIQNIDALLHQSIGSTLYNKIYLYENMNINNLTATLGADLVDS
IDNIKINRGIFNEFKKNFKYSISSNYMIVDINERPALDNERLKWRIQLSPDTRAGYLENGKLILQRNIGL
EIKDVQIIKQSEKEYIRIDAKVVPKSKIDTKIQEAQLNINQEWNKALGLPKYTKLITENVHNRYASNIVE
SAYLILNEWKNNIQSDLIKKVINYLVDGNGRFVFIDITLPNIAEQYTHQDEIYEQVHSKGLYVPESRSIL
LHGPSKGVELRNDSEGFIHEFGHAVDDYAGYLLDKNQSDLVINSKKFIDIFKEEGSNLTSYGRTNEAEFF
AEAFRLMHSTDHAERLKVQKNAPKTFQFINDQIKFIINS (SEQ ID NO: 5)

c. AhpC, Alkyl hydroperoxide reductase subunit C [Bacillus anthracis
str. Ames]
NP_842892.1 alkyl hydroperoxide reductase subunit C [Bacillus
anthracis str. Ames]
MLLIGTEVKPFKANAYHNGEFIQVIDESLKGKWSVVCFYPADFIFVCPTELEDLQNQYAILKELGVEVYS
VSIDTHFTHKAWHDSSETIGKIEYIMIGDPIRTITTNFNVLMEEEGLAARGIFIIDPDGVIQSMEINADG
IGRDASILVNKIKAAQYVRNNPGEVCPAKWQEGSATLKPSLDLVGKI (SEQ ID NO: 7)

Yersinia pestis polypeptide sequences
a. F1 capsule antigen
NP_395430.1 F1 capsule antigen (plasmid) [Yersinia pestis CO92]
MKKISSVIAIALFGTIATANAADLTASTTATATLVEPARITLTYKEGAPITIMDNGNIDTELLVGILTLG
GYKTGITSTSVNFTDAAGDPMYLIFTSQDGNNHQFTTKVIGKDSRDFDISPKVNGENLVGDDVVLATGSQ
DFFVRSIGSKGGKLAAGKYTDAVIVIVSNQ (SEQ ID NO: 8)
```

SEQUENCES b. V antigen (LcrV) protein
NP_395165.1 secreted effector protein (plasmid) [*Yersinia pestis* CO92]
MIRAYEQNPQHFIEDLEKVRVEQLIGHGSSVLEELVQLVKDKNIDISIKYDPRKDSEVFANRVITDDIEL
LKKILAYFLPEDAILKGGHYDNQLQNGIKRVKEFLESSPNTQWELRAFMAVMHFSLTADRIDDDILKVIV
DSMNHHGDARSKLREELAELTAELKIYSVIQAEINKHLSSSGTINIHDKSINLMDKNLYGYTDEEIFKAS
AEYKILEKMPQTTIQVDGSEKKIVSIKDFLGSENKRTGALGNLKNSYSYNKDNNELSHFATTCSDKSRPL
NDLVSQKTTQLSDITSRFNSAIEALNRFIQKYDSVMQRLLDDTSGK (SEQ ID NO: 9)

c. YscF
NP_395189.1 needle complex major subunit (plasmid) [*Yersinia pestis* CO92]
MSNFSGETKGTDIADLDAVAQTLKKPADDANKAVNDSIAALKDKPDNPALLADLQHSINKWSVIYNINST
IVRSMKDLMQGILQKFP (SEQ ID NO: 10)

d. YopE
AJJ86307.1 outer membrane virulence protein yopE (plasmid) [*Yersinia pestis* CO92]
MKISSFISTSLPLPTSVSGSSSVGEMSGRSVSQQTSDQYANNLAGRTESPQGSSLASRIIERLSSVAHSV
IGFIQRMFSEGSHKPVVTPAPTPAQMPSPTSFSDSIKQLAAETLPKYMQQLNSLDAEMLQKNHDQFATGS
GPLRGSITQCQGLMQFCGGELQAEASAILNTPVCGIPFSQWGTIGGAASAYVASGVDLTQAANEIKGLAQ
QMQKLLSLM (SEQ ID NO: 11)

e. Ybt/pesticin receptor Psn [*Yersinia pestis*]
AAC69592.1 Ybt/pesticin receptor Psn [*Yersinia pestis*]
MKMTRLYPLALGGLLLPAIANAQTSQQDESTLVVTASKQSSRSASANNVSSTVVSAPELSDAGVTASDKL
PRVLPGLNIENSGNMLFSTISLRGVSSAQDFYNPAVTLYVDGVPQLSTNTIQALTDVQSVELLRGPQGTL
YGKSAQGGIINIVTQQPDSTPRGYIEGGVSSRDSYRSKFNLSGPIQDGLLYGSVTLLRQVDDGDMINPAT
GSDDLGGTRASIGNVKLRLAPDDQPWEMGFAASRECTRATQDAYVGWNDIKGRKLSISDGSPDPYMRRCT
DSQTLSGKYTTDDWVFNLISAWQQQHYSRTFPSGSLIVNMPQRWNQDVQELRAATLGDARTVDMVFGLYR
QNTREKLNSAYDMPTMPYLSSTGYTTAETLAAYSDLTWHLTDRFDIGGGVRFSHDKSSTQYHGSMLGNPF
GDQGKSNDDQVLGQLSAGYMLTDDWRVYTRVAQGYKPSGYNIVPTAGLDAKPFVAEKSINYELGTRYETA
DVTLQAATFYTHTKDMQLYSGPVRMQTLSNAGKADATGVELEAKWRFAPGWSWDINGNVIRSEFTNDSEL
YHGNRVPFVPRYGAGSSVNGVIDTRYGALMPRLAVNLVGPHYFDGDNQLRQGTYATLDSSLGWQATERMN
ISVYVDNLFDRRYRTYGYMNGSSAVAQVNMGRTVGINTRIDFF (SEQ ID NO: 12)

*F. tularensis* polypeptide sequences
a. IglA (intracellular growth locus, subunit A) [*Francisella tularensis* subsp. *tularensis* SCHU S4]
CAG45992.1 intracellular growth locus, subunit A [*Francisella tularensis* subsp. *tularensis* SCHU S4]
MLIRCCEKKDNKMAKNKIPNSRLMINYETNVDGVLKKKELPYRVLVVGDLSKGRSVDAKKEFADREVRRV
NNGVDRVLEEMNISFDFEAPNFVSKDRSNLKVNYRIESVKDFRPDAVAKKVPEIRALLEMKEILASFAKD
IENNRNLKKTIDMIFSDSNELESLKSKIPALTNYTIKDSCDAAESQDLSNQQVDGK (SEQ ID NO: 2)

b. IglB (intracellular growth locus, subunit B) [*Francisella tularensis* subsp. *tularensis* SCHU S4]
CAG45991.1 intracellular growth locus, subunit B [*Francisella tularensis* subsp. *tularensis* SCHU S4]
MVSREDFIMTINKLSLIDELLNNFGGSTEVDSVLKNIDFDVSDDASKVLSLSIDYNARNLMALSLVLANN
DNINNYNQKYIQKVITVIDKLIDLQVNSIISNDEFRALEQEWLKVQEVCQEDYDNVEVSILDVKKEELQY
DFERNLYDISSSDFFKKVYVSEFDQYGGEPYGAILGLYNFENTINDIIWLIGMGMVAKNSHAPFIASIDK
SFFGVKDLSEITHIKSFEALLEHPRYKEWNDFRNLDVAAYIGLTVGDFMLRQPYNPENNPVQYKLMEGFN
EFVDYDKNESYLWGPASIHLVKNMMRSYDKTRWFQYIRGVESGGYVKNLVACVYDNKGILETKSPLNVLF
ADYMELSLANIGLIPFVSEKGISNACFFSVNSAKKVEEFVDGFDSANSRLIANLSYTMCISRISHYIKCV
IRDKIGSIVDVESIQKILSDWISEFVTIVYQPIPLEMARYPFRNVSIEVETIPGKPGWYSCKINVIPHIQ
FEGMNITMTIDIRLEPELFGINNN (SEQ ID NO: 3)

c. IglC (intracellular growth locus, subunit C) [*Francisella tularensis* subsp. *tularensis* SCHU S4]
CAG45990.1 intracellular growth locus, subunit C [*Francisella tularensis* subsp. *tularensis* SCHU S4]
MIMSEMITRQQVISGETIHVRTDPTACIGSHPNCRLFIDSLTIAGEKLDKNIVAIDGGEDVIKADSATAA
ASVIRLSITPGSINPTISITLGVLIKSNVRTKIEEKVSSILQASATDMKIKLGNSNKKQEYKTDEAWGIM
IDLSNLELYPISAKAFSISIEPTELMGVSKDGMRYHIISIDGLITSQGSLPVCCAASTDKGVAKIGYIAA
A (SEQ ID NO: 4)

d. VgrG, conserved hypothetical protein [*Francisella tularensis* subsp. *tularensis* SCHU S4]
CAG45980.1 conserved hypothetical protein [*Francisella tularensis* subsp. *tularensis* SCHU S4]
MSKADHIFNLEEQGLLIDIKDDSKGCTTKLESSGKITHNATESIESSADKQIIENVKDSKISITEKEIL
LATKKSSIMLSEDKIVIKIGNSLIILDDSNISLESATINIKSSANINIQASQNIDIKSLNNSIKADVNL
NAEGLDVNIKGSVTASIKGSTATMVG (SEQ ID NO: 15)

| SEQUENCES |
|---| e. capsule biosynthesis protein CapB [*Francisella tularensis*]
MTTLDFWLIVVVFVILCVYLIIENIVHNNSIKSIPIRIHNGTRGKSSVARLIAAGVRAGGYRTVAKTTG
TLARYIDVDGSETPVFRIGSNIAEQVKIMFKARRAKADAIVIECMALQPLLQSLCELKLIKATHGVLTN
ARPDHLDVMGPTERDVAKALAATVPVGAKYFTAEDIHLDFFEYACKDRGELIAATAQDAEKISDEEINK
FVYSEPKINVALALKVIDDLGIPREIALKGMWEATPDPGAMTEYNFNIKAEINFANAFAANDPVSTKML
WDKLCAKYSGCDKKVLVVNCRDDREDRSKQMAEAALGWQKQDLIVLIGTGTEVFTSFYKYAKSLNKPMT
KVIVCEEMTPIQILEKTVDSNPANSYILVGVGNIKDIGMELVDYCDTSHKKKHNL (SEQ ID NO: 1)

*Francisella tularensis* promoter sequences
a. Promoter for *Francisella tularensis* subsp. *holarctica* FTL_0617
(bacterioferritin, bfr)
CP009694.1:1332650-1332938 *Francisella tularensis* subsp. *holarctica*
LVS, complete genome
TTGTTACCTCCATTATTTAAAACTCTAATCATTATAATCAACATACTAACTAGTATAATTCATATTAGCA
ATCAAGTTAGCATACAAAAGAAAATTTAATTCTTTATAAGTTATCAATTTAGTATCTAATTATATATCAA
AATATCTAAGAATTCAACCTAGATATTTTAATAAAAATGATATTATGCTATTTTTAGATAAGTTAAATTT
ACTATTTTTAATAATAATATTTAAGAAAAATAAATGAAGAAAATTAATTTTAATATTGTGATGATGGCAA
TAGTAACCA (SEQ ID NO: 13)

b. Promoter for *Francisella tularensis* subsp. *novicida* FTN_1451
(omp26, omp)
CP009633.1:589316-589474 *Francisella tularensis* subsp. *novicida* U112,
complete genome
TTTGGGTTGTCACTCATCGTATTTGGTTTATAATTTTAAGCTAATAACCTAATTATAACTAATTAATAGT
TTTGTATCTTGAAAAAATAGCTATAAAACTTATTTAAATAACGAAGATTTTTGTGTATAAAATATTTATA
ACAAAAAAGGAGACTAAA (SEQ ID NO: 14)

*Burkholderia pseudomallei* polypeptide sequences
Hcp-1
type VI secretion system [*Burkholderia pseudomallei*]
GenBank: CRY35672.1
>CRY35672.1 type VI secretion system [*Burkholderia pseudomallei*]
MLHMHLKFGSPAIKGESADKDHEGWIELKSWDHSIVQPRSATASTAGGHTATRCEHGDMVFTKEIDSSSP
LLYQHASGGTTFDEVTIDFLRADGEGQRVKYLEIKLKYVIISSIAPSVHTEGLPVETFSLKYAAVQWKQT
QQKIGGNQGGNTQGAWSLTKNDKTYAV (SEQ ID NO: 35)

Hcp-2 (T6SS)
type VI secretion system [*Burkholderia pseudomallei*]
GenBank: CPN31289.1
>CPN31289.1 type VI secretion system [*Burkholderia pseudomallei*]
MSHDIFLKINGIDGEAEDATHKGEIEVLSWSWNVSQQSNMHLGSGGGAGKATIDDLQFEHYIDRASPNLV
QYCLLGKHIDEARLVVRKAGGSPLEYIKLTMSDVLVTQVSPAGVAQDESRPRELVRLSFSRLKQEYVVQN
PQGGSGGAITATFDIKKNAA (SEQ ID NO: 36)

Hcp-3 (T6SS)
type VI secretion system [*Burkholderia pseudomallei*]
GenBank: CRY29196.1
>CRY29196.1 type VI secretion system [*Burkholderia pseudomallei*]
MAQDIFLKIDGINGESLDDSHKDEIEVLNWNWEIQQESTMHIGSGGGAGKASVKDLIFEHAIDRASPNLM
KYALIGKHVDQAVLVMRKAGGNPLEYLKLIMSDVIITRVRPSGSRDDTERSRETVSLSFAKVKQEYVVQN
AQGGSGGAVITSFDIKGNKEA (SEQ ID NO: 37)

Hcp-4 (T6SS)
type VI secretion system [*Burkholderia pseudomallei*]
GenBank: CRY33495.1
>CRY33495.1 type VI secretion system [*Burkholderia pseudomallei*]
MANALVDYFLQIDGVEGESTDQQYPGLIQIQSWQWAEENSGRWGFGSGGGAGKVEMKDFEFRMVSNKASP
KLFLMCATGEHIQNAKLICRKSGKGQQEFLTISFASGLVSSFRILGNMPISQLGHASGEVDGVLPTDQIR
INFAQIEFEYREQRNDGTMGAVIKAGYDLKQNAPI (SEQ ID NO: 38)

Hcp-6 (T6SS)
type VI secretion system [*Burkholderia pseudomallei*]
GenBank: CRY19699.1
>CRY19699.1 type VI secretion system [*Burkholderia pseudomallei*]
MGVAMPFMKVDGVTGESADAQHKGWIDIQSFSWGASQPGAMASGSGGNAGKASFNDLVVAAYMDKGATAII
KNCASGKHLPTVEISACKTGGSQIEFMRVILQEVLVISAQIAGVDPGDAADRLMMQYGFQAAKVKKQYWQ
QNDNGGKGAEVSVGWNIKENTEM (SEQ ID NO: 39)

LolC (ATP binding cassette system)
lipoprotein-releasing system transmembrane subunit LolC [*Burkholderia
pseudomallei*]
NCBI Reference Sequence: WP_050865936.1
>WP_050865936.1 lipoprotein-releasing system transmembrane subunit
LolC [*Burkholderia pseudomallei*]
MKLPYEWQIGWRYTRAGKRAIGNGFISFIALVSMLGIALGVAALIVVLSVMNGFQKEVRDRMLSVLAHVE
IFSPIGSMPDWQLTAKEARLNRSVIGAAPYVDAQALLTRQDAVSGVMLRGVEPSLEPQVSDIGKDMKAGA

| SEQUENCES |
| --- |
| LTALAPGQFGIVLGNALAGNLGVGVGDKVILVAPEGTITPAGMMPRLKQFTVVGIFESGHYEYDSTLAMI<br>DIQDAQALFRLPAPTGVRLRLTDMQKAPQVARELAHTLSGDLYIRDWIQQNKTWFSAVQIEKRMMFIILT<br>LIIAVAAFNLVSSLVMTVINKQADIAILRILGAQPGSIMKIFVVQGVTIGFVGTATGVALGCLIAWSIPW<br>LIPMIEHAFGVQFLPPSVYFISELPSELVAGDVIKIGVIAFALSALATLYPSWRGAKVRPAEALRYE<br>(SEQ ID NO: 40)<br><br>TypA<br>GTP-binding protein TypA [Burkholderia pseudomallei]<br>GenBank: CRY12842.1<br>>CRY12842.1 GTP-binding protein TypA [Burkholderia pseudomallei]<br>MTRALRNIAIIAHVDHGKITLVDQLLRQSGTFRENQQVAERVMDSNDIEKERGITILAKNCAVEYEGTHI<br>NIVDTPGHADFGGEVERVLSMVDSVLLLVDAVEGPMPQTREVIKKALALGLKPIVVINKIDRPGARIDWV<br>INQTFDLFDKLGATEEQLDFPIVYASGLNGYASLDPAARDGDMRPLFEAILQHVPVRPADPDAPLQLQIT<br>SLDYSTYVGRIGVGRITRGRIKPGQPVVMRFGPEGDVLNRKINQVLSFQGLERVQVDSAEAGDIVLINGI<br>EDVGIGATICAVEAPEALPMITVDEPTLIMNFLVNSSPLAGREGKEVISRQIRDRLMKELNHNVALRVKD<br>TGDETVFEVSGRGELHLTILVENMRREGYELAVSRPRVVMQEIDGVKHEPYELLTVDLEDEHQGGVMEEL<br>GRRKGEMLDMVSDGRGRIRLEYRIPARGLIGFQSEFLILTRGTGLMSHIFDSYAPVKEGSVGERRNGVLI<br>SQDDGAAVAYALWKLQDRGRMFVKPGDALYEGMIIGIHSRDNDLVVNPIKGKQLINVRASGTDEAVRLVP<br>PIQMSLEYAVEFIDDDELVEVTPQSIRLRKRHLKEHERRRASREAEAG (SEQ ID NO: 41)<br><br>BipB<br>BipB [Burkholderia pseudomallei]<br>GenBank:AB026356.1<br>>AB026356.1 BipB [Burkholderia pseudomallei]<br>MSSGVQGGPAAHANAYQTHPLRDAASALGTLSPQAYVDVVSAAQRNFLERMSQLASEQCDAQPAAHDARL<br>DDKPALRAPQERDAPPLGASDTGSRASGAAKLTELLGVLMSVISASSLDELKQRSDIWNQMSKAAQDNLS<br>RLSDAFQRATDEAKAAADAAEQAAAAAKQAGADAKAADAAVDAAQKRYDDAVKQGLPDDRLQSLKAALEQ<br>ARQQAGDAHGRADALQADATKKLDAASALATQARACEQQVDDAVNQATQQYGASASLRTPQSPRLSGAAE<br>LTAVLGKLQELISSGNVKELESKQKLFTEMQAKREAELQKKSDEYQAQVKKAEEMQKTMGCIGKIVGWVI<br>TAVSFAAAAFTGGASLALAAVGLALAVGDEISRATTGVSFMDKLMQPVMDAILKPLMEMISSLITKALVA<br>CGVDQQKAELAGAILGAVVTGVALVAAAFVGASAVKAVASKVIDAMAGQLTKLMDSAIGKMLVQLIEKFS<br>EKSGLQALGSRTATAMTRMRRAIGVEAKEDGMLLANRFEKAGTVMNVGNQVSQAAGGIVVGVERAKAMGL<br>LADVKEAMYDIKLLGDLLKQAVDAFAEHNRVLAQLMQQMSDAGEMQTSTGKLILRNARAV (SEQ ID<br>NO: 42)<br><br>BipC<br>BipC [Burkholderia pseudomallei]<br>GenBank: AB026357.1<br>>AB026357.1 BipC [Burkholderia pseudomallei]<br>MSIGVQSSGINISHAELSRLVDAGKSEQGDKAVRDDGRALARADAALAAVVGERVAARRDAVAGSGAQRV<br>ELARPKPDAQTRATDRRTVSGLEREHKRLAASQTPRVTGMHDALVQRHVSLDGAKAAHGEGVKRAAGDAP<br>RAAADAPQRFAFADDKAFDAMLALGAAMQKNVQSDLAMQGKLTMLAHDAMMSAAAQDRSIGAAQMTAAIA<br>GGALQATTSLGGAMQQMKSLSTKSMSIEKELKPQAELKQFHAEQALELRGINKPVLSNDEVSHVKIKRDT<br>GETVRHEIDHGGERMSDEHASVLAQEAPARQHRIDMHGMRHEENLVKASRQQMKGDLLQSGGQIGKNQID<br>GASAQQQGADRAEQKEDENAQQTAMAAASTRDEAAHRSREAAQKAIDAAKSQVANDNAVAAQVAGNLRT<br>(SEQ ID NO: 43)<br><br>BipD<br>BipD [Burkholderia pseudomallei]<br>GenBank: ABL67521.1<br>>ABL67521.1 BipD [Burkholderia pseudomallei]<br>MNMHVDMGRALTVRDWPALEALAKTMPADAGAREMTDDDLRAAGVDRRVPEQKLGAAIDEFASLRLPDRI<br>DGRFVDGRRANLTVFDDARVAVRGHARAQRNLLERLETELLGGTLDTAGDEGGIQPDPILQGLVDVIGQG<br>KSDIDAYATIVEGLTKYFQSVADVMSKLQDYISAKDDKNMKIDGGKIKALIQQVIDHLPTMQLPKGADIA<br>RWRKELGDAVSISDSGVVTINPDKLIKMRDSLPPDGTVWDTARYQAWNTAFSGQKDNIQNDVQTLVEKYS<br>HQNSNFDNLVKMLSGAISTLTDAAKSYLQI (SEQ ID NO: 44)<br><br>Omp3<br>OmpA family protein [Burkholderia pseudomallei]<br>GenBank: ACN64870.1<br>>ACN64870.1 OmpA family protein [Burkholderia pseudomallei]<br>MNKLSKLAFIAATAVMAASASAQSVPASRQAVNDNWVNGTGEWVWMNGTNELCWRDAFWTPATANAKCDG<br>ALVAQAPAPAPVAPVAPAITSQKITYQADTLFDFDKAVLKPAGKQKLDELAAKIQGMNVEVVVATGYTDR<br>IGSDKYNDRLSLRRAQAVKSYLVSKGVPANKVYTEGKGKRNPVTGNTCKQKNRKQLIACLAPDRRVEVEV<br>VGTQEVQKTTVPAQ (SEQ ID NO: 45)<br><br>Omp7<br>OmpA family lipoprotein [Burkholderia pseudomallei]<br>GenBank: ACN64871.1<br>>ACN64871.1 OmpA family lipoprotein [Burkholderia pseudomallei]<br>MTTRRVTMMSKKLRLAFAMLMIGALAACKSGVKLDEHANQGDAVSTQPNPENVAQVTVDPLNDPNSPLAK<br>RSVYFDFDSYSVQDQYQALLQQHAQYLKSHPQRHILIQGNTDERGTSEYNLALGQKRAEAVRRALSLLGV<br>GDAQMEAVSLGKEKPVALGHDEASWAQNRRADLVYQQ (SEQ ID NO: 46) |

-continued

| SEQUENCES |
| --- |

Omp85
putative outer membrane protein [*Burkholderia pseudomallei* K96243]
GenBank: CAH36153.1
>CAH36153.1 putative outer membrane protein [*Burkholderia pseudomallei* K96243]
MLFKPHREVPKTVAAAALAAHGLAAHATAPFVVQDIKIEGLQRVEAGSVFAYLPIKQGDTFTDDKASEAI
RALYATGFFNDVRIATQGGVVIVQVQERPAIASIDFTGIKEFDKDNLNKALKAVGLSQGRYYDKALVDKA
EQELKRQYLTRGFYAAEVSTTVTPVDANRVSILFAVAEGPSAKIRQINFIGNKAFKTSTLRDEMQLSTPN
WFSWYTKNDLYSKEKLTGDLENVRSYYLNRGYLEFNIESTQVSISPDKKDMYLTVALHEGEPYTVSSVKL
AGNLLDRQAELEKLVKIKPGDRFSAEKLQQTTKAIVDKLGQYGYAFATVNAQPEIDQATHKVGLTLVVDP
SRRVYVRRINIVGNTRTRDEVVRREMRQLESSWFDSSRLALSKDRVNRLGYFTDVDVTTVPVEGTNDQVD
VNVKVAEKPTGAITLGAGESSTDKVVLSAGISQDNVEGSGTSLAVNVNTAKSYRTLTVTQVDPYFTVDGI
KRITDVEYRTYQPLYYSTNSSFRIITAGGNLKEGIPFSETDTVYFGAGFEQNRLDVDSNTPQSYQDYVNE
FGRVSNTVPLTIGWSRDARDSALIPSRGYFTQANAEYGVPVGKIQYYKMDVQGQYYYSFARGFILGLNFQ
AGYGNGIGNPYPIFKNYYAGGIGSVRGYEPSSLGPRDTKTNDPIGGSKMVVGNIELTFPLPGTGYDRTLR
VFTFLDGGNVWGNAPGGTSTGANGLRYGYGIGLAWISPIGPLKLSLGFPLQKHEGDQYQKFQFQIGTAF
(SEQ ID NO: 47)

OmpW
outer membrane protein W [*Burkholderia pseudomallei*]
GenBank: A1173329.1
>ALJ73329.1 outer membrane protein W [*Burkholderia pseudomallei*]
MGDKHRRRRARRDWRAPVSCWLGATLLACAWSAHAQDSGAARWRDGADGIGFFPGGDAPGFDARAWGPVP
GDARRAAASDARNGVAASAGSEATAAAPAADANAAPARKLTEERITLGERVAPVADAARRVRADGDDGIG
FADAPGGPPAGGATPSAACDDGACVPDGGDAGRAPRRPPAGATPRFIAGVRYDRMPYELHPIDPERLPDL
PEAQGPTLLEQLQGDDSNMIGVGWHYVLSTGRSTPVTTSTAALGIGSFANPGSAVSISNTNTPAFTFTHF
FGEHVAAEIVAGIPPELTMRGHGSIGLPFDKIFPGVQGRLPLVDLGNTQSNPLGTTRAWLGSAVFKYYLG
KREDRLRPYVGLGLSYTRFTNTNLNPVFAHKLASLGGLLSAGISLGDLQSLLTDSGALDRLLQAGANLIL
PNGVRATADVKSAWTPVFVVGANYQLTRQLSLSTALSYIPLKAAITVNINDTKGILASNTTTLSANVLLC
TMLLNFRF (SEQ ID NO: 48)

PotF
spermidine/putrescine ABC transporter substrate-binding protein PotF [*Burkholderia pseudomallei*]
GenBank: ANW57327.1
>ANW57327.1 spermidine/putrescine ABC transporter substrate-binding protein PotF [*Burkholderia pseudomallei*]
MKRIAWLAAVLASLACAAARAAGGNVLNIYNWAEYFAPDTIAGFEKETGIKVRLDVYDSNEALQTKLTTG
NSGYDLVFPSNDFLARQIQAGLYRKLDKSRLPNLTNLDPAIVARAAEVDPGNQYSVPYMQGTFGLGLNVA
KVKQALGGPLPANTLELIFNPAYAAKLERCGIAFNDAGSEVFPLALRYIGRDPNTTDPRDYEAALDMMKK
IRPTIRQFIATPVMNDLATGDVCVVTGYSGAVLVAARRAAEAKNGQQIVYSLPSAGAPFWFDSMAIPKGA
AHADHALRFIDYILRPDVVAKISNKVMYPNPNRVATPLVDRRLTANPAIYPDAATMRTLWVKRPMPPQAM
RMQTRYWTRFKTGY (SEQ ID NO: 49)

OppA
oligopeptide ABC transporter periplasmic oligopeptide-binding protein [*Burkholderia pseudomallei*]
GenBank: CRY20041.1
>CRY20041.1 oligopeptide ABC transporter periplasmic oligopeptide-binding protein [*Burkholderia pseudomallei*]
MKHTHAFAAVLAALALTIAPSAPAVTVASNVTLADQQDLTRQVPAEVESLDPAHIESWTGNTIGLDLFEG
LARIDASGAVVPGVAQAWEHKAPDTWIFKLRRDAKWSNGQPVTAADFVYAWQRLADPKTGSKYTILVEFV
KNASAIIAGKQPPGDLGIRAIDPYTIEVKTEVPVSYFPELTAMAPLTPVNKDAVAKFGDAWTRPKNIVSN
GPYTLVDWQPNNRIVMAKSDKYWNARNVVIRKVTYLPIENDETALRMYQAGQIDYTYSIPAGGFGQISKQ
FGKELRPGLQLATYYYYLKNSDPALKDKRVREALAMVLDREILTSKITQAGEVPMYGLMPKGVKGVQRPF
TPDWASWPMARRVDYAKNLLKQAGHGDANPLTFTLTYNTNDLHKKVALFAASEWRTKLGVTAKLENVEFK
VLMKQRHDGKVQVARDGWFADYNDAMTFFDLIRCGSSQNTVGYCNPKVDSLVAEANQKLDDGARAALLTQ
AHDLAMNDYPMVPLFQYSADRLVKSYVGGYTLTNYIDMRASQDMYLIKH (SEQ ID NO: 50)

BopA (Type III Effector)
BopA protein [*Burkholderia pseudomallei*]
GenBank: CRY24966.1
>CRY24966.1 BopA protein [*Burkholderia pseudomallei*]
MINVGAFVASARSGARVVVGGDARGPVVSAARLGMKERLFAFLAHVPLLKHCDAVRRYAEQVRMENRRSL
EVFVLALSKRYGPEGAKAAFDYGARRDGAPLDQRRVRNMVSIAEHFHGTGDAKPLARQMVERSWECRGLD
HPGHASLTIKNQADADAGRHVYEHVSWWPNQRLGSKEHFDRIEPKTLDGYRIDKRSEISSATEQRLREGD
AARRKILADGFKYANQDERHDARFFPRAGQKLDKDAEWGLSARKVYFPAIGFNHDRRDTDRPRAFVLFGL
NEAAMLRDARTVKEGAKSGELKYRMISKKENCASMALRVLRAGGAEHFVPYTAAWISEDPNHAHAYALAV
QARIDALNQRRADVERRCERLRDSASVRQAWRAFSEAGGASASPLAEDAGRGRASAHMRQARLDEHAREV
ERIGAYFAELSAGRSGKHRDRADAALADAMKRCAPSARDDVAALTRKASVLVETLGRHLDAPPPSDSSAL
RRLAAHAMIGRIEAFMAAAIAA (SEQ ID NO: 51)

SEQUENCES

BimA (Autotransporter protein)
BimA [*Burkholderia pseudomallei*]
GenBank: ACF94992.1
>ACF94992.1 BimA [*

SEQUENCES

*Burkholderia mallei* polypeptide sequences
BMA_A0768 mannitol dehydrogenase family protein
mannitol dehydrogenase family protein [*Burkholderia mallei* ATCC 23344]
GenBank: AAU46944.1
>AAU46944.1 mannitol dehydrogenase family protein [*Burkholderia mallei* ATCC 23344]
MPLLSSDHCRALPPEVSRPRYDRRALRTGIVHLGLGAFHRAHQACYTETLVERGDLRWGIAGVELRRRHT
VERLAAQDHLYSVTERAGDAARTRVVGAVHRTLFAPQALATLLGLIADPSVSIVSLTVTEKGYYRRPGGG
GLDLDDPAIRRDLAQPHAPSTTLGVLAAGIRLRAAHAPLSVLSCDNMPSNGDTLRALLAQYAEQTDGALA
RRIRCDVAFPNTMVDRIVPAATPESLDWVQSRIGVRDEAAIVCEPFAQWVFEDRFAGARPRWEDAGALVA
ADVRPYEKMKLRLLNGSHSAIAYAGQLRGRRTVSDAMADPLIDALARGVMTRELLATLDVPAGYDVRAYC
ASLIERFRNPALAHRTAQIATDGTQKVPLRWLPALAESAAAGVERPPFLERSLAMWLHYVEVARDESGRPL
VLEDPGAQALAARLHGAPGATDAVRAALGLIASRDAARWPEALTARVGAHLETVRTRGTDALLRPLLDA
(SEQ ID NO: 58)

BMA_2821ABC Transporter ATP binding protein
glutathione ABC transporter ATP-binding protein [*Burkholderia mallei*]
GenBank: KKM47108.1
>KKM47108.1 glutathione ABC transporter ATP-binding protein
[*Burkholderia mallei*]
MSASRAAPSLPDARVLAVDGLTVTFRREDAAFVAVRDLSFHVDRGETLAIVGESGSGKSVTSLALMRLVE
HGGGAIAGGAIALRRRGGAVLDLARATPSTLRTVRGADVAMIFQEPMTSLNPVETVGDQISEAIALHQHK
SAGEARAETLRLLDLVRIPEARRVFARHPHQLSGGMRQRVMIAMALSCRPALLIADEPTTALDVTIQAQI
LQLIRGLQDEMDMGVIFITHDMGVVAEVADRVLVMYRGEKVEEGACDAIFAAPSHPYTKALLAAVPRLGS
MRGIDAPAKFPLLRFDPAAGDALVVAGGDATAASGDAARESVLFVDSDAAAASAASTASTASAASAASAA
PTACARPAIDAGAPPLLRVRELVIRFPVKSGVFGRVSQYVHAVERVSFELRAGETLALVGESGCGKSITG
RSLLRLVERVSGSIEFEGREIGALKGRELQALRRNIQFIFQDPFASLNPRLTVGFSIMEPLLVHGVASGR
QAQARVDWLLERVGLPADAARRYPHEFSGGQRQRIAIARALALNPKVVVADESVSALDVSVQAQIVNLML
DLQRELGVAYLFISHDMAVVERISHRVAVMYLGQIVEIGPRRAVFETPRHPYIKKLMSAVPIADPACRHA
PRTLPADELPSPIRALGDEPEVAPLVAVGPAHFVAEHRVGGAY (SEQ ID NO: 59)

BMA_0816 maltooligosyl trehalose synthase
maltooligosyl trehalose synthase, putative [*Burkholderia mallei* ATCC 23344]
GenBank: AAU49513 .1
>AAU49513.1 maltooligosyl trehalose synthase, putative [*Burkholderia mallei* ATCC 23344]
MKPRATLRLQLHAGFTFDDAAAHVGYFARLGVSHLYLSPITAAEPGSRHGYDVIDYSTVNPELGGEAAFV
RLIDALRRRGMGAIVDIVPNHMGVGGSSNRWWNDVLEWGARSRFARHFDIDWHASDPALQRKVLLPCLGR
PYGEALAAGDIALRADAAHGRFAIACAGRILPVQIGAYPDILRAANRSDLNALAERFDAPGARPSNHARL
DAAHAALRDYAAARGPGALDAVLHGFDPRIARSREMLHRLLEQQHYRLAWWRIATDEINWRRFFDISTLA
CMRIEDAAVFDDVHALLWRLYAAGLVDGVRIDHVDGLADPRGYCRQLRGRLAALRDGEPYIVVEKILAPD
ERLPEDWRVDGTTGYDFMNDVSALLHDAAGAAPLAALWADMTGAETTFAREALDGKRRVLARQFAAEHER
VARAMHRLARASRDARDFALNPIRRAVAELAIRLPVYRLYPSAGAPQRTDRALLAGAWQAARSAIAPADR
AALDYVAATLGLPGVARAVAGLGDPARLAARVGFAQLTAPLAAKGVEDTACYRYGRLLSRNEVGAHADAL
SLAPGAFHTRNRRRRRTFPGALLATATHDHKRGEDARARLAVLSEAHRAWRAAALDWAAFNAPHHHGAPA
AADRIPGPAAEAMLYQTLVGAWPPALAPDDAPGLAALTDRVERWQLKALREAKRDTDWLEPNLGYEAGCA
AFLRAIMTPRGPDDFAHRLHRLVARIAPAGIVNSLSQAALRLLSPGVPDLYQGAQTWDHTLVDPDNRADV
PFARYAAQRIDAPVAAYLRDWADGRVKHALIGRLLALRAAHPETFAAGAYVPLHVRGTRRGHALAFARRD
ASTTIVVIATRLAYPLLGDAPARPCVEAACWADTAVGLAPGFAGPWRDMLNDGTLDAPSGMLPLAAALAH
LPVAVLIREGGAADTPRRGA (SEQ ID NO: 60)

GroEL
molecular chaperone GroEL [*Burkholderia mallei* ATCC 23344]
NCBI Reference Sequence: YP _103588.1
>YP_103588.1 molecular chaperone GroEL [*Burkholderia mallei* ATCC 23344]
MAAKDVVEGDSARAKMVEGVNILANAVKVTLGPKGRNVVLERSEGGPTVTKDGVSVAKEIELKDKLQNMG
AQMVKEVASKTSDNAGDGTTTATVLAQSIVREGMKYVASGMNPMDLKRGIDKAVAAAVEELKKISKPCTT
NKEIAQVGAISANSDSSIGDRIAEAMDKVGKEGVITVEDGKSLADELDVVEGMQFDRGYLSPYFINNPDK
QVAVLENPFVLLHDKKVSNIRDLLPVLEQVAKAGRPLLIIAEDVEGEALATLVVNNIRGILKTVAVKAPG -continued

SEQUENCES

FGDRRKAMLEDIAILTGGQVIAEETGLTLEKATLAELGQAKRIEVGKENTTIIDGAGEAMNIEARVKQIR
TQIEEATSDYDREKLQERVAKLAGGVAVIKVGAATEVEMKEKKARVEDALHATRAAVEEGIVPGGGVALI
RARTAIASLTGVNADQNAGIKIVLRAMEEPLRQIVTNGGEEASVVVAAVAAGKGNYGYNAATGEYVDMVE
AGVVDPTKVTRTALQNAASVAGLLLTTDAAVAELPKEDAPMPGGMPGGMGGMGMGMGMDM
(SEQ ID NO: 61)

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. An immunogenic composition comprising:
   a recombinant attenuated *Francisella tularensis* subspecies holarctica live vaccine Strain (LVS) having a deleted CapB gene (SEQ ID NO: 1) which comprises a *F. tularensis* promoter that expresses a fusion protein comprising an antigenic polypeptide epitope present in a *Burkholderia pseudomallei* polypeptide;
   wherein:
   the fusion protein expressed by the *F. tularensis* promoter is less than 80 kilodaltons in size; and
   the antigenic polypeptide epitope elicits an immune response in a mammalian host when the immunogenic composition is administered orally, intradermally (i.d.), subcutaneously (s.q.), intramuscularly (i.m.), or intranasally (i.n.) to the mammalian host.

2. The immunogenic composition of claim 1, wherein the antigenic polypeptide epitope is present in a *Burkholderia pseudomallei* polypeptide selected from:
Hcp-1 (SEQ ID NO: 35),
Hcp-2 (SEQ ID NO: 36),
Hcp-3 (SEQ ID NO: 37),
Hcp-4 (SEQ ID NO: 38),
Hcp-6 (SEQ ID NO: 39),
LolC (SEQ ID NO: 40),
TypA (SEQ ID NO: 41),
BipB (SEQ ID NO: 42),
BipC (SEQ ID NO: 43),
BipD (SEQ ID NO: 44),
Omp3 (SEQ ID NO: 45),
Omp7 (SEQ ID NO: 46),
Omp85 (SEQ ID NO: 47),
OmpW (SEQ ID NO: 48),
PotF (SEQ ID NO: 49),
OppA (SEQ ID NO: 50),
BopA (SEQ ID NO: 51),
BimA (SEQ ID NO: 52),
BPSL1897 (SEQ ID NO: 53),
BPSL3369 (SEQ ID NO: 54),
BPSL2287 (SEQ ID NO: 55),
BPSL2765 (SEQ ID NO: 56), and
VgrG5 (SEQ ID NO: 57).

3. The immunogenic composition of claim 1, wherein the *F. tularensis* promoter comprises a bfr promoter (SEQ ID NO: 13) and/or an omp promoter (SEQ ID NO: 14).

4. The immunogenic composition of claim 1, wherein the LVS expresses two or more antigenic polypeptide epitopes present in a *Burkholderia pseudomallei* polypeptide.

5. A method of generating an immune response in a mammal comprising administering the immunogenic composition of claim 1 to the mammal so that an immune response is generated to the antigenic polypeptide epitope present in a *Burkholderia pseudomallei* polypeptide.

6. The method of claim 5, wherein the method comprises administering the immunogenic composition of claim 1 in a primary vaccination; and administering the immunogenic composition of claim 1 in a subsequent homologous booster vaccination.

7. The method of claim 5, wherein the method consists essentially of administering the immunogenic composition of claim 1 in a primary vaccination; and administering the immunogenic composition of claim 1 in a subsequent homologous booster vaccination.

8. The method of claim 6, wherein the method comprises administering the immunogenic composition to the mammal less than 4 times.

9. The method of claim 5, wherein the method comprises administering the composition of claim 1 in a primary vaccination; and administering a second heterologous immunogenic composition comprising the antigenic polypeptide epitope present in a *Burkholderia pseudomallei* polypeptide in a subsequent booster vaccination.

10. The method of claim 9, wherein the second immunogenic composition comprises an attenuated strain of *Listeria monocytogenes* expressing the antigenic polypeptide epitope.

11. The method of claim 1, wherein the fusion protein is less than 50 kilodaltons.

12. The method of claim 10, wherein the method comprises administering the composition of claim 1 and the second immunogenic composition to the mammal less than a total of four times.

13. The method of claim 12 wherein method comprises administering a single dose of the composition of claim 1, and one or more doses of the second immunogenic composition.

14. An immunogenic composition comprising:
    a recombinant attenuated *Francisella tularensis* subspecies holarctica live vaccine Strain (LVS) having a deleted CapB gene (SEQ ID NO: 1) which comprises a *F. tularensis* promoter that expresses a fusion protein comprising an antigenic polypeptide epitope present in a *Burkholderia pseudomallei* polypeptide;
    wherein:
    the *F. tularensis* promoter comprises a bfr promoter (SEQ ID NO: 13);
    the antigenic polypeptide epitope is present in a *Burkholderia pseudomallei* Hcp-6 (SEQ ID NO: 39) polypeptide;
    the fusion protein is less than 80 kilodaltons in size; and
    the antigenic polypeptide epitope elicits an immune response in a mammalian host when the immunogenic composition is administered orally, intradermally (i.d.), subcutaneously (s.q.), intramuscularly (i.m.), or intranasally (i.n.) to the mammalian host.

* * * * *

SEQUENCE LISTING

<160> NUMBER OF SEQ ID NOS: 66

<210> SEQ ID NO 1
<211> LENGTH: 400
<212> TYPE: PRT
<213> ORGANISM: Francisella tularensis

<400> SEQUENCE: 1

```
Met Thr Thr Leu Asp Phe Trp Leu Ile Val Val Phe Val Ile Leu
1               5                   10                  15

Cys Val Tyr Leu Ile Ile Glu Asn Ile Val His Asn Asn Ser Ile Lys
                20                  25                  30

Ser Ile Pro Ile Arg Ile His Asn Gly Thr Arg Gly Lys Ser Ser Val
                35                  40                  45

Ala Arg Leu Ile Ala Ala Gly Val Arg Ala Gly Gly Tyr Arg Thr Val
                50                  55                  60

Ala Lys Thr Thr Gly Thr Leu Ala Arg Tyr Ile Asp Val Asp Gly Ser
65                  70                  75                  80

Glu Thr Pro Val Phe Arg Ile Gly Ser Asn Ile Ala Glu Gln Val Lys
                    85                  90                  95

Ile Met Phe Lys Ala Arg Arg Ala Lys Ala Asp Ala Ile Val Ile Glu
                    100                 105                 110

Cys Met Ala Leu Gln Pro Leu Leu Gln Ser Leu Cys Glu Leu Lys Leu
                    115                 120                 125

Ile Lys Ala Thr His Gly Val Leu Thr Asn Ala Arg Pro Asp His Leu
                    130                 135                 140

Asp Val Met Gly Pro Thr Glu Arg Asp Val Ala Lys Ala Leu Ala Ala
145                 150                 155                 160

Thr Val Pro Val Gly Ala Lys Tyr Phe Thr Ala Glu Asp Ile His Leu
                    165                 170                 175

Asp Phe Phe Glu Tyr Ala Cys Lys Asp Arg Gly Glu Leu Ile Ala Ala
                    180                 185                 190

Thr Ala Gln Asp Ala Glu Lys Ile Ser Asp Glu Glu Ile Asn Lys Phe
                    195                 200                 205

Val Tyr Ser Glu Phe Lys Ile Asn Val Ala Leu Ala Leu Lys Val Ile
                    210                 215                 220

Asp Asp Leu Gly Ile Pro Arg Glu Ile Ala Leu Lys Gly Met Trp Glu
225                 230                 235                 240
```

```
Ala Thr Pro Asp Pro Gly Ala Met Thr Glu Tyr Asn Phe Asn Ile Lys
            245                 250                 255

Ala Glu Ile Asn Phe Ala Asn Ala Phe Ala Ala Asn Asp Pro Val Ser
            260                 265                 270

Thr Lys Met Leu Trp Asp Lys Leu Cys Ala Lys Tyr Ser Gly Cys Asp
            275                 280                 285

Lys Lys Val Leu Val Val Asn Cys Arg Asp Asp Arg Glu Asp Arg Ser
            290                 295                 300

Lys Gln Met Ala Glu Ala Leu Gly Trp Gln Lys Gln Asp Leu Ile
305                 310                 315                 320

Val Leu Ile Gly Thr Gly Thr Glu Val Phe Thr Ser Phe Tyr Lys Tyr
            325                 330                 335

Ala Lys Ser Leu Asn Lys Pro Met Thr Lys Val Ile Val Cys Glu Glu
            340                 345                 350

Met Thr Pro Ile Gln Ile Leu Glu Lys Thr Val Asp Ser Asn Pro Ala
            355                 360                 365

Asn Ser Tyr Ile Leu Val Gly Val Gly Asn Ile Lys Asp Ile Gly Met
            370                 375                 380

Glu Leu Val Asp Tyr Cys Asp Thr Ser His Lys Lys His Asn Leu
385                 390                 395                 400

<210> SEQ ID NO 2
<211> LENGTH: 196
<212> TYPE: PRT
<213> ORGANISM: Francisella tularensis

<400> SEQUENCE: 2

Met Leu Ile Arg Cys Cys Glu Lys Lys Asp Asn Lys Met Ala Lys Asn
1               5                   10                  15

Lys Ile Pro Asn Ser Arg Leu Met Ile Asn Tyr Glu Thr Asn Val Asp
            20                  25                  30

Gly Val Leu Lys Lys Lys Glu Leu Pro Tyr Arg Val Leu Val Val Gly
            35                  40                  45

Asp Leu Ser Lys Gly Arg Ser Val Asp Ala Lys Lys Glu Phe Ala Asp
        50                  55                  60

Arg Glu Val Arg Arg Val Asn Asn Gly Val Asp Arg Val Leu Glu Glu
65                  70                  75                  80

Met Asn Ile Ser Phe Asp Phe Glu Ala Pro Asn Phe Val Ser Lys Asp
                85                  90                  95

Arg Ser Asn Leu Lys Val Asn Tyr Arg Ile Glu Ser Val Lys Asp Phe
            100                 105                 110

Arg Pro Asp Ala Val Ala Lys Lys Val Pro Glu Ile Arg Ala Leu Leu
            115                 120                 125

Glu Met Lys Glu Ile Leu Ala Ser Phe Ala Lys Asp Ile Glu Asn Asn
        130                 135                 140

Arg Asn Leu Lys Lys Thr Ile Asp Met Ile Phe Ser Asp Ser Asn Glu
145                 150                 155                 160

Leu Glu Ser Leu Lys Ser Lys Ile Pro Ala Leu Thr Asn Tyr Thr Ile
                165                 170                 175

Lys Asp Ser Cys Asp Ala Ala Glu Ser Gln Asp Leu Ser Asn Gln Gln
            180                 185                 190

Val Asp Gly Lys
            195

<210> SEQ ID NO 3
```

<211> LENGTH: 514
<212> TYPE: PRT
<213> ORGANISM: Francisella tularensis

<400> SEQUENCE: 3

| | | | | | | | | | | | | | | |
|---|---|---|---|---|---|---|---|---|---|---|---|---|---|---|
| Met | Val | Ser | Arg | Glu | Asp | Phe | Ile | Met | Thr | Ile | Asn | Lys | Leu | Ser | Leu |
| 1 | | | | 5 | | | | | 10 | | | | | 15 | |

| Thr | Asp | Glu | Leu | Leu | Asn | Asn | Phe | Gly | Gly | Ser | Thr | Glu | Val | Asp | Ser |
| | | | 20 | | | | | 25 | | | | | 30 | | |

| Val | Leu | Lys | Asn | Ile | Asp | Phe | Asp | Val | Ser | Asp | Asp | Ala | Ser | Lys | Val |
| | | | 35 | | | | | 40 | | | | | 45 | | |

| Leu | Ser | Leu | Ser | Thr | Asp | Tyr | Asn | Ala | Arg | Asn | Leu | Met | Ala | Leu | Ser |
| | 50 | | | | | 55 | | | | | 60 | | | | |

| Leu | Val | Leu | Ala | Asn | Asn | Asp | Asn | Ile | Asn | Asn | Tyr | Asn | Gln | Lys | Tyr |
| 65 | | | | | 70 | | | | | 75 | | | | | 80 |

| Ile | Gln | Lys | Val | Ile | Thr | Val | Ile | Asp | Lys | Leu | Ile | Asp | Leu | Gln | Val |
| | | | | 85 | | | | | 90 | | | | | 95 | |

| Asn | Ser | Ile | Ile | Ser | Asn | Asp | Glu | Phe | Arg | Ala | Leu | Glu | Gln | Glu | Trp |
| | | | 100 | | | | | 105 | | | | | 110 | | |

| Leu | Lys | Val | Gln | Glu | Val | Cys | Gln | Glu | Asp | Tyr | Asp | Asn | Val | Glu | Val |
| | | 115 | | | | | 120 | | | | | 125 | | | |

| Ser | Ile | Leu | Asp | Val | Lys | Lys | Glu | Leu | Gln | Tyr | Asp | Phe | Glu | Arg |
| | 130 | | | | | 135 | | | | | 140 | | | | |

| Asn | Leu | Tyr | Asp | Ile | Ser | Ser | Asp | Phe | Phe | Lys | Lys | Val | Tyr | Val |
| 145 | | | | | 150 | | | | | 155 | | | | | 160 |

| Ser | Glu | Phe | Asp | Gln | Tyr | Gly | Gly | Glu | Pro | Tyr | Gly | Ala | Ile | Leu | Gly |
| | | | | 165 | | | | | 170 | | | | | 175 | |

| Leu | Tyr | Asn | Phe | Glu | Asn | Thr | Thr | Asn | Asp | Ile | Ile | Trp | Leu | Thr | Gly |
| | | | 180 | | | | | 185 | | | | | 190 | | |

| Met | Gly | Met | Val | Ala | Lys | Asn | Ser | His | Ala | Pro | Phe | Ile | Ala | Ser | Ile |
| | | 195 | | | | | 200 | | | | | 205 | | | |

| Asp | Lys | Ser | Phe | Phe | Gly | Val | Lys | Asp | Leu | Ser | Glu | Ile | Thr | His | Ile |
| | 210 | | | | | 215 | | | | | 220 | | | | |

| Lys | Ser | Phe | Glu | Ala | Leu | Leu | Glu | His | Pro | Arg | Tyr | Lys | Glu | Trp | Asn |
| 225 | | | | | 230 | | | | | 235 | | | | | 240 |

| Asp | Phe | Arg | Asn | Leu | Asp | Val | Ala | Ala | Tyr | Ile | Gly | Leu | Thr | Val | Gly |
| | | | | 245 | | | | | 250 | | | | | 255 | |

| Asp | Phe | Met | Leu | Arg | Gln | Pro | Tyr | Asn | Pro | Glu | Asn | Asn | Pro | Val | Gln |
| | | | 260 | | | | | 265 | | | | | 270 | | |

| Tyr | Lys | Leu | Met | Glu | Gly | Phe | Asn | Glu | Phe | Val | Asp | Tyr | Asp | Lys | Asn |
| | | 275 | | | | | 280 | | | | | 285 | | | |

| Glu | Ser | Tyr | Leu | Trp | Gly | Pro | Ala | Ser | Ile | His | Leu | Val | Lys | Asn | Met |
| | 290 | | | | | 295 | | | | | 300 | | | | |

| Met | Arg | Ser | Tyr | Asp | Lys | Thr | Arg | Trp | Phe | Gln | Tyr | Ile | Arg | Gly | Val |
| 305 | | | | | 310 | | | | | 315 | | | | | 320 |

| Glu | Ser | Gly | Gly | Tyr | Val | Lys | Asn | Leu | Val | Ala | Cys | Val | Tyr | Asp | Asn |
| | | | | 325 | | | | | 330 | | | | | 335 | |

| Lys | Gly | Ile | Leu | Glu | Thr | Lys | Ser | Pro | Leu | Asn | Val | Leu | Phe | Ala | Asp |
| | | | 340 | | | | | 345 | | | | | 350 | | |

| Tyr | Met | Glu | Leu | Ser | Leu | Ala | Asn | Ile | Gly | Leu | Ile | Pro | Phe | Val | Ser |
| | | 355 | | | | | 360 | | | | | 365 | | | |

| Glu | Lys | Gly | Thr | Ser | Asn | Ala | Cys | Phe | Phe | Ser | Val | Asn | Ser | Ala | Lys |
| | 370 | | | | | 375 | | | | | 380 | | | | |

| Lys | Val | Glu | Glu | Phe | Val | Asp | Gly | Phe | Asp | Ser | Ala | Asn | Ser | Arg | Leu |

```
                385                 390                 395                 400
Ile Ala Asn Leu Ser Tyr Thr Met Cys Ile Ser Arg Ile Ser His Tyr
                    405                 410                 415
Ile Lys Cys Val Ile Arg Asp Lys Ile Gly Ser Ile Val Asp Val Glu
                420                 425                 430
Ser Ile Gln Lys Ile Leu Ser Asp Trp Ile Ser Glu Phe Val Thr Thr
                435                 440                 445
Val Tyr Gln Pro Thr Pro Leu Glu Met Ala Arg Tyr Pro Phe Arg Asn
            450                 455                 460
Val Ser Ile Glu Val Glu Thr Ile Pro Gly Lys Pro Gly Trp Tyr Ser
465                 470                 475                 480
Cys Lys Ile Asn Val Ile Pro His Ile Gln Phe Gly Met Asn Thr
                    485                 490                 495
Thr Met Thr Ile Asp Thr Arg Leu Glu Pro Glu Leu Phe Gly Thr Asn
                500                 505                 510
Asn Asn

<210> SEQ ID NO 4
<211> LENGTH: 211
<212> TYPE: PRT
<213> ORGANISM: Francisella tularensis

<400> SEQUENCE: 4

Met Ile Met Ser Glu Met Ile Thr Arg Gln Gln Val Thr Ser Gly Glu
1               5                   10                  15
Thr Ile His Val Arg Thr Asp Pro Thr Ala Cys Ile Gly Ser His Pro
                20                  25                  30
Asn Cys Arg Leu Phe Ile Asp Ser Leu Thr Ile Ala Gly Glu Lys Leu
            35                  40                  45
Asp Lys Asn Ile Val Ala Ile Asp Gly Gly Glu Asp Val Thr Lys Ala
        50                  55                  60
Asp Ser Ala Thr Ala Ala Ala Ser Val Ile Arg Leu Ser Ile Thr Pro
65                  70                  75                  80
Gly Ser Ile Asn Pro Thr Ile Ser Ile Thr Leu Gly Val Leu Ile Lys
                85                  90                  95
Ser Asn Val Arg Thr Lys Ile Glu Lys Val Ser Ser Ile Leu Gln
                100                 105                 110
Ala Ser Ala Thr Asp Met Lys Ile Lys Leu Gly Asn Ser Asn Lys Lys
            115                 120                 125
Gln Glu Tyr Lys Thr Asp Glu Ala Trp Gly Ile Met Ile Asp Leu Ser
        130                 135                 140
Asn Leu Glu Leu Tyr Pro Ile Ser Ala Lys Ala Phe Ser Ile Ser Ile
145                 150                 155                 160
Glu Pro Thr Glu Leu Met Gly Val Ser Lys Asp Gly Met Arg Tyr His
                165                 170                 175
Ile Ile Ser Ile Asp Gly Leu Thr Thr Ser Gln Gly Ser Leu Pro Val
                180                 185                 190
Cys Cys Ala Ala Ser Thr Asp Lys Gly Val Ala Lys Ile Gly Tyr Ile
            195                 200                 205
Ala Ala Ala
        210

<210> SEQ ID NO 5
<211> LENGTH: 809
<212> TYPE: PRT
```

<213> ORGANISM: Bacillus anthracis

<400> SEQUENCE: 5

| | | | | | | | | | | | | | | | |
|---|---|---|---|---|---|---|---|---|---|---|---|---|---|---|---|
| Met | Asn | Ile | Lys | Lys | Glu | Phe | Ile | Lys | Val | Ile | Ser | Met | Ser | Cys | Leu |
| 1 | | | | 5 | | | | | 10 | | | | | 15 | |
| Val | Thr | Ala | Ile | Thr | Leu | Ser | Gly | Pro | Val | Phe | Ile | Pro | Leu | Val | Gln |
| | | | 20 | | | | | 25 | | | | | 30 | | |
| Gly | Ala | Gly | Gly | His | Gly | Asp | Val | Gly | Met | His | Val | Lys | Glu | Lys | Glu |
| | | | 35 | | | | | 40 | | | | | 45 | | |
| Lys | Asn | Lys | Asp | Glu | Asn | Lys | Arg | Lys | Asp | Glu | Glu | Arg | Asn | Lys | Thr |
| | | 50 | | | | | 55 | | | | | 60 | | | |
| Gln | Glu | Glu | His | Leu | Lys | Glu | Ile | Met | Lys | His | Ile | Val | Lys | Ile | Glu |
| 65 | | | | | 70 | | | | | 75 | | | | | 80 |
| Val | Lys | Gly | Glu | Glu | Ala | Val | Lys | Lys | Glu | Ala | Ala | Glu | Lys | Leu | Leu |
| | | | | 85 | | | | | 90 | | | | | 95 | |
| Glu | Lys | Val | Pro | Ser | Asp | Val | Leu | Glu | Met | Tyr | Lys | Ala | Ile | Gly | Gly |
| | | | 100 | | | | | 105 | | | | | 110 | | |
| Lys | Ile | Tyr | Ile | Val | Asp | Gly | Asp | Ile | Thr | Lys | His | Ile | Ser | Leu | Glu |
| | | | 115 | | | | | 120 | | | | | 125 | | |
| Ala | Leu | Ser | Glu | Asp | Lys | Lys | Ile | Lys | Asp | Ile | Tyr | Gly | Lys | Asp |
| | 130 | | | | | 135 | | | | | 140 | | | | |
| Ala | Leu | Leu | His | Glu | His | Tyr | Val | Tyr | Ala | Lys | Glu | Gly | Tyr | Glu | Pro |
| 145 | | | | | 150 | | | | | 155 | | | | | 160 |
| Val | Leu | Val | Ile | Gln | Ser | Ser | Glu | Asp | Tyr | Val | Glu | Asn | Thr | Glu | Lys |
| | | | | 165 | | | | | 170 | | | | | 175 | |
| Ala | Leu | Asn | Val | Tyr | Tyr | Glu | Ile | Gly | Lys | Ile | Leu | Ser | Arg | Asp | Ile |
| | | | 180 | | | | | 185 | | | | | 190 | | |
| Leu | Ser | Lys | Ile | Asn | Gln | Pro | Tyr | Gln | Lys | Phe | Leu | Asp | Val | Leu | Asn |
| | | | 195 | | | | | 200 | | | | | 205 | | |
| Thr | Ile | Lys | Asn | Ala | Ser | Asp | Ser | Asp | Gly | Gln | Asp | Leu | Leu | Phe | Thr |
| | 210 | | | | | 215 | | | | | 220 | | | | |
| Asn | Gln | Leu | Lys | Glu | His | Pro | Thr | Asp | Phe | Ser | Val | Glu | Phe | Leu | Glu |
| 225 | | | | | 230 | | | | | 235 | | | | | 240 |
| Gln | Asn | Ser | Asn | Glu | Val | Gln | Glu | Val | Phe | Ala | Lys | Ala | Phe | Ala | Tyr |
| | | | | 245 | | | | | 250 | | | | | 255 | |
| Tyr | Ile | Glu | Pro | Gln | His | Arg | Asp | Val | Leu | Gln | Leu | Tyr | Ala | Pro | Glu |
| | | | 260 | | | | | 265 | | | | | 270 | | |
| Ala | Phe | Asn | Tyr | Met | Asp | Lys | Phe | Asn | Glu | Gln | Glu | Ile | Asn | Leu | Ser |
| | | | 275 | | | | | 280 | | | | | 285 | | |
| Leu | Glu | Glu | Leu | Lys | Asp | Gln | Arg | Met | Leu | Ser | Arg | Tyr | Glu | Lys | Trp |
| | 290 | | | | | 295 | | | | | 300 | | | | |
| Glu | Lys | Ile | Lys | Gln | His | Tyr | Gln | His | Trp | Ser | Asp | Ser | Leu | Ser | Glu |
| 305 | | | | | 310 | | | | | 315 | | | | | 320 |
| Glu | Gly | Arg | Gly | Leu | Leu | Lys | Lys | Leu | Gln | Ile | Pro | Ile | Glu | Pro | Lys |
| | | | | 325 | | | | | 330 | | | | | 335 | |
| Lys | Asp | Asp | Ile | Ile | His | Ser | Leu | Ser | Gln | Glu | Glu | Lys | Glu | Leu | Leu |
| | | | 340 | | | | | 345 | | | | | 350 | | |
| Lys | Arg | Ile | Gln | Ile | Asp | Ser | Ser | Asp | Phe | Leu | Ser | Thr | Glu | Glu | Lys |
| | | | 355 | | | | | 360 | | | | | 365 | | |
| Glu | Phe | Leu | Lys | Lys | Leu | Gln | Ile | Asp | Ile | Arg | Asp | Ser | Leu | Ser | Glu |
| | 370 | | | | | 375 | | | | | 380 | | | | |
| Glu | Glu | Lys | Glu | Leu | Leu | Asn | Arg | Ile | Gln | Val | Asp | Ser | Ser | Asn | Pro |
| 385 | | | | | 390 | | | | | 395 | | | | | 400 |

-continued

```
Leu Ser Glu Lys Glu Lys Glu Phe Leu Lys Lys Leu Lys Leu Asp Ile
            405                 410                 415
Gln Pro Tyr Asp Ile Asn Gln Arg Leu Gln Asp Thr Gly Gly Leu Ile
        420                 425                 430
Asp Ser Pro Ser Ile Asn Leu Asp Val Arg Lys Gln Tyr Lys Arg Asp
    435                 440                 445
Ile Gln Asn Ile Asp Ala Leu Leu His Gln Ser Ile Gly Ser Thr Leu
450                 455                 460
Tyr Asn Lys Ile Tyr Leu Tyr Glu Asn Met Asn Ile Asn Asn Leu Thr
465                 470                 475                 480
Ala Thr Leu Gly Ala Asp Leu Val Asp Ser Thr Asp Asn Thr Lys Ile
                485                 490                 495
Asn Arg Gly Ile Phe Asn Glu Phe Lys Lys Asn Phe Lys Tyr Ser Ile
            500                 505                 510
Ser Ser Asn Tyr Met Ile Val Asp Ile Asn Glu Arg Pro Ala Leu Asp
        515                 520                 525
Asn Glu Arg Leu Lys Trp Arg Ile Gln Leu Ser Pro Asp Thr Arg Ala
    530                 535                 540
Gly Tyr Leu Glu Asn Gly Lys Leu Ile Leu Gln Arg Asn Ile Gly Leu
545                 550                 555                 560
Glu Ile Lys Asp Val Gln Ile Ile Lys Gln Ser Glu Lys Glu Tyr Ile
                565                 570                 575
Arg Ile Asp Ala Lys Val Val Pro Lys Ser Lys Ile Asp Thr Lys Ile
            580                 585                 590
Gln Glu Ala Gln Leu Asn Ile Asn Gln Glu Trp Asn Lys Ala Leu Gly
        595                 600                 605
Leu Pro Lys Tyr Thr Lys Leu Ile Thr Phe Asn Val His Asn Arg Tyr
    610                 615                 620
Ala Ser Asn Ile Val Glu Ser Ala Tyr Leu Ile Leu Asn Glu Trp Lys
625                 630                 635                 640
Asn Asn Ile Gln Ser Asp Leu Ile Lys Lys Val Thr Asn Tyr Leu Val
                645                 650                 655
Asp Gly Asn Gly Arg Phe Val Phe Thr Asp Ile Thr Leu Pro Asn Ile
            660                 665                 670
Ala Glu Gln Tyr Thr His Gln Asp Glu Ile Tyr Glu Gln Val His Ser
        675                 680                 685
Lys Gly Leu Tyr Val Pro Glu Ser Arg Ser Ile Leu Leu His Gly Pro
    690                 695                 700
Ser Lys Gly Val Glu Leu Arg Asn Asp Ser Glu Gly Phe Ile His Glu
705                 710                 715                 720
Phe Gly His Ala Val Asp Asp Tyr Ala Gly Tyr Leu Leu Asp Lys Asn
                725                 730                 735
Gln Ser Asp Leu Val Thr Asn Ser Lys Lys Phe Ile Asp Ile Phe Lys
            740                 745                 750
Glu Glu Gly Ser Asn Leu Thr Ser Tyr Gly Arg Thr Asn Glu Ala Glu
        755                 760                 765
Phe Phe Ala Glu Ala Phe Arg Leu Met His Ser Thr Asp His Ala Glu
    770                 775                 780
Arg Leu Lys Val Gln Lys Asn Ala Pro Lys Thr Phe Gln Phe Ile Asn
785                 790                 795                 800
Asp Gln Ile Lys Phe Ile Ile Asn Ser
                805
```

<210> SEQ ID NO 6
<211> LENGTH: 764
<212> TYPE: PRT
<213> ORGANISM: Bacillus anthracis

<400> SEQUENCE: 6

| Met | Lys | Lys | Arg | Lys | Val | Leu | Ile | Pro | Leu | Met | Ala | Leu | Ser | Thr | Ile |
|---|---|---|---|---|---|---|---|---|---|---|---|---|---|---|---|
| 1 | | | | 5 | | | | | 10 | | | | | 15 | |

| Leu | Val | Ser | Ser | Thr | Gly | Asn | Leu | Glu | Val | Ile | Gln | Ala | Glu | Val | Lys |
| | | | 20 | | | | | 25 | | | | | 30 | | |

| Gln | Glu | Asn | Arg | Leu | Leu | Asn | Glu | Ser | Glu | Ser | Ser | Gln | Gly | Leu |
| | | | 35 | | | | | 40 | | | | | 45 | | |

| Leu | Gly | Tyr | Tyr | Phe | Ser | Asp | Leu | Asn | Phe | Gln | Ala | Pro | Met | Val | Val |
| | 50 | | | | | 55 | | | | | 60 | | | | |

| Thr | Ser | Ser | Thr | Thr | Gly | Asp | Leu | Ser | Ile | Pro | Ser | Ser | Glu | Leu | Glu |
| 65 | | | | | 70 | | | | | 75 | | | | | 80 |

| Asn | Ile | Pro | Ser | Glu | Asn | Gln | Tyr | Phe | Gln | Ser | Ala | Ile | Trp | Ser | Gly |
| | | | | 85 | | | | | 90 | | | | | 95 | |

| Phe | Ile | Lys | Val | Lys | Lys | Ser | Asp | Glu | Tyr | Thr | Phe | Ala | Thr | Ser | Ala |
| | | | 100 | | | | | 105 | | | | | 110 | | |

| Asp | Asn | His | Val | Thr | Met | Trp | Val | Asp | Gln | Glu | Val | Ile | Asn | Lys |
| | | 115 | | | | | 120 | | | | | 125 | | | |

| Ala | Ser | Asn | Ser | Asn | Lys | Ile | Arg | Leu | Glu | Lys | Gly | Arg | Leu | Tyr | Gln |
| | 130 | | | | | 135 | | | | | 140 | | | | |

| Ile | Lys | Ile | Gln | Tyr | Gln | Arg | Glu | Asn | Pro | Thr | Glu | Lys | Gly | Leu | Asp |
| 145 | | | | | 150 | | | | | 155 | | | | | 160 |

| Phe | Lys | Leu | Tyr | Trp | Thr | Asp | Ser | Gln | Asn | Lys | Lys | Glu | Val | Ile | Ser |
| | | | | 165 | | | | | 170 | | | | | 175 | |

| Ser | Asp | Asn | Leu | Gln | Leu | Pro | Glu | Leu | Lys | Gln | Lys | Ser | Ser | Asn | Ser |
| | | | 180 | | | | | 185 | | | | | 190 | | |

| Arg | Lys | Lys | Arg | Ser | Thr | Ser | Ala | Gly | Pro | Thr | Val | Pro | Asp | Arg | Asp |
| | | 195 | | | | | 200 | | | | | 205 | | | |

| Asn | Asp | Gly | Ile | Pro | Asp | Ser | Leu | Glu | Val | Glu | Gly | Tyr | Thr | Val | Asp |
| | 210 | | | | | 215 | | | | | 220 | | | | |

| Val | Lys | Asn | Lys | Arg | Thr | Phe | Leu | Ser | Pro | Trp | Ile | Ser | Asn | Ile | His |
| 225 | | | | | 230 | | | | | 235 | | | | | 240 |

| Glu | Lys | Lys | Gly | Leu | Thr | Lys | Tyr | Lys | Ser | Ser | Pro | Glu | Lys | Trp | Ser |
| | | | | 245 | | | | | 250 | | | | | 255 | |

| Thr | Ala | Ser | Asp | Pro | Tyr | Ser | Asp | Phe | Glu | Lys | Val | Thr | Gly | Arg | Ile |
| | | | 260 | | | | | 265 | | | | | 270 | | |

| Asp | Lys | Asn | Val | Ser | Pro | Glu | Ala | Arg | His | Pro | Leu | Val | Ala | Ala | Tyr |
| | | 275 | | | | | 280 | | | | | 285 | | | |

| Pro | Ile | Val | His | Val | Asp | Met | Glu | Asn | Ile | Ile | Leu | Ser | Lys | Asn | Glu |
| | 290 | | | | | 295 | | | | | 300 | | | | |

| Asp | Gln | Ser | Thr | Gln | Asn | Thr | Asp | Ser | Glu | Thr | Arg | Thr | Ile | Ser | Lys |
| 305 | | | | | 310 | | | | | 315 | | | | | 320 |

| Asn | Thr | Ser | Thr | Ser | Arg | Thr | His | Thr | Ser | Glu | Val | His | Gly | Asn | Ala |
| | | | | 325 | | | | | 330 | | | | | 335 | |

| Glu | Val | His | Ala | Ser | Phe | Phe | Asp | Ile | Gly | Gly | Ser | Val | Ser | Ala | Gly |
| | | | 340 | | | | | 345 | | | | | 350 | | |

| Phe | Ser | Asn | Ser | Asn | Ser | Ser | Thr | Val | Ala | Ile | Asp | His | Ser | Leu | Ser |
| | | | 355 | | | | | 360 | | | | | 365 | | |

| Leu | Ala | Gly | Glu | Arg | Thr | Trp | Ala | Glu | Thr | Met | Gly | Leu | Asn | Thr | Ala |
| | 370 | | | | | 375 | | | | | 380 | | | | |

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
            405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
            485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
            565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
            645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
            675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
            725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
            755                 760

<210> SEQ ID NO 7
<211> LENGTH: 187
<212> TYPE: PRT
<213> ORGANISM: Bacillus anthracis

<400> SEQUENCE: 7

```
Met Leu Leu Ile Gly Thr Glu Val Lys Pro Phe Lys Ala Asn Ala Tyr
1               5                   10                  15

His Asn Gly Glu Phe Ile Gln Val Thr Asp Glu Ser Leu Lys Gly Lys
            20                  25                  30

Trp Ser Val Val Cys Phe Tyr Pro Ala Asp Phe Thr Phe Val Cys Pro
            35                  40                  45

Thr Glu Leu Glu Asp Leu Gln Asn Gln Tyr Ala Thr Leu Lys Glu Leu
50                  55                  60

Gly Val Glu Val Tyr Ser Val Ser Thr Asp Thr His Phe Thr His Lys
65                  70                  75                  80

Ala Trp His Asp Ser Ser Glu Thr Ile Gly Lys Ile Glu Tyr Ile Met
                85                  90                  95

Ile Gly Asp Pro Thr Arg Thr Ile Thr Thr Asn Phe Asn Val Leu Met
                100                 105                 110

Glu Glu Glu Gly Leu Ala Ala Arg Gly Thr Phe Ile Ile Asp Pro Asp
            115                 120                 125

Gly Val Ile Gln Ser Met Glu Ile Asn Ala Asp Gly Ile Gly Arg Asp
130                 135                 140

Ala Ser Ile Leu Val Asn Lys Ile Lys Ala Ala Gln Tyr Val Arg Asn
145                 150                 155                 160

Asn Pro Gly Glu Val Cys Pro Ala Lys Trp Gln Glu Gly Ser Ala Thr
                165                 170                 175

Leu Lys Pro Ser Leu Asp Leu Val Gly Lys Ile
                180                 185

<210> SEQ ID NO 8
<211> LENGTH: 170
<212> TYPE: PRT
<213> ORGANISM: Yersinia pestis

<400> SEQUENCE: 8

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
                100                 105                 110

Asp Ser Arg Asp Phe Asp Ile Ser Pro Lys Val Asn Gly Glu Asn Leu
            115                 120                 125

Val Gly Asp Asp Val Val Leu Ala Thr Gly Ser Gln Asp Phe Phe Val
130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170
```

<210> SEQ ID NO 9
<211> LENGTH: 326
<212> TYPE: PRT
<213> ORGANISM: Yersinia pestis

<400> SEQUENCE: 9

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 10
<211> LENGTH: 87
<212> TYPE: PRT
<213> ORGANISM: Yersinia pestis

<400> SEQUENCE: 10

Met Ser Asn Phe Ser Gly Phe Thr Lys Gly Thr Asp Ile Ala Asp Leu

```
                1               5                   10                  15
Asp Ala Val Ala Gln Thr Leu Lys Lys Pro Ala Asp Asp Ala Asn Lys
                    20                  25                  30

Ala Val Asn Asp Ser Ile Ala Ala Leu Lys Asp Lys Pro Asp Asn Pro
                    35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                    85

<210> SEQ ID NO 11
<211> LENGTH: 219
<212> TYPE: PRT
<213> ORGANISM: Yersinia pestis

<400> SEQUENCE: 11

Met Lys Ile Ser Ser Phe Ile Ser Thr Ser Leu Pro Leu Pro Thr Ser
1               5                   10                  15

Val Ser Gly Ser Ser Val Gly Glu Met Ser Gly Arg Ser Val Ser
                    20                  25                  30

Gln Gln Thr Ser Asp Gln Tyr Ala Asn Asn Leu Ala Gly Arg Thr Glu
                    35                  40                  45

Ser Pro Gln Gly Ser Ser Leu Ala Ser Arg Ile Ile Glu Arg Leu Ser
    50                  55                  60

Ser Val Ala His Ser Val Ile Gly Phe Ile Gln Arg Met Phe Ser Glu
65                  70                  75                  80

Gly Ser His Lys Pro Val Val Thr Pro Ala Pro Thr Pro Ala Gln Met
                    85                  90                  95

Pro Ser Pro Thr Ser Phe Ser Asp Ser Ile Lys Gln Leu Ala Ala Glu
                    100                 105                 110

Thr Leu Pro Lys Tyr Met Gln Gln Leu Asn Ser Leu Asp Ala Glu Met
                    115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                    165                 170                 175

Pro Phe Ser Gln Trp Gly Thr Ile Gly Gly Ala Ala Ser Ala Tyr Val
                    180                 185                 190

Ala Ser Gly Val Asp Leu Thr Gln Ala Ala Asn Glu Ile Lys Gly Leu
                    195                 200                 205

Ala Gln Gln Met Gln Lys Leu Leu Ser Leu Met
    210                 215

<210> SEQ ID NO 12
<211> LENGTH: 673
<212> TYPE: PRT
<213> ORGANISM: Yersinia pestis

<400> SEQUENCE: 12

Met Lys Met Thr Arg Leu Tyr Pro Leu Ala Leu Gly Gly Leu Leu Leu
1               5                   10                  15

Pro Ala Ile Ala Asn Ala Gln Thr Ser Gln Gln Asp Glu Ser Thr Leu
```

-continued

```
                 20                  25                  30
Val Val Thr Ala Ser Lys Gln Ser Arg Ala Ser Ala Asn Asn
             35                  40                  45
Val Ser Ser Thr Val Val Ser Ala Pro Glu Leu Ser Asp Ala Gly Val
         50                  55                  60
Thr Ala Ser Asp Lys Leu Pro Arg Val Leu Pro Gly Leu Asn Ile Glu
 65                  70                  75                  80
Asn Ser Gly Asn Met Leu Phe Ser Thr Ile Ser Leu Arg Gly Val Ser
                 85                  90                  95
Ser Ala Gln Asp Phe Tyr Asn Pro Ala Val Thr Leu Tyr Val Asp Gly
                100                 105                 110
Val Pro Gln Leu Ser Thr Asn Thr Ile Gln Ala Leu Thr Asp Val Gln
                115                 120                 125
Ser Val Glu Leu Leu Arg Gly Pro Gln Gly Thr Leu Tyr Gly Lys Ser
                130                 135                 140
Ala Gln Gly Gly Ile Ile Asn Ile Val Thr Gln Gln Pro Asp Ser Thr
145                 150                 155                 160
Pro Arg Gly Tyr Ile Glu Gly Gly Val Ser Ser Arg Asp Ser Tyr Arg
                165                 170                 175
Ser Lys Phe Asn Leu Ser Gly Pro Ile Gln Asp Gly Leu Leu Tyr Gly
                180                 185                 190
Ser Val Thr Leu Leu Arg Gln Val Asp Asp Gly Asp Met Ile Asn Pro
                195                 200                 205
Ala Thr Gly Ser Asp Asp Leu Gly Gly Thr Arg Ala Ser Ile Gly Asn
                210                 215                 220
Val Lys Leu Arg Leu Ala Pro Asp Asp Gln Pro Trp Glu Met Gly Phe
225                 230                 235                 240
Ala Ala Ser Arg Glu Cys Thr Arg Ala Thr Gln Asp Ala Tyr Val Gly
                245                 250                 255
Trp Asn Asp Ile Lys Gly Arg Lys Leu Ser Ile Ser Asp Gly Ser Pro
                260                 265                 270
Asp Pro Tyr Met Arg Arg Cys Thr Asp Ser Gln Thr Leu Ser Gly Lys
                275                 280                 285
Tyr Thr Thr Asp Asp Trp Val Phe Asn Leu Ile Ser Ala Trp Gln Gln
                290                 295                 300
Gln His Tyr Ser Arg Thr Phe Pro Ser Gly Ser Leu Ile Val Asn Met
305                 310                 315                 320
Pro Gln Arg Trp Asn Gln Asp Val Gln Glu Leu Arg Ala Ala Thr Leu
                325                 330                 335
Gly Asp Ala Arg Thr Val Asp Met Val Phe Gly Leu Tyr Arg Gln Asn
                340                 345                 350
Thr Arg Glu Lys Leu Asn Ser Ala Tyr Asp Met Pro Thr Met Pro Tyr
                355                 360                 365
Leu Ser Ser Thr Gly Tyr Thr Thr Ala Glu Thr Leu Ala Ala Tyr Ser
                370                 375                 380
Asp Leu Thr Trp His Leu Thr Asp Arg Phe Asp Ile Gly Gly Gly Val
385                 390                 395                 400
Arg Phe Ser His Asp Lys Ser Thr Gln Tyr His Gly Ser Met Leu
                405                 410                 415
Gly Asn Pro Phe Gly Asp Gln Gly Lys Ser Asn Asp Asp Gln Val Leu
                420                 425                 430
Gly Gln Leu Ser Ala Gly Tyr Met Leu Thr Asp Asp Trp Arg Val Tyr
                435                 440                 445
```

Thr Arg Val Ala Gln Gly Tyr Lys Pro Ser Gly Tyr Asn Ile Val Pro
    450                 455                 460

Thr Ala Gly Leu Asp Ala Lys Pro Phe Val Ala Glu Lys Ser Ile Asn
465                 470                 475                 480

Tyr Glu Leu Gly Thr Arg Tyr Glu Thr Ala Asp Val Thr Leu Gln Ala
                485                 490                 495

Ala Thr Phe Tyr Thr His Thr Lys Asp Met Gln Leu Tyr Ser Gly Pro
            500                 505                 510

Val Arg Met Gln Thr Leu Ser Asn Ala Gly Lys Ala Asp Ala Thr Gly
        515                 520                 525

Val Glu Leu Glu Ala Lys Trp Arg Phe Ala Pro Gly Trp Ser Trp Asp
    530                 535                 540

Ile Asn Gly Asn Val Ile Arg Ser Glu Phe Thr Asn Asp Ser Glu Leu
545                 550                 555                 560

Tyr His Gly Asn Arg Val Pro Phe Val Pro Arg Tyr Gly Ala Gly Ser
                565                 570                 575

Ser Val Asn Gly Val Ile Asp Thr Arg Tyr Gly Ala Leu Met Pro Arg
            580                 585                 590

Leu Ala Val Asn Leu Val Gly Pro His Tyr Phe Asp Gly Asp Asn Gln
        595                 600                 605

Leu Arg Gln Gly Thr Tyr Ala Thr Leu Asp Ser Ser Leu Gly Trp Gln
    610                 615                 620

Ala Thr Glu Arg Met Asn Ile Ser Val Tyr Val Asp Asn Leu Phe Asp
625                 630                 635                 640

Arg Arg Tyr Arg Thr Tyr Gly Tyr Met Asn Gly Ser Ser Ala Val Ala
                645                 650                 655

Gln Val Asn Met Gly Arg Thr Val Gly Ile Asn Thr Arg Ile Asp Phe
            660                 665                 670

Phe

<210> SEQ ID NO 13
<211> LENGTH: 289
<212> TYPE: DNA
<213> ORGANISM: Francisella tularensis

<400> SEQUENCE: 13
ttgttacctc cattatttaa aactctaatc attataatca acatactaac tagtataatt    60
catattagca atcaagttag catacaaaag aaaatttaat tctttataag ttatcaattt   120
agtatctaat tatatatcaa aatatctaag aattcaacct agatatttta ataaaaatga   180
tattatgcta ttttagata agttaaattt actattttta ataataatat ttaagaaaaa    240
taaatgaaga aaattaattt taatattgtg atgatggcaa tagtaacca                289

<210> SEQ ID NO 14
<211> LENGTH: 159
<212> TYPE: DNA
<213> ORGANISM: Francisella tularensis

<400> SEQUENCE: 14 tttggggttgt cactcatcgt atttggttta taattttaag ctaataacct aattataact    60
aattaatagt tttgtatctt gaaaaaatag ctataaaact tatttaaata cgaagatttt   120
ttgtgtataa aatatttata acaaaaaaag gagactaaa                           159

<210> SEQ ID NO 15

```
<211> LENGTH: 164
<212> TYPE: PRT
<213> ORGANISM: Francisella tularensis

<400> SEQUENCE: 15

Met Ser Lys Ala Asp His Ile Phe Asn Leu Glu Glu Gln Gly Leu Leu
1               5                   10                  15

Ile Asp Ile Lys Asp Asp Ser Lys Gly Cys Thr Thr Lys Leu Glu Ser
            20                  25                  30

Ser Gly Lys Ile Thr His Asn Ala Thr Glu Ser Ile Glu Ser Ser Ala
        35                  40                  45

Asp Lys Gln Ile Ile Glu Asn Val Lys Asp Ser Lys Ile Ser Ile Thr
50                  55                  60

Glu Lys Glu Ile Leu Leu Ala Thr Lys Lys Ser Ser Ile Met Leu Ser
65                  70                  75                  80

Glu Asp Lys Ile Val Ile Lys Ile Gly Asn Ser Leu Ile Ile Leu Asp
                85                  90                  95

Asp Ser Asn Ile Ser Leu Glu Ser Ala Thr Ile Asn Ile Lys Ser Ser
            100                 105                 110

Ala Asn Ile Asn Ile Gln Ala Ser Gln Asn Ile Asp Ile Lys Ser Leu
        115                 120                 125

Asn Asn Ser Ile Lys Ala Asp Val Asn Leu Asn Ala Glu Gly Leu Asp
130                 135                 140

Val Asn Ile Lys Gly Ser Val Thr Ala Ser Ile Lys Gly Ser Thr Ala
145                 150                 155                 160

Thr Met Val Gly

<210> SEQ ID NO 16
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Gly Gly His Gly Asp Val Gly Met His Val Lys Glu Lys Glu
1               5                   10                  15

Lys Asn Lys Asp Glu Asn Lys Arg Lys Asp Glu Glu Arg Asn Lys Thr
            20                  25                  30

Gln Glu Glu His Leu Lys Glu Ile Met Lys His Ile Val Lys Ile Glu
        35                  40                  45

Val Lys Gly Glu Glu Ala Val Lys Lys Glu Ala Ala Glu Lys Leu Leu
    50                  55                  60

Glu Lys Val Pro Ser Asp Val Leu Glu Met Tyr Lys Ala Ile Gly Gly
65                  70                  75                  80

Lys Ile Tyr Ile Val Asp Gly Asp Ile Thr Lys His Ile Ser Leu Glu
                85                  90                  95

Ala Leu Ser Glu Asp Lys Lys Lys Ile Lys Asp Ile Tyr Gly Lys Asp
            100                 105                 110

Ala Leu Leu His Glu His Tyr Val Tyr Ala Lys Glu Gly Tyr Glu Pro
        115                 120                 125

Val Leu Val Ile Gln Ser Ser Glu Asp Tyr Val Glu Asn Thr Glu Lys
    130                 135                 140

Ala Leu Asn Val Tyr Tyr Glu Ile Gly Lys Ile Leu Ser Arg Asp Ile
145                 150                 155                 160
```

Leu Ser Lys Ile Asn Gln Pro Tyr Gln Lys Phe Leu Asp Val Leu Asn
            165                 170                 175

Thr Ile Lys Asn Ala Ser Asp Ser Asp Gly Gln Asp Leu Leu Phe Thr
        180                 185                 190

Asn Gln Leu Lys Glu His Pro Thr Asp Phe Ser Val Glu Phe Leu Glu
    195                 200                 205

Gln Asn Ser Asn Glu Val Gln Glu Val Phe Ala Lys Ala Phe Ala Tyr
210                 215                 220

Tyr Ile Glu Pro Gln His Arg Asp Val Leu Gln Leu Tyr Ala Pro Glu
225                 230                 235                 240

Ala Phe Asn Tyr Met Asp Lys Phe Asn Glu Gln Glu Ile Asn Leu Gly
                245                 250                 255

Gly Ser Gly Asn Phe Asp Gln Gln Thr Ser Gln Asn Ile Lys Asn Gln
            260                 265                 270

Leu Ala Glu Leu Asn Ala Thr Asn Ile Tyr Thr Val Leu Asp Lys Ile
        275                 280                 285

Lys Leu Asn Ala Lys Met Asn Ile Leu Ile Arg Asp Lys Arg Phe His
    290                 295                 300

Tyr Asp Arg Asn Asn Ile Ala Val Gly Ala Asp Glu Ser Val Val Lys
305                 310                 315                 320

Glu Ala His Arg Glu Val Ile Asn Ser Ser Thr Glu Gly Leu Leu Leu
                325                 330                 335

Asn Ile Asp Lys Asp Ile Arg Lys Ile Leu Ser Gly Tyr Ile Val Glu
            340                 345                 350

Ile Glu Asp Thr Glu Gly Leu Lys Glu Val Ile Asn Asp Arg Tyr Asp
        355                 360                 365

Met Leu Asn Ile Ser Ser Leu Arg Gln Asp Gly Lys Thr Phe Ile Asp
    370                 375                 380

Phe Lys Lys Tyr Asn Asp Lys Leu Pro Leu Tyr Ile Ser Asn Pro Asn
385                 390                 395                 400

Tyr Lys Val Asn Val Tyr Ala Val Thr Lys Glu Asn Thr Ile Ile Asn
                405                 410                 415

Pro Ser Glu Asn Gly Asp Thr Ser Thr Asn Gly Ile Lys Lys Ile Leu
            420                 425                 430

Ile Phe Ser Lys Lys Gly Tyr Glu Ile Gly
        435                 440

<210> SEQ ID NO 17
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Gly Gly His Gly Asp Val Gly Met His Val Lys Glu Lys Glu
1               5                   10                  15

Lys Asn Lys Asp Glu Asn Lys Arg Lys Asp Glu Glu Arg Asn Lys Thr
            20                  25                  30

Gln Glu Glu His Leu Lys Glu Ile Met Lys His Ile Val Lys Ile Glu
        35                  40                  45

Val Lys Gly Glu Glu Ala Val Lys Lys Glu Ala Ala Glu Lys Leu Leu
    50                  55                  60

Glu Lys Val Pro Ser Asp Val Leu Glu Met Tyr Lys Ala Ile Gly Gly
65                  70                  75                  80

Lys Ile Tyr Ile Val Asp Gly Asp Ile Thr Lys His Ile Ser Leu Glu
                85                  90                  95

Ala Leu Ser Glu Asp Lys Lys Ile Lys Asp Ile Tyr Gly Lys Asp
            100                 105                 110

Ala Leu Leu His Glu His Tyr Val Tyr Ala Lys Glu Gly Tyr Glu Pro
            115                 120                 125

Val Leu Val Ile Gln Ser Ser Glu Asp Tyr Val Glu Asn Thr Glu Lys
        130                 135                 140

Ala Leu Asn Val Tyr Tyr Glu Ile Gly Lys Ile Leu Ser Arg Asp Ile
145                 150                 155                 160

Leu Ser Lys Ile Asn Gln Pro Tyr Gln Lys Phe Leu Asp Val Leu Asn
                165                 170                 175

Thr Ile Lys Asn Ala Ser Asp Ser Asp Gly Gln Asp Leu Leu Phe Thr
            180                 185                 190

Asn Gln Leu Lys Glu His Pro Thr Asp Phe Ser Val Glu Phe Leu Glu
        195                 200                 205

Gln Asn Ser Asn Glu Val Gln Glu Val Phe Ala Lys Ala Phe Ala Tyr
    210                 215                 220

Tyr Ile Glu Pro Gln His Arg Asp Val Leu Gln Leu Tyr Ala Pro Glu
225                 230                 235                 240

Ala Phe Asn Tyr Met Asp Lys Phe Asn Glu Gln Glu Ile Asn Leu Gly
                245                 250                 255

Ser Ser Gly Gly Ser Ser Gly Asn Phe Asp Gln Gln Thr Ser Gln Asn
            260                 265                 270

Ile Lys Asn Gln Leu Ala Glu Leu Asn Ala Thr Asn Ile Tyr Thr Val
        275                 280                 285

Leu Asp Lys Ile Lys Leu Asn Ala Lys Met Asn Ile Leu Ile Arg Asp
    290                 295                 300

Lys Arg Phe His Tyr Asp Arg Asn Asn Ile Ala Val Gly Ala Asp Glu
305                 310                 315                 320

Ser Val Val Lys Glu Ala His Arg Glu Val Ile Asn Ser Ser Thr Glu
                325                 330                 335

Gly Leu Leu Leu Asn Ile Asp Lys Asp Ile Arg Lys Ile Leu Ser Gly
            340                 345                 350

Tyr Ile Val Glu Ile Glu Asp Thr Glu Gly Leu Lys Glu Val Ile Asn
        355                 360                 365

Asp Arg Tyr Asp Met Leu Asn Ile Ser Ser Leu Arg Gln Asp Gly Lys
    370                 375                 380

Thr Phe Ile Asp Phe Lys Lys Tyr Asn Asp Lys Leu Pro Leu Tyr Ile
385                 390                 395                 400

Ser Asn Pro Asn Tyr Lys Val Asn Val Tyr Ala Val Thr Lys Glu Asn
                405                 410                 415

Thr Ile Ile Asn Pro Ser Glu Asn Gly Asp Thr Ser Thr Asn Gly Ile
            420                 425                 430

Lys Lys Ile Leu Ile Phe Ser Lys Lys Gly Tyr Glu Ile Gly
        435                 440                 445

<210> SEQ ID NO 18
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
        35                  40                  45

Pro Ile Thr Ile Met Asp Asn Gly Asn Ile Asp Thr Glu Leu Leu Val
50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln Met Ile Arg Ala Tyr Glu
                165                 170                 175

Gln Asn Pro Gln His Phe Ile Glu Asp Leu Glu Lys Val Arg Val Glu
            180                 185                 190

Gln Leu Thr Gly His Gly Ser Ser Val Leu Glu Glu Leu Val Gln Leu
        195                 200                 205

Val Lys Asp Lys Asn Ile Asp Ile Ser Ile Lys Tyr Asp Pro Arg Lys
210                 215                 220

Asp Ser Glu Val Phe Ala Asn Arg Val Ile Thr Asp Ile Glu Leu
225                 230                 235                 240

Leu Lys Lys Ile Leu Ala Tyr Phe Leu Pro Glu Asp Ala Ile Leu Lys
                245                 250                 255

Gly Gly His Tyr Asp Asn Gln Leu Gln Asn Gly Ile Lys Arg Val Lys
            260                 265                 270

Glu Phe Leu Glu Ser Ser Pro Asn Thr Gln Trp Glu Leu Arg Ala Phe
        275                 280                 285

Met Ala Val Met His Phe Ser Leu Thr Ala Asp Arg Ile Asp Asp
290                 295                 300

Ile Leu Lys Val Ile Val Asp Ser Met Asn His His Gly Asp Ala Arg
305                 310                 315                 320

Ser Lys Leu Arg Glu Glu Leu Ala Glu Leu Thr Ala Glu Leu Lys Ile
                325                 330                 335

Tyr Ser Val Ile Gln Ala Glu Ile Asn Lys His Leu Ser Ser Ser Gly
            340                 345                 350

Thr Ile Asn Ile His Asp Lys Ser Ile Asn Leu Met Asp Lys Asn Leu
        355                 360                 365

Tyr Gly Tyr Thr Asp Glu Glu Ile Phe Lys Ala Ser Ala Glu Tyr Lys
370                 375                 380

Ile Leu Glu Lys Met Pro Gln Thr Thr Ile Gln Val Asp Gly Ser Glu
385                 390                 395                 400

Lys Lys Ile Val Ser Ile Lys Asp Phe Leu Gly Ser Glu Asn Lys Arg
                405                 410                 415
```

```
Thr Gly Ala Leu Gly Asn Leu Lys Asn Ser Tyr Ser Tyr Asn Lys Asp
            420                 425                 430

Asn Asn Glu Leu Ser His Phe Ala Thr Thr Cys Ser Asp Lys Ser Arg
            435                 440                 445

Pro Leu Asn Asp Leu Val Ser Gln Lys Thr Thr Gln Leu Ser Asp Ile
450                 455                 460

Thr Ser Arg Phe Asn Ser Ala Ile Glu Ala Leu Asn Arg Phe Ile Gln
465                 470                 475                 480

Lys Tyr Asp Ser Val Met Gln Arg Leu Leu Asp Asp Thr Ser Gly Lys
                485                 490                 495

<210> SEQ ID NO 19
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
                20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln Gly Gly Ser Gly Met Ile
                165                 170                 175

Arg Ala Tyr Glu Gln Asn Pro Gln His Phe Ile Glu Asp Leu Glu Lys
            180                 185                 190

Val Arg Val Glu Gln Leu Thr Gly His Gly Ser Ser Val Leu Glu Glu
        195                 200                 205

Leu Val Gln Leu Val Lys Asp Lys Asn Ile Asp Ile Ser Ile Lys Tyr
210                 215                 220

Asp Pro Arg Lys Asp Ser Glu Val Phe Ala Asn Arg Val Ile Thr Asp
225                 230                 235                 240

Asp Ile Glu Leu Leu Lys Lys Ile Leu Ala Tyr Phe Leu Pro Glu Asp
                245                 250                 255

Ala Ile Leu Lys Gly Gly His Tyr Asp Asn Gln Leu Gln Asn Gly Ile
            260                 265                 270

Lys Arg Val Lys Glu Phe Leu Glu Ser Ser Pro Asn Thr Gln Trp Glu
```

```
                275                 280                 285
Leu Arg Ala Phe Met Ala Val Met His Phe Ser Leu Thr Ala Asp Arg
    290                 295                 300

Ile Asp Asp Asp Ile Leu Lys Val Ile Val Asp Ser Met Asn His His
305                 310                 315                 320

Gly Asp Ala Arg Ser Lys Leu Arg Glu Glu Leu Ala Glu Leu Thr Ala
                325                 330                 335

Glu Leu Lys Ile Tyr Ser Val Ile Gln Ala Glu Ile Asn Lys His Leu
            340                 345                 350

Ser Ser Ser Gly Thr Ile Asn Ile His Asp Lys Ser Ile Asn Leu Met
        355                 360                 365

Asp Lys Asn Leu Tyr Gly Tyr Thr Asp Glu Ile Phe Lys Ala Ser
    370                 375                 380

Ala Glu Tyr Lys Ile Leu Glu Lys Met Pro Gln Thr Thr Ile Gln Val
385                 390                 395                 400

Asp Gly Ser Glu Lys Lys Ile Val Ser Ile Lys Asp Phe Leu Gly Ser
                405                 410                 415

Glu Asn Lys Arg Thr Gly Ala Leu Gly Asn Leu Lys Asn Ser Tyr Ser
            420                 425                 430

Tyr Asn Lys Asp Asn Asn Glu Leu Ser His Phe Ala Thr Thr Cys Ser
        435                 440                 445

Asp Lys Ser Arg Pro Leu Asn Asp Leu Val Ser Gln Lys Thr Thr Gln
    450                 455                 460

Leu Ser Asp Ile Thr Ser Arg Phe Asn Ser Ala Ile Glu Ala Leu Asn
465                 470                 475                 480

Arg Phe Ile Gln Lys Tyr Asp Ser Val Met Gln Arg Leu Leu Asp Asp
                485                 490                 495

Thr Ser Gly Lys
            500

<210> SEQ ID NO 20
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125
```

-continued

```
Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys Gly Gly Gly Ser Gly Gly Gly Ser
                325                 330                 335

Gly Gly Gly Gly Ser Ala Asp Leu Thr Ala Ser Thr Thr Ala Thr Ala
            340                 345                 350

Thr Leu Val Glu Pro Ala Arg Ile Thr Leu Thr Tyr Lys Glu Gly Ala
    355                 360                 365

Pro Ile Thr Ile Met Asp Asn Gly Asn Ile Asp Thr Glu Leu Leu Val
370                 375                 380

Gly Thr Leu Thr Leu Gly Gly Tyr Lys Thr Gly Thr Thr Ser Thr Ser
385                 390                 395                 400

Val Asn Phe Thr Asp Ala Ala Gly Asp Pro Met Tyr Leu Thr Phe Thr
                405                 410                 415

Ser Gln Asp Gly Asn Asn His Gln Phe Thr Thr Lys Val Ile Gly Lys
            420                 425                 430

Asp Ser Arg Asp Phe Asp Ile Ser Pro Lys Val Asn Gly Glu Asn Leu
        435                 440                 445

Val Gly Asp Asp Val Val Leu Ala Thr Gly Ser Gln Asp Phe Phe Val
    450                 455                 460

Arg Ser Ile Gly Ser Lys Gly Gly Lys Leu Ala Ala Gly Lys Tyr Thr
465                 470                 475                 480

Asp Ala Val Thr Val Thr Val Ser Asn Gln Gly Gly Gly Ser Gly
                485                 490                 495

Gly Gly Gly Ser Gly Gly Gly Ser Met Ser Asn Phe Ser Gly Phe
            500                 505                 510

Thr Lys Gly Thr Asp Ile Ala Asp Leu Asp Ala Val Ala Gln Thr Leu
        515                 520                 525

Lys Lys Pro Ala Asp Asp Ala Asn Lys Ala Val Asn Asp Ser Ile Ala
    530                 535                 540

Ala Leu Lys Asp Lys Pro Asp Asn Pro Ala Leu Leu Ala Asp Leu Gln
```

His Ser Ile Asn Lys Trp Ser Val Ile Tyr Asn Ile Asn Ser Thr Ile
545                 550                 555                 560

Val Arg Ser Met Lys Asp Leu Met Gln Gly Ile Leu Gln Lys Phe Pro
            565                 570                 575

580                 585                 590

<210> SEQ ID NO 21
<211> LENGTH: 285
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Leu Val Val Gly Asp Leu Ser Lys Gly Arg Ser Val Asp Ala Lys
1               5                   10                  15

Lys Glu Phe Ala Asp Arg Glu Val Arg Val Asn Asn Gly Val Asp
            20                  25                  30

Arg Val Leu Glu Glu Met Asn Ile Ser Phe Asp Phe Glu Ala Pro Asn
            35                  40                  45

Phe Val Ser Lys Asp Arg Ser Asn Leu Lys Val Asn Tyr Arg Ile Glu
            50                  55                  60

Ser Val Lys Asp Phe Arg Pro Asp Ala Val Lys Lys Val Pro Glu
65              70                  75                  80

Ile Arg Ala Leu Leu Glu Met Lys Glu Ile Leu Ala Ser Phe Ala Lys
                85                  90                  95

Asp Ile Glu Asn Asn Gln Leu Pro Leu Glu Met Ala Arg Tyr Pro Phe
            100                 105                 110

Arg Asn Val Ser Ile Glu Val Glu Thr Ile Pro Gly Lys Pro Gly Trp
            115                 120                 125

Tyr Ser Cys Lys Ile Asn Val Ile Pro His Ile Gln Phe Glu Gly Met
130                 135                 140

Asn Thr Thr Met Thr Ile Asp Thr Arg Leu Glu Pro Glu Leu Phe Gly
145                 150                 155                 160

Thr Asn Asn Thr Gly Asn Cys Arg Leu Phe Ile Asp Ser Leu Thr
                165                 170                 175

Ile Ala Gly Glu Lys Leu Asp Lys Asn Ile Val Ala Ile Asp Gly Gly
            180                 185                 190

Glu Asp Val Thr Lys Ala Asp Ser Ala Thr Ala Ala Ser Val Ile
            195                 200                 205

Arg Leu Ser Ile Thr Pro Gly Ser Ile Asn Pro Thr Ile Ser Ile Thr
210                 215                 220

Leu Gly Val Leu Ile Lys Ser Asn Val Arg Thr Lys Ile Glu Glu Lys
225                 230                 235                 240

Val Ser Ser Ile Leu Gln Ala Ser Ala Thr Asp Met Lys Ile Lys Leu
                245                 250                 255

Gly Asn Ser Asn Lys Lys Gln Glu Tyr Lys Thr Asp Glu Ala Trp Gly
            260                 265                 270

Ile Met Ile Asp Leu Ser Asn Leu Glu Leu Tyr Pro Ile
            275                 280                 285

<210> SEQ ID NO 22
<211> LENGTH: 292
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 22

Met Leu Val Val Gly Asp Leu Ser Lys Gly Arg Ser Val Asp Ala Lys
1               5                   10                  15

Lys Glu Phe Ala Asp Arg Glu Val Arg Arg Val Asn Asn Gly Val Asp
            20                  25                  30

Arg Val Leu Glu Glu Met Asn Ile Ser Phe Asp Phe Glu Ala Pro Asn
        35                  40                  45

Phe Val Ser Lys Asp Arg Ser Asn Leu Lys Val Asn Tyr Arg Ile Glu
    50                  55                  60

Ser Val Lys Asp Phe Arg Pro Asp Ala Val Ala Lys Lys Val Pro Glu
65                  70                  75                  80

Ile Arg Ala Leu Leu Glu Met Lys Glu Ile Leu Ala Ser Phe Ala Lys
                85                  90                  95

Asp Ile Glu Asn Asn Gln Leu Gly Gly Ser Gly Pro Leu Glu Met Ala
            100                 105                 110

Arg Tyr Pro Phe Arg Asn Val Ser Ile Glu Val Glu Thr Ile Pro Gly
        115                 120                 125

Lys Pro Gly Trp Tyr Ser Cys Lys Ile Asn Val Ile Pro His Ile Gln
    130                 135                 140

Phe Glu Gly Met Asn Thr Thr Met Thr Ile Asp Thr Arg Leu Glu Pro
145                 150                 155                 160

Glu Leu Phe Gly Thr Asn Asn Asn Gly Gly Ser Gly Thr Gly Asn Cys
                165                 170                 175

Arg Leu Phe Ile Asp Ser Leu Thr Ile Ala Gly Glu Lys Asp Lys Asn
            180                 185                 190

Ile Val Ala Ile Asp Gly Gly Glu Asp Val Thr Lys Ala Asp Ser Ala
        195                 200                 205

Thr Ala Ala Ser Val Ile Arg Leu Ser Ile Thr Pro Gly Ser Ile
    210                 215                 220

Asn Pro Thr Ile Ser Ile Thr Leu Gly Val Leu Ile Lys Ser Asn Val
225                 230                 235                 240

Arg Thr Lys Ile Glu Glu Lys Val Ser Ser Ile Leu Gln Ala Ser Ala
                245                 250                 255

Thr Asp Met Lys Ile Lys Leu Gly Asn Ser Asn Lys Lys Gln Glu Tyr
            260                 265                 270

Lys Thr Asp Glu Ala Trp Gly Ile Met Ile Asp Leu Ser Asn Leu Glu
        275                 280                 285

Leu Tyr Pro Ile
    290

<210> SEQ ID NO 23
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Leu Val Val Gly Asp Leu Ser Lys Gly Arg Ser Val Asp Ala Lys
1               5                   10                  15

Lys Glu Phe Ala Asp Arg Glu Val Arg Arg Val Asn Asn Gly Val Asp
            20                  25                  30

Arg Val Leu Glu Glu Met Asn Ile Ser Phe Asp Phe Glu Ala Pro Asn
            35                  40                  45

Phe Val Ser Lys Asp Arg Ser Asn Leu Lys Val Asn Tyr Arg Ile Glu
 50                  55                  60

Ser Val Lys Asp Phe Arg Pro Asp Ala Val Ala Lys Lys Val Pro Glu
65                  70                  75                  80

Ile Arg Ala Leu Leu Glu Met Lys Glu Ile Leu Ala Ser Phe Ala Lys
                85                  90                  95

Asp Ile Glu Asn Asn Gln Leu Gly Gly Ser Gly Gly Ser Gly Pro
                100                 105                 110

Leu Glu Met Ala Arg Tyr Pro Phe Arg Asn Val Ser Ile Glu Val Glu
            115                 120                 125

Thr Ile Pro Gly Lys Pro Gly Trp Tyr Ser Cys Lys Ile Asn Val Ile
130                 135                 140

Pro His Ile Gln Phe Glu Gly Met Asn Thr Thr Met Thr Ile Asp Thr
145                 150                 155                 160

Arg Leu Glu Pro Glu Leu Phe Gly Thr Asn Asn Asn Gly Gly Ser Gly
                165                 170                 175

Gly Gly Ser Gly Thr Gly Asn Cys Arg Leu Phe Ile Asp Ser Leu Thr
            180                 185                 190

Ile Ala Gly Glu Lys Leu Asp Lys Asn Ile Val Ala Ile Asp Gly Gly
            195                 200                 205

Glu Asp Val Thr Lys Ala Asp Ser Ala Thr Ala Ala Ser Val Ile
            210                 215                 220

Arg Leu Ser Ile Thr Pro Gly Ser Ile Asn Pro Thr Ile Ser Ile Thr
225                 230                 235                 240

Leu Gly Val Leu Ile Lys Ser Asn Val Arg Thr Lys Ile Glu Lys
                245                 250                 255

Val Ser Ser Ile Leu Gln Ala Ser Ala Thr Asp Met Lys Ile Lys Leu
                260                 265                 270

Gly Asn Ser Asn Lys Lys Gln Glu Tyr Lys Thr Asp Glu Ala Trp Gly
                275                 280                 285

Ile Met Ile Asp Leu Ser Asn Leu Glu Leu Tyr Pro Ile
            290                 295                 300

<210> SEQ ID NO 24
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Gly Gly His Gly Asp Val Gly Met His Val Lys Glu Lys Glu
1               5                   10                  15

Lys Asn Lys Asp Glu Asn Lys Arg Lys Asp Glu Glu Arg Asn Lys Thr
                20                  25                  30

Gln Glu Glu His Leu Lys Glu Ile Met Lys His Ile Val Lys Ile Glu
            35                  40                  45

Val Lys Gly Glu Glu Ala Val Lys Lys Glu Ala Ala Glu Lys Leu Leu
 50                  55                  60

Glu Lys Val Pro Ser Asp Val Leu Glu Met Tyr Lys Ala Ile Gly Gly
65                  70                  75                  80

Lys Ile Tyr Ile Val Asp Gly Asp Ile Thr Lys His Ile Ser Leu Glu
                85                  90                  95

```
Ala Leu Ser Glu Asp Lys Lys Ile Lys Asp Ile Tyr Gly Lys Asp
            100                 105                 110

Ala Leu Leu His Glu His Tyr Val Tyr Ala Lys Glu Gly Tyr Glu Pro
            115                 120                 125

Val Leu Val Ile Gln Ser Ser Glu Asp Tyr Val Glu Asn Thr Glu Lys
130                 135                 140

Ala Leu Asn Val Tyr Tyr Glu Ile Gly Lys Ile Leu Ser Arg Asp Ile
145                 150                 155                 160

Leu Ser Lys Ile Asn Gln Pro Tyr Gln Lys Phe Leu Asp Val Leu Asn
                165                 170                 175

Thr Ile Lys Asn Ala Ser Asp Ser Asp Gly Gln Asp Leu Leu Phe Thr
            180                 185                 190

Asn Gln Leu Lys Glu His Pro Thr Asp Phe Ser Val Glu Phe Leu Glu
            195                 200                 205

Gln Asn Ser Asn Glu Val Gln Glu Val Phe Ala Lys Ala Phe Ala Tyr
            210                 215                 220

Tyr Ile Glu Pro Gln His Arg Asp Val Leu Gln Leu Tyr Ala Pro Glu
225                 230                 235                 240

Ala Phe Asn Tyr Met Asp Lys Phe Asn Glu Gln Glu Ile Asn Leu Gly
                245                 250                 255

Gly Ser Gly Asn Phe Asp Gln Gln Thr Ser Gln Asn Ile Lys Asn Gln
            260                 265                 270

Leu Ala Glu Leu Asn Ala Thr Asn Ile Tyr Thr Val Leu Asp Lys Ile
            275                 280                 285

Lys Leu Asn Ala Lys Met Asn Ile Leu Ile Arg Asp Lys Arg Phe His
            290                 295                 300

Tyr Asp Arg Asn Asn Ile Ala Val Gly Ala Asp Glu Ser Val Val Lys
305                 310                 315                 320

Glu Ala His Arg Glu Val Ile Asn Ser Ser Thr Glu Gly Leu Leu Leu
                325                 330                 335

Asn Ile Asp Lys Asp Ile Arg Lys Ile Leu Ser Gly Tyr Ile Val Glu
            340                 345                 350

Ile Glu Asp Thr Glu Gly Leu Lys Glu Val Ile Asn Asp Arg Tyr Asp
            355                 360                 365

Met Leu Asn Ile Ser Ser Leu Arg Gln Asp Gly Lys Thr Phe Ile Asp
            370                 375                 380

Phe Lys Lys Tyr Asn Asp Lys Leu Pro Leu Tyr Ile Ser Asn Pro Asn
385                 390                 395                 400

Tyr Lys Val Asn Val Tyr Ala Val Thr Lys Glu Asn Thr Ile Ile Asn
                405                 410                 415

Pro Ser Glu Asn Gly Asp Thr Ser Thr Asn Gly Ile Lys Lys Ile Leu
            420                 425                 430

Ile Phe Ser Lys Lys Gly Tyr Glu Ile Gly
            435                 440
```

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
agatgctacg taatgctagt tgttggcgat ttatca                        36

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
attattttca atgtccttag caa                                              23

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gacattgaaa ataatcaatt gcctttagaa atggcgagat atcctttc                   48

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttattattt gtaccgaata attc                                             24

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtacaaata ataacaccgg taattgtaga ttatttattg attcttta                   48

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agatgcggat ccctattata ttggatataa ctctaaatta ga                         42

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagtaacaat tgggtggttc tggtccttta gaaatggcga gatatccttt c               51

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagtaaaccg gttccagaac caccgttatt atttgtaccg aataattctg g          51

<210> SEQ ID NO 33
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aagtaacaat tgggtggttc tggtggtggt tctggtcctt tagaaatggc gagatatcct    60
ttc                                                                 63

<210> SEQ ID NO 34
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aagtaaaccg gttccagaac caccaccaga accaccgtta ttatttgtac cgaataattc    60
tgg                                                                 63

<210> SEQ ID NO 35
<211> LENGTH: 167
<212> TYPE: PRT
<213> ORGANISM: Burkholderia pseudomallei

<400> SEQUENCE: 35

Met Leu His Met His Leu Lys Phe Gly Ser Pro Ala Ile Lys Gly Glu
1               5                   10                  15

Ser Ala Asp Lys Asp His Glu Gly Trp Ile Glu Leu Lys Ser Trp Asp
            20                  25                  30

His Ser Ile Val Gln Pro Arg Ser Ala Thr Ala Ser Thr Ala Gly Gly
        35                  40                  45

His Thr Ala Thr Arg Cys Glu His Gly Asp Met Val Phe Thr Lys Glu
    50                  55                  60

Ile Asp Ser Ser Pro Leu Leu Tyr Gln His Ala Ser Gly Gly Thr
65                  70                  75                  80

Thr Phe Asp Glu Val Thr Ile Asp Phe Leu Arg Ala Asp Gly Glu Gly
                85                  90                  95

Gln Arg Val Lys Tyr Leu Glu Ile Lys Leu Lys Tyr Val Ile Ile Ser
            100                 105                 110

Ser Ile Ala Pro Ser Val His Thr Glu Gly Leu Pro Val Glu Thr Phe
        115                 120                 125

Ser Leu Lys Tyr Ala Ala Val Gln Trp Lys Gln Thr Gln Gln Lys Ile
    130                 135                 140

Gly Gly Asn Gln Gly Gly Asn Thr Gln Gly Ala Trp Ser Leu Thr Lys 145                 150                 155                 160

Asn Asp Lys Thr Tyr Ala Val
                165

<210> SEQ ID NO 36
<211> LENGTH: 160
<212> TYPE: PRT
<213> ORGANISM: Burkholderia pseudomallei

<400> SEQUENCE: 36

Met Ser His Asp Ile Phe Leu Lys Ile Asn Gly Ile Asp Gly Glu Ala
1               5                   10                  15

Glu Asp Ala Thr His Lys Gly Glu Ile Glu Val Leu Ser Trp Ser Trp
            20                  25                  30

Asn Val Ser Gln Gln Ser Asn Met His Leu Gly Ser Gly Gly Gly Ala
        35                  40                  45

Gly Lys Ala Thr Ile Asp Asp Leu Gln Phe Glu His Tyr Ile Asp Arg
    50                  55                  60

Ala Ser Pro Asn Leu Val Gln Tyr Cys Leu Leu Gly Lys His Ile Asp
65                  70                  75                  80

Glu Ala Arg Leu Val Val Arg Lys Ala Gly Gly Ser Pro Leu Glu Tyr
                85                  90                  95

Ile Lys Leu Thr Met Ser Asp Val Leu Val Thr Gln Val Ser Pro Ala
            100                 105                 110

Gly Val Ala Gln Asp Glu Ser Arg Pro Arg Glu Leu Val Arg Leu Ser
        115                 120                 125

Phe Ser Arg Leu Lys Gln Glu Tyr Val Val Gln Asn Pro Gln Gly Gly
    130                 135                 140

Ser Gly Gly Ala Ile Thr Ala Thr Phe Asp Ile Lys Lys Asn Ala Ala
145                 150                 155                 160

<210> SEQ ID NO 37
<211> LENGTH: 161
<212> TYPE: PRT
<213> ORGANISM: Burkholderia pseudomallei

<400> SEQUENCE: 37

Met Ala Gln Asp Ile Phe Leu Lys Ile Asp Gly Ile Asn Gly Glu Ser
1               5                   10                  15

Leu Asp Asp Ser His Lys Asp Glu Ile Glu Val Leu Asn Trp Asn Trp
            20                  25                  30

Glu Ile Gln Gln Glu Ser Thr Met His Thr Gly Ser Gly Gly Gly Ala
        35                  40                  45

Gly Lys Ala Ser Val Lys Asp Leu Thr Phe Glu His Ala Ile Asp Arg
    50                  55                  60

Ala Ser Pro Asn Leu Met Lys Tyr Ala Leu Thr Gly Lys His Val Asp
65                  70                  75                  80

Gln Ala Val Leu Val Met Arg Lys Ala Gly Gly Asn Pro Leu Glu Tyr
                85                  90                  95

Leu Lys Leu Thr Met Ser Asp Val Ile Ile Thr Arg Val Arg Pro Ser
            100                 105                 110

Gly Ser Arg Asp Asp Thr Glu Arg Ser Arg Glu Thr Val Ser Leu Ser
        115                 120                 125

Phe Ala Lys Val Lys Gln Glu Tyr Val Val Gln Asn Ala Gln Gly Gly
    130                 135                 140

Ser Gly Gly Ala Val Thr Thr Ser Phe Asp Ile Lys Gly Asn Lys Glu

```
                145                 150                 155                 160
Ala

<210> SEQ ID NO 38
<211> LENGTH: 175
<212> TYPE: PRT
<213> ORGANISM: Burkholderia pseudomallei

<400> SEQUENCE: 38

Met Ala Asn Ala Leu Val Asp Tyr Phe Leu Gln Ile Asp Gly Val Glu
1               5                   10                  15

Gly Glu Ser Thr Asp Gln Gln Tyr Pro Gly Leu Ile Gln Ile Gln Ser
            20                  25                  30

Trp Gln Trp Ala Glu Glu Asn Ser Gly Arg Trp Gly Phe Gly Ser Gly
        35                  40                  45

Gly Gly Ala Gly Lys Val Glu Met Lys Asp Phe Glu Phe Arg Met Val
    50                  55                  60

Ser Asn Lys Ala Ser Pro Lys Leu Phe Leu Met Cys Ala Thr Gly Glu
65                  70                  75                  80

His Ile Gln Asn Ala Lys Leu Ile Cys Arg Lys Ser Gly Lys Gly Gln
                85                  90                  95

Gln Glu Phe Leu Thr Ile Ser Phe Ala Ser Gly Leu Val Ser Ser Phe
            100                 105                 110

Arg Thr Leu Gly Asn Met Pro Ile Ser Gln Leu Gly His Ala Ser Gly
        115                 120                 125

Glu Val Asp Gly Val Leu Pro Thr Asp Gln Ile Arg Ile Asn Phe Ala
    130                 135                 140

Gln Ile Glu Phe Glu Tyr Arg Glu Gln Arg Asn Asp Gly Thr Met Gly
145                 150                 155                 160

Ala Val Ile Lys Ala Gly Tyr Asp Leu Lys Gln Asn Ala Pro Ile
                165                 170                 175

<210> SEQ ID NO 39
<211> LENGTH: 163
<212> TYPE: PRT
<213> ORGANISM: Burkholderia pseudomallei

<400> SEQUENCE: 39

Met Gly Val Ala Met Phe Met Lys Val Asp Gly Val Thr Gly Glu Ser
1               5                   10                  15

Ala Asp Ala Gln His Lys Gly Trp Thr Asp Ile Gln Ser Phe Ser Trp
            20                  25                  30

Gly Ala Ser Gln Pro Gly Ala Met Ala Ser Gly Ser Gly Gly Asn Ala
        35                  40                  45

Gly Lys Ala Ser Phe Asn Asp Leu Val Val Ala Ala Tyr Met Asp Lys
    50                  55                  60

Gly Ala Thr Ala Ile Ile Lys Asn Cys Ala Ser Gly Lys His Leu Pro
65                  70                  75                  80

Thr Val Glu Ile Ser Ala Cys Lys Thr Gly Gly Ser Gln Ile Glu Phe
                85                  90                  95

Met Arg Val Thr Leu Gln Glu Val Leu Val Thr Ser Ala Gln Ile Ala
            100                 105                 110

Gly Val Asp Pro Gly Asp Ala Ala Asp Arg Leu Met Met Gln Tyr Gly
        115                 120                 125

Phe Gln Ala Ala Lys Val Lys Lys Gln Tyr Trp Gln Gln Asn Asp Asn
    130                 135                 140
```

Gly Gly Lys Gly Ala Glu Val Ser Val Gly Trp Asn Ile Lys Glu Asn
145                 150                 155                 160

Thr Glu Met

<210> SEQ ID NO 40
<211> LENGTH: 417
<212> TYPE: PRT
<213> ORGANISM: Burkholderia pseudomallei

<400> SEQUENCE: 40

Met Lys Leu Pro Tyr Glu Trp Gln Ile Gly Trp Arg Tyr Thr Arg Ala
1               5                   10                  15

Gly Lys Arg Ala Thr Gly Asn Gly Phe Ile Ser Phe Ile Ala Leu Val
                20                  25                  30

Ser Met Leu Gly Ile Ala Leu Gly Val Ala Ala Leu Ile Val Val Leu
            35                  40                  45

Ser Val Met Asn Gly Phe Gln Lys Glu Val Arg Asp Arg Met Leu Ser
50                  55                  60

Val Leu Ala His Val Glu Ile Phe Ser Pro Thr Gly Ser Met Pro Asp
65                  70                  75                  80

Trp Gln Leu Thr Ala Lys Glu Ala Arg Leu Asn Arg Ser Val Ile Gly
                85                  90                  95

Ala Ala Pro Tyr Val Asp Ala Gln Ala Leu Leu Thr Arg Gln Asp Ala
            100                 105                 110

Val Ser Gly Val Met Leu Arg Gly Val Glu Pro Ser Leu Glu Pro Gln
        115                 120                 125

Val Ser Asp Ile Gly Lys Asp Met Lys Ala Gly Ala Leu Thr Ala Leu
130                 135                 140

Ala Pro Gly Gln Phe Gly Ile Val Leu Gly Asn Ala Leu Ala Gly Asn
145                 150                 155                 160

Leu Gly Val Gly Val Gly Asp Lys Val Thr Leu Val Ala Pro Glu Gly
                165                 170                 175

Thr Ile Thr Pro Ala Gly Met Met Pro Arg Leu Lys Gln Phe Thr Val
            180                 185                 190

Val Gly Ile Phe Glu Ser Gly His Tyr Glu Tyr Asp Ser Thr Leu Ala
        195                 200                 205

Met Ile Asp Ile Gln Asp Ala Gln Ala Leu Phe Arg Leu Pro Ala Pro
210                 215                 220

Thr Gly Val Arg Leu Arg Leu Thr Asp Met Gln Lys Ala Pro Gln Val
225                 230                 235                 240

Ala Arg Glu Leu Ala His Thr Leu Ser Gly Asp Leu Tyr Ile Arg Asp
                245                 250                 255

Trp Thr Gln Gln Asn Lys Thr Trp Phe Ser Ala Val Gly Ile Glu Lys
            260                 265                 270

Arg Met Met Phe Ile Ile Leu Thr Leu Ile Ile Ala Val Ala Ala Phe
        275                 280                 285

Asn Leu Val Ser Ser Leu Val Met Thr Val Thr Asn Lys Gln Ala Asp
290                 295                 300

Ile Ala Ile Leu Arg Thr Leu Gly Ala Gln Pro Gly Ser Ile Met Lys
305                 310                 315                 320

Ile Phe Val Val Gln Gly Val Thr Ile Gly Phe Val Gly Thr Ala Thr
                325                 330                 335

Gly Val Ala Leu Gly Cys Leu Ile Ala Trp Ser Ile Pro Trp Leu Ile
            340                 345                 350

-continued

```
Pro Met Ile Glu His Ala Phe Gly Val Gln Phe Leu Pro Ser Val
        355                 360                 365

Tyr Phe Ile Ser Glu Leu Pro Ser Glu Leu Val Ala Gly Asp Val Ile
370                 375                 380

Lys Ile Gly Val Ile Ala Phe Ala Leu Ser Ala Leu Ala Thr Leu Tyr
385                 390                 395                 400

Pro Ser Trp Arg Gly Ala Lys Val Arg Pro Ala Glu Ala Leu Arg Tyr
                405                 410                 415

Glu

<210> SEQ ID NO 41
<211> LENGTH: 608
<212> TYPE: PRT
<213> ORGANISM: Burkholderia pseudomallei

<400> SEQUENCE: 41

Met Thr Arg Ala Leu Arg Asn Ile Ala Ile Ala His Val Asp His
1               5                   10                  15

Gly Lys Thr Thr Leu Val Asp Gln Leu Leu Arg Gln Ser Gly Thr Phe
                20                  25                  30

Arg Glu Asn Gln Gln Val Ala Glu Arg Val Met Asp Ser Asn Asp Ile
            35                  40                  45

Glu Lys Glu Arg Gly Ile Thr Ile Leu Ala Lys Asn Cys Ala Val Glu
50                  55                  60

Tyr Glu Gly Thr His Ile Asn Ile Val Asp Thr Pro Gly His Ala Asp
65                  70                  75                  80

Phe Gly Gly Glu Val Glu Arg Val Leu Ser Met Val Asp Ser Val Leu
                85                  90                  95

Leu Leu Val Asp Ala Val Glu Gly Pro Met Pro Gln Thr Arg Phe Val
                100                 105                 110

Thr Lys Lys Ala Leu Ala Leu Gly Leu Lys Pro Ile Val Val Ile Asn
            115                 120                 125

Lys Ile Asp Arg Pro Gly Ala Arg Ile Asp Trp Val Ile Asn Gln Thr
130                 135                 140

Phe Asp Leu Phe Asp Lys Leu Gly Ala Thr Glu Glu Gln Leu Asp Phe
145                 150                 155                 160

Pro Ile Val Tyr Ala Ser Gly Leu Asn Gly Tyr Ala Ser Leu Asp Pro
                165                 170                 175

Ala Ala Arg Asp Gly Asp Met Arg Pro Leu Phe Glu Ala Ile Leu Gln
            180                 185                 190

His Val Pro Val Arg Pro Ala Asp Pro Asp Ala Pro Leu Gln Leu Gln
        195                 200                 205

Ile Thr Ser Leu Asp Tyr Ser Thr Tyr Val Gly Arg Ile Gly Val Gly
    210                 215                 220

Arg Ile Thr Arg Gly Arg Ile Lys Pro Gly Gln Pro Val Val Met Arg
225                 230                 235                 240

Phe Gly Pro Glu Gly Asp Val Leu Asn Arg Lys Ile Asn Gln Val Leu
                245                 250                 255

Ser Phe Gln Gly Leu Glu Arg Val Gln Val Asp Ser Ala Glu Ala Gly
            260                 265                 270

Asp Ile Val Leu Ile Asn Gly Ile Glu Asp Val Gly Ile Gly Ala Thr
        275                 280                 285

Ile Cys Ala Val Glu Ala Pro Glu Ala Leu Pro Met Ile Thr Val Asp
    290                 295                 300
```

```
Glu Pro Thr Leu Thr Met Asn Phe Leu Val Asn Ser Pro Leu Ala
305                 310                 315                 320

Gly Arg Glu Gly Lys Phe Val Thr Ser Arg Gln Ile Arg Asp Arg Leu
            325                 330                 335

Met Lys Glu Leu Asn His Asn Val Ala Leu Arg Val Lys Asp Thr Gly
            340                 345                 350

Asp Glu Thr Val Phe Glu Val Ser Gly Arg Gly Glu Leu His Leu Thr
            355                 360                 365

Ile Leu Val Glu Asn Met Arg Arg Glu Gly Tyr Glu Leu Ala Val Ser
370                 375                 380

Arg Pro Arg Val Val Met Gln Glu Ile Asp Gly Val Lys His Glu Pro
385                 390                 395                 400

Tyr Glu Leu Leu Thr Val Asp Leu Glu Asp Glu His Gln Gly Gly Val
            405                 410                 415

Met Glu Glu Leu Gly Arg Arg Lys Gly Glu Met Leu Asp Met Val Ser
            420                 425                 430

Asp Gly Arg Gly Arg Thr Arg Leu Glu Tyr Arg Ile Pro Ala Arg Gly
            435                 440                 445

Leu Ile Gly Phe Gln Ser Glu Phe Leu Thr Leu Thr Arg Gly Thr Gly
            450                 455                 460

Leu Met Ser His Ile Phe Asp Ser Tyr Ala Pro Val Lys Glu Gly Ser
465                 470                 475                 480

Val Gly Glu Arg Arg Asn Gly Val Leu Ile Ser Gln Asp Asp Gly Ala
            485                 490                 495

Ala Val Ala Tyr Ala Leu Trp Lys Leu Gln Asp Arg Gly Arg Met Phe
            500                 505                 510

Val Lys Pro Gly Asp Ala Leu Tyr Glu Gly Met Ile Ile Gly Ile His
            515                 520                 525

Ser Arg Asp Asn Asp Leu Val Val Asn Pro Ile Lys Gly Lys Gln Leu
530                 535                 540

Thr Asn Val Arg Ala Ser Gly Thr Asp Glu Ala Val Arg Leu Val Pro
545                 550                 555                 560

Pro Ile Gln Met Ser Leu Glu Tyr Ala Val Glu Phe Ile Asp Asp
            565                 570                 575

Glu Leu Val Glu Val Thr Pro Gln Ser Ile Arg Leu Arg Lys Arg His
            580                 585                 590

Leu Lys Glu His Glu Arg Arg Ala Ser Arg Glu Ala Glu Ala Gly
            595                 600                 605
```

<210> SEQ ID NO 42
<211> LENGTH: 620
<212> TYPE: PRT
<213> ORGANISM: Burkholderia pseudomallei

<400> SEQUENCE: 42

```
Met Ser Ser Gly Val Gln Gly Gly Pro Ala Ala His Ala Asn Ala Tyr
1               5                   10                  15

Gln Thr His Pro Leu Arg Asp Ala Ala Ser Ala Leu Gly Thr Leu Ser
            20                  25                  30

Pro Gln Ala Tyr Val Asp Val Ser Ala Ala Gln Arg Asn Phe Leu
            35                  40                  45

Glu Arg Met Ser Gln Leu Ala Ser Glu Gln Cys Asp Ala Gln Pro Ala
50                  55                  60

Ala His Asp Ala Arg Leu Asp Asp Lys Pro Ala Leu Arg Ala Pro Gln
```

```
            65                  70                  75                  80
Glu Arg Asp Ala Pro Leu Gly Ala Ser Asp Thr Gly Ser Arg Ala
                    85                  90                  95
Ser Gly Ala Ala Lys Leu Thr Glu Leu Leu Gly Val Leu Met Ser Val
                100                 105                 110
Ile Ser Ala Ser Ser Leu Asp Glu Leu Lys Gln Arg Ser Asp Ile Trp
                115                 120                 125
Asn Gln Met Ser Lys Ala Ala Gln Asp Asn Leu Ser Arg Leu Ser Asp
            130                 135                 140
Ala Phe Gln Arg Ala Thr Asp Glu Ala Lys Ala Ala Asp Ala Ala
145                 150                 155                 160
Glu Gln Ala Ala Ala Ala Lys Gln Ala Gly Ala Asp Ala Lys Ala
                165                 170                 175
Ala Asp Ala Ala Val Asp Ala Ala Gln Lys Arg Tyr Asp Ala Val
                180                 185                 190
Lys Gln Gly Leu Pro Asp Asp Arg Leu Gln Ser Leu Lys Ala Ala Leu
                195                 200                 205
Glu Gln Ala Arg Gln Gln Ala Gly Asp Ala His Gly Arg Ala Asp Ala
            210                 215                 220
Leu Gln Ala Asp Ala Thr Lys Lys Leu Asp Ala Ala Ser Ala Leu Ala
225                 230                 235                 240
Thr Gln Ala Arg Ala Cys Glu Gln Gln Val Asp Asp Ala Val Asn Gln
                245                 250                 255
Ala Thr Gln Gln Tyr Gly Ala Ser Ala Ser Leu Arg Thr Pro Gln Ser
                260                 265                 270
Pro Arg Leu Ser Gly Ala Ala Glu Leu Thr Ala Val Leu Gly Lys Leu
            275                 280                 285
Gln Glu Leu Ile Ser Ser Gly Asn Val Lys Glu Leu Glu Ser Lys Gln
            290                 295                 300
Lys Leu Phe Thr Glu Met Gln Ala Lys Arg Glu Ala Glu Leu Gln Lys
305                 310                 315                 320
Lys Ser Asp Glu Tyr Gln Ala Gln Val Lys Lys Ala Glu Glu Met Gln
                325                 330                 335
Lys Thr Met Gly Cys Ile Gly Lys Ile Val Gly Trp Val Ile Thr Ala
                340                 345                 350
Val Ser Phe Ala Ala Ala Phe Thr Gly Gly Ala Ser Leu Ala Leu
                355                 360                 365
Ala Ala Val Gly Leu Ala Leu Ala Val Gly Asp Glu Ile Ser Arg Ala
            370                 375                 380
Thr Thr Gly Val Ser Phe Met Asp Lys Leu Met Gln Pro Val Met Asp
385                 390                 395                 400
Ala Ile Leu Lys Pro Leu Met Glu Met Ile Ser Ser Leu Ile Thr Lys
                405                 410                 415
Ala Leu Val Ala Cys Gly Val Asp Gln Gln Lys Ala Glu Leu Ala Gly
                420                 425                 430
Ala Ile Leu Gly Ala Val Val Thr Gly Val Ala Leu Val Ala Ala Ala
            435                 440                 445
Phe Val Gly Ala Ser Ala Val Lys Ala Val Ala Ser Lys Val Ile Asp
                450                 455                 460
Ala Met Ala Gly Gln Leu Thr Lys Leu Met Asp Ser Ala Ile Gly Lys
465                 470                 475                 480
Met Leu Val Gln Leu Ile Glu Lys Phe Ser Glu Lys Ser Gly Leu Gln
                485                 490                 495
```

```
Ala Leu Gly Ser Arg Thr Ala Thr Ala Met Thr Arg Met Arg Arg Ala
                500                 505                 510

Ile Gly Val Glu Ala Lys Glu Asp Gly Met Leu Leu Ala Asn Arg Phe
            515                 520                 525

Glu Lys Ala Gly Thr Val Met Asn Val Gly Asn Gln Val Ser Gln Ala
        530                 535                 540

Ala Gly Ile Val Val Gly Val Glu Arg Ala Lys Ala Met Gly Leu
545                 550                 555                 560

Leu Ala Asp Val Lys Glu Ala Met Tyr Asp Ile Lys Leu Leu Gly Asp
                565                 570                 575

Leu Leu Lys Gln Ala Val Asp Ala Phe Ala Glu His Asn Arg Val Leu
            580                 585                 590

Ala Gln Leu Met Gln Met Ser Asp Ala Gly Glu Met Gln Thr Ser
        595                 600                 605

Thr Gly Lys Leu Ile Leu Arg Asn Ala Arg Ala Val
    610                 615                 620

<210> SEQ ID NO 43
<211> LENGTH: 419
<212> TYPE: PRT
<213> ORGANISM: Burkholderia pseudomallei

<400> SEQUENCE: 43

Met Ser Ile Gly Val Gln Ser Gly Ile Asn Ile Ser His Ala Glu
1               5                   10                  15

Leu Ser Arg Leu Val Asp Ala Gly Lys Ser Glu Gln Gly Asp Lys Ala
            20                  25                  30

Val Arg Asp Asp Gly Arg Ala Leu Ala Arg Ala Asp Ala Leu Ala
        35                  40                  45

Ala Val Val Gly Glu Arg Val Ala Arg Arg Asp Ala Val Ala Gly
50                  55                  60

Ser Gly Ala Gln Arg Val Glu Leu Ala Arg Pro Lys Pro Asp Ala Gln
65                  70                  75                  80

Thr Arg Ala Thr Asp Arg Arg Thr Val Ser Gly Leu Glu Arg Glu His
                85                  90                  95

Lys Arg Leu Ala Ala Ser Gln Thr Pro Arg Val Thr Gly Met His Asp
            100                 105                 110

Ala Leu Val Gln Arg His Val Ser Leu Asp Gly Ala Lys Ala Ala His
        115                 120                 125

Gly Glu Gly Val Lys Arg Ala Gly Asp Ala Pro Arg Ala Ala Ala
    130                 135                 140

Asp Ala Pro Gln Arg Phe Ala Phe Ala Asp Lys Ala Phe Asp Ala
145                 150                 155                 160

Met Leu Ala Leu Gly Ala Ala Met Gln Lys Asn Val Gln Ser Asp Leu
                165                 170                 175

Ala Met Gln Gly Lys Leu Thr Met Leu Ala His Asp Ala Met Met Ser
            180                 185                 190

Ala Ala Ala Gln Asp Arg Ser Ile Gly Ala Ala Gln Met Thr Ala Ala
        195                 200                 205

Ile Ala Gly Gly Ala Leu Gln Ala Thr Thr Ser Leu Gly Gly Ala Met
    210                 215                 220

Gln Gln Met Lys Ser Leu Ser Thr Lys Ser Met Ser Ile Glu Lys Glu
225                 230                 235                 240

Leu Lys Pro Gln Ala Glu Leu Lys Gln Phe His Ala Glu Gln Ala Leu
```

-continued

```
                245                 250                 255
Glu Leu Arg Gly Ile Asn Lys Pro Val Leu Ser Asn Asp Glu Val Ser
            260                 265                 270

His Val Lys Ile Lys Arg Asp Thr Gly Glu Thr Val Arg His Glu Ile
        275                 280                 285

Asp His Gly Gly Glu Arg Met Ser Asp Glu His Ala Ser Val Leu Ala
    290                 295                 300

Gln Glu Ala Pro Ala Arg Gln His Arg Ile Asp Met His Gly Met Arg
305                 310                 315                 320

His Glu Glu Asn Leu Val Lys Ala Ser Arg Gln Gln Met Lys Gly Asp
                325                 330                 335

Leu Leu Gln Ser Gly Gly Gln Ile Gly Lys Asn Gln Ile Asp Gly Ala
            340                 345                 350

Ser Ala Gln Gln Gln Gly Ala Asp Arg Ala Glu Gln Lys Glu Asp Glu
        355                 360                 365

Asn Ala Gln Gln Thr Ala Met Ala Ala Ala Ser Thr Arg Asp Glu Ala
    370                 375                 380

Ala His Arg Ser Arg Glu Ala Ala Gln Lys Ala Ile Asp Ala Ala Lys
385                 390                 395                 400

Ser Gln Val Ala Asn Asp Asn Ala Val Ala Ala Gln Val Ala Gly Asn
                405                 410                 415

Leu Arg Thr

<210> SEQ ID NO 44
<211> LENGTH: 310
<212> TYPE: PRT
<213> ORGANISM: Burkholderia pseudomallei

<400> SEQUENCE: 44

Met Asn Met His Val Asp Met Gly Arg Ala Leu Thr Val Arg Asp Trp
1               5                   10                  15

Pro Ala Leu Glu Ala Leu Ala Lys Thr Met Pro Ala Asp Ala Gly Ala
            20                  25                  30

Arg Glu Met Thr Asp Asp Leu Arg Ala Ala Gly Val Asp Arg Arg
        35                  40                  45

Val Pro Glu Gln Lys Leu Gly Ala Ala Ile Asp Glu Phe Ala Ser Leu
    50                  55                  60

Arg Leu Pro Asp Arg Ile Asp Gly Arg Phe Val Asp Gly Arg Arg Ala
65                  70                  75                  80

Asn Leu Thr Val Phe Asp Asp Ala Arg Val Ala Val Arg Gly His Ala
                85                  90                  95

Arg Ala Gln Arg Asn Leu Leu Glu Arg Leu Glu Thr Glu Leu Leu Gly
            100                 105                 110

Gly Thr Leu Asp Thr Ala Gly Asp Glu Gly Gly Ile Gln Pro Asp Pro
        115                 120                 125

Ile Leu Gln Gly Leu Val Asp Val Ile Gly Gln Gly Lys Ser Asp Ile
    130                 135                 140

Asp Ala Tyr Ala Thr Ile Val Glu Gly Leu Thr Lys Tyr Phe Gln Ser
145                 150                 155                 160

Val Ala Asp Val Met Ser Lys Leu Gln Asp Tyr Ile Ser Ala Lys Asp
                165                 170                 175

Asp Lys Asn Met Lys Ile Asp Gly Gly Lys Ile Lys Ala Leu Ile Gln
            180                 185                 190

Gln Val Ile Asp His Leu Pro Thr Met Gln Leu Pro Lys Gly Ala Asp
```

```
                    195                 200                 205
Ile Ala Arg Trp Arg Lys Glu Leu Gly Asp Ala Val Ser Ile Ser Asp
    210                 215                 220

Ser Gly Val Val Thr Ile Asn Pro Asp Lys Leu Ile Lys Met Arg Asp
225                 230                 235                 240

Ser Leu Pro Pro Asp Gly Thr Val Trp Asp Thr Ala Arg Tyr Gln Ala
                245                 250                 255

Trp Asn Thr Ala Phe Ser Gly Gln Lys Asp Asn Ile Gln Asn Asp Val
            260                 265                 270

Gln Thr Leu Val Glu Lys Tyr Ser His Gln Asn Ser Asn Phe Asp Asn
        275                 280                 285

Leu Val Lys Met Leu Ser Gly Ala Ile Ser Thr Leu Thr Asp Ala Ala
    290                 295                 300

Lys Ser Tyr Leu Gln Ile
305                 310

<210> SEQ ID NO 45
<211> LENGTH: 224
<212> TYPE: PRT
<213> ORGANISM: Burkholderia pseudomallei

<400> SEQUENCE: 45

Met Asn Lys Leu Ser Lys Leu Ala Phe Ile Ala Ala Thr Ala Val Met
1               5                   10                  15

Ala Ala Ser Ala Ser Ala Gln Ser Val Pro Ala Ser Arg Gln Ala Val
            20                  25                  30

Asn Asp Asn Trp Val Asn Gly Thr Gly Glu Trp Val Trp Met Asn Gly
        35                  40                  45

Thr Asn Glu Leu Cys Trp Arg Asp Ala Phe Trp Thr Pro Ala Thr Ala
    50                  55                  60

Asn Ala Lys Cys Asp Gly Ala Leu Val Ala Gln Ala Pro Ala Pro Ala
65                  70                  75                  80

Pro Val Ala Pro Val Ala Pro Ile Thr Ser Gln Lys Ile Thr Tyr
                85                  90                  95

Gln Ala Asp Thr Leu Phe Asp Phe Asp Lys Ala Val Leu Lys Pro Ala
            100                 105                 110

Gly Lys Gln Lys Leu Asp Glu Leu Ala Ala Lys Ile Gln Gly Met Asn
        115                 120                 125

Val Glu Val Val Val Ala Thr Gly Tyr Thr Asp Arg Ile Gly Ser Asp
    130                 135                 140

Lys Tyr Asn Asp Arg Leu Ser Leu Arg Arg Ala Gln Ala Val Lys Ser
145                 150                 155                 160

Tyr Leu Val Ser Lys Gly Val Pro Ala Asn Lys Val Tyr Thr Glu Gly
                165                 170                 175

Lys Gly Lys Arg Asn Pro Val Thr Gly Asn Thr Cys Lys Gln Lys Asn
            180                 185                 190

Arg Lys Gln Leu Ile Ala Cys Leu Ala Pro Asp Arg Val Glu Val
        195                 200                 205

Glu Val Val Gly Thr Gln Glu Val Gln Lys Thr Thr Val Pro Ala Gln
    210                 215                 220

<210> SEQ ID NO 46
<211> LENGTH: 177
<212> TYPE: PRT
<213> ORGANISM: Burkholderia pseudomallei
```

-continued

```
<400> SEQUENCE: 46

Met Thr Thr Arg Arg Val Thr Met Met Ser Lys Lys Leu Arg Leu Ala
1               5                   10                  15

Phe Ala Met Leu Met Ile Gly Ala Leu Ala Ala Cys Lys Ser Gly Val
            20                  25                  30

Lys Leu Asp Glu His Ala Asn Gln Gly Asp Ala Val Ser Thr Gln Pro
        35                  40                  45

Asn Pro Glu Asn Val Ala Gln Val Thr Val Asp Pro Leu Asn Asp Pro
    50                  55                  60

Asn Ser Pro Leu Ala Lys Arg Ser Val Tyr Phe Asp Phe Asp Ser Tyr
65                  70                  75                  80

Ser Val Gln Asp Gln Tyr Gln Ala Leu Leu Gln His Ala Gln Tyr
                85                  90                  95

Leu Lys Ser His Pro Gln Arg His Ile Leu Ile Gln Gly Asn Thr Asp
            100                 105                 110

Glu Arg Gly Thr Ser Glu Tyr Asn Leu Ala Leu Gly Gln Lys Arg Ala
        115                 120                 125

Glu Ala Val Arg Arg Ala Leu Ser Leu Leu Gly Val Gly Asp Ala Gln
    130                 135                 140

Met Glu Ala Val Ser Leu Gly Lys Glu Lys Pro Val Ala Leu Gly His
145                 150                 155                 160

Asp Glu Ala Ser Trp Ala Gln Asn Arg Arg Ala Asp Leu Val Tyr Gln
                165                 170                 175

Gln

<210> SEQ ID NO 47
<211> LENGTH: 769
<212> TYPE: PRT
<213> ORGANISM: Burkholderia pseudomallei

<400> SEQUENCE: 47

Met Leu Phe Lys Pro His Arg Phe Val Pro Lys Thr Val Ala Ala Ala
1               5                   10                  15

Ala Leu Ala Ala His Gly Leu Ala Ala His Ala Thr Ala Pro Phe Val
            20                  25                  30

Val Gln Asp Ile Lys Ile Glu Gly Leu Gln Arg Val Glu Ala Gly Ser
        35                  40                  45

Val Phe Ala Tyr Leu Pro Ile Lys Gln Gly Asp Thr Phe Thr Asp Asp
    50                  55                  60

Lys Ala Ser Glu Ala Ile Arg Ala Leu Tyr Ala Thr Gly Phe Phe Asn
65                  70                  75                  80

Asp Val Arg Ile Ala Thr Gln Gly Gly Val Val Ile Gln Val Gln
                85                  90                  95

Glu Arg Pro Ala Ile Ala Ser Ile Asp Phe Thr Gly Ile Lys Glu Phe
            100                 105                 110

Asp Lys Asp Asn Leu Asn Lys Ala Leu Lys Ala Val Gly Leu Ser Gln
        115                 120                 125

Gly Arg Tyr Tyr Asp Lys Ala Leu Val Asp Lys Ala Glu Gln Glu Leu
    130                 135                 140

Lys Arg Gln Tyr Leu Thr Arg Gly Phe Tyr Ala Ala Glu Val Ser Thr
145                 150                 155                 160

Thr Val Thr Pro Val Asp Ala Asn Arg Val Ser Ile Leu Phe Ala Val
                165                 170                 175

Ala Glu Gly Pro Ser Ala Lys Ile Arg Gln Ile Asn Phe Ile Gly Asn
```

```
                180                 185                 190
Lys Ala Phe Lys Thr Ser Thr Leu Arg Asp Glu Met Gln Leu Ser Thr
                195                 200                 205

Pro Asn Trp Phe Ser Trp Tyr Thr Lys Asn Asp Leu Tyr Ser Lys Glu
        210                 215                 220

Lys Leu Thr Gly Asp Leu Glu Asn Val Arg Ser Tyr Tyr Leu Asn Arg
225                 230                 235                 240

Gly Tyr Leu Glu Phe Asn Ile Glu Ser Thr Gln Val Ser Ile Ser Pro
                245                 250                 255

Asp Lys Lys Asp Met Tyr Leu Thr Val Ala Leu His Glu Gly Glu Pro
        260                 265                 270

Tyr Thr Val Ser Ser Val Lys Leu Ala Gly Asn Leu Leu Asp Arg Gln
        275                 280                 285

Ala Glu Leu Glu Lys Leu Val Lys Ile Lys Pro Gly Asp Arg Phe Ser
        290                 295                 300

Ala Glu Lys Leu Gln Gln Thr Thr Lys Ala Ile Val Asp Lys Leu Gly
305                 310                 315                 320

Gln Tyr Gly Tyr Ala Phe Ala Thr Val Asn Ala Gln Pro Glu Ile Asp
                325                 330                 335

Gln Ala Thr His Lys Val Gly Leu Thr Leu Val Val Asp Pro Ser Arg
        340                 345                 350

Arg Val Tyr Val Arg Arg Ile Asn Ile Val Gly Asn Thr Arg Thr Arg
        355                 360                 365

Asp Glu Val Val Arg Arg Glu Met Arg Gln Leu Glu Ser Ser Trp Phe
        370                 375                 380

Asp Ser Ser Arg Leu Ala Leu Ser Lys Asp Arg Val Asn Arg Leu Gly
385                 390                 395                 400

Tyr Phe Thr Asp Val Asp Val Thr Val Pro Val Glu Gly Thr Asn
                405                 410                 415

Asp Gln Val Asp Val Asn Val Lys Val Ala Glu Lys Pro Thr Gly Ala
        420                 425                 430

Ile Thr Leu Gly Ala Gly Phe Ser Ser Thr Asp Lys Val Val Leu Ser
        435                 440                 445

Ala Gly Ile Ser Gln Asp Asn Val Phe Gly Ser Gly Thr Ser Leu Ala
        450                 455                 460

Val Asn Val Asn Thr Ala Lys Ser Tyr Arg Thr Leu Thr Val Thr Gln
465                 470                 475                 480

Val Asp Pro Tyr Phe Thr Val Asp Gly Ile Lys Arg Ile Thr Asp Val
                485                 490                 495

Phe Tyr Arg Thr Tyr Gln Pro Leu Tyr Tyr Ser Thr Asn Ser Ser Phe
                500                 505                 510

Arg Ile Ile Thr Ala Gly Gly Asn Leu Lys Phe Gly Ile Pro Phe Ser
                515                 520                 525

Glu Thr Asp Thr Val Tyr Phe Gly Ala Gly Phe Glu Gln Asn Arg Leu
        530                 535                 540

Asp Val Asp Ser Asn Thr Pro Gln Ser Tyr Gln Asp Tyr Val Asn Glu
545                 550                 555                 560

Phe Gly Arg Val Ser Asn Thr Pro Leu Thr Ile Gly Trp Ser Arg
                565                 570                 575

Asp Ala Arg Asp Ser Ala Leu Ile Pro Ser Arg Gly Tyr Phe Thr Gln
                580                 585                 590

Ala Asn Ala Glu Tyr Gly Val Pro Val Gly Lys Ile Gln Tyr Tyr Lys
                595                 600                 605
```

```
Met Asp Val Gln Gly Gln Tyr Tyr Tyr Ser Phe Ala Arg Gly Phe Ile
            610                 615                 620

Leu Gly Leu Asn Phe Gln Ala Gly Tyr Gly Asn Gly Ile Gly Asn Pro
625                 630                 635                 640

Tyr Pro Ile Phe Lys Asn Tyr Tyr Ala Gly Gly Ile Gly Ser Val Arg
                645                 650                 655

Gly Tyr Glu Pro Ser Ser Leu Gly Pro Arg Asp Thr Lys Thr Asn Asp
            660                 665                 670

Pro Ile Gly Gly Ser Lys Met Val Val Gly Asn Ile Glu Leu Thr Phe
            675                 680                 685

Pro Leu Pro Gly Thr Gly Tyr Asp Arg Thr Leu Arg Val Phe Thr Phe
690                 695                 700

Leu Asp Gly Gly Asn Val Trp Gly Asn Ala Pro Gly Gly Thr Ser Thr
705                 710                 715                 720

Gly Ala Asn Gly Leu Arg Tyr Gly Tyr Gly Ile Gly Leu Ala Trp Ile
                725                 730                 735

Ser Pro Ile Gly Pro Leu Lys Leu Ser Leu Gly Phe Pro Leu Gln Lys
                740                 745                 750

His Glu Gly Asp Gln Tyr Gln Lys Phe Gln Phe Gln Ile Gly Thr Ala
            755                 760                 765

Phe

<210> SEQ ID NO 48
<211> LENGTH: 498
<212> TYPE: PRT
<213> ORGANISM: Burkholderia pseudomallei

<400> SEQUENCE: 48

Met Gly Asp Lys His Arg Arg Arg Ala Arg Arg Asp Trp Arg Ala
1               5                   10                  15

Pro Val Ser Cys Trp Leu Gly Ala Thr Leu Leu Ala Cys Ala Trp Ser
                20                  25                  30

Ala His Ala Gln Asp Ser Gly Ala Ala Arg Trp Arg Asp Gly Ala Asp
            35                  40                  45

Gly Ile Gly Phe Phe Pro Gly Gly Asp Ala Pro Gly Phe Asp Ala Arg
        50                  55                  60

Ala Trp Gly Pro Val Pro Gly Asp Ala Arg Arg Ala Ala Ser Asp
65                  70                  75                  80

Ala Arg Asn Gly Val Ala Ala Ser Ala Gly Ser Glu Ala Thr Ala Ala
                85                  90                  95

Ala Pro Ala Ala Asp Ala Asn Ala Ala Pro Ala Arg Lys Leu Thr Glu
            100                 105                 110

Glu Arg Ile Thr Leu Gly Glu Arg Val Ala Pro Val Ala Asp Ala Ala
        115                 120                 125

Arg Arg Val Arg Ala Asp Gly Asp Gly Ile Gly Phe Ala Asp Ala
130                 135                 140

Pro Gly Gly Pro Pro Ala Gly Gly Ala Thr Pro Ser Ala Ala Cys Asp
145                 150                 155                 160

Asp Gly Ala Cys Val Pro Asp Gly Gly Asp Ala Gly Arg Ala Pro Arg
                165                 170                 175

Arg Pro Pro Ala Gly Ala Thr Pro Arg Phe Ile Ala Gly Val Arg Tyr
            180                 185                 190

Asp Arg Met Pro Tyr Glu Leu His Pro Ile Asp Pro Glu Arg Leu Pro
        195                 200                 205
```

```
Asp Leu Pro Glu Ala Gln Gly Pro Thr Leu Leu Gln Leu Gln Gly
    210                 215                 220

Asp Asp Ser Asn Met Ile Gly Val Gly Trp His Tyr Val Leu Ser Thr
225                 230                 235                 240

Gly Arg Ser Thr Pro Val Thr Thr Ser Thr Ala Ala Leu Gly Ile Gly
                245                 250                 255

Ser Phe Ala Asn Pro Gly Ser Ala Val Ser Ile Ser Asn Thr Asn Thr
            260                 265                 270

Pro Ala Phe Thr Phe Thr His Phe Gly Glu His Val Ala Ala Glu
        275                 280                 285

Ile Val Ala Gly Ile Pro Pro Glu Leu Thr Met Arg Gly His Gly Ser
290                 295                 300

Ile Gly Leu Pro Phe Asp Lys Ile Phe Pro Gly Val Gln Gly Arg Leu
305                 310                 315                 320

Pro Leu Val Asp Leu Gly Asn Thr Gln Ser Asn Pro Leu Gly Thr Thr
                325                 330                 335

Arg Ala Trp Leu Gly Ser Ala Val Phe Lys Tyr Tyr Leu Gly Lys Arg
            340                 345                 350

Glu Asp Arg Leu Arg Pro Tyr Val Gly Leu Gly Leu Ser Tyr Thr Arg
        355                 360                 365

Phe Thr Asn Thr Asn Leu Asn Pro Val Phe Ala His Lys Leu Ala Ser
    370                 375                 380

Leu Gly Gly Leu Leu Ser Ala Gly Ile Ser Leu Gly Asp Leu Gln Ser
385                 390                 395                 400

Leu Leu Thr Asp Ser Gly Ala Leu Asp Arg Leu Leu Gln Ala Gly Ala
                405                 410                 415

Asn Leu Ile Leu Pro Asn Gly Val Arg Ala Thr Ala Asp Val Lys Ser
            420                 425                 430

Ala Trp Thr Pro Val Phe Val Val Gly Ala Asn Tyr Gln Leu Thr Arg
        435                 440                 445

Gln Leu Ser Leu Ser Thr Ala Leu Ser Tyr Ile Pro Leu Lys Ala Ala
    450                 455                 460

Ile Thr Val Asn Ile Asn Asp Thr Lys Gly Ile Leu Ala Ser Asn Thr
465                 470                 475                 480

Thr Thr Leu Ser Ala Asn Val Leu Leu Cys Thr Met Leu Leu Asn Phe
                485                 490                 495

Arg Phe

<210> SEQ ID NO 49
<211> LENGTH: 364
<212> TYPE: PRT
<213> ORGANISM: Burkholderia pseudomallei

<400> SEQUENCE: 49

Met Lys Arg Ile Ala Trp Leu Ala Ala Val Leu Ala Ser Leu Ala Cys
1               5                   10                  15

Ala Ala Ala Arg Ala Ala Gly Gly Asn Val Leu Asn Ile Tyr Asn Trp
                20                  25                  30

Ala Glu Tyr Phe Ala Pro Asp Thr Ile Ala Gly Phe Glu Lys Glu Thr
            35                  40                  45

Gly Ile Lys Val Arg Leu Asp Val Tyr Asp Ser Asn Glu Ala Leu Gln
        50                  55                  60

Thr Lys Leu Thr Thr Gly Asn Ser Gly Tyr Asp Leu Val Phe Pro Ser
65                  70                  75                  80
```

```
Asn Asp Phe Leu Ala Arg Gln Ile Gln Ala Gly Leu Tyr Arg Lys Leu
                85                  90                  95

Asp Lys Ser Arg Leu Pro Asn Leu Thr Asn Leu Asp Pro Ala Ile Val
            100                 105                 110

Ala Arg Ala Ala Glu Val Asp Pro Gly Asn Gln Tyr Ser Val Pro Tyr
        115                 120                 125

Met Gln Gly Thr Phe Gly Leu Gly Leu Asn Val Ala Lys Val Lys Gln
    130                 135                 140

Ala Leu Gly Gly Pro Leu Pro Ala Asn Thr Leu Glu Leu Ile Phe Asn
145                 150                 155                 160

Pro Ala Tyr Ala Ala Lys Leu Glu Arg Cys Gly Ile Ala Phe Asn Asp
                165                 170                 175

Ala Gly Ser Glu Val Phe Pro Leu Ala Leu Arg Tyr Ile Gly Arg Asp
            180                 185                 190

Pro Asn Thr Thr Asp Pro Arg Asp Tyr Glu Ala Ala Leu Asp Met Met
        195                 200                 205

Lys Lys Ile Arg Pro Thr Ile Arg Gln Phe Ile Ala Thr Pro Val Met
    210                 215                 220

Asn Asp Leu Ala Thr Gly Asp Val Cys Val Val Thr Gly Tyr Ser Gly
225                 230                 235                 240

Ala Val Leu Val Ala Ala Arg Arg Ala Ala Glu Ala Lys Asn Gly Gln
                245                 250                 255

Gln Ile Val Tyr Ser Leu Pro Ser Ala Gly Ala Pro Phe Trp Phe Asp
            260                 265                 270

Ser Met Ala Ile Pro Lys Gly Ala His Ala Asp His Ala Leu Arg
        275                 280                 285

Phe Ile Asp Tyr Ile Leu Arg Pro Asp Val Val Ala Lys Ile Ser Asn
    290                 295                 300

Lys Val Met Tyr Pro Asn Pro Asn Arg Val Ala Thr Pro Leu Val Asp
305                 310                 315                 320

Arg Arg Leu Thr Ala Asn Pro Ala Ile Tyr Pro Asp Ala Ala Thr Met
                325                 330                 335

Arg Thr Leu Trp Val Lys Arg Pro Met Pro Pro Gln Ala Met Arg Met
            340                 345                 350

Gln Thr Arg Tyr Trp Thr Arg Phe Lys Thr Gly Tyr
        355                 360

<210> SEQ ID NO 50
<211> LENGTH: 539
<212> TYPE: PRT
<213> ORGANISM: Burkholderia pseudomallei

<400> SEQUENCE: 50

Met Lys His Thr His Ala Phe Ala Ala Val Leu Ala Ala Leu Ala Leu
1               5                   10                  15

Thr Ile Ala Pro Ser Ala Pro Ala Val Thr Val Ala Ser Asn Val Thr
                20                  25                  30

Leu Ala Asp Gln Gln Asp Leu Thr Arg Gln Val Pro Ala Glu Val Glu
            35                  40                  45

Ser Leu Asp Pro Ala His Ile Glu Ser Trp Thr Gly Asn Thr Ile Gly
        50                  55                  60

Leu Asp Leu Phe Glu Gly Leu Ala Arg Ile Asp Ala Ser Gly Ala Val
65                  70                  75                  80

Val Pro Gly Val Ala Gln Ala Trp Glu His Lys Ala Pro Asp Thr Trp
```

```
                    85                  90                  95
Ile Phe Lys Leu Arg Arg Asp Ala Lys Trp Ser Asn Gly Gln Pro Val
                100                 105                 110

Thr Ala Ala Asp Phe Val Tyr Ala Trp Gln Arg Leu Ala Asp Pro Lys
                115                 120                 125

Thr Gly Ser Lys Tyr Thr Ile Leu Val Glu Phe Val Lys Asn Ala Ser
                130                 135                 140

Ala Ile Ile Ala Gly Lys Gln Pro Pro Gly Asp Leu Gly Ile Arg Ala
145                 150                 155                 160

Ile Asp Pro Tyr Thr Ile Glu Val Lys Thr Glu Val Pro Val Ser Tyr
                165                 170                 175

Phe Pro Glu Leu Thr Ala Met Ala Pro Leu Thr Pro Val Asn Lys Asp
                180                 185                 190

Ala Val Ala Lys Phe Gly Asp Ala Trp Thr Arg Pro Lys Asn Ile Val
                195                 200                 205

Ser Asn Gly Pro Tyr Thr Leu Val Asp Trp Gln Pro Asn Asn Arg Ile
                210                 215                 220

Val Met Ala Lys Ser Asp Lys Tyr Trp Asn Ala Arg Asn Val Val Ile
225                 230                 235                 240

Arg Lys Val Thr Tyr Leu Pro Ile Glu Asn Asp Glu Thr Ala Leu Arg
                245                 250                 255

Met Tyr Gln Ala Gly Gln Ile Asp Tyr Thr Tyr Ser Ile Pro Ala Gly
                260                 265                 270

Gly Phe Gly Gln Ile Ser Lys Gln Phe Gly Lys Glu Leu Arg Pro Gly
                275                 280                 285

Leu Gln Leu Ala Thr Tyr Tyr Tyr Leu Lys Asn Ser Asp Pro Ala
                290                 295                 300

Leu Lys Asp Lys Arg Val Arg Glu Ala Leu Ala Met Val Leu Asp Arg
305                 310                 315                 320

Glu Ile Leu Thr Ser Lys Ile Thr Gln Ala Gly Glu Val Pro Met Tyr
                325                 330                 335

Gly Leu Met Pro Lys Gly Val Lys Gly Val Gln Arg Pro Phe Thr Pro
                340                 345                 350

Asp Trp Ala Ser Trp Pro Met Ala Arg Arg Val Asp Tyr Ala Lys Asn
                355                 360                 365

Leu Leu Lys Gln Ala Gly His Gly Asp Ala Asn Pro Leu Thr Phe Thr
                370                 375                 380

Leu Thr Tyr Asn Thr Asn Asp Leu His Lys Lys Val Ala Leu Phe Ala
385                 390                 395                 400

Ala Ser Glu Trp Arg Thr Lys Leu Gly Val Thr Ala Lys Leu Glu Asn
                405                 410                 415

Val Glu Phe Lys Val Leu Met Lys Gln Arg His Asp Gly Lys Val Gln
                420                 425                 430

Val Ala Arg Asp Gly Trp Phe Ala Asp Tyr Asn Asp Ala Met Thr Phe
                435                 440                 445

Phe Asp Leu Ile Arg Cys Gly Ser Ser Gln Asn Thr Val Gly Tyr Cys
                450                 455                 460

Asn Pro Lys Val Asp Ser Leu Val Ala Glu Ala Asn Gln Lys Leu Asp
465                 470                 475                 480

Asp Gly Ala Arg Ala Ala Leu Leu Thr Gln Ala His Asp Leu Ala Met
                485                 490                 495

Asn Asp Tyr Pro Met Val Pro Leu Phe Gln Tyr Ser Ala Asp Arg Leu
                500                 505                 510
```

Val Lys Ser Tyr Val Gly Gly Tyr Thr Leu Thr Asn Tyr Ile Asp Met
            515                 520                 525

Arg Ala Ser Gln Asp Met Tyr Leu Ile Lys His
            530                 535

<210> SEQ ID NO 51
<211> LENGTH: 512
<212> TYPE: PRT
<213> ORGANISM: Burkholderia pseudomallei

<400> SEQUENCE: 51

Met Ile Asn Val Gly Ala Phe Val Ala Ser Ala Arg Ser Gly Ala Arg
1               5                   10                  15

Val Val Val Gly Gly Asp Ala Arg Gly Pro Val Val Ser Ala Ala Arg
            20                  25                  30

Leu Gly Met Lys Glu Arg Leu Phe Ala Phe Leu Ala His Val Pro Leu
        35                  40                  45

Leu Lys His Cys Asp Ala Val Arg Arg Tyr Ala Glu Gln Val Arg Met
    50                  55                  60

Glu Asn Arg Arg Ser Leu Glu Val Phe Val Leu Ala Leu Ser Lys Arg
65                  70                  75                  80

Tyr Gly Pro Glu Gly Ala Lys Ala Ala Phe Asp Tyr Gly Ala Arg Arg
                85                  90                  95

Asp Gly Ala Pro Leu Asp Gln Arg Arg Val Arg Asn Met Val Ser Ile
            100                 105                 110

Ala Glu His Phe His Gly Thr Gly Asp Ala Lys Pro Leu Ala Arg Gln
        115                 120                 125

Met Val Phe Arg Ser Trp Glu Cys Arg Gly Leu Asp His Pro Gly His
    130                 135                 140

Ala Ser Leu Thr Ile Lys Asn Gln Ala Asp Ala Asp Ala Gly Arg His
145                 150                 155                 160

Val Tyr Glu His Val Ser Trp Trp Pro Asn Gln Arg Leu Gly Ser Lys
                165                 170                 175

Glu His Phe Asp Arg Ile Glu Pro Lys Thr Leu Asp Gly Tyr Arg Ile
            180                 185                 190

Asp Lys Arg Ser Glu Ile Ser Ser Ala Thr Glu Gln Arg Leu Arg Glu
        195                 200                 205

Gly Asp Ala Ala Arg Arg Lys Ile Leu Ala Asp Gly Phe Lys Tyr Ala
    210                 215                 220

Asn Gln Asp Glu Arg His Asp Ala Arg Phe Phe Pro Arg Ala Gly Gln
225                 230                 235                 240

Lys Leu Asp Lys Asp Ala Glu Trp Gly Leu Ser Ala Arg Lys Val Tyr
                245                 250                 255

Phe Pro Ala Ile Gly Phe Asn His Asp Arg Arg Asp Thr Asp Arg Pro
            260                 265                 270

Arg Ala Phe Val Leu Phe Gly Leu Asn Glu Ala Ala Met Leu Arg Asp
        275                 280                 285

Ala Arg Thr Val Lys Glu Gly Ala Lys Ser Gly Glu Leu Lys Tyr Arg
    290                 295                 300

Met Ile Ser Lys Lys Glu Asn Cys Ala Ser Met Ala Leu Arg Val Leu
305                 310                 315                 320

Arg Ala Gly Gly Ala Glu His Phe Val Pro Tyr Thr Ala Ala Trp Ile
                325                 330                 335

Ser Glu Asp Pro Asn His Ala His Ala Tyr Ala Leu Ala Val Gln Ala

```
            340                 345                 350

Arg Ile Asp Ala Leu Asn Gln Arg Arg Ala Asp Val Glu Arg Arg Cys
        355                 360                 365

Glu Arg Leu Arg Asp Ser Ala Ser Val Arg Gln Ala Trp Arg Ala Phe
    370                 375                 380

Ser Glu Ala Gly Gly Ala Ser Ala Ser Pro Leu Ala Glu Asp Ala Gly
385                 390                 395                 400
Arg Gly Arg Ala Ser Ala His Met Arg Gln Ala Arg Leu Asp Glu His
                405                 410                 415
Ala Arg Glu Val Glu Arg Ile Gly Ala Tyr Phe Ala Glu Leu Ser Ala
            420                 425                 430

Gly Arg Ser Gly Lys His Arg Asp Arg Ala Asp Ala Ala Leu Ala Asp
        435                 440                 445

Ala Met Lys Arg Cys Ala Pro Ser Ala Arg Asp Asp Val Ala Ala Leu
    450                 455                 460
Thr Arg Lys Ala Ser Val Leu Val Glu Thr Leu Gly Arg His Leu Asp
465                 470                 475                 480
Ala Pro Pro Pro Ser Asp Ser Ser Ala Leu Arg Arg Leu Ala Ala His
                485                 490                 495

Ala Met Ile Gly Arg Ile Glu Ala Phe Met Ala Ala Ala Ile Ala Ala
            500                 505                 510

<210> SEQ ID NO 52
<211> LENGTH: 516
<212> TYPE: PRT
<213> ORGANISM: Burkholderia pseudomallei

<400> SEQUENCE: 52

Met His Ala Lys Ala Ser Ser Ser His Ala Pro Asp Ala Pro Lys Pro
1               5                   10                  15

Ser Ser Ile Ala Thr Thr Leu Cys Arg Ala Leu Ala Ser Leu Ser Leu
            20                  25                  30

Gly Leu Ser Met Asp Ala Glu Ala Asn Pro Pro Glu Pro Pro Gly Gly
        35                  40                  45

Thr Asn Ile Pro Val Pro Pro Pro Met Pro Gly Gly Gly Ala Asn Ile
    50                  55                  60

Pro Val Pro Pro Pro Met Pro Gly Gly Gly Ala Asn Ile Pro Pro Pro
65                  70                  75                  80

Pro Pro Pro Pro Gly Gly Ile Gly Gly Ala Thr Pro Ser Pro Pro Pro
                85                  90                  95

Leu Thr Pro Val Asn Gly Asn Pro Gly Ala Ser Thr Pro Thr Lys Thr
            100                 105                 110

Gly Leu Leu Lys Thr Leu Asn Arg Leu Ser Ala Glu Leu Gln Asn Asn
        115                 120                 125

Pro Arg Val Thr Glu Asp Val Val Asp Asn Val Asp Ala Val Ile Arg
    130                 135                 140

Asn Ala Val Asn Leu Ala Pro Asp Ala Asn Gly Asp Phe Ser Gly Arg
145                 150                 155                 160

Ser Ala Met Pro Ile Glu Met Ala Ala Asn Ala Ala Leu Arg Ser Leu
                165                 170                 175

Lys Lys Asn Pro Gly Asp Ala Gly His Ala Ala Pro Ala Tyr Leu Pro
            180                 185                 190

Ala Glu Arg Ile Gly Gln Leu Arg Glu Lys Val Arg Arg Thr Ile Glu
        195                 200                 205
```

Ala Leu Glu Ser Asn Arg Pro Pro Lys Pro Gln Pro Arg Ser Thr Pro
    210                 215                 220

Pro Gln Ser Thr Pro Pro Lys Pro Thr Gln His Pro Thr Ala Pro Asn
225                 230                 235                 240

Pro Asn Val Pro Asp Ala Ser Thr Pro Asp Ala Ser Thr Pro Asp Ala
            245                 250                 255

Ser Thr Pro Asp Ala Ser Thr Pro Asp Ala Ser Thr Pro Ser Arg Pro
        260                 265                 270

Ala Pro Ala Pro Arg Ala Gly Thr Gly Ala Pro Ala Ala Ser Ala Ala
    275                 280                 285

Thr Arg Ala Pro Ala Phe Ala Asn Arg Val Arg Lys Pro Asn Pro Ala
    290                 295                 300

Met Pro Ala Ala Ser Ser His Ala Ile Ala Ser Asp Phe Ala Ser Ser
305                 310                 315                 320

Asn Ala Phe Ala Ile Gly Asp Asp Ser Thr Ala Val Gly Ala Gln Ala
                325                 330                 335

Ile Ala Phe Ser Glu Gln Ser Ile Ala Ile Gly Ser Arg Ala Ile Ala
            340                 345                 350

Ala Gly Ala Arg Ser Ile Ala Val Gly Thr Asp Ala Thr Ala Ala Ala
    355                 360                 365

Pro Asp Ser Val Ala Leu Gly Ser Gly Ser Ile Ala Glu Arg Glu Gly
    370                 375                 380

Thr Val Ser Val Gly Arg Asp Gly His Glu Arg Gln Ile Thr His Val
385                 390                 395                 400

Ala Ser Gly Thr Glu Pro Thr Asp Ala Val Asn Val Thr Gln Leu Arg
                405                 410                 415

Ala Ala Met Ser Asn Ala Asn Ala Tyr Thr Asn Gln Arg Ile Gly Asp
            420                 425                 430

Leu Gln Gln Ser Ile Thr Asp Thr Ala Arg Asp Ala Tyr Ser Gly Val
        435                 440                 445

Ala Ala Ala Thr Ala Leu Thr Met Ile Pro Asp Val Asp Arg Asp Lys
    450                 455                 460

Arg Val Ser Ile Gly Val Gly Gly Ala Val Tyr Lys Gly His Arg Ala
465                 470                 475                 480

Val Ala Leu Gly Gly Thr Ala Arg Ile Asn Glu Asn Leu Lys Val Arg
                485                 490                 495

Ala Gly Val Ala Met Ser Ala Gly Gly Asn Ala Val Gly Ile Gly Met
            500                 505                 510

Ser Trp Gln Trp
        515

<210> SEQ ID NO 53
<211> LENGTH: 155
<212> TYPE: PRT
<213> ORGANISM: Burkholderia pseudomallei

<400> SEQUENCE: 53

Met Thr Arg Ala Leu Gly Arg Leu Arg Ser Pro Arg Arg Gln Arg Gly
1               5                   10                  15

Ala Thr Ala Ile Glu Phe Ala Ile Leu Phe Pro Met Phe Phe Leu Ile
            20                  25                  30

Leu Tyr Gly Ile Ile Thr Tyr Gly Met Ile Phe Ala Ala Gln Gln Ser
        35                  40                  45

Leu Thr Leu Ala Ala Thr Glu Gly Ala Arg Ala Ala Leu Asn Tyr Gln
    50                  55                  60

Val Ala Gln Thr Gln Ser Ala Ala Leu Gly Leu Arg Ala Ala Ala
65                  70                  75                  80

Cys Thr Ala Ala Asn Asn Leu Thr Gly Trp Leu Ser Gly Ala Thr Cys
85 90 95

Thr Thr Ser Thr Asn Tyr Thr Cys Ser Tyr Asp Ser Thr Met Tyr Cys
100 105 110

Ile Gln Val Thr Leu Thr Tyr Pro Tyr Ala Ala Asn Pro Leu Val Pro
115 120 125

Ala Val Ala Leu Phe Asp Ala Val Leu Pro Thr Thr Leu Thr Ser Arg
130 135 140

Ala Thr Val Gln Ile Asn Pro Thr Asn Ile Ile
145 150 155

<210> SEQ ID NO 54
<211> LENGTH: 506
<212> TYPE: PRT
<213> ORGANISM: Burkholderia pseudomallei

<400> SEQUENCE: 54

Met Asn His Ala Asp Met Gln His Leu Asn Ile Glu Phe Pro Tyr Arg
1 5 10 15

Lys Gln Tyr Gly Asn Phe Ile Gly Gly Glu Trp Val Ala Pro Val Gly
20 25 30

Gly Glu Tyr Phe Asp Asn Val Ser Pro Val Thr Gly Arg Pro Phe Thr
35 40 45

Ala Ile Pro Arg Ser Arg Glu Ala Asp Ile Glu Leu Ala Leu Asp Ala
50 55 60

Ala His Ala Ala Lys Ala Gly Trp Ala Ala Lys Gly Ala Ala Glu Arg
65 70 75 80

Ala Asn Val Leu Leu Arg Ile Ala Asp Arg Met Glu Ala Asn Leu Thr
85 90 95

Arg Leu Ala Val Ala Glu Thr Ile Asp Asn Gly Lys Pro Leu Arg Glu
100 105 110

Thr Thr Ala Ala Asp Val Pro Leu Ala Ile Asp His Phe Arg Tyr Phe
115 120 125

Ala Gly Cys Ile Arg Ala Gln Glu Gly Ser Ile Ala Asp Ile Gly Gly
130 135 140

Asp Met Val Ala Tyr His Phe His Glu Pro Leu Gly Val Val Gly Gln
145 150 155 160

Ile Ile Pro Trp Asn Phe Pro Leu Leu Met Ala Ala Trp Lys Leu Ala
165 170 175

Pro Ala Leu Ala Ala Gly Asn Cys Val Val Leu Lys Pro Ala Glu Gln
180 185 190

Thr Pro Ala Ser Ile Leu Val Phe Ala Glu Leu Ile Gln Asp Leu Leu
195 200 205

Pro Pro Gly Val Leu Asn Ile Val Asn Gly Phe Gly Leu Glu Ala Gly
210 215 220

Lys Pro Leu Ala Ser Ser Lys Arg Ile Ala Lys Ile Ala Phe Thr Gly
225 230 235 240

Glu Thr Ser Thr Gly Arg Leu Ile Met Gln Tyr Ala Ser Glu Asn Leu
245 250 255

Ile Pro Val Thr Leu Glu Leu Gly Gly Lys Ser Pro Asn Ile Phe Phe
260 265 270

Ala Asp Val Met Asp Arg Asp Asp Ser Tyr Phe Asp Lys Ala Leu Glu

```
                275                 280                 285
Gly Phe Ala Met Phe Ala Leu Asn Gln Gly Glu Val Cys Thr Cys Pro
    290                 295                 300
Ser Arg Ala Leu Val Glu Glu Ser Ile Tyr Asp Arg Phe Ile Glu Arg
305                 310                 315                 320
Ala Leu Lys Arg Val Glu Ala Ile Lys Gln Gly His Pro Leu Asp Ser
                325                 330                 335
Gln Thr Met Ile Gly Ala Gln Ala Ser Ala Glu Gln Leu Glu Lys Ile
            340                 345                 350
Leu Ser Tyr Ile Asp Ile Gly Arg Gly Glu Gly Ala Gln Cys Leu Thr
                355                 360                 365
Gly Gly Glu Arg Asn Val Leu Gly Gly Glu Leu Ala Glu Gly Tyr Tyr
    370                 375                 380
Val Lys Pro Thr Val Phe Arg Gly His Asn Lys Met Arg Ile Phe Gln
385                 390                 395                 400
Glu Glu Ile Phe Gly Pro Val Leu Ala Val Thr Thr Phe Lys Thr Glu
                405                 410                 415
Glu Glu Ala Leu Glu Ile Ala Asn Asp Thr Leu Tyr Gly Leu Gly Ala
            420                 425                 430
Gly Val Trp Thr Arg Asp Gly Asn Arg Ala Tyr Arg Phe Gly Arg Gly
                435                 440                 445
Ile Gln Ala Gly Arg Val Trp Thr Asn Cys Tyr His Ala Tyr Pro Ala
    450                 455                 460
His Ala Ala Phe Gly Gly Tyr Lys Gln Ser Gly Ile Gly Arg Glu Thr
465                 470                 475                 480
His Lys Met Met Leu Asp His Tyr Gln Gln Thr Lys Asn Leu Leu Val
                485                 490                 495
Ser Tyr Ser Glu Lys Pro Leu Gly Phe Phe
            500                 505

<210> SEQ ID NO 55
<211> LENGTH: 107
<212> TYPE: PRT
<213> ORGANISM: Burkholderia pseudomallei

<400> SEQUENCE: 55

Met Ala Ile Thr Leu Thr Glu Lys Ala Ala Gln His Val Gln Lys Tyr
1               5                   10                  15
Leu Ala Arg Arg Gly Lys Gly Leu Gly Leu Arg Leu Gly Val Arg Thr
            20                  25                  30
Thr Gly Cys Ser Gly Leu Ala Tyr Lys Leu Glu Tyr Val Asp Glu Leu
        35                  40                  45
Thr Pro Glu Asp Gln Met Phe Glu Ser His Gly Val Lys Val Phe Val
    50                  55                  60
Asp Pro Lys Ser Leu Ala Tyr Ile Asp Gly Thr Glu Leu Asp Phe Ala
65                  70                  75                  80
Arg Glu Gly Leu Asn Glu Gly Phe Lys Phe Asn Pro Asn Val Lys
                85                  90                  95
Asp Glu Cys Gly Cys Gly Glu Ser Phe Arg Val
            100                 105

<210> SEQ ID NO 56
<211> LENGTH: 170
<212> TYPE: PRT
<213> ORGANISM: Burkholderia pseudomallei
```

```
<400> SEQUENCE: 56

Met Met Ser Lys Lys Leu Arg Leu Ala Phe Ala Met Leu Met Ile Gly
1               5                   10                  15

Ala Leu Ala Ala Cys Lys Ser Gly Val Lys Leu Asp Glu His Ala Asn
            20                  25                  30

Gln Gly Asp Ala Val Ser Thr Gln Pro Asn Pro Glu Asn Val Ala Gln
        35                  40                  45

Val Thr Val Asp Pro Leu Asn Asp Pro Asn Ser Pro Leu Ala Lys Arg
    50                  55                  60

Ser Val Tyr Phe Asp Phe Asp Ser Tyr Ser Val Gln Asp Gln Tyr Gln
65                  70                  75                  80

Ala Leu Leu Gln Gln His Ala Gln Tyr Leu Lys Ser His Pro Gln Arg
                85                  90                  95

His Ile Leu Ile Gln Gly Asn Thr Asp Glu Arg Gly Thr Ser Glu Tyr
            100                 105                 110

Asn Leu Ala Leu Gly Gln Lys Arg Ala Glu Ala Val Arg Arg Ala Leu
        115                 120                 125

Ser Leu Leu Gly Val Gly Asp Ala Gln Met Glu Ala Val Ser Leu Gly
    130                 135                 140

Lys Glu Lys Pro Val Ala Leu Gly His Asp Glu Ala Ser Trp Ala Gln
145                 150                 155                 160

Asn Arg Arg Ala Asp Leu Val Tyr Gln Gln
                165                 170

<210> SEQ ID NO 57
<211> LENGTH: 762
<212> TYPE: PRT
<213> ORGANISM: Burkholderia pseudomallei

<400> SEQUENCE: 57

Met Arg Leu Ile Glu Leu Arg Ser Pro Leu Leu Asp Pro Asp Ala Val
1               5                   10                  15

Ala Leu Ser Phe Val Val His Glu Asn Leu Ser Gln Glu Pro Ser Tyr
            20                  25                  30

Gln Leu Asp Leu Leu Ser His Asp Ser Asn Leu Asp Phe Asp Ala Leu
        35                  40                  45

Leu Gly Ser Thr Leu Ser Ala Asp Ile Asp Leu Gly Glu Gly Asp Ile
    50                  55                  60

Arg Thr Phe Asn Thr His Val Phe Gly Gly Tyr Asp Thr Gly Gln Met
65                  70                  75                  80

Ser Gly Gln Tyr Thr Tyr Thr Leu Glu Leu Arg Ser Trp Leu Ser Phe
                85                  90                  95

Leu Ala Glu Asn Arg Asn Ser Arg Ile Phe Gln Asp Leu Ser Val Pro
            100                 105                 110

Gln Ile Val Glu Gln Val Phe Gln Gly His Gln Arg Asn Gly Tyr Arg
        115                 120                 125

Phe Glu Leu Glu Gly Thr Tyr Glu Pro Arg Glu Tyr Cys Val Gln Phe
    130                 135                 140

Gln Glu Thr Asp Leu Asn Phe Val Lys Arg Leu Leu Glu Asp Glu Gly
145                 150                 155                 160

Ile Tyr Phe Trp Val Glu His Glu Pro Asp Arg His Val Val Ile
                165                 170                 175

Ser Asp Thr Gln Arg Phe Glu Asp Leu Pro Leu Pro Asn Asp Thr Leu
            180                 185                 190
```

```
Glu Tyr Leu Pro Asp Gly Glu Ser Arg Ala Ile Gln Gly Arg Glu
            195                 200                 205
Gly Val Gln Arg Leu Gln Arg Thr Arg Ile Lys Ser Asn Asn Val
210                 215                 220
Ala Leu Arg Asp Phe Asp Tyr His Ala Pro Ser Lys Gln Leu Asp Ser
225                 230                 235                 240
Asp Ala Gln Val Glu Gln Gln Ser Leu Gly Gly Ile Pro Leu Glu Tyr
                245                 250                 255
Tyr Asp Tyr Ala Ala Gly Tyr Arg Asp Pro Glu Gln Gly Glu Arg Leu
            260                 265                 270
Ala Arg Leu Arg Leu Glu Ala Ile Gln Ala Asp Ala His Ala Leu Gly
            275                 280                 285
Gly Glu Ala Asn Ala Arg Ala Leu Ala Val Gly Arg Ala Phe Thr Leu
290                 295                 300
Val Gly His Pro Ala Leu Ser Arg Asn Arg Arg Tyr Tyr Val Thr Asn
305                 310                 315                 320
Ser Glu Leu Thr Phe Ile Gln Asp Gly Pro Asp Ser Thr Ser Gln Gly
                325                 330                 335
Arg Asn Val Ala Val Lys Phe Arg Ala Leu Ala Asp Asp Gln Pro Phe
            340                 345                 350
Arg Pro Leu Leu Val Thr Lys Arg Pro Arg Val Pro Gly Ile Gln Ser
            355                 360                 365
Ala Thr Val Val Gly Pro Glu Met Ser Glu Val His Thr Asp Lys Leu
            370                 375                 380
Gly Arg Ile Arg Val His Phe His Trp Asp Arg Tyr Lys Thr Thr Glu
385                 390                 395                 400
Ala Asp Ala Ser Cys Trp Ile Arg Val Thr Gln Ala Trp Ala Gly Lys
                405                 410                 415
Gly Trp Gly Val Leu Ala Met Pro Arg Val Gly Gln Glu Val Ile Val
            420                 425                 430
Val Tyr Val Asp Gly Asp Leu Asp Arg Pro Leu Ala Thr Gly Ile Val
            435                 440                 445
Tyr Asn Gly Glu Asn Pro Thr Pro Tyr Asp Leu Pro Lys Asp Ile Arg
450                 455                 460
Tyr Thr Gly Leu Val Thr Arg Ser Ile Lys Arg Ala Gly Gly Ile Pro
465                 470                 475                 480
Asn Ala Ser Gln Leu Thr Phe Asp Asp Gln His Gly Ala Glu Arg Val
                485                 490                 495
Met Ile His Ala Glu Arg Asp Leu Gln Gln Thr Val Glu Arg Asn Ser
            500                 505                 510
Ser Thr Ser Ile Ala Gln Asp Leu Asn Leu Ser Val Lys Gly Thr Ser
            515                 520                 525
Thr Ser Val Val Gly Ile Ser Val Ser Phe Thr Gly Ile Ser Val Ser
            530                 535                 540
Tyr Thr Gly Leu Ser Val Ser Phe Thr Gly Val Ser Ala Arg Phe Thr
545                 550                 555                 560
Gly Val Ser Thr Ser Phe Thr Gly Val Ser Thr Ser Phe Thr Gly Val
                565                 570                 575
Ser Thr Ser Phe Thr Gly Val Asp Ser Phe Thr Gly Val Ser Thr
            580                 585                 590
Gly Phe Lys Gly Val Asp Thr Ser Phe Thr Gly Val Ala Thr Ser Met
            595                 600                 605
Val Gly Val Ser Thr Ser Ile Thr Gly Ser Ser Asn Ser Val Thr Gly
```

Val Ser Asn Ser Met Thr Gly Ile Ser Ser Trp Lys Asp Val Ser
625                 630                 635                 640

Met Ser Thr Thr Gly Gln Ser Glu Ser Ile Thr Gly Val Ser Leu Ser
            645                 650                 655

Tyr Thr Gly Thr Ser Asn Ser Met Thr Gly Thr Ser Thr Ser Val Thr
            660                 665                 670

Gly Thr Ser Thr Ser Ile Thr Gly Thr Ser Met Ser Asn Thr Gly Ser
            675                 680                 685

Ser Thr Ser Ile Thr Gly Thr Ser Met Ser Thr Gly Ser Ser Val
690                 695                 700

Ser Thr Thr Gly Ser Ser Met Ser Ala Thr Gly Ser Ser Val Gly Thr
705                 710                 715                 720

Thr Gly Ser Ser Val Ser Thr Thr Gly Ser Lys Met Ser Val Thr Gly
                725                 730                 735

Phe Ser Phe Ser Tyr Thr Gly Ala Ser Tyr Glu Asp Val Gly Val Asp
            740                 745                 750

Leu Lys Lys Leu Gly Met Gln Thr Lys Asn
            755                 760

<210> SEQ ID NO 58
<211> LENGTH: 489
<212> TYPE: PRT
<213> ORGANISM: Burkholderia mallei

<400> SEQUENCE: 58

Met Pro Leu Leu Ser Ser Asp His Cys Arg Ala Leu Pro Pro Glu Val
1               5                   10                  15

Ser Arg Pro Arg Tyr Asp Arg Arg Ala Leu Arg Thr Gly Ile Val His
            20                  25                  30

Leu Gly Leu Gly Ala Phe His Arg Ala His Gln Ala Cys Tyr Thr Glu
            35                  40                  45

Thr Leu Val Glu Arg Gly Asp Leu Arg Trp Gly Ile Ala Gly Val Glu
50                  55                  60

Leu Arg Arg Arg His Thr Val Glu Arg Leu Ala Ala Gln Asp His Leu
65                  70                  75                  80

Tyr Ser Val Thr Glu Arg Ala Gly Asp Ala Ala Arg Thr Arg Val Val
                85                  90                  95

Gly Ala Val His Arg Thr Leu Phe Ala Pro Gln Ala Leu Ala Thr Leu
            100                 105                 110

Leu Gly Leu Ile Ala Asp Pro Ser Val Ser Ile Val Ser Leu Thr Val
            115                 120                 125

Thr Glu Lys Gly Tyr Tyr Arg Arg Pro Gly Gly Gly Leu Asp Leu
130                 135                 140

Asp Asp Pro Ala Ile Arg Arg Asp Leu Ala Gln Pro His Ala Pro Ser
145                 150                 155                 160

Thr Thr Leu Gly Val Leu Ala Ala Gly Ile Arg Leu Arg Ala Ala His
            165                 170                 175

Ala Pro Leu Ser Val Leu Ser Cys Asp Asn Met Pro Ser Asn Gly Asp
            180                 185                 190

Thr Leu Arg Ala Leu Leu Ala Gln Tyr Ala Glu Gln Thr Asp Gly Ala
            195                 200                 205

Leu Ala Arg Arg Ile Arg Cys Asp Val Ala Phe Pro Asn Thr Met Val
210                 215                 220

```
Asp Arg Ile Val Pro Ala Ala Thr Pro Glu Ser Leu Asp Trp Val Gln
225                 230                 235                 240

Ser Arg Ile Gly Val Arg Asp Glu Ala Ala Ile Val Cys Glu Pro Phe
            245                 250                 255

Ala Gln Trp Val Phe Glu Asp Arg Phe Ala Gly Ala Arg Pro Arg Trp
            260                 265                 270

Glu Asp Ala Gly Ala Leu Val Ala Ala Asp Val Arg Pro Tyr Glu Lys
            275                 280                 285

Met Lys Leu Arg Leu Leu Asn Gly Ser His Ser Ala Ile Ala Tyr Ala
290                 295                 300

Gly Gln Leu Arg Gly Arg Thr Val Ser Asp Ala Met Ala Asp Pro
305                 310                 315                 320

Leu Ile Asp Ala Leu Ala Arg Gly Val Met Thr Arg Glu Leu Leu Ala
            325                 330                 335

Thr Leu Asp Val Pro Ala Gly Tyr Asp Val Arg Ala Tyr Cys Ala Ser
            340                 345                 350

Leu Ile Glu Arg Phe Arg Asn Pro Ala Leu Ala His Arg Thr Ala Gln
            355                 360                 365

Ile Ala Thr Asp Gly Thr Gln Lys Val Pro Leu Arg Trp Leu Pro Ala
370                 375                 380

Leu Ala Glu Ser Ala Ala Ala Gly Val Glu Arg Pro Phe Leu Glu Arg
385                 390                 395                 400

Ser Leu Ala Met Trp Leu His Tyr Val Glu Val Ala Arg Asp Glu Ser
            405                 410                 415

Gly Arg Pro Leu Val Leu Glu Asp Pro Gly Ala Gln Ala Leu Ala Ala
            420                 425                 430

Arg Leu His Gly Ala Pro Gly Ala Thr Asp Ala Val Arg Ala Ala Leu
            435                 440                 445

Gly Leu Ile Ala Ser Arg Asp Ala Ala Arg Trp Pro Glu Ala Leu Thr
450                 455                 460

Ala Arg Val Gly Ala His Leu Glu Thr Val Arg Thr Arg Gly Thr Asp
465                 470                 475                 480

Ala Leu Leu Arg Pro Leu Leu Asp Ala
            485

<210> SEQ ID NO 59
<211> LENGTH: 673
<212> TYPE: PRT
<213> ORGANISM: Burkholderia mallei

<400> SEQUENCE: 59

Met Ser Ala Ser Arg Ala Ala Pro Ser Leu Pro Asp Ala Arg Val Leu
1               5                   10                  15

Ala Val Asp Gly Leu Thr Val Thr Phe Arg Arg Glu Asp Ala Ala Phe
            20                  25                  30

Val Ala Val Arg Asp Leu Ser Phe His Val Asp Arg Gly Glu Thr Leu
        35                  40                  45

Ala Ile Val Gly Glu Ser Gly Ser Gly Lys Ser Val Thr Ser Leu Ala
50                  55                  60

Leu Met Arg Leu Val Glu His Gly Gly Ala Ile Ala Gly Ala
65                  70                  75                  80

Ile Ala Leu Arg Arg Gly Gly Ala Val Leu Asp Leu Ala Arg Ala
            85                  90                  95

Thr Pro Ser Thr Leu Arg Thr Val Arg Gly Ala Asp Val Ala Met Ile
            100                 105                 110
```

```
Phe Gln Glu Pro Met Thr Ser Leu Asn Pro Val Phe Thr Val Gly Asp
            115                 120                 125
Gln Ile Ser Glu Ala Ile Ala Leu His Gln His Lys Ser Ala Gly Glu
        130                 135                 140
Ala Arg Ala Glu Thr Leu Arg Leu Leu Asp Leu Val Arg Ile Pro Glu
145                 150                 155                 160
Ala Arg Arg Val Phe Ala Arg His Pro His Gln Leu Ser Gly Gly Met
                165                 170                 175
Arg Gln Arg Val Met Ile Ala Met Ala Leu Ser Cys Arg Pro Ala Leu
            180                 185                 190
Leu Ile Ala Asp Glu Pro Thr Thr Ala Leu Asp Val Thr Ile Gln Ala
        195                 200                 205
Gln Ile Leu Gln Leu Ile Arg Gly Leu Gln Asp Glu Met Asp Met Gly
    210                 215                 220
Val Ile Phe Ile Thr His Asp Met Gly Val Ala Glu Val Ala Asp
225                 230                 235                 240
Arg Val Leu Val Met Tyr Arg Gly Glu Lys Val Glu Gly Ala Cys
                245                 250                 255
Asp Ala Ile Phe Ala Ala Pro Ser His Pro Tyr Thr Lys Ala Leu Leu
            260                 265                 270
Ala Ala Val Pro Arg Leu Gly Ser Met Arg Gly Thr Asp Ala Pro Ala
        275                 280                 285
Lys Phe Pro Leu Leu Arg Phe Asp Pro Ala Ala Gly Asp Ala Leu Val
    290                 295                 300
Val Ala Gly Gly Asp Ala Thr Ala Ala Ser Gly Asp Ala Ala Arg Glu
305                 310                 315                 320
Ser Val Leu Phe Val Asp Ser Asp Ala Ala Ala Ser Ala Ala Ser
                325                 330                 335
Thr Ala Ser Thr Ala Ser Ala Ala Ser Ala Ala Ser Ala Ala Pro Thr
            340                 345                 350
Ala Cys Ala Arg Pro Ala Ile Asp Ala Gly Ala Pro Pro Leu Leu Arg
        355                 360                 365
Val Arg Glu Leu Val Thr Arg Phe Pro Val Lys Ser Gly Val Phe Gly
    370                 375                 380
Arg Val Ser Gln Tyr Val His Ala Val Glu Arg Val Ser Phe Glu Leu
385                 390                 395                 400
Arg Ala Gly Glu Thr Leu Ala Leu Val Gly Glu Ser Gly Cys Gly Lys
                405                 410                 415
Ser Thr Thr Gly Arg Ser Leu Leu Arg Leu Val Glu Arg Val Ser Gly
            420                 425                 430
Ser Ile Glu Phe Glu Gly Arg Glu Ile Gly Ala Leu Lys Gly Arg Glu
        435                 440                 445
Leu Gln Ala Leu Arg Arg Asn Ile Gln Phe Ile Phe Gln Asp Pro Phe
    450                 455                 460
Ala Ser Leu Asn Pro Arg Leu Thr Val Gly Phe Ser Ile Met Glu Pro
465                 470                 475                 480
Leu Leu Val His Gly Val Ala Ser Gly Arg Gln Ala Gln Ala Arg Val
                485                 490                 495
Asp Trp Leu Leu Glu Arg Val Gly Leu Pro Ala Asp Ala Ala Arg Arg
            500                 505                 510
Tyr Pro His Glu Phe Ser Gly Gly Gln Arg Gln Arg Ile Ala Ile Ala
        515                 520                 525
```

-continued

Arg Ala Leu Ala Leu Asn Pro Lys Val Val Ala Asp Glu Ser Val
    530                 535                 540

Ser Ala Leu Asp Val Ser Val Gln Ala Gln Ile Val Asn Leu Met Leu
545                 550                 555                 560

Asp Leu Gln Arg Glu Leu Gly Val Ala Tyr Leu Phe Ile Ser His Asp
            565                 570                 575

Met Ala Val Val Glu Arg Ile Ser His Arg Val Ala Val Met Tyr Leu
        580                 585                 590

Gly Gln Ile Val Glu Ile Gly Pro Arg Arg Ala Val Phe Glu Thr Pro
            595                 600                 605

Arg His Pro Tyr Thr Lys Lys Leu Met Ser Ala Val Pro Ile Ala Asp
    610                 615                 620

Pro Ala Cys Arg His Ala Pro Arg Thr Leu Pro Ala Asp Glu Leu Pro
625                 630                 635                 640

Ser Pro Ile Arg Ala Leu Gly Asp Glu Pro Glu Val Ala Pro Leu Val
            645                 650                 655

Ala Val Gly Pro Ala His Phe Val Ala Glu His Arg Val Gly Gly Ala
        660                 665                 670

Tyr

<210> SEQ ID NO 60
<211> LENGTH: 930
<212> TYPE: PRT
<213> ORGANISM: Burkholderia mallei

<400> SEQUENCE: 60

Met Lys Pro Arg Ala Thr Leu Arg Leu Gln Leu His Ala Gly Phe Thr
1               5                   10                  15

Phe Asp Asp Ala Ala His Val Gly Tyr Phe Ala Arg Leu Gly Val
            20                  25                  30

Ser His Leu Tyr Leu Ser Pro Ile Thr Ala Ala Glu Pro Gly Ser Arg
        35                  40                  45

His Gly Tyr Asp Val Ile Asp Tyr Ser Thr Val Asn Pro Glu Leu Gly
    50                  55                  60

Gly Glu Ala Ala Phe Val Arg Leu Ile Asp Ala Leu Arg Arg Arg Gly
65                  70                  75                  80

Met Gly Ala Ile Val Asp Ile Val Pro Asn His Met Gly Val Gly Gly
                85                  90                  95

Ser Ser Asn Arg Trp Trp Asn Asp Val Leu Glu Trp Gly Ala Arg Ser
            100                 105                 110

Arg Phe Ala Arg His Phe Asp Ile Asp Trp His Ala Ser Asp Pro Ala
        115                 120                 125

Leu Gln Arg Lys Val Leu Leu Pro Cys Leu Gly Arg Pro Tyr Gly Glu
    130                 135                 140

Ala Leu Ala Ala Gly Asp Ile Ala Leu Arg Ala Asp Ala Ala His Gly
145                 150                 155                 160

Arg Phe Ala Ile Ala Cys Ala Gly Arg Thr Leu Pro Val Gln Ile Gly
                165                 170                 175

Ala Tyr Pro Asp Ile Leu Arg Ala Ala Asn Arg Ser Asp Leu Asn Ala
            180                 185                 190

Leu Ala Glu Arg Phe Asp Ala Pro Gly Ala Arg Pro Ser Asn His Ala
        195                 200                 205

Arg Leu Asp Ala Ala His Ala Ala Leu Arg Asp Tyr Ala Ala Ala Arg
    210                 215                 220

```
Gly Pro Gly Ala Leu Asp Ala Val Leu His Gly Phe Asp Pro Arg Ile
225                 230                 235                 240

Ala Arg Ser Arg Glu Met Leu His Arg Leu Leu Glu Gln Gln His Tyr
            245                 250                 255

Arg Leu Ala Trp Trp Arg Thr Ala Thr Asp Glu Ile Asn Trp Arg Arg
            260                 265                 270

Phe Phe Asp Ile Ser Thr Leu Ala Cys Met Arg Ile Glu Asp Ala Ala
            275                 280                 285

Val Phe Asp Asp Val His Ala Leu Leu Trp Arg Leu Tyr Ala Ala Gly
    290                 295                 300

Leu Val Asp Gly Val Arg Ile Asp His Val Asp Gly Leu Ala Asp Pro
305                 310                 315                 320

Arg Gly Tyr Cys Arg Gln Leu Arg Gly Arg Leu Ala Ala Leu Arg Asp
                325                 330                 335

Gly Glu Pro Tyr Ile Val Val Glu Lys Ile Leu Ala Pro Asp Glu Arg
                340                 345                 350

Leu Pro Glu Asp Trp Arg Val Asp Gly Thr Thr Gly Tyr Asp Phe Met
            355                 360                 365

Asn Asp Val Ser Ala Leu Leu His Asp Ala Ala Gly Ala Ala Pro Leu
370                 375                 380

Ala Ala Leu Trp Ala Asp Met Thr Gly Ala Glu Thr Thr Phe Ala Arg
385                 390                 395                 400

Glu Ala Leu Asp Gly Lys Arg Arg Val Leu Ala Arg Gln Phe Ala Ala
                405                 410                 415

Glu His Glu Arg Val Ala Arg Ala Met His Arg Leu Ala Arg Ala Ser
            420                 425                 430

Arg Asp Ala Arg Asp Phe Ala Leu Asn Pro Ile Arg Arg Ala Val Ala
            435                 440                 445

Glu Leu Ala Ile Arg Leu Pro Val Tyr Arg Leu Tyr Pro Ser Ala Gly
450                 455                 460

Ala Pro Gln Arg Thr Asp Arg Ala Leu Leu Ala Gly Ala Trp Gln Ala
465                 470                 475                 480

Ala Arg Ser Ala Ile Ala Pro Ala Asp Arg Ala Ala Leu Asp Tyr Val
            485                 490                 495

Ala Ala Thr Leu Gly Leu Pro Gly Val Ala Arg Ala Val Ala Gly Leu
            500                 505                 510

Gly Asp Pro Ala Arg Leu Ala Ala Arg Val Gly Phe Ala Gln Leu Thr
            515                 520                 525

Ala Pro Leu Ala Ala Lys Gly Val Glu Asp Thr Ala Cys Tyr Arg Tyr
530                 535                 540

Gly Arg Leu Leu Ser Arg Asn Glu Val Gly Ala His Ala Asp Ala Leu
545                 550                 555                 560

Ser Leu Ala Pro Gly Ala Phe His Thr Arg Asn Arg Arg Arg Arg Arg
            565                 570                 575

Thr Phe Pro Gly Ala Leu Leu Ala Thr Ala Thr His Asp His Lys Arg
            580                 585                 590

Gly Glu Asp Ala Arg Ala Arg Leu Ala Val Leu Ser Glu Ala His Arg
            595                 600                 605

Ala Trp Arg Ala Ala Ala Leu Asp Trp Ala Ala Phe Asn Ala Pro His
            610                 615                 620

His His Gly Ala Pro Ala Ala Asp Arg Ile Pro Gly Pro Ala Ala
625                 630                 635                 640

Glu Ala Met Leu Tyr Gln Thr Leu Val Gly Ala Trp Pro Pro Ala Leu
```

```
                645                 650                 655
Ala Pro Asp Asp Ala Pro Gly Leu Ala Ala Leu Thr Asp Arg Val Glu
                660                 665                 670

Arg Trp Gln Leu Lys Ala Leu Arg Glu Ala Lys Arg Asp Thr Asp Trp
            675                 680                 685

Leu Glu Pro Asn Leu Gly Tyr Glu Ala Gly Cys Ala Ala Phe Leu Arg
        690                 695                 700

Ala Ile Met Thr Pro Arg Gly Pro Asp Phe Ala His Arg Leu His
705                 710                 715                 720

Arg Leu Val Ala Arg Ile Ala Pro Ala Gly Ile Val Asn Ser Leu Ser
                725                 730                 735

Gln Ala Ala Leu Arg Leu Leu Ser Pro Gly Val Pro Asp Leu Tyr Gln
            740                 745                 750

Gly Ala Gln Thr Trp Asp His Thr Leu Val Asp Pro Asp Asn Arg Ala
        755                 760                 765

Asp Val Pro Phe Ala Arg Tyr Ala Ala Gln Arg Ile Asp Ala Pro Val
    770                 775                 780

Ala Ala Tyr Leu Arg Asp Trp Ala Asp Gly Arg Val Lys His Ala Leu
785                 790                 795                 800

Ile Gly Arg Leu Leu Ala Leu Arg Ala Ala His Pro Glu Thr Phe Ala
                805                 810                 815

Ala Gly Ala Tyr Val Pro Leu His Val Arg Gly Thr Arg Arg Gly His
            820                 825                 830

Ala Leu Ala Phe Ala Arg Arg Asp Ala Ser Thr Thr Ile Val Val Ile
        835                 840                 845

Ala Thr Arg Leu Ala Tyr Pro Leu Leu Gly Asp Ala Pro Ala Arg Pro
850                 855                 860

Cys Val Glu Ala Ala Cys Trp Ala Asp Thr Ala Val Gly Leu Ala Pro
865                 870                 875                 880

Gly Phe Ala Gly Pro Trp Arg Asp Met Leu Asn Asp Gly Thr Leu Asp
                885                 890                 895

Ala Pro Ser Gly Met Leu Pro Leu Ala Ala Ala Leu Ala His Leu Pro
            900                 905                 910

Val Ala Val Leu Ile Arg Glu Gly Gly Ala Ala Asp Thr Pro Arg Arg
        915                 920                 925

Gly Ala
    930

<210> SEQ ID NO 61
<211> LENGTH: 550
<212> TYPE: PRT
<213> ORGANISM: Burkholderia mallei

<400> SEQUENCE: 61

Met Ala Ala Lys Asp Val Val Phe Gly Asp Ser Ala Arg Ala Lys Met
1               5                   10                  15

Val Glu Gly Val Asn Ile Leu Ala Asn Ala Val Lys Val Thr Leu Gly
                20                  25                  30

Pro Lys Gly Arg Asn Val Val Leu Glu Arg Ser Phe Gly Gly Pro Thr
            35                  40                  45

Val Thr Lys Asp Gly Val Ser Val Ala Lys Glu Ile Glu Leu Lys Asp
        50                  55                  60

Lys Leu Gln Asn Met Gly Ala Gln Met Val Lys Glu Val Ala Ser Lys
65                  70                  75                  80
```

-continued

```
Thr Ser Asp Asn Ala Gly Asp Gly Thr Thr Thr Ala Thr Val Leu Ala
             85                  90                  95
Gln Ser Ile Val Arg Glu Gly Met Lys Tyr Val Ala Ser Gly Met Asn
            100                 105                 110
Pro Met Asp Leu Lys Arg Gly Ile Asp Lys Ala Val Ala Ala Val
            115                 120                 125
Glu Glu Leu Lys Lys Ile Ser Lys Pro Cys Thr Thr Asn Lys Glu Ile
130                 135                 140
Ala Gln Val Gly Ala Ile Ser Ala Asn Ser Asp Ser Ile Gly Asp
145                 150                 155                 160
Arg Ile Ala Glu Ala Met Asp Lys Val Gly Lys Glu Gly Val Ile Thr
                165                 170                 175
Val Glu Asp Gly Lys Ser Leu Ala Asp Glu Leu Asp Val Val Glu Gly
            180                 185                 190
Met Gln Phe Asp Arg Gly Tyr Leu Ser Pro Tyr Phe Ile Asn Asn Pro
        195                 200                 205
Asp Lys Gln Val Ala Val Leu Glu Asn Pro Phe Val Leu Leu His Asp
    210                 215                 220
Lys Lys Val Ser Asn Ile Arg Asp Leu Leu Pro Val Leu Glu Gln Val
225                 230                 235                 240
Ala Lys Ala Gly Arg Pro Leu Leu Ile Ile Ala Glu Asp Val Glu Gly
                245                 250                 255
Glu Ala Leu Ala Thr Leu Val Val Asn Asn Ile Arg Gly Ile Leu Lys
            260                 265                 270
Thr Val Ala Val Lys Ala Pro Gly Phe Gly Asp Arg Arg Lys Ala Met
        275                 280                 285
Leu Glu Asp Ile Ala Ile Leu Thr Gly Gly Gln Val Ile Ala Glu Glu
    290                 295                 300
Thr Gly Leu Thr Leu Glu Lys Ala Thr Leu Ala Glu Leu Gly Gln Ala
305                 310                 315                 320
Lys Arg Ile Glu Val Gly Lys Glu Asn Thr Thr Ile Ile Asp Gly Ala
                325                 330                 335
Gly Glu Ala Val Asn Ile Glu Ala Arg Val Lys Gln Ile Arg Thr Gln
            340                 345                 350
Ile Glu Glu Ala Thr Ser Asp Tyr Asp Arg Glu Lys Leu Gln Glu Arg
        355                 360                 365
Val Ala Lys Leu Ala Gly Gly Val Ala Val Ile Lys Val Gly Ala Ala
    370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Ile Val Pro Gly Gly Gly
                405                 410                 415
Val Ala Leu Ile Arg Ala Arg Thr Ala Ile Ala Ser Leu Thr Gly Val
            420                 425                 430
Asn Ala Asp Gln Asn Ala Gly Ile Lys Ile Val Leu Arg Ala Met Glu
        435                 440                 445
Glu Pro Leu Arg Gln Ile Val Thr Asn Gly Gly Glu Glu Ala Ser Val
    450                 455                 460
Val Val Ala Ala Val Ala Gly Lys Gly Asn Tyr Gly Tyr Asn Ala
465                 470                 475                 480
Ala Thr Gly Glu Tyr Val Asp Met Val Glu Ala Gly Val Val Asp Pro
                485                 490                 495
Thr Lys Val Thr Arg Thr Ala Leu Gln Asn Ala Ala Ser Val Ala Gly
```

500                 505                 510
Leu Leu Leu Thr Thr Asp Ala Ala Val Ala Glu Leu Pro Lys Glu Asp
        515                 520                 525

Ala Pro Met Pro Gly Gly Met Pro Gly Gly Met Gly Gly Met Gly Met
    530                 535                 540

Gly Met Gly Met Asp Met
545                 550

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Ser Gly
1

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Ser Gly Gly Gly Ser Gly
1               5

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Asp Glu Ala Trp Gly Ile Met Ile Asp Leu Ser Asn Leu Glu
1               5                   10                  15

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ser Ser Gly Gly Ser Ser Gly
1               5

<210> SEQ ID NO 66
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 66

Gly Gly Gly Ser Gly Gly Gly Ser Gly Gly Gly Ser
1               5                   10
```